(12) United States Patent
Liu et al.

(10) Patent No.: US 9,322,006 B2
(45) Date of Patent: Apr. 26, 2016

(54) EVALUATION AND IMPROVEMENT OF NUCLEASE CLEAVAGE SPECIFICITY

(71) Applicant: President and Fellows of Harvard College, Cambridge, MA (US)

(72) Inventors: David R. Liu, Lexington, MA (US); John Paul Guilinger, Ridgway, CO (US); Vikram Pattanayak, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/320,271

(22) Filed: Jun. 30, 2014

(65) Prior Publication Data
US 2015/0010526 A1    Jan. 8, 2015

Related U.S. Application Data

(63) Continuation of application No. 14/234,031, filed as application No. PCT/US2012/047778 on Jul. 22, 2012.

(60) Provisional application No. 61/510,841, filed on Jul. 22, 2011.

(51) Int. Cl.
*C12P 19/34* (2006.01)
*C12Q 1/68* (2006.01)
(Continued)

(52) U.S. Cl.
CPC .. *C12N 9/22* (2013.01); *C12Q 1/44* (2013.01); *C12Q 1/6802* (2013.01); *C12Q 1/6874* (2013.01)

(58) Field of Classification Search
USPC ......... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS 5,780,053 A    7/1998  Ashley et al.
6,057,153 A    5/2000  George et al.
(Continued)

FOREIGN PATENT DOCUMENTS

AU    2012244264       11/2012
CN    103233028 A      8/2013
(Continued)

OTHER PUBLICATIONS

Pattanayak et al., Determining the Specificities of TALENs, Cas9, and Other Genome-Editing Enzymes. Enzymology, 546, 47-78, 2014.*
(Continued)

*Primary Examiner* — Frank Lu
(74) *Attorney, Agent, or Firm* — Wolf, Greenfield & Sacks, P.C.

(57) ABSTRACT

Engineered nucleases are promising tools for genome manipulation and determining off-target cleavage sites of these enzymes is of great interest. We developed an in vitro selection method that interrogates $10^{11}$ DNA sequences for their ability to be cleaved by nucleases. The method revealed hundreds of thousands of DNA sequences that can be cleaved in vitro by two ZFNs, CCR5-224 and VF2468, which target the endogenous human CCR5 and VEGF-A genes, respectively. Analysis of the identified sites in cultured human cells revealed CCR5-224-induced mutagenesis at nine off-target loci. Similarly, we observed 31 off-target sites cleaved by VF2468 in cultured human cells. Our findings establish an energy compensation model of ZFN specificity in which excess binding energy contributes to off-target ZFN cleavage and suggest strategies for the improvement of future nuclease design. It was also observed that TALENs can achieve cleavage specificity similar to or higher than that observed in ZFNs.

26 Claims, 67 Drawing Sheets

(51) Int. Cl.
*C07H 21/02* (2006.01)
*C07H 21/04* (2006.01)
*C07H 21/00* (2006.01)
*C12N 9/22* (2006.01)
*C12Q 1/44* (2006.01)

(56) References Cited

U.S. PATENT DOCUMENTS

| | | |
|---|---|---|
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,479,573 B2 | 1/2009 | Chu et al. |
| 7,794,931 B2 | 9/2010 | Breaker et al. |
| 7,919,277 B2 | 4/2011 | Russell et al. |
| 8,361,725 B2 | 1/2013 | Russell et al. |
| 8,546,553 B2 | 10/2013 | Terns et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,846,578 B2 | 9/2014 | McCray et al. |
| 2006/0088864 A1 | 4/2006 | Smolke et al. |
| 2008/0124725 A1 | 5/2008 | Barrangou et al. |
| 2008/0182254 A1 | 7/2008 | Hall et al. |
| 2009/0130718 A1 | 5/2009 | Short |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2011/0104787 A1 | 5/2011 | Church et al. |
| 2011/0189776 A1 | 8/2011 | Terns et al. |
| 2011/0217739 A1 | 9/2011 | Terns et al. |
| 2012/0141523 A1 | 6/2012 | Castado et al. |
| 2012/0270273 A1 | 10/2012 | Zhang et al. |
| 2013/0130248 A1 | 5/2013 | Haurwitz et al. |
| 2013/0158245 A1 | 6/2013 | Russell et al. |
| 2013/0344117 A1 | 12/2013 | Mirosevich et al. |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |

FOREIGN PATENT DOCUMENTS

| | | |
|---|---|---|
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 104004778 A | 8/2014 |
| CN | 104109687 A | 10/2014 |
| CN | 104178461 A | 12/2014 |
| CN | 104342457 | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104593418 A | 5/2015 |
| CN | 104593422 A | 5/2015 |
| CN | 104611370 A | 5/2015 |
| WO | WO 2006/002547 A1 | 1/2006 |
| WO | WO 2006/042112 A2 | 4/2006 |
| WO | WO 2007/025097 A2 | 3/2007 |
| WO | WO 2007/136815 A2 | 11/2007 |
| WO | WO 2010/054108 A2 | 5/2010 |
| WO | WO 2010/054154 A2 | 5/2010 |
| WO | WO 2010/075424 A2 | 7/2010 |
| WO | WO 2011/017293 A2 | 2/2011 |
| WO | WO 2011/053982 A2 | 5/2011 |
| WO | WO 2012/054726 A1 | 4/2012 |
| WO | WO 2012/138927 A2 | 10/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO 2013/013105 A2 | 1/2013 |
| WO | WO 2013/066438 A2 | 5/2013 |
| WO | WO 2013/098244 A1 | 7/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142378 A9 | 9/2013 |
| WO | WO 2013/142578 A2 | 9/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A2 | 11/2013 |
| WO | WO 2013/176915 A1 | 11/2013 |
| WO | WO 2013/176916 A1 | 11/2013 |

(56) References Cited

FOREIGN PATENT DOCUMENTS

| | | |
|---|---|---|
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/113493 A1 | 7/2014 |
| WO | WO 2014/124226 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130955 A1 | 8/2014 |
| WO | WO 2014/131833 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/145599 A2 | 9/2014 |
| WO | WO 2014/150624 A1 | 9/2014 |
| WO | WO 2014/152432 A2 | 9/2014 |
| WO | WO 2014/153470 A2 | 9/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165825 A2 | 10/2014 |
| WO | WO 2014/172458 A1 | 10/2014 |
| WO | WO 2014/172470 A | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006498 A2 | 1/2015 |
| WO | WO 2015/006747 A2 | 1/2015 |
| WO | WO 2015/010114 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/031619 A1 | 3/2015 |
| WO | WO 2015/031775 A1 | 3/2015 |
| WO | WO 2015/033293 A1 | 3/2015 |
| WO | WO 2015/034872 A2 | 3/2015 |
| WO | WO 2015/035136 A2 | 3/2015 |
| WO | WO 2015/035139 A2 | 3/2015 |
| WO | WO 2015/040075 A1 | 3/2015 |
| WO | WO 2015/040402 A1 | 3/2015 |
| WO | WO 2015/048577 A2 | 4/2015 |
| WO | WO 2015/048690 A1 | 4/2015 |
| WO | WO 2015/052133 A1 | 4/2015 |
| WO | WO 2015/052231 A2 | 4/2015 |
| WO | WO 2015/053995 A1 | 4/2015 |
| WO | WO 2015/054253 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066637 A1 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |

(56) References Cited

FOREIGN PATENT DOCUMENTS

WO    WO 2015/073867 A1    5/2015
WO    WO 2015/073990 A1    5/2015

OTHER PUBLICATIONS

International Search Report and Written Opinion for PCT/US2014/050283, mailed Nov. 6, 2014.
GENBANK Submission; NIH/NCBI, Accession No. J04623. Kita et al., Apr. 26, 1993. 2 pages.
Barrangou, RNA-mediated programmable DNA cleavage. Nat Biotechnol. Sep. 2012;30(9):836-8. doi: 10.1038/nbt.2357.
Carroll, A CRISPR approach to gene targeting. Mol Ther. Sep. 2012;20(9):1658-60. doi: 10.1038/mt.2012.171.
Fuchs et al., Polyarginine as a multifunctional fusion tag. Protein Sci. Jun. 2005;14(6):1538-44.
O'Connell et al., Programmable RNA recognition and cleavage by CRISPR/Cas9. Nature. Sep. 28, 2014. doi: 10.1038/nature13769.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 14/258,458, filed Apr. 22, 2014, Cong.
International Search Report and Written Opinion for PCT/US2012/047778, mailed May 30, 2013.
International Preliminary Report on Patentability for PCT/US2012/047778, mailed Feb. 6, 2014.
International Search Report for PCT/US2013/032589, mailed Jul. 26, 2013.
GENBANK Submission; NIH/NCBI, Accession No. J04623. Kita et al., Aug. 26, 1993. 2 pages.
GENBANK Submission; NIH/NCBI, Accession No. NC_002737.1. Ferretti et al., Jun. 27, 2013. 1 page.
GENBANK Submission; NIH/NCBI, Accession No. NC_015683.1. Trost et al., Jul. 6, 2013. 1 page.
GENBANK Submission; NIH/NCBI, Accession No. NC_016782.1. Trost et al., Jun. 11, 2013. 1 page.
GENBANK Submission; NIH/NCBI, Accession No. NC_016786.1. Trost et al., Aug. 28, 2013. 1 page.
GENBANK Submission; NIH/NCBI, Accession No. NC_017053.1. Fittipaldi et al., Jul. 6, 2013. 1 page.
GENBANK Submission; NIH/NCBI, Accession No. NC_017317.1. Trost et al., Jun. 11, 2013. 1 page.
GENBANK Submission; NIH/NCBI, Accession No. NC_017861.1. Heidelberg et al., Jun. 11, 2013. 1 page.
GENBANK Submission; NIH/NCBI, Accession No. NC_018010.1. Lucas et al., Jun. 11, 2013. 2 pages.
GENBANK Submission; NIH/NCBI, Accession No. NC_018721.1. Feng et al., Jun. 11, 2013. 1 pages.
GENBANK Submission; NIH/NCBI, Accession No. NC_021284.1. Ku et al., Jul. 12, 2013. 1 page.
GENBANK Submission; NIH/NCBI, Accession No. NC_021314.1. Zhang et al., Jul. 15, 2013. 1 page.
GENBANK Submission; NIH/NCBI, Accession No. NC_021846.1. Lo et al., Jul. 22, 2013. 1 page.
GENBANK Submission; NIH/NCBI, Accession No. NP_472073.1. Glaser et al., Jun. 27, 2013. 2 pages.
GENBANK Submission; NIH/NCBI, Accession No. P42212. Prasher et al., Mar. 19, 2014. 7 pages.
GENBANK Submission; NIH/NCBI, Accession No. YP_002342100.1. Bernardini et al., Jun. 10, 2013. 2 pages.
GENBANK Submission; NIH/NCBI, Accession No. YP_002344900.1. Gundogdu et al., Mar. 19, 2014. 2 pages.
GENBANK Submission; NIH/NCBI, Accession No. YP_820832.1. Makarova et al., Aug. 27, 2013. 2 pages.
UNIPROT Submission; UniProt, Accession No. P04275. Last modified Jul. 9, 2014, version 107. 29 pages.
UNIPROT Submission; UniProt, Accession No. P04264. Last modified Jun. 11, 2014, version 6. 15 pages.
UNIPROT Submission; UniProt, Accession No. P01011. Last modified Jun. 11, 2014, version 2. 15 pages.
Barrangou et al., CRISPR provides acquired resistance against viruses in prokaryotes. Science. Mar. 23, 2007;315(5819):1709-12.
Bedell et al., In vivo genome editing using a high-efficiency TALEN system. Nature. Nov. 1, 2012;491(7422):114-8. Doi: 10.1038/nature11537. Epub Sep. 23, 2012.
Beumer et al., Efficient gene targeting in *Drosophila* with zinc-finger nucleases. Genetics. Apr. 2006;172(4):2391-403. Epub Feb. 1, 2006.
Bibikova et al., Stimulation of homologous recombination through targeted cleavage by chimeric nucleases. Mol Cell Biol. Jan. 2001;21(1):289-97.
Bibikova et al., Targeted chromosomal cleavage and mutagenesis in *Drosophila* using zinc-finger nucleases. Genetics. Jul. 2002;161(3):1169-75.
Boch et al., Breaking the code of DNA binding specificity of TAL-type III effectors. Science. Dec. 11, 2009;326(5959):1509-12. Doi: 10.1126/science.1178811.
Boch, TALEs of genome targeting. Nat Biotechnol. Feb. 2011;29(2):135-6. Doi: 10.1038/nbt.1767.
Bulyk et al., Exploring the DNA-binding specificities of zinc fingers with DNA microarrays. Proc Natl Acad Sci U S A. Jun. 19, 2001;98(13):7158-63. Epub Jun. 12, 2001.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Carroll et al., Gene targeting in *Drosophila* and *Caenorhabditis elegans* with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Charpentier et al., Biotechnology: Rewriting a genome. Nature. Mar. 7, 2013;495(7439):50-1. doi: 10.1038/495050a.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2012;186(2):757-61. Doi: 10.1534/genetics.110.120717. Epub Jul. 26, 2010.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012. Review.
Cong et al., Comprehensive interrogation of natural TALE DNA-binding modules and transcriptional repressor domains. Nat Commun. Jul. 24, 2012;3:968. doi: 10.1038/ncomms1962.
Cong et al., Multiplex genome engineering using CRISPR/Cas systems. Science. Feb. 15, 2013;339(6121):819-23. doi: 10.1126/science.1231143. Epub Jan. 3, 2013.

(56) References Cited

OTHER PUBLICATIONS

Cornu et al., DNA-binding specificity is a major determinant of the activity and toxicity of zinc-finger nucleases. Mol Ther. Feb. 2008;16(2):352-8. Epub Nov. 20, 2007.

Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.

Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.

Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.

Dahlem et al., Simple methods for generating and detecting locus-specific mutations induced with TALENs in the zebrafish genome. PLoS Genet. 2012;8(8):e1002861. doi: 10.1371/journal.pgen. 1002861. Epub Aug. 16, 2012.

De Souza, Primer: genome editing with engineered nucleases. Nat Methods. Jan. 2012;9(1):27.

Deltcheva et al., CRISPR RNA maturation by trans-encoded small RNA and host factor RNase III. Nature. Mar. 31, 2011;471(7340):602-7. doi: 10.1038/nature09886.

Dicarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.

Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.

Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.

Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.

Esvelt et al., A system for the continuous directed evolution of biomolecules. Nature. Apr. 28, 2011;472(7344):499-503. doi: 10.1038/nature09929. Epub Apr. 10, 2011.

Esvelt et al., Genome-scale engineering for systems and synthetic biology. Mol Syst Biol. 2013;9:641. doi: 10.1038/msb.2012.66.

Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.

Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.

Gabriel et al., An unbiased genome-wide analysis of zinc-finger nuclease specificity. Nat Biotechnol. Aug. 7, 2011;29(9):816-23. doi: 10.1038/nbt.1948.

Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.

Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.

Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.

Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.

Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.

Gilbert et al., CRISPR-mediated modular RNA-guided regulation of transcription in eukaryotes. Cell. 2013 154(2):442-51.

Gordley et al., Evolution of programmable zinc finger-recombinases with activity in human cells. J Mol Biol. Mar. 30, 2007;367(3):802-13. Epub Jan. 12, 2007.

Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.

Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.

Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.

Gupta et al., Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.

Hale et al., RNA-guided RNA cleavage by a CRISPR RNA-Cas protein complex. Cell. Nov. 25, 2009;139(5):945-56. doi: 10.1016/j.cell.2009.07.040.

Händel et al., Expanding or restricting the target site repertoire of zinc-finger nucleases: the inter-domain linker as a major determinant of target site selectivity. Mol Ther. Jan. 2009;17(1):104-11. doi: 10.1038/mt.2008.233. Epub Nov. 11, 2008.

Hartung et al., Cre mutants with altered DNA binding properties. J Biol Chem. Sep. 4, 1998;273(36):22884-91.

Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.

Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockemeyer et al., Genetic engineering of human pluripotent cells using TALE nucleases. Nat Biotechnol. Jul. 7, 2011;29(8):731-4. doi: 10.1038/nbt.1927.

Horvath et al., CRISPR/Cas, the immune system of bacteria and archaea. Science. Jan. 8, 2010;327(5962):167-70. doi: 10.1126/science.1179555.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Huang et al., Heritable gene targeting in zebrafish using customized TALENs. Nat Biotechnol. Aug. 5, 2011;29(8):699-700. doi: 10.1038/nbt.1939.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Jamieson et al., Drug discovery with engineered zinc-finger proteins. Nat Rev Drug Discov. May 2003;2(5):361-8.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

(56) References Cited

OTHER PUBLICATIONS

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.
Kaiser et al., Gene therapy. Putting the fingers on gene repair. Science. Dec. 23, 2005;310(5756):1894-6.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Karpenshif et al., From yeast to mammals: recent advances in genetic control of homologous recombination. DNA Repair (Amst). Oct. 1, 2012;11(10):781-8. doi: 10.1016/j.dnarep.2012.07.001.Epub Aug. 11, 2012. Review.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Hybrid restriction enzymes: zinc finger fusions to Fok I cleavage domain. Proc Natl Acad Sci U S A. Feb. 6, 1996;93(3):1156-60.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Klug et al., Zinc fingers: a novel protein fold for nucleic acid recognition. Cold Spring Harb Symp Quant Biol. 1987;52:473-82.
Krishna et al., Structural classification of zinc fingers: survey and summary. Nucleic Acids Res. Jan. 15, 2003;31(2):532-50.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design of polydactyl zinc-finger proteins for unique addressing within complex genomes. Proc Natl Acad Sci U S A. May 27, 1997;94(11):5525-30.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Mak et al., The crystal structure of TAL effector PthXo1 bound to its DNA target. Science. Feb. 10, 2012;335(6069):716-9. doi: 10.1126/science.1216211. Epub Jan. 5, 2012.
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Mani et al., Design, engineering, and characterization of zinc finger nucleases. Biochem Biophys Res Commun. Sep. 23, 2005;335(2):447-57.
Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.
Meng et al., Profiling the DNA-binding specificities of engineered Cys2His2 zinc finger domains using a rapid cell-based method. Nucleic Acids Res. 2007;35(11):e81. Epub May 30, 2007.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Moscou et al., A simple cipher governs DNA recognition by TAL effectors. Science. Dec. 11, 2009;326(5959):1501. doi: 10.1126/science.1178817.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Narayanan et al., Clamping down on weak terminal base pairs: oligonucleotides with molecular caps as fidelity-enhancing elements at the 5'- and 3'- terminal residues. Nucleic Acids Res. May 20, 2004;32(9):2901-11. Print 2004.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Osborn et al., TALEN-based gene correction for epidermolysis bullosa. Mol Ther. Jun. 2013;21(6):1151-9. doi: 10.1038/mt.2013.56. Epub Apr. 2, 2013.
Pabo et al., Design and selection of novel Cys2His2 zinc finger proteins. Annu Rev Biochem. 2001;70:313-40.
Pan et al., Biological and biomedical applications of engineered nucleases. Mol Biotechnol. Sep. 2013;55(1):54-62. doi: 10.1007/s12033-012-9613-9.

(56) References Cited

OTHER PUBLICATIONS

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Pattanayak et al., Revealing off-target cleavage specificities of zinc-finger nucleases by in vitro selection. Nat Methods. Aug. 7, 2011;8(9):765-70. doi: 10.1038/nmeth.1670.

Pavletich et al., Zinc finger-DNA recognition: crystal structure of a Zif268-DNA complex at 2.1 A. Science. May 10, 1991;252(5007):809-17.

Pennisi et al., The CRISPR craze. Science. Aug. 23, 2013;341(6148):833-6. doi: 10.1126/science.341.6148.833.

Pennisi et al., The tale of the TALEs. Science. Dec. 14, 2012;338(6113):1408-11. doi: 10.1126/science.338.6113.1408.

Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Petek et al., Frequent endonuclease cleavage at off-target locations in vivo. Mol Ther. May 2010;18(5):983-6. Doi: 10.1038/mt.2010.35. Epub Mar. 9, 2010.

Porteus, Design and testing of zinc finger nucleases for use in mammalian cells. Methods Mol Biol. 2008;435:47-61. doi: 10.1007/978-1-59745-232-8_4.

Proudfoot et al., Zinc finger recombinases with adaptable DNA sequence specificity. PLoS One. Apr. 29, 2011;6(4):e19537. doi: 10.1371/journal.pone.0019537.

Qi et al., Repurposing CRISPR as an RNA-guided platform for sequence-specific control of gene expression. Cell. Feb. 28, 2013;152(5):1173-83. doi: 10.1016/j.cell.2013.02.022.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.

Reyon et al., FLASH assembly of TALENs for high-throughput genome editing. Nat Biotechnol. May 2012;30(5):460-5. doi: 10.1038/nbt.2170.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.

Sander et al., Targeted gene disruption in somatic zebrafish cells using engineered TALENs. Nat Biotechnol. Aug. 5, 2011;29(8):697-8. doi: 10.1038/nbt.1934.

Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.

Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Segal et al., Evaluation of a modular strategy for the construction of novel polydactyl zinc finger DNA-binding proteins. Biochemistry. Feb. 25, 2003;42(7):2137-48.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Sheridan, First CRISPR-Cas patent opens race to stake out intellectual property. Nat Biotechnol. 2014;32(7):599-601.

Sheridan, Gene therapy finds its niche. Nat Biotechnol. Feb. 2011;29(2):121-8. doi: 10.1038/nbt.1769.

Shimizu et al., Adding fingers to an engineered zinc finger nuclease can reduce activity. Biochemistry. Jun. 7, 2011;50(22):5033-41. doi: 10.1021/bi200393g. Epub May 11, 2011.

Siebert et al., An improved PCR method for walking in uncloned genomic DNA. Nucleic Acids Res. Mar. 25, 1995;23(6):1087-8.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Szczepek et al., Structure-based redesign of the dimerization interface reduces the toxicity of zinc-finger nucleases. Nat Biotechnol. Jul. 2007;25(7):786-93. Epub Jul. 1, 2007.

Tebas et al., Gene editing of CCR5 in autologous CD4 T cells of persons infected with HIV. N Engl J Med. Mar. 6, 2014;370(10):901-10. doi: 10.1056/NEJMoa1300662.

Tesson et al., Knockout rats generated by embryo microinjection of TALENs. Nat Biotechnol. Aug. 5, 2011;29(8):695-6. doi: 10.1038/nbt.1940.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Van Duyne et al., Teaching Cre to follow directions. Proc Natl Acad Sci U S A. Jan. 6, 2009;106(1):4-5. doi: 10.1073/pnas.0811624106. Epub Dec. 31, 2008.

Vanamee et al., FokI requires two specific DNA sites for cleavage. J Mol Biol. May 25, 2001;309(1):69-78.

Wah et al., Structure of FokI has implications for DNA cleavage. Proc Natl Acad Sci U S A. Sep. 1, 1998;95(18):10564-9.

Wang et al., Genetic screens in human cells using the CRISPR-Cas9 system. Science. Jan. 3, 2014;343(6166):80-4. doi: 10.1126/science.1246981. Epub Dec. 12, 2013.

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

(56) References Cited

OTHER PUBLICATIONS

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Weber et al., Assembly of designer TAL effectors by Golden Gate cloning. PLoS One. 2011;6(5):e19722. doi:10.1371/journal.pone.0019722. Epub May 19, 2011.
Wiedenheft et al., RNA-guided genetic silencing systems in bacteria and archaea. Nature. Feb. 15, 2012;482(7385):331-8. doi: 10.1038/nature10886. Review.
Wolfe et al., Analysis of zinc fingers optimized via phage display: evaluating the utility of a recognition code. J Mol Biol. Feb. 5, 1999;285(5):1917-34.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Partial Supplementary European Search Report for Application No. EP 12845790.0, mailed Mar. 18, 2015.
International Search Report and Written Opinion for PCT/US2014/052231, mailed Dec. 4, 2014.
International Search Report and Written Opinion for PCT/US2014/052231, mailed Jan. 30, 2015.
International Search Report and Written Opinion for PCT/US2014/054247, mailed Mar. 27, 2015.
International Search Report and Written Opinion for PCT/US2014/054291, mailed Mar. 27, 2015.
Invitation to Pay Additional Fees for PCT/US2014/054291, mailed Dec. 18, 2014.
International Search Report and Written Opinion for PCT/US2014/054252, mailed Mar. 5, 2015.
International Search Report and Written Opinion for PCT/US2014/070038, mailed Apr. 14, 2015.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Chung-Il et al., Artificial control of gene expression in mammalian cells by modulating RNA interference through aptamer-small molecule interaction. RNA. May 2006;12(5):710-6. Epub Apr. 10, 2006.
Cradick et al., ZFN-site searches genomes for zinc finger nuclease target sites and off-target sites. BMC Bioinformatics. May 13, 2011;12:152. doi: 10.1186/1471-2105-12-152.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Guo et al., Protein tolerance to random amino acid change. J Gene Med. Mar.-Apr. 2002;4(2):195-204.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hill et al., Functional analysis of conserved histidines in ADP-glucose pyrophosphorylase from *Escherichia coli*.Biochem Biophys Res Commun. Mar. 17, 1998;244(2):573-7.
Houdebine, The methods to generate transgenic animals and to control transgene expression. J Biotechnol. Sep. 25, 2002;98(2-3):145-60.
Kappel et al., Regulating gene expression in transgenic animals.Curr Opin Biotechnol. Oct. 1992;3(5):548-53.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Lazar et al., Transforming growth factor alpha: mutation of aspartic acid 47 and leucine 48 results in different biological activities. Mol Cell Biol. Mar. 1988;8(3):1247-52.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Liu et al., Fast Colorimetric Sensing of Adenosine and Cocaine Based on a General Sensor Design Involving Aptamers and Nanoparticles. Angew Chem. 2006;118(1):96-100.
Lundberg et al., Delivery of short interfering RNA using endosomolytic cell-penetrating peptides. FASEB J. Sep. 2007;21(11):2664-71. Epub Apr. 26, 2007.
Mullins et al., Transgenesis in nonmurine species. Hypertension. Oct. 1993;22(4):630-3.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
NCBI Reference Sequence: NM_002427.3. Wu et al., May 3, 2014. 5 pages.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Phillips, The challenge of gene therapy and DNA delivery. J Pharm Pharmacol. Sep. 2001;53(9):1169-74.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Samal et al., Cationic polymers and their therapeutic potential. Chem Soc Rev. Nov. 7, 2012;41(21):7147-94. doi: 10.1039/c2cs35094g. Epub Aug. 10, 2012.
Sang, Prospects for transgenesis in the chick. Mech Dev. Sep. 2004;121(9):1179-86.
Schwarze et al., In vivo protein transduction: delivery of a biologically active protein into the mouse. Science. Sep. 3, 1999;285(5433):1569-72.
Sells et al., Delivery of protein into cells using polycationic liposomes. Biotechniques. Jul. 1995;19(1):72-6, 78.
Thorpe et al., Functional correction of episomal mutations with short DNA fragments and RNA-DNA oligonucleotides. J Gene Med. Mar.-Apr. 2002;4(2):195-204.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.

(56) References Cited

OTHER PUBLICATIONS

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Winkler et al., Thiamine derivatives bind messenger RNAs directly to regulate bacterial gene expression. Nature. Oct. 31, 2002;419(6910):952-6. Epub Oct. 16, 2002.

Zelphati et al., Intracellular delivery of proteins with a new lipid-mediated delivery system. J Biol Chem. Sep. 14, 2001;276(37):35103-10. Epub Jul. 10, 2001.

\* cited by examiner

|  | (+) site (5'->3') | (-) site (5'->3') | 4 nM | 2 nM | 1 nM | 0.5 nM |
|---|---|---|---|---|---|---|
| wt | GAT GAG GAT GAC | AAA CTG GAA AAG | X | X | X | X |
| 5-4 | GAT GAG Ggg cga | AAA CTG GAA AAG | X | X | X | X |
| 5-3 | GAT GAG Gca cga | AAA CTG GAA AAG | X | X | X |  |
| 5-2 | GcT GAG GAT aAC | AAA aTG gAA cAG | X | X |  |  |
| 5-1 | GAT aca GAT GAC | AAA CTG gAA AAa | X |  |  |  |

|  | (+) site (5'->3') | (-) site (5'->3') | 4 nM | 2 nM | 1 nM | 0.5 nM |
|---|---|---|---|---|---|---|
| wt | GAG TGA GGA | GAC GCT GCT | X | X | X | X |
| 4-4 | GAG TGA aac | GAC GtT GCT | X | X | X | X |
| 4-3 | GAG TGA Gtc | GAC GtT aCT | X | X | X |  |
| 4-2 | GtG TGA aaA | GAC GtT GCT | X | X |  |  |
| 4-1 | GAG TGA GGA | GAC Gaa aCc | X |  |  |  |

Target Site

TALNS
L18 5'-TTCATTACACCTGCAGCT

TTCATTACACCTGCAGCTCTCATTTTCCATACAGTCAGTATCA
AAGTAATGTGGACGTCGAGAGTAAAAGGTATGTCAGTCATAGT

R18                    AGTATCAATTCTGGAAGA-5'

TALNS
```
L16    5'-TCTTCATTACACCTGC
L13       5'-TCATTACACCTGC
L10          5'-TTACACCTGC
          TCTTCATTACACCTGCAGCTCTCATTTTCCATACAGTCAGTATCA
          AGAAGTAATGTGGACGTCGAGAGTAAAAGGTATGTCAGTCATAGT
R16                                  GTATGTCAGTCATAGT-5'
R13                                  GTATGTCAGTCAT-5'
R10                                  GTATGTCAGT-5'
```

| Length Recognized | TALN Pair | Mutations in Common TS | |
|---|---|---|---|
| | | Mean | Std Dev. |
| 32 | L16+R16 | 1.61 | 1.19 |
| 29 | L16+R13 | 1.43 | 1.36 |
|  | L13+R16 | 1.33 | 1.26 |
| 26 | L16+R10 | 1.04 | 1.09 |
|  | L13+R13 | 1.11 | 1.37 |
|  | L10+R16 | 1.22 | 1.13 |
| 23 | L13+R10 | 0.87 | 1.26 |
|  | L10+R13 | 0.94 | 1.20 |
| 20 | L10+R10 | 0.77 | 1.10 |
|  | Library | 4.17 | 1.97 |

| Length Recognized | TALN Pair | TALN Digestion Mutations in Target Site | | | Pre-Selection Library |
|---|---|---|---|---|---|
| | | Mean | Std Dev. | Std. Error | Mean |
| 32 | L16+R16 | 2.257 | 1.487 | 0.007 | 6.500 |
| 29 | L16+R13 | 1.894 | 1.723 | 0.008 | 5.914 |
| | L13+R16 | 1.735 | 1.567 | 0.007 | 5.969 |
| 26 | L16+R10 | 1.303 | 1.224 | 0.006 | 5.273 |
| | L13+R13 | 1.326 | 1.663 | 0.007 | 5.383 |
| | L10+R16 | 1.516 | 1.260 | 0.006 | 5.396 |
| 23 | L13+R10 | 0.965 | 1.383 | 0.005 | 4.742 |
| | L10+R13 | 1.028 | 1.310 | 0.005 | 4.810 |
| 20 | L10+R10 | 0.769 | 1.101 | 0.004 | 4.169 |

Hypothesis: There are two distinct off-target populations

◯ sites similar to the on-target sequence with exponential enrichment vs. mutations ◯ sites highly mutant to the on-target sequence

EVALUATION AND IMPROVEMENT OF NUCLEASE CLEAVAGE SPECIFICITY

RELATED APPLICATION

This application is a continuation of and claims priority under 35 U.S.C. §120 to U.S. application, U.S. Ser. No. 14/234,031, filed Mar. 24, 2014, which is a national stage filing under 35 U.S.C. §371 of international PCT application, PCT/US2012/047778, filed Jul. 22, 2012, which claims priority under 35 U.S.C. §119(e) to U.S. provisional patent application, U.S. Ser. No. 61/510,841, filed Jul. 22, 2011, the entire contents of each of which are incorporated herein by reference.

GOVERNMENT SUPPORT

This invention was made with U.S. Government support under grant numbers R01 GM065400 and R01 GM088040 awarded by the National Institutes of Health/National Institute of General Medical Sciences, under grant number HR0011-11-2-0003 awarded by the Defense Advanced Research Projects Agency, and under grant number DP1 OD006862 awarded by the National Institutes of Health. The U.S. Government has certain rights in the invention.

BACKGROUND OF THE INVENTION

Site-specific endonucleases theoretically allow for the targeted manipulation of a single site within a genome, and are useful in the context of gene targeting as well as for therapeutic applications. In a variety of organisms, including mammals, site-specific endonucleases, for example, zinc-finger nucleases (ZFNs), have been used for genome engineering by stimulating either non-homologous end joining or homologous recombination. In addition to providing powerful research tools, ZFNs also have potential as gene therapy agents, and two ZFNs have recently entered clinical trials: one, CCR5-2246, targeting a human CCR-5 allele as part of an anti-HIV therapeutic approach (NCT00842634, NCT01044654, NCT01252641), and the other one, VF24684, targeting the human VEGF-A promoter as part of an anti-cancer therapeutic approach (NCT01082926).

Precise targeting of the intended target site is crucial for minimizing undesired off-target effects of site-specific nucleases, particularly in therapeutic applications, as imperfect specificity of some engineered site-specific binding domains has been linked to cellular toxicity. However, the site preferences for engineered site-specific nucleases, including current ZFNs, which cleave their target site after dimerization, has previously only been evaluated in vitro or in silico using methods that are limited to calculating binding and cleavage specificity for monomeric proteins.

Therefore, improved systems for evaluating the off-target sites of nucleases and other nucleic acid cleaving agents are needed and would be useful in the design of nucleases with better specificity, especially for therapeutic applications.

SUMMARY OF THE INVENTION

This invention is at least partly based on the recognition that the reported toxicity of some engineered site-specific endonucleases is based on off-target DNA cleavage, rather than on off-target binding alone. Information about the specificity of site-specific nucleases to date has been based on the assumptions that (i) dimeric nucleases cleave DNA with the same sequence specificity with which isolated monomeric domains bind DNA; and that (ii) the binding of one domain does not influence the binding of the other domain in a given dimeric nuclease. No study to date has reported a method for determining the broad DNA cleavage specificity of active, dimeric site-specific nucleases. Such a method would not only be useful in determining the DNA cleavage specificity of nucleases but would also find use in evaluating the cleavage specificity of other DNA cleaving agents, such as small molecules that cleave DNA.

This invention addresses the shortcomings of previous attempts to evaluate and characterize the sequence specificity of site-specific nucleases, and in particular of nucleases that dimerize or multimerize in order to cleave their target sequence. Some aspects of this invention provide an in vitro selection method to broadly examine the cleavage specificity of active nucleases. In some aspects, the invention provide methods of identifying suitable nuclease target sites that are sufficiently different from any other site within a genome to achieve specific cleavage by a given nuclease without any or at least minimal off-target cleavage. The invention provide methods of evaluating, selecting, and/or designing site specific nucleases with enhanced specificity as compared to current nucleases. Methods for minimizing off-target cleavage by a given nuclease, for example, by enhancing nuclease specificity by designing variant nucleases with binding domains having decreased binding affinity, by lowering the final concentration of the nuclease, and by choosing target sites that differ by at least three base pairs from their closest sequence relatives in the genome are provided. Compositions and kits useful in the practice of the inventive methods are also provided. The provided methods, compositions and kits are also useful in the evaluation, design, and selection of other nucleic acid (e.g., DNA) cleaving agents as would be appreciated by one of skill in the art.

In another aspect, the invention provides nucleases and other nucleic acid cleaving agents designed or selected using the provided system. Isolated ZFNs and TALENs designed, evaluated, or selected according to methods provided herein and pharmaceutical compositions comprising such nucleases are also provided.

Some aspects of this invention provide a method for identifying a target site of a nuclease. In some embodiments, the method comprises (a) providing a nuclease that cuts a double-stranded nucleic acid target site and creates a 5' overhang, wherein the target site comprises a [left-half site]-[spacer sequence]-[right-half site] (LSR) structure, and the nuclease cuts the target site within the spacer sequence. In some embodiments, the method comprises (b) contacting the nuclease with a library of candidate nucleic acid molecules, wherein each nucleic acid molecule comprises a concatemer of a sequence comprising a candidate nuclease target site and a constant insert sequence, under conditions suitable for the nuclease to cut a candidate nucleic acid molecule comprising a target site of the nuclease. In some embodiments, the method comprises (c) filling in the 5' overhangs of a nucleic acid molecule that has been cut twice by the nuclease and comprises a constant insert sequence flanked by a left half-site and cut spacer sequence on one side, and a right half-site and cut spacer sequence on the other side, thereby creating blunt ends. In some embodiments, the method comprises (d) identifying the nuclease target site cut by the nuclease by determining the sequence of the left-half site, the right-half-site, and/or the spacer sequence of the nucleic acid molecule of step (c). In some embodiments, determining the sequence of step (d) comprises ligating sequencing adapters to the blunt ends of the nucleic acid molecule of step (c) and amplifying and/or sequencing the nucleic acid molecule. In some embodiments, the method comprises amplifying the nucleic acid molecule after ligation of the sequencing adapters via PCR. In some embodiments, the method further comprises a step of enriching the nucleic acid molecules of step (c) or step (d) for molecules comprising a single constant insert sequence. In some embodiments, the step of enriching comprises a size fractionation. In some embodiments, the size fractionation is done by gel purification. In some embodiments, the method further comprises discarding any sequences determined in step (d) if the nucleic acid molecule did not comprise a complementary pair of filled-in 5' overhangs. In some embodiments, the method further comprises compiling a plurality of nuclease target sites identified in step (d), thereby generating a nuclease target site profile. In some embodiments, the nuclease is a therapeutic nuclease which cuts a specific nuclease target site in a gene associated with a disease. In some embodiments, the method further comprises determining a maximum concentration of the therapeutic nuclease at which the therapeutic nuclease cuts the specific nuclease target site, and does not cut more than 10, more than 5, more than 4, more than 3, more than 2, more than 1, or no additional nuclease target sites. In some embodiments, the method further comprises administering the therapeutic nuclease to a subject in an amount effective to generate a final concentration equal or lower than the maximum concentration. In some embodiments, the nuclease comprises an unspecific nucleic acid cleavage domain. In some embodiments, the nuclease comprises a FokI cleavage domain. In some embodiments, the nuclease comprises a nucleic acid cleavage domain that cleaves a target sequence upon cleavage domain dimerization. In some embodiments, the nuclease comprises a binding domain that specifically binds a nucleic acid sequence. In some embodiments, the binding domain comprises a zinc finger. In some embodiments, the binding domain comprises at least 2, at least 3, at least 4, or at least 5 zinc fingers. In some embodiments, the nuclease is a Zinc Finger Nuclease. In some embodiments, the binding domain comprises a Transcriptional Activator-Like Element. In some embodiments, the nuclease is a Transcriptional Activator-Like Element Nuclease (TALEN). In some embodiments, the nuclease comprises an organic compound. In some embodiments, the nuclease comprises an enediyne. In some embodiments, the nuclease is an antibiotic. In some embodiments, the compound is dynemicin, neocarzinostatin, calicheamicin, esperamicin, bleomycin, or a derivative thereof. In some embodiments, the nuclease is a homing endonuclease.

Some aspects of this invention provide libraries of nucleic acid molecule. In some embodiments, a library of nucleic acid molecules is provided that comprises a plurality of nucleic acid molecules, wherein each nucleic acid molecule comprises a concatemer of a candidate nuclease target site and a constant insert sequence spacer sequence. In some embodiments, the candidate nuclease target site comprises a [left-half site]-[spacer sequence]-[right-half site] (LSR) structure. In some embodiments, the left-half site and/or the right-half site is between 10-18 nucleotides long. In some embodiments, the library comprises candidate nuclease target sites that can be cleaved by a nuclease comprising a FokI cleavage domain. In some embodiments, the library comprises candidate nuclease target sites that can be cleaved by a Zinc Finger Nuclease (ZFN), a Transcription Activator-Like Effector Nuclease (TALEN), a homing endonuclease, an organic compound nuclease, an enediyne, an antibiotic nuclease, dynemicin, neocarzinostatin, calicheamicin, esperamicin, and/or bleomycin. In some embodiments, the library comprises at least $10^5$, at least $10^6$, at least $10^7$, at least $10^8$, at least $10^9$, at least $10^{10}$, at least $10^{11}$, or at least $10^{12}$ different candidate nuclease target sites. In some embodiments, the library comprises nucleic acid molecules of a molecular weight of at least 5 kDa, at least 6 kDa, at least 7 kDa, at least 8 kDa, at least 9 kDa, at least 10 kDa, at least 12 kDa, or at least 15 kDa. In some embodiments, the candidate nuclease target sites comprise a partially randomized left-half site, a partially randomized right-half site, and/or a partially randomized spacer sequence. In some embodiments, the library is templated on a known target site of a nuclease of interest. In some embodiments, the nuclease of interest is a ZFN, a TALEN, a homing endonuclease, an organic compound nuclease, an enediyne, an antibiotic nuclease, dynemicin, neocarzinostatin, calicheamicin, esperamicin, bleomycin, or a derivative thereof. In some embodiments, partial randomized sites differ from the consensus site by more than 5%, more than 10%, more than 15%, more than 20%, more than 25%, or more than 30% on average, distributed binomially. In some embodiments, partial randomized sites differ from the consensus site by no more than 10%, no more than 15%, no more than 20%, no more than 25%, nor more than 30%, no more than 40%, or no more than 50% on average, distributed binomially. In some embodiments, the candidate nuclease target sites comprise a randomized spacer sequence.

Some aspects of this invention provide methods of selecting a nuclease based on an evaluation of cleavage specificity. In some embodiments, a method of selecting a nuclease that specifically cuts a consensus target site from a plurality of nucleases is provided. In some embodiments, the method comprises (a) providing a plurality of candidate nucleases that cut the same consensus sequence; (b) for each of the candidate nucleases of step (a), identifying a nuclease target site cleaved by the candidate nuclease that differ from the consensus target site; and (c) selecting a nuclease based on the nuclease target site(s) identified in step (b). In some embodiments, the nuclease selected in step (c) is the nuclease that cleaves the consensus target site with the highest specificity. In some embodiments, the nuclease that cleaves the consensus target site with the highest specificity is the candidate nuclease that cleaves the lowest number of target sites that differ from the consensus site. In some embodiments, the candidate nuclease that cleaves the consensus target site with the highest specificity is the candidate nuclease that cleaves the lowest number of target sites that are different from the consensus site in the context of a target genome. In some embodiments, the candidate nuclease selected in step (c) is a nuclease that does not cleave any target site other than the consensus target site. In some embodiments, the candidate nuclease selected in step (c) is a nuclease that does not cleave any target site other than the consensus target site within the genome of a subject at a therapeutically effective concentration of the nuclease. In some embodiments, the method further comprises contacting a genome with the nuclease selected in step (c). In some embodiments, the genome is a vertebrate, mammalian, human, non-human primate, rodent, mouse rat, hamster, goat, sheep, cattle, dog, cat, reptile, amphibian, fish, nematode, insect, or fly genome. In some embodiments, the genome is within a living cell. In some embodiments, the genome is within a subject. In some embodiments, the consensus target site is within an allele that is associated with a disease or disorder. In some embodiments, cleavage of the consensus target site results in treatment or prevention of the disease or disorder. In some embodiments, cleavage of the consensus target site results in the alleviation of a symptom of the disease or disorder. In some embodiments, the disease is HIV/AIDS, or a proliferative disease. In some embodiments, the allele is a CCR5 or VEGFA allele.

Some aspects of this invention provide a method for selecting a nuclease target site within a genome. In some embodiments, the method comprises (a) identifying a candidate nuclease target site; and (b) using a general purpose computer, comparing the candidate nuclease target site to other sequences within the genome, wherein if the candidate nuclease target site differs from any other sequence within the genome by at least 3, at least 4, at least 5, at least 6, at least 7, at least 8, at least 9, or at least 10 nucleotides, selecting the candidate nuclease site. In some embodiments, the candidate nuclease target site comprises a [left-half site]-[spacer sequence]-[right-half site] (LSR) structure. In some embodiments, the left-half site and/or the right-half site is 10-18 nucleotides long. In some embodiments, the spacer is 10-24 nucleotides long. In some embodiments, the method further comprises designing and/or generating a nuclease targeting the candidate nuclease site selected in step (b). In some embodiments, designing and/or generating is done by recombinant technology. In some embodiments, designing and/or generating comprises designing a binding domain that specifically binds the selected candidate target site, or a half-site thereof. In some embodiments, designing and/or generating comprises conjugating the binding domain with a nucleic acid cleavage domain. In some embodiments, the nucleic acid cleavage domain is a non-specific cleavage domain and/or wherein the nucleic acid cleavage domain must dimerize or multimerize in order to cut a nucleic acid. In some embodiments, the nucleic acid cleavage domain comprises a FokI cleavage domain. In some embodiments, the method further comprises isolating the nuclease. In some embodiments, the nuclease is a Zinc Finger Nuclease (ZFN) or a Transcription Activator-Like Effector Nuclease (TALEN), a homing endonuclease, or is or comprises an organic compound nuclease, an enediyne, an antibiotic nuclease, dynemicin, neocarzinostatin, calicheamicin, esperamicin, bleomycin, or a derivative thereof. In some embodiments, the candidate target site is within a genomic sequence the cleavage of which is known to be associated with an alleviation of a symptom of a disease or disorder. In some embodiments, the disease is HIV/AIDS, or a proliferative disease. In some embodiments, the genomic sequence is a CCR5 or VEGFA sequence.

Some aspects of this invention provide isolated nucleases with enhanced specificity and nucleic acids encoding such nucleases. In some embodiments, an isolated nuclease is provided that has been engineered to cleave a target site within a genome, wherein the nuclease has been selected according to any of the selection methods described herein. In some embodiments, an isolated nuclease is provided that cuts a target site selected according to any of the methods described herein. In some embodiments, an isolated nuclease is provided that is designed or engineered according to any of the concepts or parameters described herein. In some embodiments, the nuclease is a Zinc Finger Nuclease (ZFN) or a Transcription Activator-Like Effector Nuclease (TALEN), a homing endonuclease, or is or comprises an organic compound nuclease, an enediyne, an antibiotic nuclease, dynemicin, neocarzinostatin, calicheamicin, esperamicin, bleomycin, or a derivative thereof.

Some aspects of this invention provide kits comprising nucleases and nuclease compositions. In some embodiments, a kit is provided that comprises an isolated nuclease described herein. In some embodiments, the kit further comprises a nucleic acid comprising a target site of the isolated nuclease. In some embodiments, the kit comprises an excipient and instructions for contacting the nuclease with the excipient to generate a composition suitable for contacting a nucleic acid with the nuclease. In some embodiments, the nucleic acid is a genome or part of a genome. In some embodiments, the genome is within a cell. In some embodiments, the genome is within a subject and the excipient is a pharmaceutically acceptable excipient.

Some aspects of this invention provide pharmaceutical compositions comprising a nuclease or a nucleic acid encoding a nuclease as described herein. In some embodiments, pharmaceutical composition for administration to a subject is provided. In some embodiments, the composition comprises an isolated nuclease described herein or a nucleic acid encoding such a nuclease and a pharmaceutically acceptable excipient.

Other advantages, features, and uses of the invention will be apparent from the detailed description of certain non-limiting embodiments; the drawings, which are schematic and not intended to be drawn to scale; and the claims.

DEFINITIONS

Figure 1:
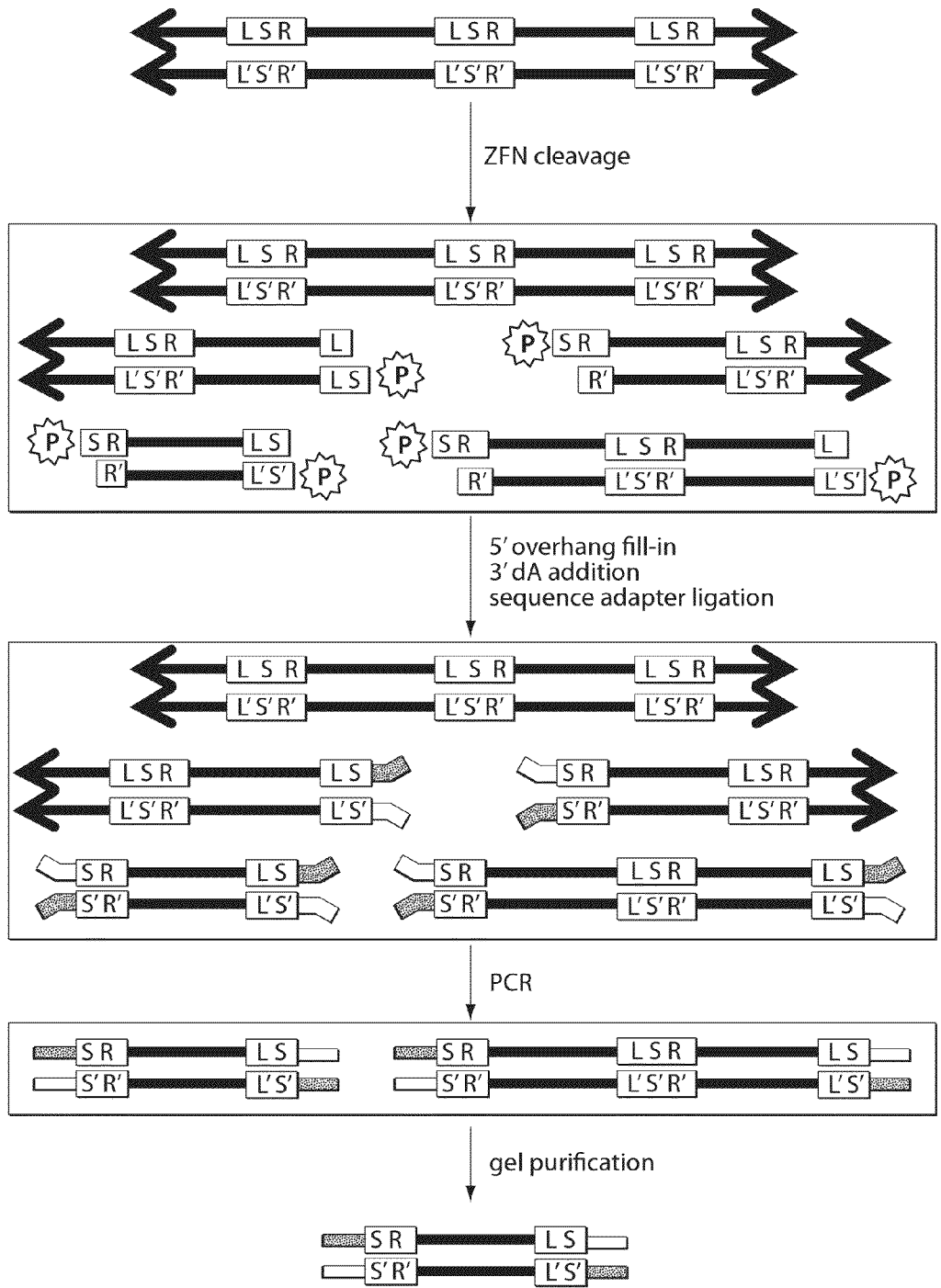
FIG. 1. In vitro selection for ZFN-mediated cleavage. Pre-selection library members are concatemers (represented by arrows) of identical ZFN target sites lacking 5' phosphates. L=left half-site; R=right half-site, S=spacer; L', S', R'=complementary sequences to L, S, R. ZFN cleavage reveals a 5' phosphate, which is required for sequencing adapter ligation. The only sequences that can be amplified by PCR using primers complementary to the adapters are sequences that have been cleaved twice and have adapters on both ends. DNA cleaved at adjacent sites are purified by gel electrophoresis and sequenced. A computational screening step after sequencing ensures that the filled-in spacer sequences (S and S') are complementary and therefore from the same molecule.

As used herein and in the claims, the singular forms "a," "an," and "the" include the singular and the plural reference unless the context clearly indicates otherwise. Thus, for example, a reference to "an agent" includes a single agent and a plurality of such agents.

The term "concatemer," as used herein in the context of nucleic acid molecules, refers to a nucleic acid molecule that contains multiple copies of the same DNA sequences linked in a series. For example, a concatemer comprising ten copies of a specific sequence of nucleotides (e.g., $[XYZ]_{10}$), would comprise ten copies of the same specific sequence linked to each other in series, e.g., 5'-XYZXYZXYZXYZXYZX-YZXYZXYZXYZXYZ-3'. A concatemer may comprise any number of copies of the repeat unit or sequence, e.g., at least 2 copies, at least 3 copies, at least 4 copies, at least 5 copies, at least 10 copies, at least 100 copies, at least 1000 copies, etc. An example of a concatemer of a nucleic acid sequence comprising a nuclease target site and a constant insert sequence would be [(target site)-(constant insert sequence)]$_{300}$. A concatemer may be a linear nucleic acid molecule, or may be circular.

The terms "conjugating," "conjugated," and "conjugation" refer to an association of two entities, for example, of two molecules such as two proteins, two domains (e.g., a binding domain and a cleavage domain), or a protein and an agent, e.g., a protein binding domain and a small molecule. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, or bound with the highest affinity, by a given nuclease.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term "enediyne," as used herein, refers to a class of bacterial natural products characterized by either nine- and ten-membered rings containing two triple bonds separated by a double bond (see, e.g., K. C. Nicolaou; A. L. Smith; E. W. Yue (1993). "Chemistry and biology of natural and designed enediynes". PNAS 90 (13): 5881-5888; the entire contents of which are incorporated herein by reference). Some enediynes are capable of undergoing Bergman cyclization, and the resulting diradical, a 1,4-dehydrobenzene derivative, is capable of abstracting hydrogen atoms from the sugar backbone of DNA which results in DNA strand cleavage (see, e.g., S. Walker; R. Landovitz; W. D. Ding; G. A. Ellestad; D. Kahne (1992). "Cleavage behavior of calicheamicin gamma 1 and calicheamicin T". Proc Natl Acad Sci U.S.A. 89 (10): 4608-12; the entire contents of which are incorporated herein by reference). Their reactivity with DNA confers an antibiotic character to many enediynes, and some enediynes are clinically investigated as anticancer antibiotics. Nonlimiting examples of enediynes are dynemicin, neocarzinostatin, calicheamicin, esperamicin (see, e.g., Adrian L. Smith and K. C. Bicolaou, "The Enediyne Antibiotics" J. Med. Chem., 1996, 39 (11), pp 2103-2117; and Donald Borders, "Enediyne antibiotics as antitumor agents," Informa Healthcare; 1$^{st}$ edition (Nov. 23, 1994, ISBN-10: 0824789385; the entire contents of which are incorporated herein by reference).

The term "homing endonuclease," as used herein, refers to a type of restriction enzymes typically encoded by introns or inteins Edgell DR (February 2009). "Selfish DNA: homing endonucleases find a home". Curr Biol 19 (3): R115-R117; Jasin M (June 1996). "Genetic manipulation of genomonth with rare-cutting endonucleases". Trends Genet 12 (6): 224-8; Burt A, Koufopanou V (December 2004). "Homing endonuclease genes: the rise and fall and rise again of a selfish element". Curr Opin Genet Dev 14 (6): 609-15; the entire contents of which are incorporated herein by reference. Homing endonuclease recognition sequences are long enough to occur randomly only with a very low probability (approximately once every $7 \times 10^{10}$ bp), and are normally found in only one instance per genome.

The term "library," as used herein in the context of nucleic acids or proteins, refers to a population of two or more different nucleic acids or proteins, respectively. For example, a library of nuclease target sites comprises at least two nucleic acid molecules comprising different nuclease target sites. In some embodiments, a library comprises at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ different nucleic acids or proteins. In some embodiments, the members of the library may comprise randomized sequences, for example, fully or partially randomized sequences. In some embodiments, the library comprises nucleic acid molecules that are unrelated to each other, e.g., nucleic acids comprising fully randomized sequences. In other embodiments, at least some members of the library may be related, for example, they may be variants or derivatives of a particular sequence, such as a consensus target site sequence.

The term "linker," as used herein, refers to a chemical group or a molecule linking two adjacent molecules or moieties, e.g., a binding domain and a cleavage domain of a nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The term "nuclease," as used herein, refers to an agent, for example a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease recognizes a single stranded target site, while in other embodiments, a nuclease recognizes a double-stranded target site, for example a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target site asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, zinc fingers or transcriptional activator like elements can be used as binding domains to specifically bind a desired target site, and fused or conjugated to a cleavage domain, for example, the cleavage domain of FokI, to create an engineered nuclease cleaving the target site.

The terms "nucleic acid" and "nucleic acid molecule," as used herein, refers to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications' A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administered to a subject in the context of treatment of a disease or disorder. In some embodiments, a pharmaceutical composition comprises an active ingredient, e.g. a nuclease or a nucleic acid encoding a nuclease, and a pharmaceutically acceptable excipient.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to a s cancer.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

The term "randomized," as used herein in the context of nucleic acid sequences, refers to a sequence or residue within a sequence that has been synthesized to incorporate a mixture of free nucleotides, for example, a mixture of all four nucleotides A, T, G, and C. Randomized residues are typically represented by the letter N within a nucleotide sequence. In some embodiments, a randomized sequence or residue is fully randomized, in which case the randomized residues are synthesized by adding equal amounts of the nucleotides to be incorporated (e.g., 25% T, 25% A, 25% G, and 25% C) during the synthesis step of the respective sequence residue. In some embodiments, a randomized sequence or residue is partially randomized, in which case the randomized residues are synthesized by adding non-equal amounts of the nucleotides to be incorporated (e.g., 79% T, 7% A, 7% G, and 7% C) during the synthesis step of the respective sequence residue. Partial randomization allows for the generation of sequences that are templated on a given sequence, but have incorporated mutations at a desired frequency. E.g., if a known nuclease target site is used as a synthesis template, partial randomization in which at each step the nucleotide represented at the respective residue is added to the synthesis at 79%, and the other three nucleotides are added at 7% each, will result in a mixture of partially randomized target sites being synthesized, which still represent the consensus sequence of the original target site, but which differ from the original target site at each residue with a statistical frequency of 21% for each residue so synthesized (distributed binomially). In some embodiments, a partially randomized sequence differs from the consensus sequence by more than 5%, more than 10%, more than 15%, more than 20%, more than 25%, or more than 30% on average, distributed binomially. In some embodiments, a partially randomized sequence differs from the consensus site by no more than 10%, no more than 15%, no more than 20%, no more than 25%, nor more than 30%, no more than 40%, or no more than 50% on average, distributed binomially.

The terms "small molecule" and "organic compound" are used interchangeably herein and refer to molecules, whether naturally-occurring or artificially created (e.g., via chemical synthesis) that have a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, organic compounds are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body. In certain embodiments, the organic molecule is known to bind and/or cleave a nucleic acid. In some embodiments, the organic compound is an enediyne. In some embodiments, the organic compound is an antibiotic drug, for example, an anticancer antibiotic such as dynemicin, neocarzinostatin, calicheamicin, esperamicin, bleomycin, or a derivative thereof.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode.

The terms "target nucleic acid," and "target genome," as used herein in the context of nucleases, refer to a nucleic acid molecule or a genome, respectively, that comprises at least one target site of a given nuclease.

The term "target site," used herein interchangeably with the term "nuclease target site," refers to a sequence within a nucleic acid molecule that is bound and cleaved by a nuclease. A target site may be single-stranded or double-stranded. In the context of nucleases that dimerize, for example, nucleases comprising a FokI DNA cleavage domain, a target sites typically comprises a left-half site (bound by one monomer of the nuclease), a right-half site (bound by the second monomer of the nuclease), and a spacer sequence between the half sites in which the cut is made. This structure ([left-half site]-[spacer sequence]-[right-half site]) is referred to herein as an LSR structure. In some embodiments, the left-half site and/or the right-half site is between 10-18 nucleotides long. In some embodiments, either or both half-sites are shorter or longer. In some embodiments, the left and right half sites comprise different nucleic acid sequences.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et. al. (February 2011). "A TALE nuclease architecture for efficient genome editing". Nature Biotechnology 29 (2): 143-8; Zhang, Feng; et. al. (February 2011). "Efficient construction of sequence-specific TAL effectors for modulating mammalian transcription". Nature Biotechnology 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Boch, Jens (February 2011). "TALEs of genome targeting". Nature Biotechnology 29 (2): 135-6; Boch, Jens; et. al. (December 2009). "Breaking the Code of DNA Binding Specificity of TAL-Type III Effectors". Science 326 (5959): 1509-12; and Moscou, Matthew J.; Adam J. Bogdanove (December 2009). "A Simple Cipher Governs DNA Recognition by TAL Effectors". Science 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". Nature Biotechnology 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research; Morbitzer, R.; Elsaesser, J.; Hausner, J.; Lahaye, T. (2011). "Assembly of custom TALE-type DNA binding domains by modular cloning". Nucleic Acids Research; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". PLoS ONE 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-

82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different type of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res*. 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to the design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 Å". *Science* 252 (5007): 809-17, the entire contents of which are incorporated herein). In some embodiments, separate zinc fingers that each recognize a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this nonlimiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

Introduction

Site-specific nucleases are powerful tools for the targeted modification of a genome. Some site specific nucleases can theoretically achieve a level of specificity for a target cleavage site that would allow to target a single unique site in a genome for cleaveage without affecting any other genomic site. It has been reported that nuclease cleavage in living cells triggers a DNA repair mechanism that frequently results in a modification of the cleaved, repaired genomic sequence, for example, via homologous recombination. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials.

One important aspect in the field of site-specific nuclease-mediated modification are off-target nuclease effects, e.g., the cleavage of genomic sequences that differ from the intended target sequence by one or more nucleotides. Undesired side effects of off-target cleavage ranges from insertion into unwanted loci during a gene targeting event to severe complications in a clinical scenario. Off target cleavage of sequences encoding essential gene functions or tumor suppressor genes by an andonuclease administered to a subject may result in disease or even death of the subject. Accordingly, it is desirable to characterize the cleavage preferences of a nuclease before using it in the laboratory or the clinic in order to determine its efficacy and safety. Further, the characterization of nuclease cleavager properties allows for the selection of the nuclease best suited for a specific task from a group of candidate nucleases, or for the selection of evolution products obtained from existing nucleases. Such a characterization of nuclease cleavage properties may also inform the de-novo design of nucleases with enhanced properties, such as enhanced specificity or efficiency.

In many scenarios where a nuclease is employed for the targeted manipulation of a nucleic acid, cleavage specificity is a crucial feature. The imperfect specificity of some engineered nuclease binding domains can lead to off-target cleavage and undesired effects both in vitro and in vivo. Current methods of evaluating site-specific nuclease specificity, including ELISA assays, microarrays, one-hybrid systems, SELEX and its variants, and Rosetta-based computational predictions, are all premised on the assumption that the binding specificity of nuclease molecules is equivalent or proportionate to their cleavage specificity.

However, the work presented here is based on the discovery that prediction of nuclease off-target binding effects constitutes an imperfect approximation of a nuclease's off-target cleavage effects that may result in undesired biological effects. This finding is consistent with the notion that the reported toxicity of some site specific DNA nucleases results from off-target DNA cleavage, rather than off-target binding alone.

The methods and reagents provided herein allow for an accurate evaluation of a given nuclease's target site specificity and provide strategies for the selection of suitable unique target sites and the design of highly specific nucleases for the targeted cleavage of a single site in the context of a complex genome. Further, methods, reagents, and strategies provided herein allow those of skill to enhance the specificity and minimize the off-target effects of any given site-specific nuclease. While of particular relevance to DNA and DNA-cleaving nucleases, the inventive concepts, methods, strategies, and reagents provided herein are not limited in this respect, but can be applied to any nucleic acid:nuclease pair.

Identifying Nuclease Target Sites Cleaved by a Site-specific Nuclease

Some aspects of this invention provide methods and reagents to determine the nucleic acid target sites cleaved by any site-specific nuclease. In general, such methods comprise contacting a given nuclease with a library of target sites under conditions suitable for the nuclease to bind and cut a target site, and determining which target sites the nuclease actually cuts. A determination of a nuclease's target site profile based on actual cutting has the advantage over methods that rely on binding that it measures a parameter more relevant for mediating undesired off-target effects of site-specific nucleases.

In some embodiments, a method for identifying a target site of a nuclease is provided. In some embodiments, the method comprises (a) providing a nuclease that cuts a double-stranded nucleic acid target site and creates a 5' overhang, wherein the target site comprises a [left-half site]-[spacer sequence]-[right-half site] (LSR) structure, and the nuclease cuts the target site within the spacer sequence. In some embodiments, the method comprises (b) contacting the nuclease with a library of candidate nucleic acid molecules, wherein each nucleic acid molecule comprises a concatemer of a sequence comprising a candidate nuclease target site and a constant insert sequence, under conditions suitable for the nuclease to cut a candidate nucleic acid molecule comprising a target site of the nuclease. In some embodiments, the method comprises (c) filling in the 5' overhangs of a nucleic acid molecule that has been cut twice by the nuclease and comprises a constant insert sequence flanked by a left half-site and cut spacer sequence on one side, and a right half-site and cut spacer sequence on the other side, thereby creating blunt ends. In some embodiments, the method comprises (d) identifying the nuclease target site cut by the nuclease by determining the sequence of the left-half site, the right-half-site, and/or the spacer sequence of the nucleic acid molecule of step (c). In some embodiments, the method comprises providing a nuclease and contacting the nuclease with a library of candidate nucleic acid molecules comprising candidate target sites. In some embodiments, the candidate nucleic acid molecules are double-stranded nucleic acid molecules. In some embodiments, the candidate nucleic acid molecules are DNA molecules. In some embodiments, the nuclease dimerizes at the target site, and the target site comprises an LSR structure ([left-half site]-[spacer sequence]-[right-half site]). In some embodiments, the nuclease cuts the target site within the spacer sequence. In some embodiments, the nuclease is a nuclease that cuts a double-stranded nucleic acid target site and creates a 5' overhang. In some embodiments, each nucleic acid molecule in the library comprises a concatemer of a sequence comprising a candidate nuclease target site and a constant insert sequence.

For example, in some embodiments, the candidate nucleic acid molecules of the library comprise the structure $R_1$-$[(LSR)\text{-(constant region)}]_x$-$R_2$, wherein R1 and R2 are, independently, nucleic acid sequences that may comprise a fragment of the [(LSR)-(constant region)] repeat unit, and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. The constant region, in some embodiments, is of a length that allows for efficient self ligation of a single repeat unit. Suitable lengths will be apparent to those of skill in the art. For example, in some embodiments, the constant region is between 100 and 1000 base pairs long, for example, about 100 base pairs, about 200 base pairs, about 300 base pairs, about 400 base pairs, about 450 base pairs, about 500 base pairs, about 600 base pairs, about 700 base pairs, about 800 base pairs, about 900 base pairs, or about 1000 base pairs long in some embodiments, the constant region is shorter than about 100 base pairs or longer than about 1000 base pairs.

Incubation of the nuclease with the library nucleic acids will result in cleavage of those concatemers in the library that comprise target sites that can be bound and cleaved by the nuclease. If a given nuclease cleaves a specific target site with high efficiency, a concatemer comprising target sites will be cut multiple times, resulting in the generation of fragments comprising a single repeat unit. The repeat unit released from the concatemer by nuclease cleavage will be of the structure $S_2R$-(constant region)-$LS_1$, wherein $S_1$ and $S_2$ represent complementary spacer region fragments after being cut by the nuclease. Any repeat units released from library candidate molecules can then be isolated and/or the sequence of the LSR cleaved by the nuclease identified by sequencing the $S_2R$ and $LS_1$ regions of released repeat units.

Any method suitable for isolation and sequencing of the repeat units can be employed to elucidate the LSR sequence cleaved by the nuclease. For example, since the length of the constant region is known, individual released repeat units can be separated based on their size from the larger uncut library nucleic acid molecules as well as from fragments of library nucleic acid molecules that comprise multiple repeat units (indicating non-efficient targeted cleavage by the nuclease). Suitable methods for separating and/or isolating nucleic acid molecules based on their size a well-known to those of skill in the art and include, for example, size fractionation methods, such as gel electrophoresis, density gradient centrifugation, and dialysis over a semi-permeable membrane with a suitable molecular cutoff value. The separated/isolated nucleic acid molecules can then be further characterized, for example, by ligating PCR and/or sequencing adapters to the cut ends and amplifying and/or sequencing the respective nucleic acids. Further, if the length of the constant region is selected to favor self-ligation of individual released repeat units, such individual released repeat units may be enriched by contacting the nuclease treated library molecules with a ligase and subsequent amplification and/or sequencing based on the circularized nature of the self-ligated individual repeat units.

In some embodiments, where a nuclease is used that generates 5' overhangs as a result of cutting a target nucleic acid, the 5' overhangs of the cut nucleic acid molecules are filled in. Methods for filling in 5' overhangs are well known to those of skill in the art and include, for example, methods using DNA polymerase I Klenow fragment lacking exonuclease activity (Klenow (3'->5' exo-)). Filling in 5' overhangs results in the overhang-templated extension of the recessed strand, which, in turn, results in blunt ends. In the case of single repeat units released from library concatemers, the resulting structure is a blunt-ended $S_2$'R-(constant region)-$LS_1$', with $S_1$' and $S_2$' comprising blunt ends. PCR and/or sequencing adapters can then be added to the ends by blunt end ligation and the respective repeat units (including $S_2$'R and $LS_1$' regions) can be sequenced. From the sequence data, the original LSR region can be deducted. Blunting of the overhangs created during the nuclease cleavage process also allows for distinguishing between target sites that were properly cut by the respective nuclease and target sites that were non-specifically cut e.g., based on non-nuclease effects such as physical shearing. Correctly cleaved nuclease target sites can be recognized by the existence of complementary $S_2$'R and $LS_1$' regions, which comprise a duplication of the overhang nucleotides as a result of the overhang fill in, while target sites that were not cleaved by the respective nuclease are unlikely to comprise overhang nucleotide duplications. In some embodiments, the method comprises identifying the nuclease target site cut by the nuclease by determining the sequence of the left-half site, the right-half-site, and/or the spacer sequence of a released individual repeat unit. Any suitable method for amplifying and/or sequencing can be used to identify the LSR sequence of the target site cleaved by the respective nuclease. Methods for amplifying and/or sequencing nucleic acid molecules are well known to those of skill in the art and the invention is not limited in this respect.

Some of the methods and strategies provided herein allow for the simultaneous assessment of a plurality of candidate target sites as possible cleavage targets for any given nuclease. Accordingly, the data obtained from such methods can be used to compile a list of target sites cleaved by a given nuclease, which is also referred to herein as a target site profile. If they sequencing method is used that allows for the generation of quantitative sequencing data, it is also possible to record the relative abundance of any nuclease target site detected to be cleaved by the respective nuclease. Target sites that are cleaved more efficiently by the nuclease will be detected more frequently in the sequencing step, while target sites that are not cleaved efficiently will only rarely release an individual repeat unit from a candidate concatemer, and thus, will only generate few, if any sequencing reads. Such quantitative sequencing data can be integrated into a target site profile to generate a ranked list of highly preferred and less preferred nuclease target sites.

The methods and strategies of nuclease target site profiling provided herein can be applied to any site-specific nuclease, including, for example, ZFNs, TALENs, and homing endonucleases. As described in more detail herein, nuclease specificity typically decreases with increasing nuclease concentration, and the methods described herein can be used to determine a concentration at which a given nuclease efficiently cuts its intended target site, but does not efficiently cut any off target sequences. In some embodiments, a maximum concentration of a therapeutic nuclease is determined at which the therapeutic nuclease cuts its intended nuclease target site, but does not cut more than 10, more than 5, more than 4, more than 3, more than 2, more than 1, or any additional nuclease target sites. In some embodiments, a therapeutic nuclease is administered to a subject in an amount effective to generate a final concentration equal or lower to the maximum concentration determined as described above.

Nuclease Target Site Libraries

Some embodiments of this invention provide libraries of nucleic acid molecules for nuclease target site profiling. In some embodiments such a library comprises a plurality of nucleic acid molecules, each comprising a concatemer of a candidate nuclease target site and a constant insert sequence spacer sequence. For example, in some embodiments, the candidate nucleic acid molecules of the library comprise the structure $R_1$-[(LSR)-(constant region)]$_X$-$R_2$, wherein R1 and R2 are, independently, nucleic acid sequences that may comprise a fragment of the [(LSR)-(constant region)] repeat unit, and X is an integer between 2 and y. In some embodiments, y is at least $10^1$, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$. In some embodiments, y is less than $10^2$, less than $10^3$, less than $10^4$, less than $10^5$, less than $10^6$, less than $10^7$, less than $10^8$, less than $10^9$, less than $10^{10}$, less than $10^{11}$, less than $10^{12}$, less than $10^{13}$, less than $10^{14}$, or less than $10^{15}$. The constant region, in some embodiments, is of a length that allows for efficient self ligation of a single repeat unit. In some embodiments, the constant region is of a length that allows for efficient separation of single repeat units from fragments comprising two or more repeat units. In some embodiments, the concentration is over length allows for efficient sequencing of a complete repeat unit in one sequencing read. Suitable lengths will be apparent to those of skill in the art. For example, in some embodiments, the constant region is between 100 and 1000 base pairs long, for example, about 100 base pairs, about 200 base pairs, about 300 base pairs, about 400 base pairs, about 450 base pairs, about 500 base pairs, about 600 base pairs, about 700 base pairs, about 800 base pairs, about 900 base pairs, or about 1000 base pairs long in some embodiments, the constant region is shorter than about 100 base pairs or longer than about 1000 base pairs.

An LSR site typically comprises a [left-half site]-[spacer sequence]-[right-half site] structure. The lengths of the half-size and the spacer sequence will depend on the specific nuclease to be evaluated. In general, the half-sites will be 6-30 nucleotides long, and preferably 10-18 nucleotides long. For example, each half site individually may be 6, 7, 8, 9, 10, 11, 12, 13, 14, 15, 16, 17, 18, 19, 20, 21, 22, 23, 24, 25, 26, 27, 28, 29, or 30 nucleotides long. In some embodiments, an LSR site may be longer than 30 nucleotides. In some embodiments, the left half site and the right half site of an LSR are of the same length. In some embodiments, the left half site and the right half site of an LSR are of different lengths. In some embodiments, the left half site and the right half site of an LSR are of different sequences. In some embodiments, a library is provided that comprises candidate nucleic acids which comprise LSRs that can be cleaved by a FokI cleavage domain, a Zinc Finger Nuclease (ZFN), a Transcription Activator-Like Effector Nuclease (TALEN), a homing endonuclease, an organic compound nuclease, an enediyne, an antibiotic nuclease, dynemicin, neocarzinostatin, calicheamicin, esperamicin, and/or bleomycin.

In some embodiments, a library of candidate nucleic acid molecules is provided that comprises at least $10^5$, at least $10^6$, at least $10^7$, at least $10^8$, at least $10^9$, at least $10^{10}$, at least $10^{11}$, or at least $10^{12}$ different candidate nuclease target sites. In some embodiments, the candidate nucleic acid molecules of the library are concatemers produced from a secularized templates by rolling cycle amplification. In some embodiments, the library comprises nucleic acid molecules, e.g., concatemers, of a molecular weight of at least 5 kDa, at least 6 kDa, at least 7 kDa, at least 8 kDa, at least 9 kDa, at least 10 kDa, at least 12 kDa, or at least 15 kDa. in some embodiments, the molecular weight of the nucleic acid molecules within the library may be larger than 15 kDa. In some embodiments, the library comprises nucleic acid molecules within a specific size range, for example, within a range of 5-7 kDa, 5-10 kDa, 8-12 kDa, 10-15 kDa, or 12-15 kDa, or 5-10 kDa or any possible subrange. While some methods suitable for generating nucleic acid concatemers according to some aspects of this invention result in the generation of nucleic acid molecules of greatly different molecular weights, such mixtures of nucleic acid molecules may be size fractionated to obtain a desired size distribution. Suitable methods for enriching nucleic acid molecules of a desired size or excluding nucleic acid molecules of a desired size are well known to those of skill in the art and the invention is not limited in this respect.

In some embodiments, a library is provided comprising candidate nucleic acid molecules that comprise target sites with a partially randomized left-half site, a partially randomized right-half site, and/or a partially randomized spacer sequence. In some embodiments, the library is provided comprising candidate nucleic acid molecules that comprise target sites with a partially randomized left half site, a fully randomized spacer sequence, and a partially randomized right half site. In some embodiments, partially randomized sites differ from the consensus site by more than 5%, more than 10%, more than 15%, more than 20%, more than 25%, or more than 30% on average, distributed binomially. In some embodiments, partially randomized sites differ from the consensus site by no more than 10%, no more than 15%, no more than 20%, no more than 25%, nor more than 30%, no more than 40%, or no more than 50% on average, distributed binomially. For example, in some embodiments partially randomized sites differ from the consensus site by more than 5%, but by no more than 10%; by more than 10%, but by no more than 20%; by more than 20%, but by no more than 25%; by more than 5%, but by no more than 20%, and so on. Using partially randomized nuclease target sites in the library is useful to increase the concentration of library members comprising target sites that are closely related to the consensus site, for example, that differ from the consensus sites in only one, only two, only three, only four, or only five residues. The rationale behind this is that a given nuclease, for example a given ZFN, is likely to cut its intended target site and any closely related target sites, but unlikely to cut a target sites that is vastly different from or completely unrelated to the intended target site. Accordingly, using a library comprising partially randomized target sites can be more efficient than using libraries comprising fully randomized target sites without compromising the sensitivity in detecting any off target cleavage events for any given nuclease. Thus, the use of partially randomized libraries significantly reduces the cost and effort required to produce a library having a high likelihood of covering virtually all off target sites of a given nuclease. In some embodiments however it may be desirable to use a fully randomized library of target sites, for example, in embodiments, where the specificity of a given nuclease is to be evaluated in the context of any possible site in a given genome.

Selection and Design of Site-specific Nucleases

Some aspects of this invention provide methods and strategies for selecting and designing site-specific nucleases that allow the targeted cleavage of a single, unique sites in the context of a complex genome. In some embodiments, a method is provided that comprises providing a plurality of candidate nucleases that are designed or known to cut the same consensus sequence; profiling the target sites actually cleaved by each candidate nuclease, thus detecting any cleaved off-target sites (target sites that differ from the consensus target site); and selecting a candidate nuclease based on the off-target site(s) so identified. In some embodiments, this method is used to select the most specific nuclease from a group of candidate nucleases, for example, the nuclease that cleaves the consensus target site with the highest specificity, the nuclease that cleaves the lowest number of off-target sites, the nuclease that cleaves the lowest number of off-target sites in the context of a target genome, or a nuclease that does not cleave any target site other than the consensus target site. In some embodiments, this method is used to select a nuclease that does not cleave any off-target site in the context of the genome of a subject at concentration that is equal to or higher than a therapeutically effective concentration of the nuclease.

The methods and reagents provided herein can be used, for example, to evaluate a plurality of different nucleases targeting the same intended targets site, for example, a plurality of variations of a given site-specific nuclease, for example a given zinc finger nuclease. Accordingly, such methods may be used as the selection step in evolving or designing a novel site-specific nucleases with improved specificity.

Identifying Unique Nuclease Target Sites within a Genome

Some embodiments of this invention provide a method for selecting a nuclease target site within a genome. As described in more detail elsewhere herein, it was surprisingly discovered that off target sites cleaved by a given nuclease are typically highly similar to the consensus target site, e.g., differing from the consensus target site in only one, only two, only three, only four, or only five nucleotide residues. Based on this discovery, a nuclease target sites within the genome can be selected to increase the likelihood of a nuclease targeting this site not cleaving any off target sites within the genome. For example, in some embodiments, a method is provided that comprises identifying a candidate nuclease target site; and comparing the candidate nuclease target site to other sequences within the genome. Methods for comparing candidate nuclease target sites to other sequences within the genome are well known to those of skill in the art and include for example sequence alignment methods, for example, using a sequence alignment software or algorithm such as BLAST on a general purpose computer. A suitable unique nuclease target site can then be selected based on the results of the sequence comparison. In some embodiments, if the candidate nuclease target site differs from any other sequence within the genome by at least 3, at least 4, at least 5, at least 6, at least 7, at least 8, at least 9, or at least 10 nucleotides, the nuclease target site is selected as a unique site within the genome, whereas if the site does not fulfill this criteria, the site may be discarded. In some embodiments, once a site is selected based on the sequence comparison, as outlined above, a site-specific nuclease targeting the selected site is designed. For example, a zinc finger nuclease may be designed to target any selected nuclease target site by constructing a zinc finger array binding the target site, and conjugating the zinc finger array to a DNA cleavage domain. In embodiments where the DNA cleavage domain needs to dimerize in order to cleave DNA, to zinc finger arrays will be designed, each binding a half site of the nuclease target site, and each conjugated to a cleavage domain. In some embodiments, nuclease designing and/or generating is done by recombinant technology. Suitable recombinant technologies are well known to those of skill in the art, and the invention is not limited in this respect.

In some embodiments, a site-specific nuclease designed or generated according to aspects of this invention is isolated and/or purified. The methods and strategies for designing site-specific nucleases according to aspects of this invention can be applied to design or generate any site-specific nuclease, including, but not limited to Zinc Finger Nucleases, Transcription Activator-Like Effector Nucleases (TALENs), homing endonucleases, organic compound nucleases, enediyne nucleases, antibiotic nucleases, and dynemicin, neocarzinostatin, calicheamicin, esperamicin, bleomycin, or a derivative thereof variants or derivatives.

Site-specific Nucleases

Some aspects of this invention provide isolated site-specific nucleases with enhanced specificity that are designed using the methods and strategies described herein. Some embodiments, of this invention provide nucleic acids encoding such nucleases. Some embodiments of this invention provide expression constructs comprising such encoding nucleic acids. For example, in some embodiments an isolated nuclease is provided that has been engineered to cleave a desired target site within a genome, and has been evaluated according to a method provided herein to cut less than 1, less than 2, less than 3, less than 4, less than 5, less than 6, less than 7, less than 8, less than 9 or less than 10 off-target sites at a concentration effective for the nuclease to cut its intended target site. In some embodiments an isolated nuclease is provided that has been engineered to cleave a desired unique target site that has been selected to differ from any other site within a genome by at least 3, at least 4, at least 5, at least 6, at least 7, at least 8, at least 9, or at least 10 nucleotide residues. In some embodiments, the isolated nuclease is a Zinc Finger Nuclease (ZFN) or a Transcription Activator-Like Effector Nuclease (TALEN), a homing endonuclease, or is or comprises an organic compound nuclease, an enediyne, an antibiotic nuclease, dynemicin, neocarzinostatin, calicheamicin, esperamicin, bleomycin, or a derivative thereof. In some embodiments, the isolated nuclease cleaves a consensus target site within an allele that is associated with a disease or disorder. In some embodiments, the isolated nuclease cleaves a consensus target site the cleavage of which results in treatment or prevention of a disease or disorder. In some embodiments, the disease is HIV/AIDS, or a proliferative disease. In some embodiments, the allele is a CCR5 (for treating HIV/AIDS) or a VEGFA allele (for treating a proliferative disease).

In some embodiments, the isolated nuclease is provided as part of a pharmaceutical composition. For example, some embodiments provide pharmaceutical compositions comprising a nuclease as provided herein, or a nucleic acid encoding such a nuclease, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and contacted with a nuclease or a nuclease-encoding nucleic acid ex vivo, and re-administered to the subject after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1

Zinc Finger Nucleases

Introduction

Zinc finger nucleases (ZFNs) are enzymes engineered to recognize and cleave desired target DNA sequences. A ZFN monomer consists of a zinc finger DNA-binding domain fused with a non-specific FokI restriction endonuclease cleavage domain[1]. Since the FokI nuclease domain must dimerize and bridge two DNA half-sites to cleave DNA[2], ZFNs are designed to recognize two unique sequences flanking a spacer sequence of variable length and to cleave only when bound as a dimer to DNA. ZFNs have been used for genome engineering in a variety of organisms including mammals[3-9] by stimulating either non-homologous end joining or homologous recombination. In addition to providing powerful research tools, ZFNs also have potential as gene therapy agents. Indeed, two ZFNs have recently entered clinical trials: one as part of an anti-HIV therapeutic approach (NCT00842634, NCT01044654, NCT01252641) and the other to modify cells used as anti-cancer therapeutics (NCT01082926).

DNA cleavage specificity is a crucial feature of ZFNs. The imperfect specificity of some engineered zinc fingers domains has been linked to cellular toxicity[10] and therefore determining the specificities of ZFNs is of significant interest. ELISA assays[11], microarrays[12], a bacterial one-hybrid system[13], SELEX and its variants[14-16], and Rosetta-based computational predictions[17] have all been used to characterize the DNA-binding specificity of monomeric zinc finger domains in isolation. However, the toxicity of ZFNs is believed to result from DNA cleavage, rather than binding alone[18,19]. As a result, information about the specificity of zinc finger nucleases to date has been based on the unproven assumptions that (i) dimeric zinc finger nucleases cleave DNA with the same sequence specificity with which isolated monomeric zinc finger domains bind DNA; and (ii) the binding of one zinc finger domain does not influence the binding of the other zinc finger domain in a given ZFN. The DNA-binding specificities of monomeric zinc finger domains have been used to predict potential off-target cleavage sites of dimeric ZFNs in genomes[6,20], but to our knowledge no study to date has reported a method for determining the broad DNA cleavage specificity of active, dimeric zinc finger nucleases.

In this work we present an in vitro selection method to broadly examine the DNA cleavage specificity of active ZFNs. Our selection was coupled with high-throughput DNA sequencing technology to evaluate two obligate heterodimeric ZFNs, CCR5-224[6], currently in clinical trials (NCT00842634, NCT01044654, NCT01252641), and VF2468[4], that targets the human VEGF-A promoter, for their abilities to cleave each of $10^{11}$ potential target sites. We identified 37 sites present in the human genome that can be cleaved in vitro by CCR5-224, 2,652 sites in the human genome that can be cleaved in vitro by VF2468, and hundreds of thousands of in vitro cleavable sites for both ZFNs that are not present in the human genome. To demonstrate that sites identified by our in vitro selection can also be cleaved by ZFNs in cells, we examined 34 or 90 sites for evidence of ZFN-induced mutagenesis in cultured human K562 cells expressing the CCR5-224 or VF2468 ZFNs, respectively. Ten of the CCR5-224 sites and 32 of the VF2468 sites we tested show DNA sequence changes consistent with ZFN-mediated cleavage in human cells, although we anticipate that cleavage is likely to be dependent on cell type and ZFN concentration. One CCR5-224 off-target site lies in a promoter of the malignancy-associated BTBD10 gene.

Our results, which could not have been obtained by determining binding specificities of monomeric zinc finger domains alone, indicate that excess DNA-binding energy results in increased off-target ZFN cleavage activity and suggest that ZFN specificity can be enhanced by designing ZFNs with decreased binding affinity, by lowering ZFN expression levels, and by choosing target sites that differ by at least three base pairs from their closest sequence relatives in the genome.

Results

In Vitro Selection for ZFN-mediated DNA Cleavage

Figure 5:
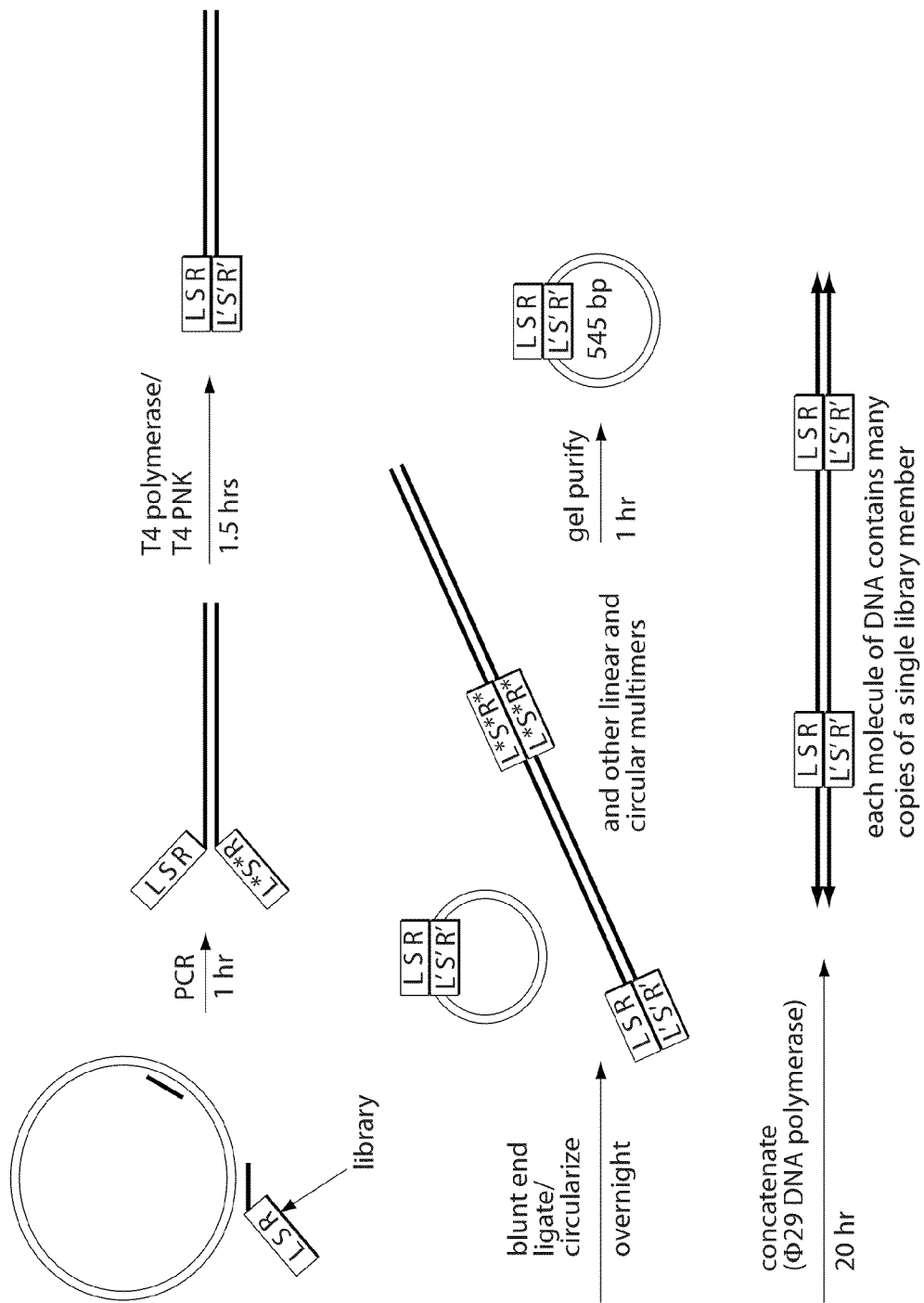
FIG. 5. In vitro synthesis of target site library. Library members consist of a partially randomized left-half site (L), a fully randomized 4-7 nucleotide spacer sequence (S), and a partially randomized right-half site (R). Library members present on DNA primers were incorporated into a linear ~545 base pair double-stranded DNA by PCR. During PCR, a primer with a library member (L S R) can anneal to a DNA strand with a different library member (L*S*R*), resulting in a double-strand DNA with two different library members at one end. The 3'-5' exonuclease and 5'-3' polymerase activities of T4 DNA polymerase removed mismatched library members and replaced them with complementary, matched library members (L'S'R'). After 5' phosphorylation with T4 polynucleotide kinase, the library DNA was subjected to blunt-end ligation, resulting in a mixture of linear and circular monomeric and multimeric species. Circular monomers were purified by gel electrophoresis and concatenated through rolling-circle amplification with Φ29 DNA polymerase.
Figure 6A:
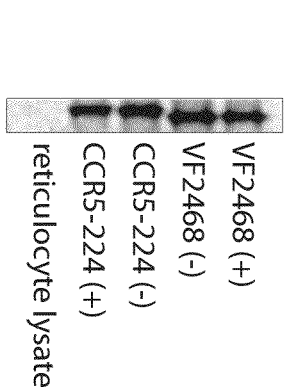
FIGS. 6A-D. Expression and quantification of ZFNs. Western blots for CCR5-224 and VF2468 are shown (a) for the ZFN samples used in the in vitro selection, and (b) for quantification. (c) Known quantities of N-terminal FLAG-tagged bacterial alkaline phosphatase (FLAG-BAP) were used to generate a standard curve for ZFN quantification. Diamonds represent the intensities of FLAG-BAP standards from the Western blot shown in (b), plus signs represent the intensities of bands of ZFNs, and the line shows the best-fit curve of FLAG-BAP standards that was used to quantify ZFNs. (d) Gels are shown of activity assays of CCR5-224 and VF2468 on an 8 nM linear substrate containing one target cleavage site. The ZFNs were each incubated with their respective substrate for 4 hours at 37° C. DNA in the "+lysate" lane was incubated with an amount of in vitro transcription/translation mixture equivalent to that used in the 2.5 nM ZFN reaction. ZFN-mediated cleavage results in two linear fragments approximately 700 bp and 300 bp in length. 2 nM CCR5-224 and 1 nM VF2468 were the amounts required for 50% cleavage of the linear substrate.
Figure 6B:
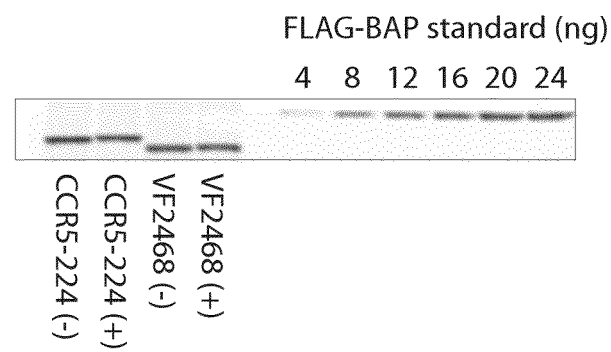
Figure 6C:
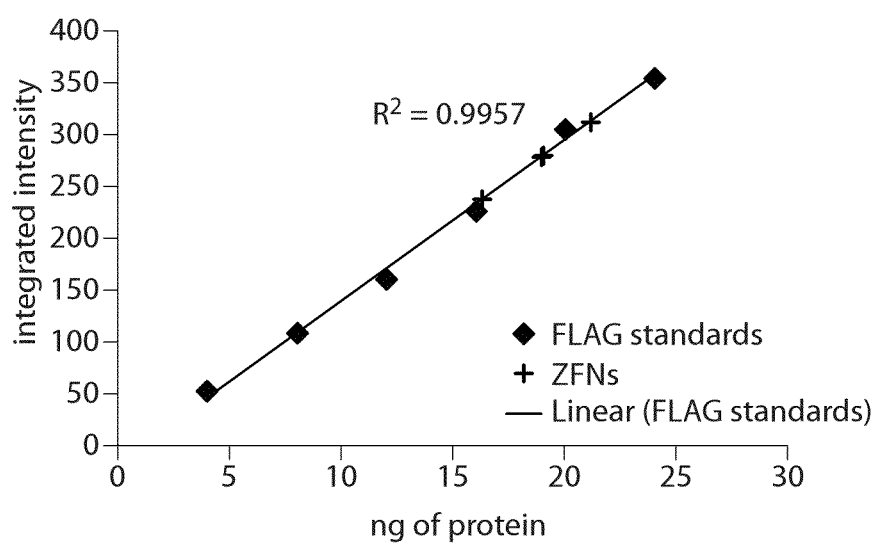
Figure 6D:
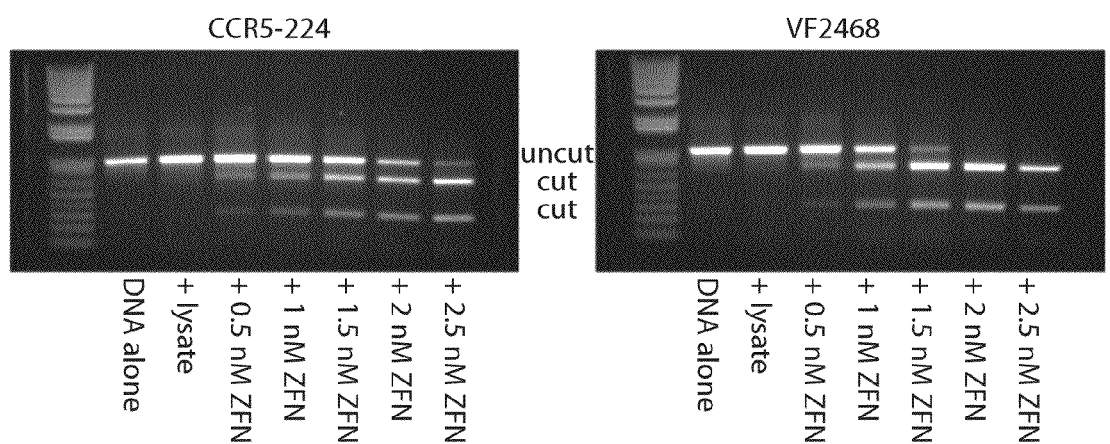

Libraries of potential cleavage sites were prepared as double-stranded DNA using synthetic primers and PCR (FIG. 5). Each partially randomized position in the primer was synthesized by incorporating a mixture containing 79% wild-type phosphoramidite and 21% of an equimolar mixture of all three other phosphoramidites. Library sequences therefore differed from canonical ZFN cleavage sites by 21% on average, distributed binomially. We used a blunt ligation strategy to create a $10^{12}$-member minicircle library. Using rolling-circle amplification, >$10^{11}$ members of this library were both amplified and concatenated into high molecular weight (>12 kb) DNA molecules. In theory, this library covers with at least 10-fold excess all DNA sequences that are seven or fewer mutations from the wild-type target sequences.

Figure 7A:
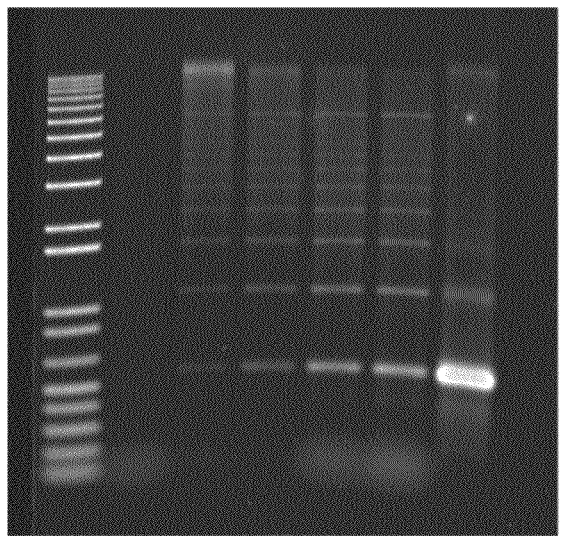
FIGS. 7A-B. Library cleavage with ZFNs. Cleavage of 1 μg of concatemeric libraries of CCR5-224 (a) or VF2468(b) target sites are shown with varying amounts CCR5-224 or VF2468, respectively. The lane labeled "+lysate" refers to pre-selection concatemeric library incubated with the volume of in vitro transcription/translation mixture contained in the samples containing 4 nM CCR5-224 or 4 nM of VF2468. Uncut DNA, which would be observed in the "+lysate" lane, is of length>12 kb and is lost upon purification due to its size and therefore is not present on the gel. The lane labeled "+PvuI" is a digest of the pre-selection library at PvuI sites introduced adjacent to library members. The laddering on the gels results from cleavage of pre-selection DNA concatemers at more than one site. There is a dose dependent increase in the amount of the bottom band, which corresponds to cleavage at two adjacent library sites in the same pre-selection DNA molecule. This bottom band of DNA was enriched by PCR and gel purification before sequencing.
Figure 7B:
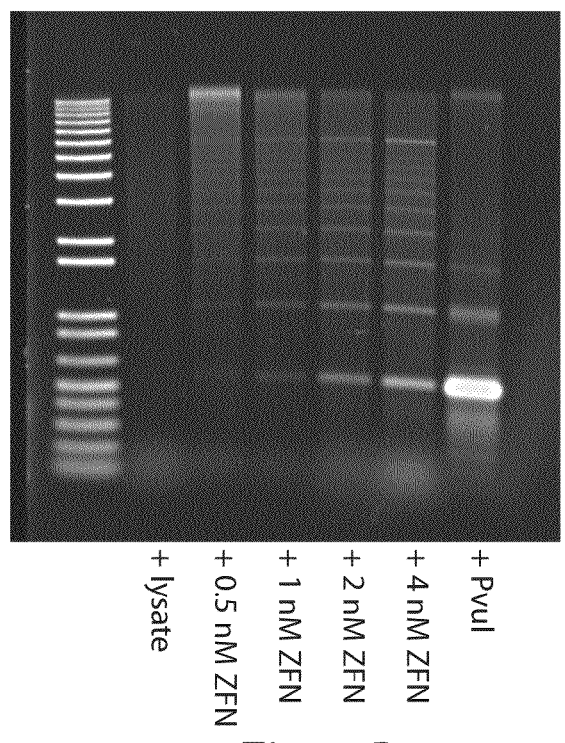
Figure 8A:
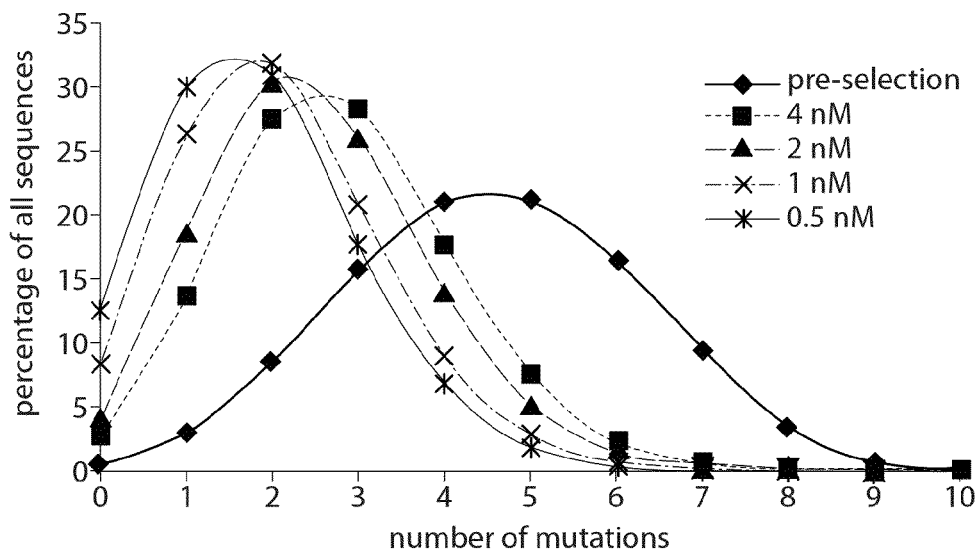
FIGS. 8A-B. ZFN off-target cleavage is dependent on enzyme concentration. For both (a) CCR5-224 and (b) VF2468 the distribution of cleavable sites revealed by in vitro selection shifts to include sites that are less similar to the target site as the concentration of ZFN increases. Both CCR5-224 and VF2468 selections enrich for sites that have fewer mutations than the pre-selection library. For comparisons between preselection and post-selection library means for all combinations of selection stringencies, P-values are 0 with the exception of the comparison between 0.5 nM and 1 nM VF2468 selections, which has a P-value of $1.7 \times 10^{-14}$.
Figure 8B:
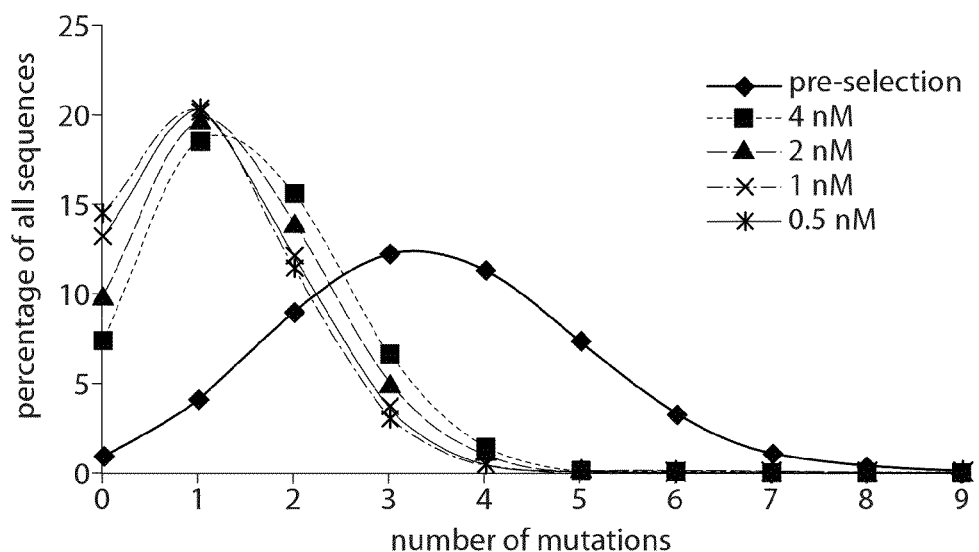

We incubated the CCR5-224 or VF2468 DNA cleavage site library at a total cleavage site concentration of 14 nM with two-fold dilutions, ranging from 0.5 nM to 4 nM, of crude in vitro-translated CCR5-224 or VF2468, respectively (FIG. 6). Following digestion, we subjected the resulting DNA molecules (FIG. 7) to in vitro selection for DNA cleavage and subsequent paired-end high-throughput DNA sequencing. Briefly, three selection steps (FIG. 1) enabled the separation of sequences that were cleaved from those that were not. First, only sites that had been cleaved contained 5' phosphates, which are necessary for the ligation of adapters required for sequencing. Second, after PCR, a gel purification step enriched the smaller, cleaved library members. Finally, a computational filter applied after sequencing only counted sequences that have filled-in, complementary 5' overhangs on both ends, the hallmark for cleavage of a target site concatemer (Table 2 and Protocols 1-9). We prepared pre-selection library sequences for sequencing by cleaving the library at a PvuI restriction endonuclease recognition site adjacent to the library sequence and subjecting the digestion products to the same protocol as the ZFN-digested library sequences. High-throughput sequencing confirmed that the rolling-circle-amplified, pre-selection library contained the expected distribution of mutations (FIG. 8).

Design of an In Vitro Selection for ZFN-mediated DNA Cleavage.

To characterize comprehensively the DNA cleavage specificity of active ZFNs, we first generated a large library of potential DNA substrates that can be selected for DNA cleavage in one step without requiring iterative enrichment steps that could amplify noise and introduce bias. We designed the substrate library such that each molecule in the library is a concatemer of one of >$10^{11}$ potential substrate sequences (FIG. 5). Incubation with ZFN results in some molecules that are uncut, some that have been cut once, and some that have been cut at least twice. Those molecules that have been cleaved at least twice have ends consisting of each half of the cleaved DNA sequence (FIG. 1). Cut library members are enriched relative to uncut library members in three ways (FIG. 1). First, sequences that have been cleaved twice have two complementary 5' overhangs, which can be identified computationally following DNA sequencing as hallmarks of bona fide cleavage products. Second, since ZFN-mediated cleavage reveals 5' phosphates that are not present in the pre-selection library, only DNA that has undergone cleavage is amenable to sequencing adapter ligation. Third, after PCR using primers complementary to the sequencing adapters, a gel purification step ensures that all sequenced material is of a length consistent with library members that have been cleaved at two adjacent sites. This gel-purified material is subjected to high-throughput DNA sequencing using the Illumina method (Bentley, D. R. et al. Accurate whole human genome sequencing using reversible terminator chemistry. Nature 456, 53-9 (2008)). Ideally, the library used in a ZFN cleavage selection would consist of every possible DNA sequence of the length recognized by the ZFN. Only one out of every 105 members of such a library, however, would contain a sequence that was within seven mutations of a 24-base pair recognition sequence. Since off-target recognition sequences most likely resemble target recognition sites, we used instead a biased library that ensures >10-fold coverage of all half-site sequences that differ from the wild-type recognition sequences by up to seven mutations. Library members consist of a fully randomized base pair adjacent to the 5' end of the recognition site, two partially randomized half sites flanking a 4-, 5-, 6-, or 7-bp fully randomized spacer, and another fully randomized base pair adjacent to the 3' end of the recognition site. A fully randomized five-base pair tag follows each library member. This tag, along with the randomized flanking base pairs and the randomized spacer sequence, was used as a unique identifier "key" for each library member. If this unique key was associated with more than one sequence read containing identical library members, these duplicate sequencing reads likely arose during PCR amplification and were therefore treated as one data point.
Analysis of CCR5-224 and VF2468 ZFNs Using the DNA Cleavage Selection.

Each member of a sequence pair consisted of a fragment of the spacer, an entire half-site, an adjacent nucleotide, and constant sequence. One end of the spacer was generally found in one sequence and the other end in its corresponding paired sequence, with the overhang sequence present in both paired sequence reads because overhangs were blunted by extension prior to ligation of adapters. The spacer sequences were reconstructed by first identifying the shared overhang sequence and then any nucleotides present between the overhang sequence and the half-site sequence. Only sequences containing no ambiguous nucleotides and overhangs of at least 4 nucleotides were analyzed. Overall, this computational screen for unique sequences that originated from two cleavage events on identical library members yielded 2.0 million total reads of cleaved library members (Table 2). There are far fewer analyzed sequences for the 0.5 nM, 1 nM, and 2 nM CCR5-224 and VF2468 selections compared to the 4 nM selections due to the presence of a large number of sequence repeats, identified through the use of the unique identifier key described above. The high abundance of repeated sequences in the 0.5 nM, 1 nM, and 2 nM selections indicate that the number of sequencing reads obtained in those selections, before repeat sequences were removed, was larger than the number of individual DNA sequences that survived all experimental selection steps. We estimated the error rate of sequencing to be 0.086% per nucleotide by analysis of a constant nucleotide in all paired reads. Using this error rate, we estimate that 98% of the post-selection ZFN target site sequences contain no errors.

Off-target Cleavage is Dependent on ZFN Concentration

Figure 9A:
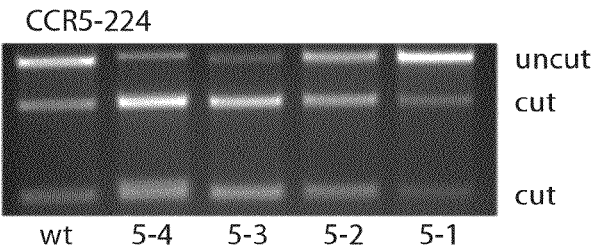
FIGS. 9A-B. Cleavage efficiency of individual sequences is related to selection stringency. In vitro DNA digests were performed on sequences identified in selections of varying stringencies (marked with 'X's). 2 nM CCR5-224 (SEQ ID NOs:7-14) (a) or 1 nM VF2468 (SEQ ID NOs:15-24) (b) was incubated with 8 nM of linear substrate containing the sequence shown. The 1 kb linear substrate contained a single cleavage site with the spacer sequence found in the genomic target of CCR5-224 ("CTGAT") or VF2468 ("TCGAA") and the indicated (+) and (−) half-sites. Mutant base pairs are represented with lowercase letters. CCR5-224 sites and VF2468 sites that were identified in the highest stringency selections (0.5 nM ZFN) are cleaved most efficiently, while sites that were identified only in the lowest stringency selections (4 nM ZFN) are cleaved least efficiently. Sequences in FIG. 9A correspond, from top to bottom, to SEQ ID NOs: 7-14. Sequences in FIG. 9B correspond, from top to bottom, to SEQ ID NOs: 15-24.
Figure 9B:
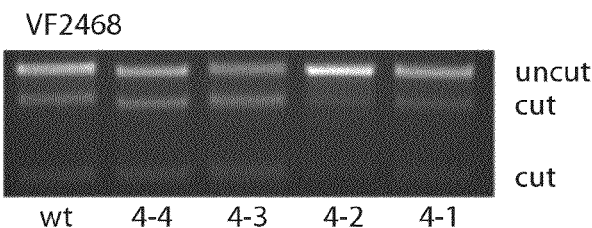

As expected, only a subset of library members was cleaved by each enzyme. The pre-selection libraries for CCR5-224 and VF2468 contained means of 4.56 and 3.45 mutations per complete target site (two half-sites), respectively, while post-selection libraries exposed to the highest concentrations of ZFN used (4 nM CCR5-224 and 4 nM VF2468) had means of 2.79 and 1.53 mutations per target site, respectively (FIG. 8). As ZFN concentration decreased, both ZFNs exhibited less tolerance for off-target sequences. At the lowest concentrations (0.5 nM CCR5-224 and 0.5 nM VF2468), cleaved sites contained an average of 1.84 and 1.10 mutations, respectively. We placed a small subset of the identified sites in a new DNA context and incubated in vitro with 2 nM CCR5-224 or 1 nM VF2468 for 4 hours at 37° C. (FIG. 9). We observed cleavage for all tested sites and those sites emerging from the more stringent (low ZFN concentration) selections were cleaved more efficiently than those from the less stringent selections. Notably, all of the tested sequences contain several mutations, yet some were cleaved in vitro more efficiently than the designed target.

Figure 2A:
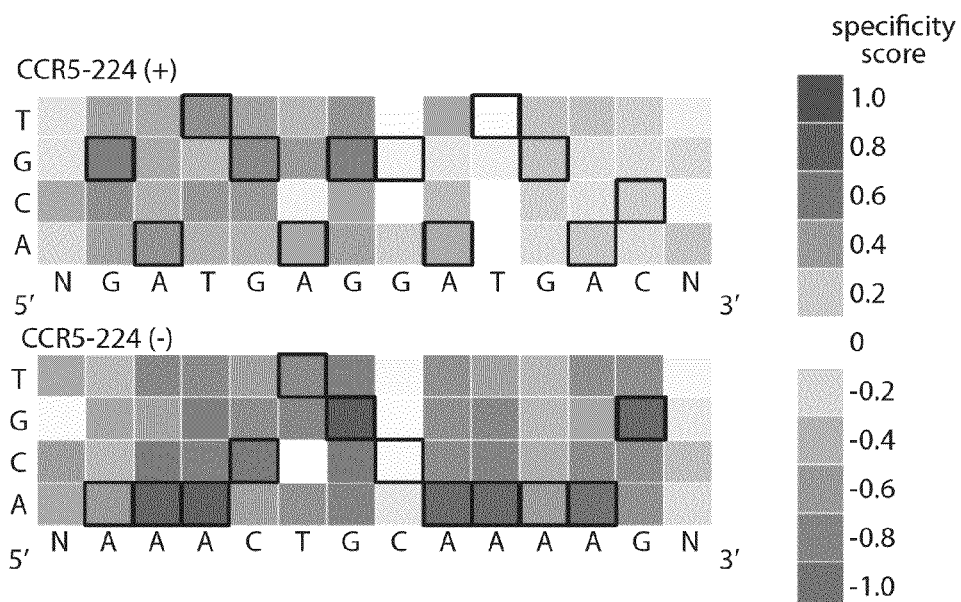
FIGS. 2A-B. DNA cleavage sequence specificity profiles for CCR5-224 and VF2468 ZFNs. The heat maps show specificity scores compiled from all sequences identified in selections for cleavage of 14 nM of DNA library with (a) 2 nM CCR5-224 or (b) 1 nM VF2468. The target DNA sequence is shown below each half-site. Black boxes indicate target base pairs. Specificity scores were calculated by dividing the change in frequency of each base pair at each position in the post-selection DNA pool compared to the pre-selection pool by the maximal possible change in frequency from pre-selection library to post-selection library of each base pair at each position. Blue boxes indicate enrichment for a base pair at a given position, white boxes indicate no enrichment, and red boxes indicate enrichment against a base pair at a given position. The darkest blue shown in the legend corresponds to absolute preference for a given base pair (specificity score=1.0), while the darkest red corresponds to an absolute preference against a given base pair (specificity score=−1.0). Sequences correspond, from top to bottom, to SEQ ID NOs: 1 and 2 (FIG. 2A) and SEQ ID NOs: 3 and 4 (FIG. 2B).
Figure 2B:
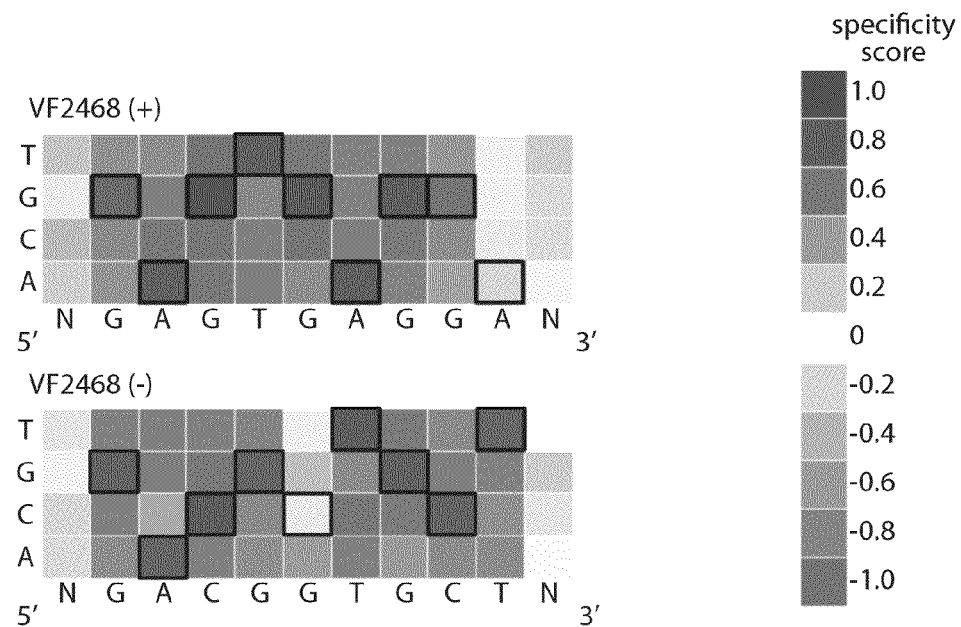
Figure 3A:
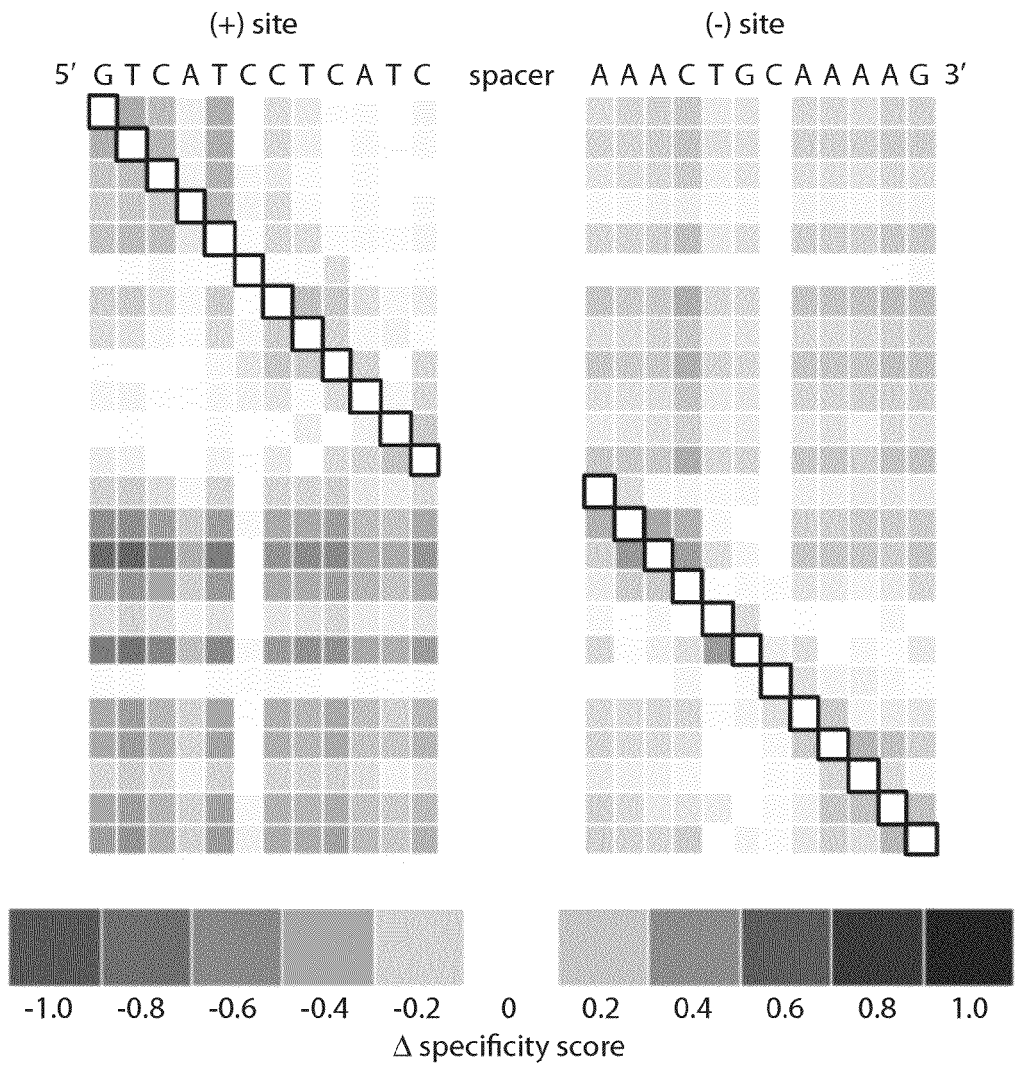
FIGS. 3A-B. Evidence for a compensation model of ZFN target site recognition. The heat maps show the changes in specificity score upon mutation at the black-boxed positions in selections with (a) 2 nM CCR5-224 or (b) 1 nM VF2468. Each row corresponds to a different mutant position (explained graphically in FIG. 12). Sites are listed in their genomic orientation; the (+) half-site of CCR5-224 and the (+) half-site of VF2468 are therefore listed as reverse complements of the sequences found in FIG. 2. Shades of blue indicate increased specificity score (more stringency) when the black boxed position is mutated and shades of red indicate decreased specificity score (less stringency). Sequences in FIG. 3A correspond, from top to bottom, to SEQ ID NOs: 5-6.
Figure 3B:
Figure 3B:
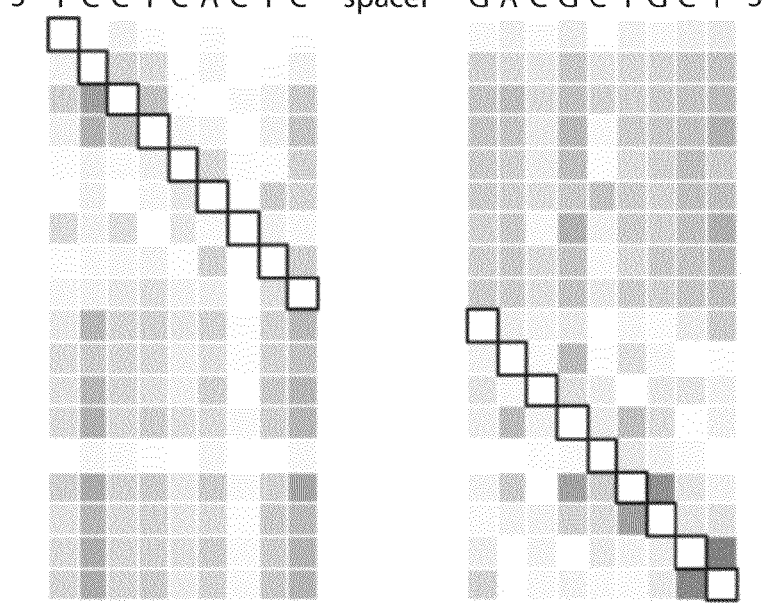
Figure 3B:
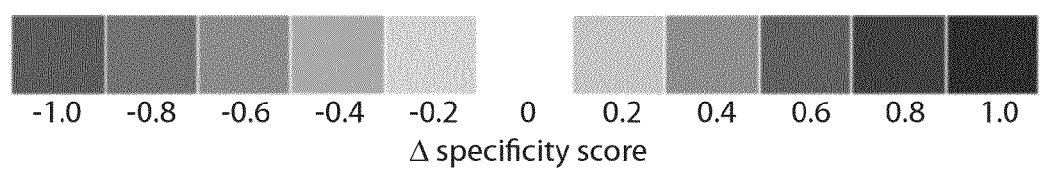
Figure 10A:
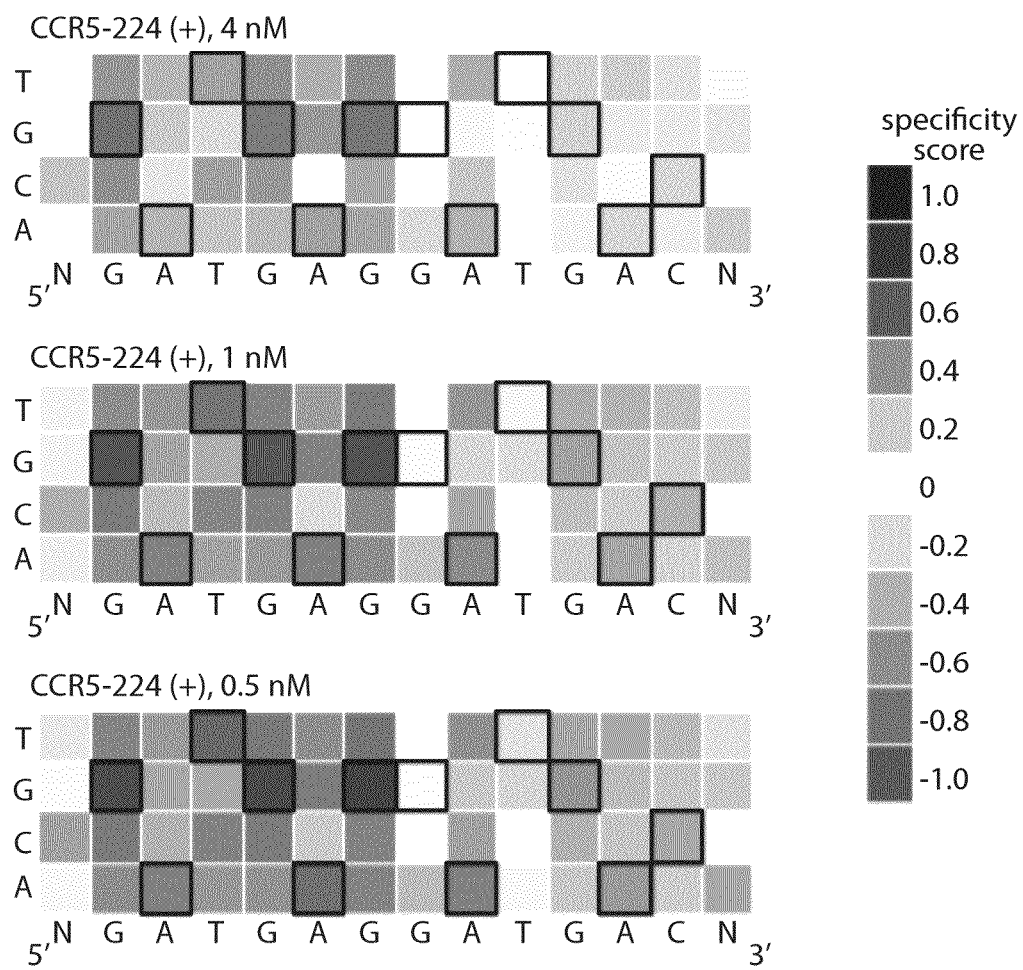
FIGS. 10A-D. Concentration-dependent sequence profiles for CCR5-224 and VF2468 ZFNs. The heat maps show specificity scores for the cleavage of 14 nM of total DNA library with varying amounts of (a-b) CCR5-224 or (c-d) VF2468. The target DNA sequence is shown below each half-site. Black boxes indicate target base pairs. Specificity scores were calculated by dividing the change in frequency of each base pair at each position in the post-selection DNA pool compared to the pre-selection pool by the maximal possible change in frequency of each base pair at each position. Blue boxes indicate specificity for a base pair at a given position, white boxes indicate no specificity, and red boxes indicate specificity against a base pair at a given position. The darkest blue shown in the legend corresponds to absolute preference for a given base pair (specificity score=1.0), while the darkest red corresponds to an absolute preference against a given base pair (specificity score=−1.0). Sequences in FIGS. 10A-D correspond, from top to bottom, to SEQ ID NOs: 25-28.
Figure 10B:
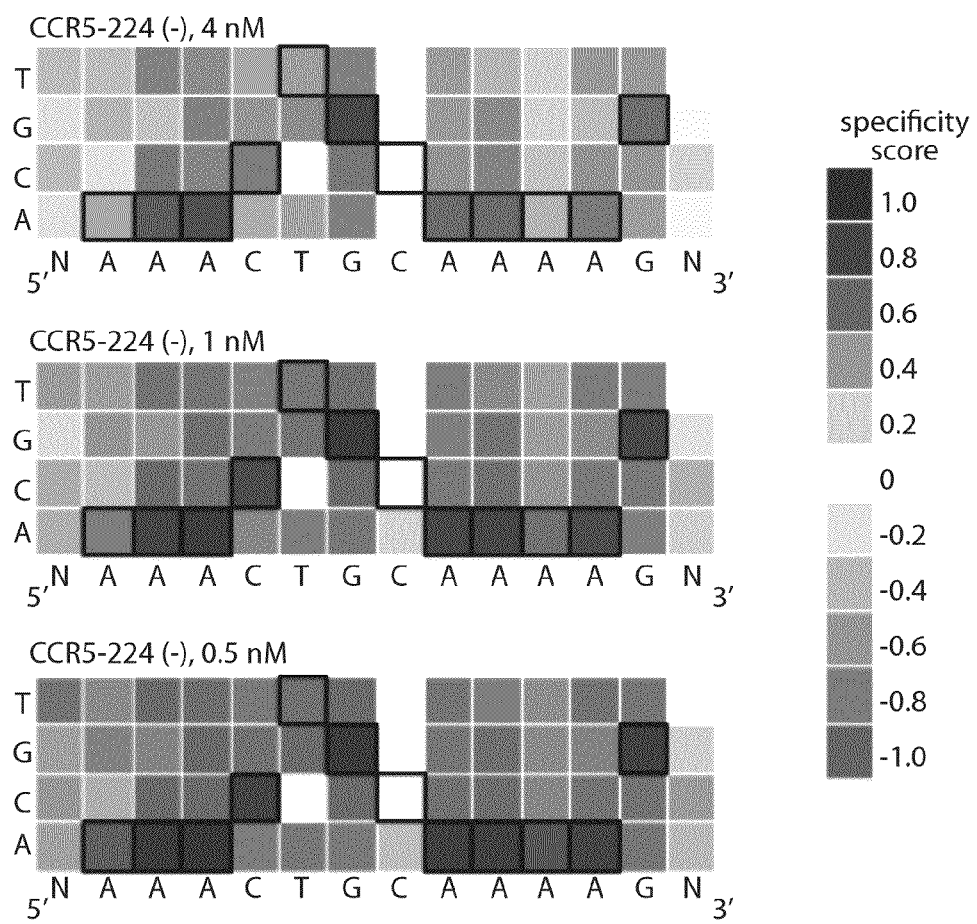
Figure 10C:
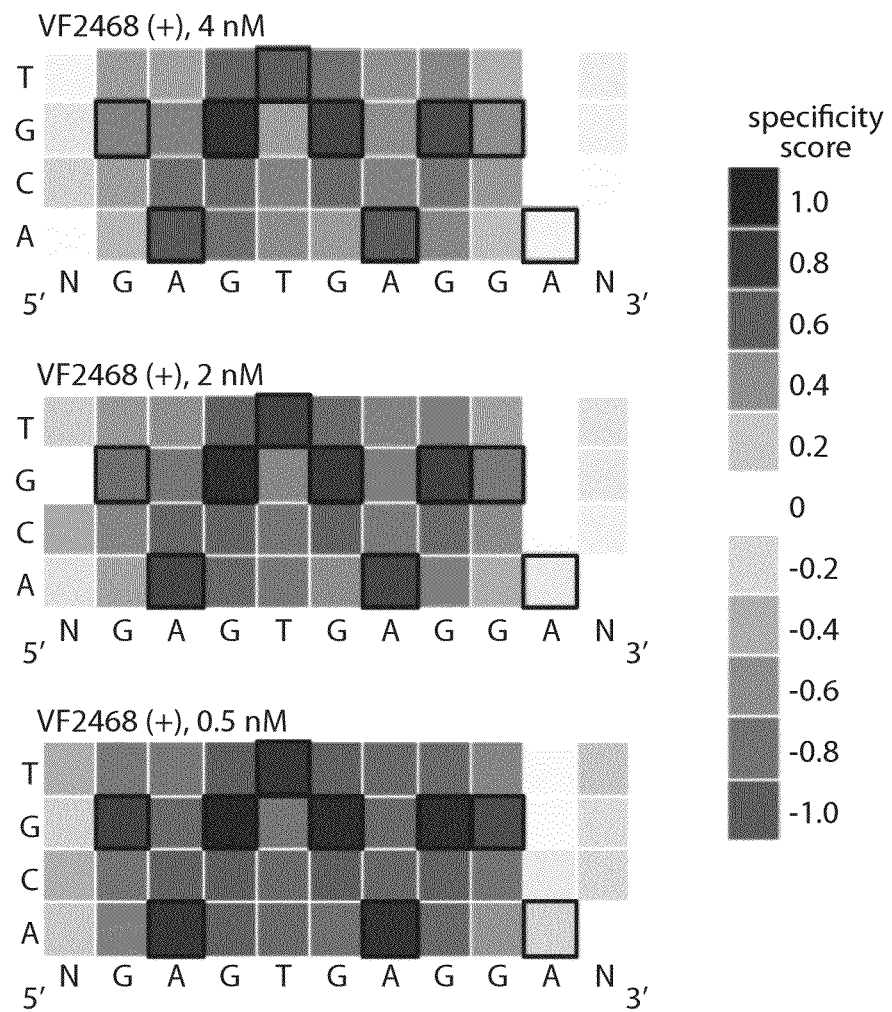
Figure 10D:
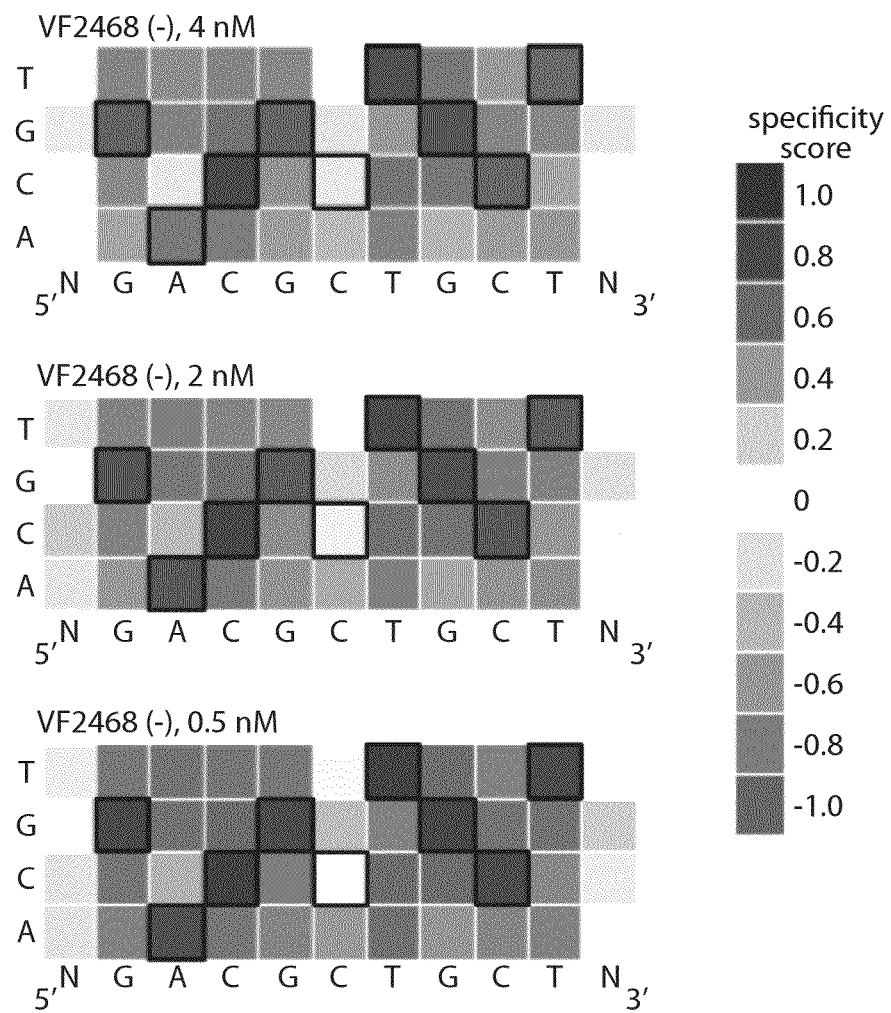

The DNA-cleavage specificity profile of the dimeric CCR5-224 ZFN (FIG. 2a and FIG. 10a,b) was notably different than the DNA-binding specificity profiles of the CCR5-224 monomers previously determined by SELEX[6]. For example, some positions, such as (+)A5 and (+)T9, exhibited tolerance for off-target base pairs in our cleavage selection that were not predicted by the SELEX study. VF2468, which had not been previously characterized with respect to either DNA-binding or DNA-cleavage specificity, revealed two positions, (−)C5 and (+)A9, that exhibited limited sequence preference, suggesting that they were poorly recognized by the ZFNs (FIG. 2b and FIG. 10c,d).

Compensation Between Half-sites Affects DNA Recognition

Figure 11:
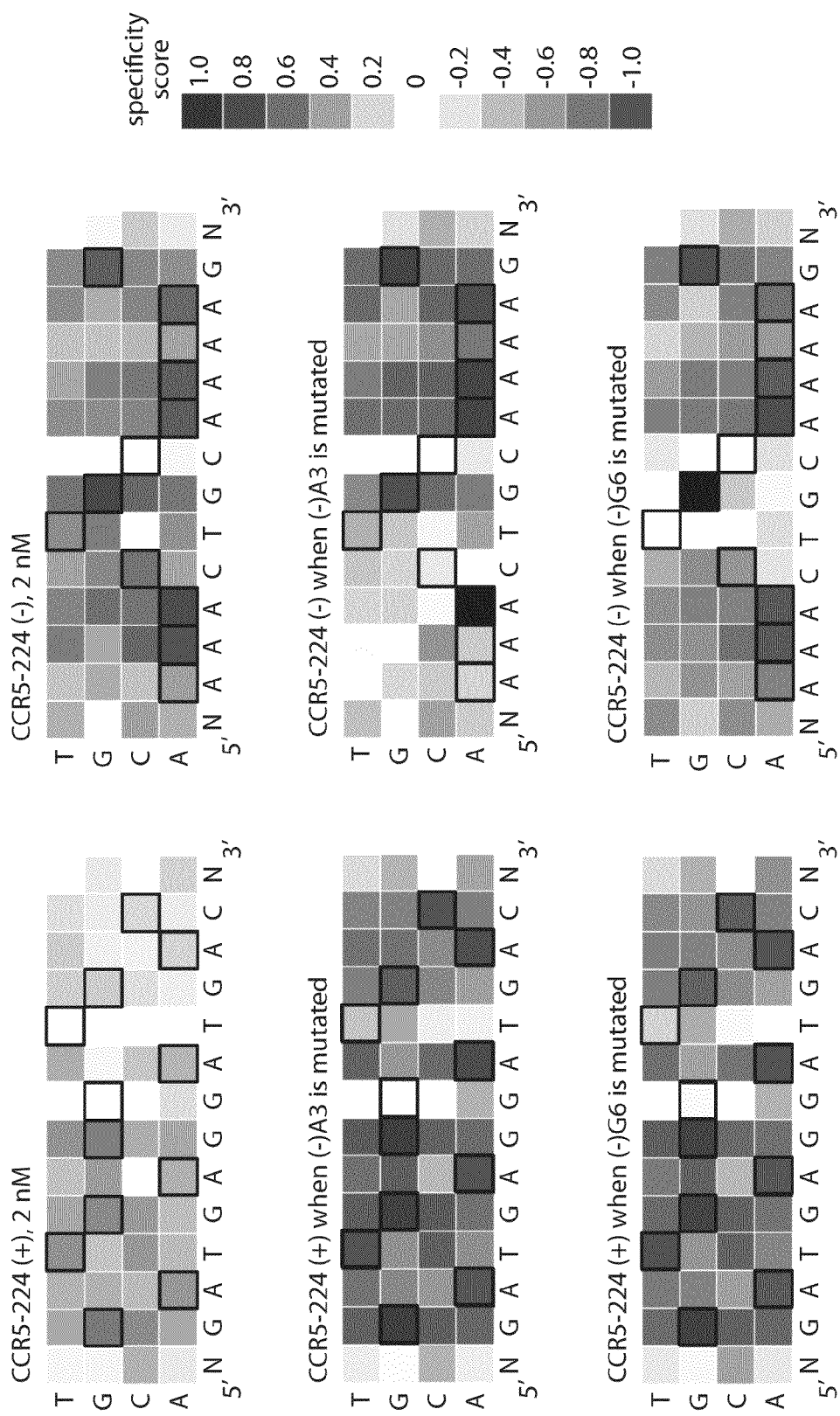
FIG. 11. Stringency at the (+) half-site increases when CCR5-224 cleaves sites with mutations at highly specified base pairs in the (−) half-site. The heat maps show specificity scores for sequences identified in the in vitro selection with 2 nM CCR5-224. For (−)A3 and (−)G6, indicated by filled black boxes, both pre-selection library sequences and post-selection sequences were filtered to exclude any sequences that contained an A at position 3 in the (−) half-site or G at position 6 in the (−) half-site, respectively, before specificity scores were calculated. For sites with either (−) half-site mutation, there is an increase in specificity at the (+) half-site. Black boxes indicate target base pairs. Specificity scores were calculated by dividing the change in frequency of each base pair at each position in the post-selection DNA pool compared to the pre-selection pool by the maximal possible change in frequency of each base pair at each position. Blue boxes indicate specificity for a base pair at a given position, white boxes indicate no specificity, and red boxes indicate specificity against a base pair at a given position. The darkest blue shown in the legend corresponds to absolute preference for a given base pair (specificity score=1.0), while the darkest red corresponds to an absolute preference against a given base pair (specificity score=−1.0). Sequences on the left correspond to SEQ ID NO: 29. Sequences on the right correspond to SEQ ID NO: 30.
Figure 12A:
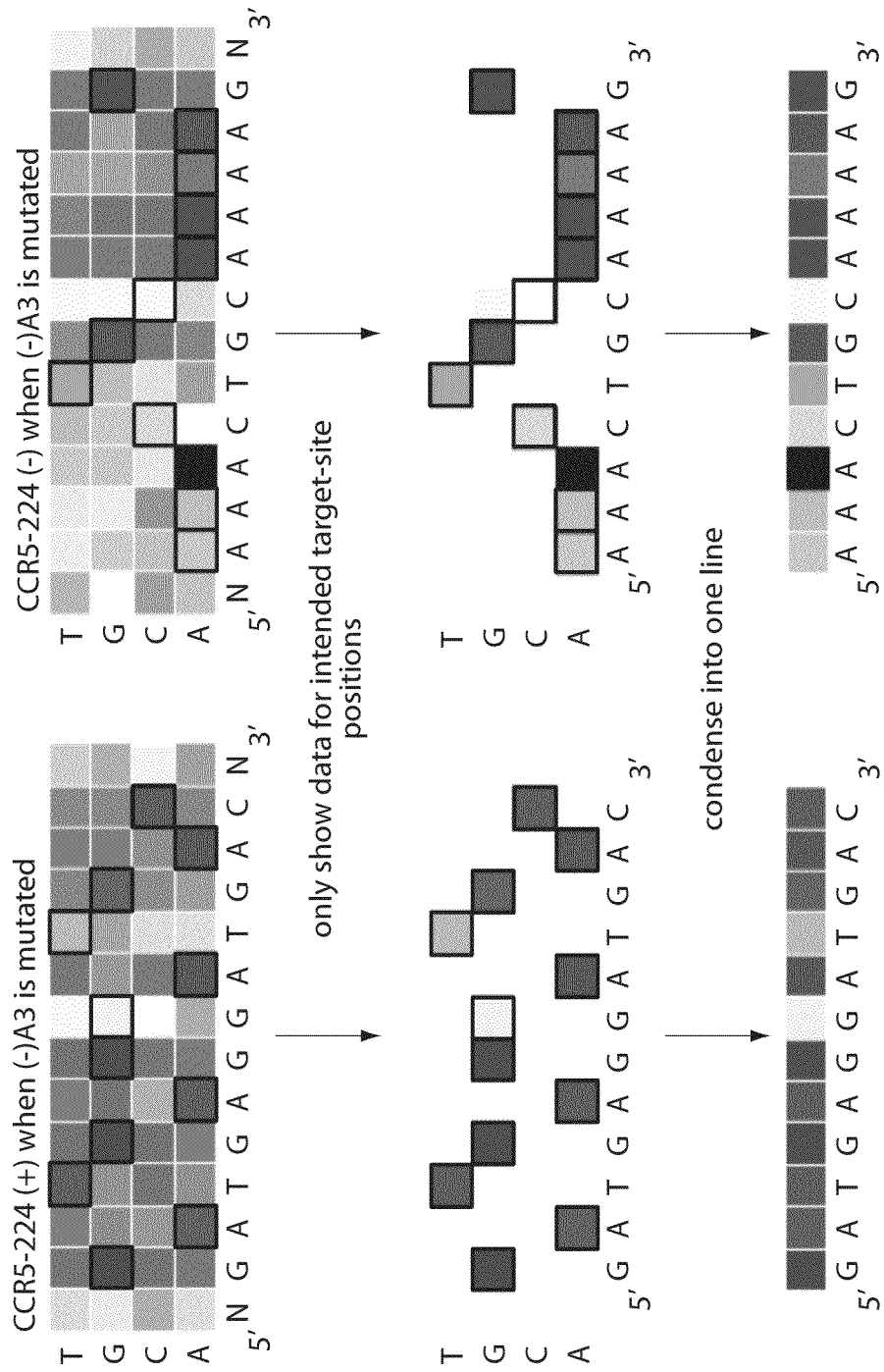
FIGS. 12A-B. Data processing steps used to create mutation compensation difference maps. The steps to create each line of the difference map in FIG. 3 are shown for the example of a mutation at position (−)A3. (a) Heat maps of the type described in FIG. 11 are condensed into one line to show only the specificity scores for intended target site nucleotides (in black outlined boxes in FIG. 11). (b) The condensed heat maps are then compared to a condensed heat map corresponding to the unfiltered baseline profile from FIG. 2, to create a condensed difference heat map that shows the relative effect of mutation at the position specified by the white box with black outline on the specificity score profile. Blue boxes indicate an increase in sequence stringency at positions in cleaved sites that contain mutations at the position indicated by the white box, while red boxes indicate a decrease in sequence stringency and white boxes, no change in sequence stringency. The (+) half-site difference map is reversed to match the orientation of the (+) half-site as it is found in the genome rather than as it is recognized by the zinc finger domain of the ZFN. Sequences in FIG. 12A correspond, from top left to bottom right, to SEQ ID NOs:31-36. Sequences in FIG. 12B correspond to SEQ ID NOs: 37 and 38 (left) and SEQ ID NO: 39 (right).
Figure 12B:
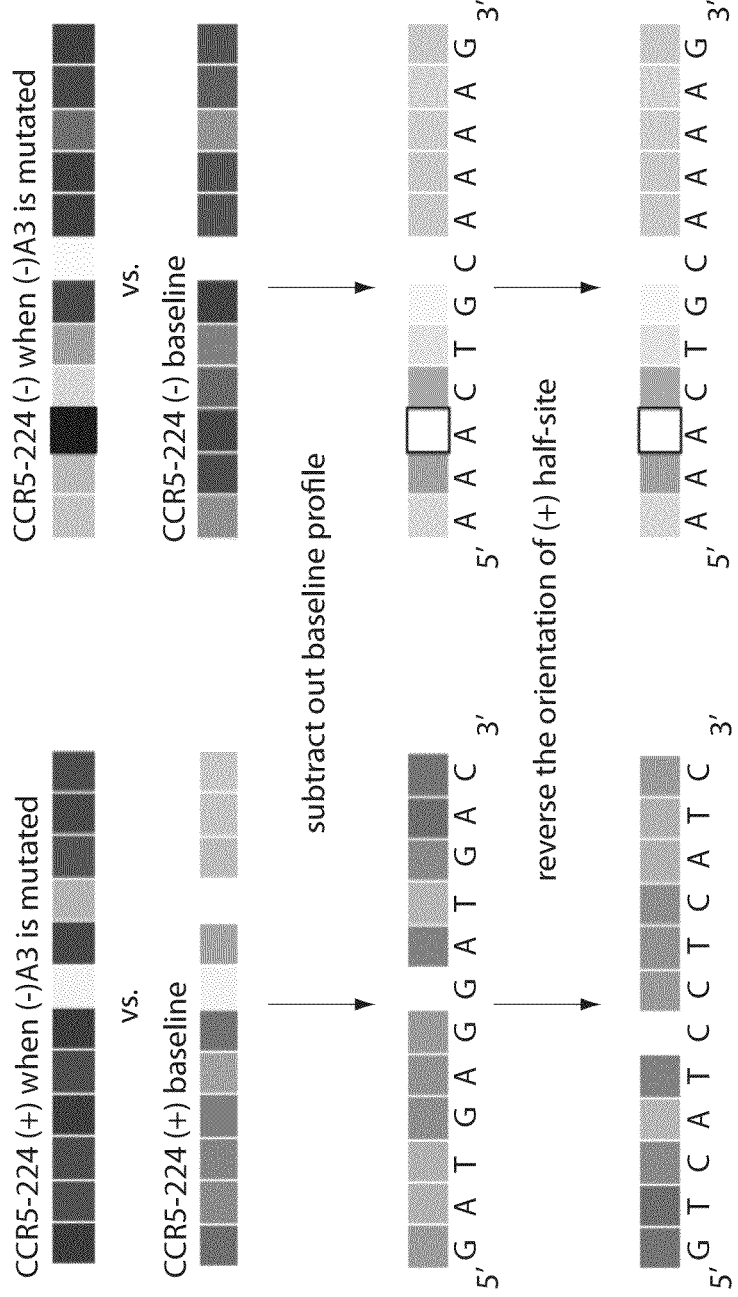
Figure 13:
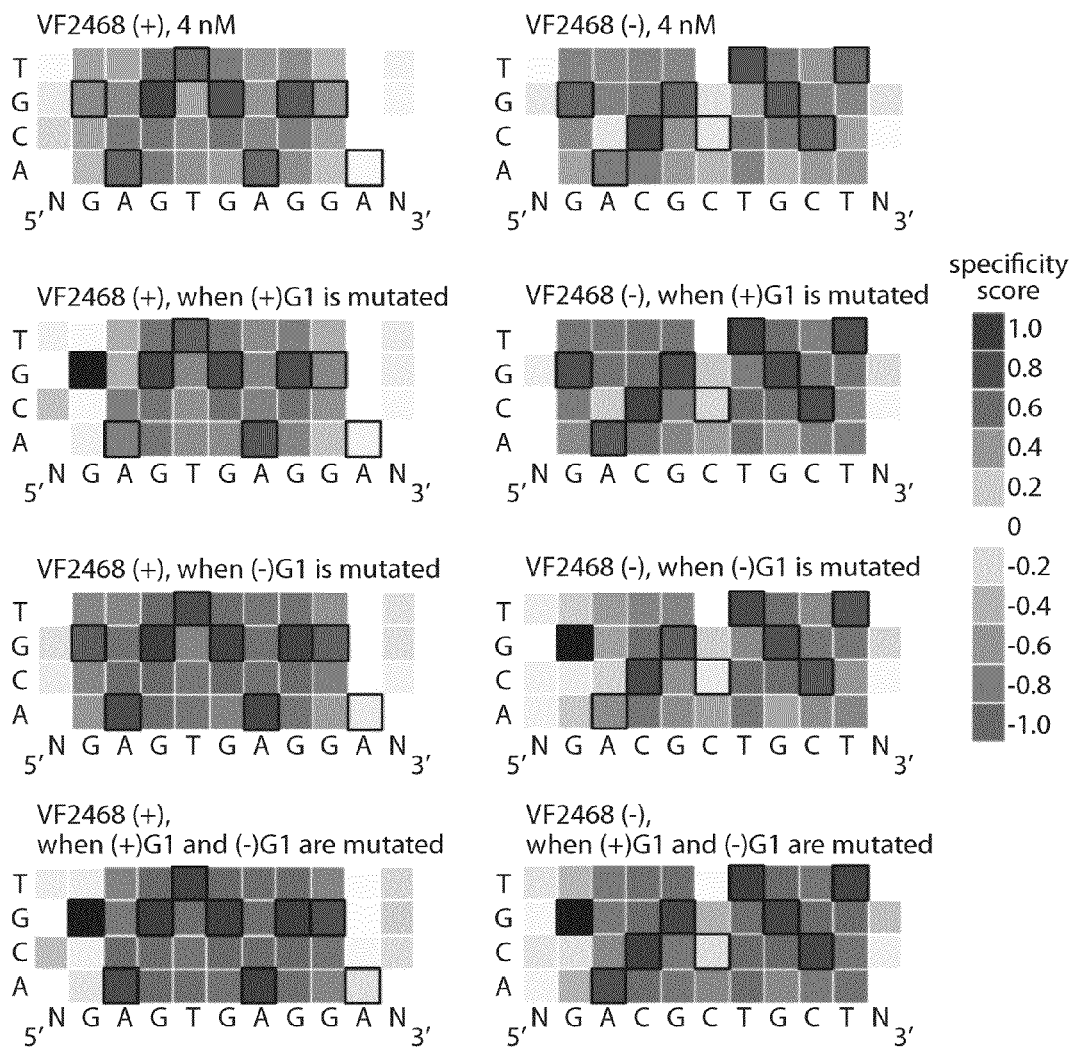
FIG. 13. Stringency at both half-sites increases when VF2468 cleaves sites with mutations at the first base pair of both half-sites. The heat maps show specificity scores for sequences identified in the in vitro selection with 4 nM VF2468. For (+)G1, (−)G1, and (+)G1/(−)G1, indicated by filled black boxes, both pre-selection library sequences and post-selection sequences were filtered to exclude any sequences that contained an G at position 1 in the (+) half-site and/or G at position 1 in the (−) half-site, before specificity scores were calculated. For sites with either mutation, there is decrease in mutational tolerance at the opposite half-site and a very slight decrease in mutational tolerance at the same half-site. Sites with both mutations show a strong increase in stringency at both half-sites. Black boxes indicate on-target base pairs. Specificity scores were calculated by dividing the change in frequency of each base pair at each position in the post-selection DNA pool compared to the pre-selection pool by the maximal possible change in frequency of each base pair at each position. Blue boxes indicate specificity for a base pair at a given position, white boxes indicate no specificity, and red boxes indicate specificity against a base pair at a given position. The darkest blue shown in the legend corresponds to absolute preference for a given base pair (specificity score=1.0), while the darkest red corresponds to an absolute preference against a given base pair (specificity score=−1.0). Sequences correspond to SEQ ID NO:40 for VF2468(+) and SEQ ID NO: 41 for VF2468(−).

Our results reveal that ZFN substrates with mutations in one half-site are more likely to have additional mutations in nearby positions in the same half-site compared to the pre-selection library and less likely to have additional mutations in the other half-site. While this effect was found to be largest when the most strongly recognized base pairs were mutated (FIG. 11), we observed this compensatory phenomenon for all specified half-site positions for both the CCR5 and VEGF-targeting ZFNs (FIG. 3 and FIG. 12). For a minority of nucleotides in cleaved sites, such as VF2468 target site positions (+)G1, (−)G1, (−)A2, and (−)C3, mutation led to decreased tolerance of mutations in base pairs in the other half-site and also a slight decrease, rather than an increase, in mutational tolerance in the same half-site. When two of these mutations, (+)G1 and (−)G1, were enforced at the same time, mutational tolerance at all other positions decreased (FIG. 13). Collectively, these results show that tolerance of mutations at one half-site is influenced by DNA recognition at the other half-site.

Figure 14A:
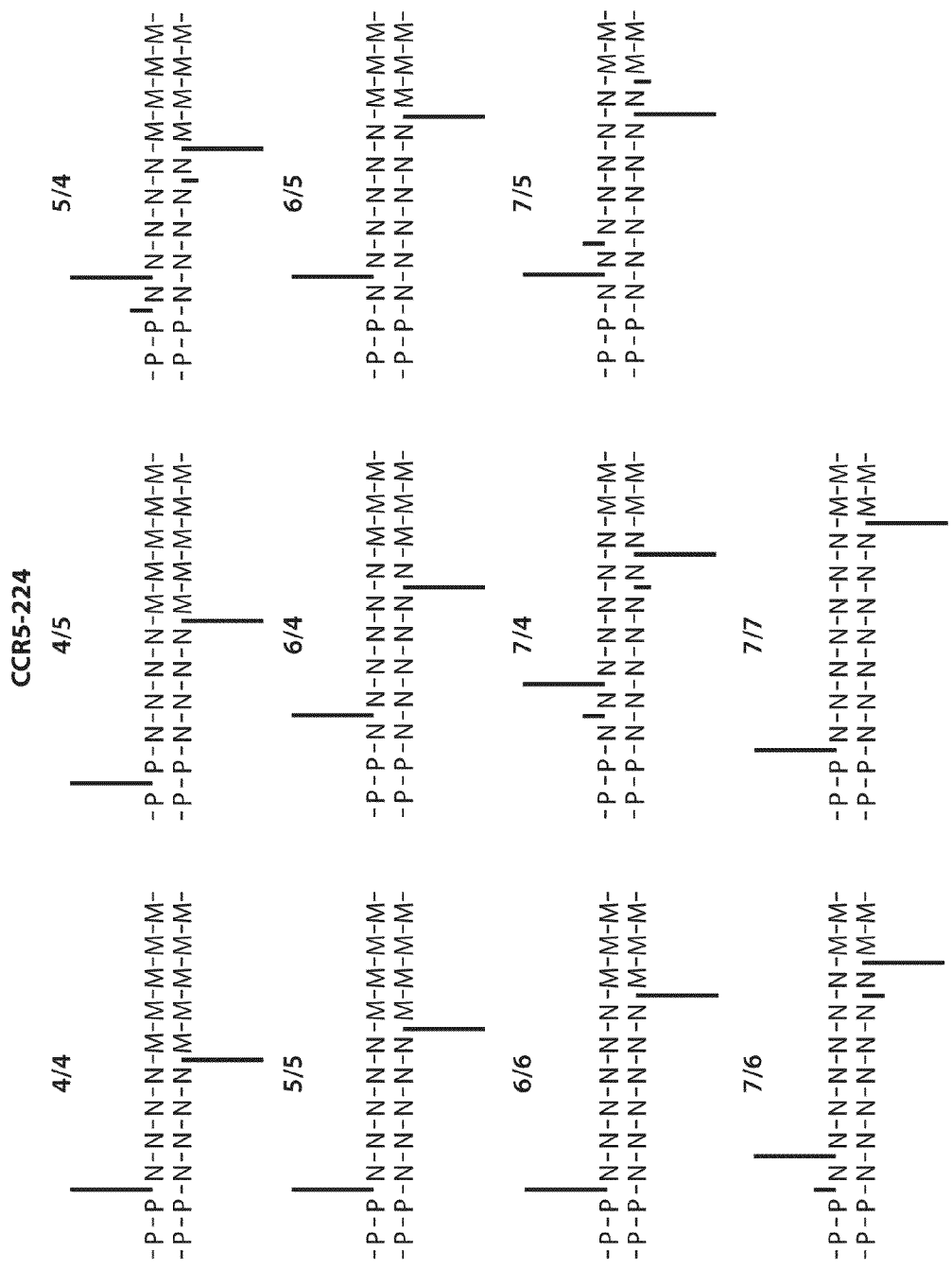
FIGS. 14A-B. ZFN cleavage occurs at characteristic locations in the DNA target site. The plots show the locations of cleavage sites identified in the in vitro selections with (a) 4 nM CCR5-224 or (b) 4 nM VF2468. The cleavage site locations show similar patterns for both ZFNs except in the case of five-base pair spacers with four-base overhangs. The titles refer to the spacer length/overhang length combination that is plotted (e.g., a site with a six base-pair spacer and a four base overhang is referred to as "6/4"). The black bars indicate the relative number of sequences cleaved for each combination of spacer length and overhang length. 'P' refers to nucleotides in the (+) target half-site, 'M' refers to nucleotides in the (−) target half site, and 'N' refers to nucleotides in the spacer. There were no "7/7" sequences from the 4 nM VF2468 selection. Only sequences with overhangs of at least 4 bases were tabulated.
Figure 14B:
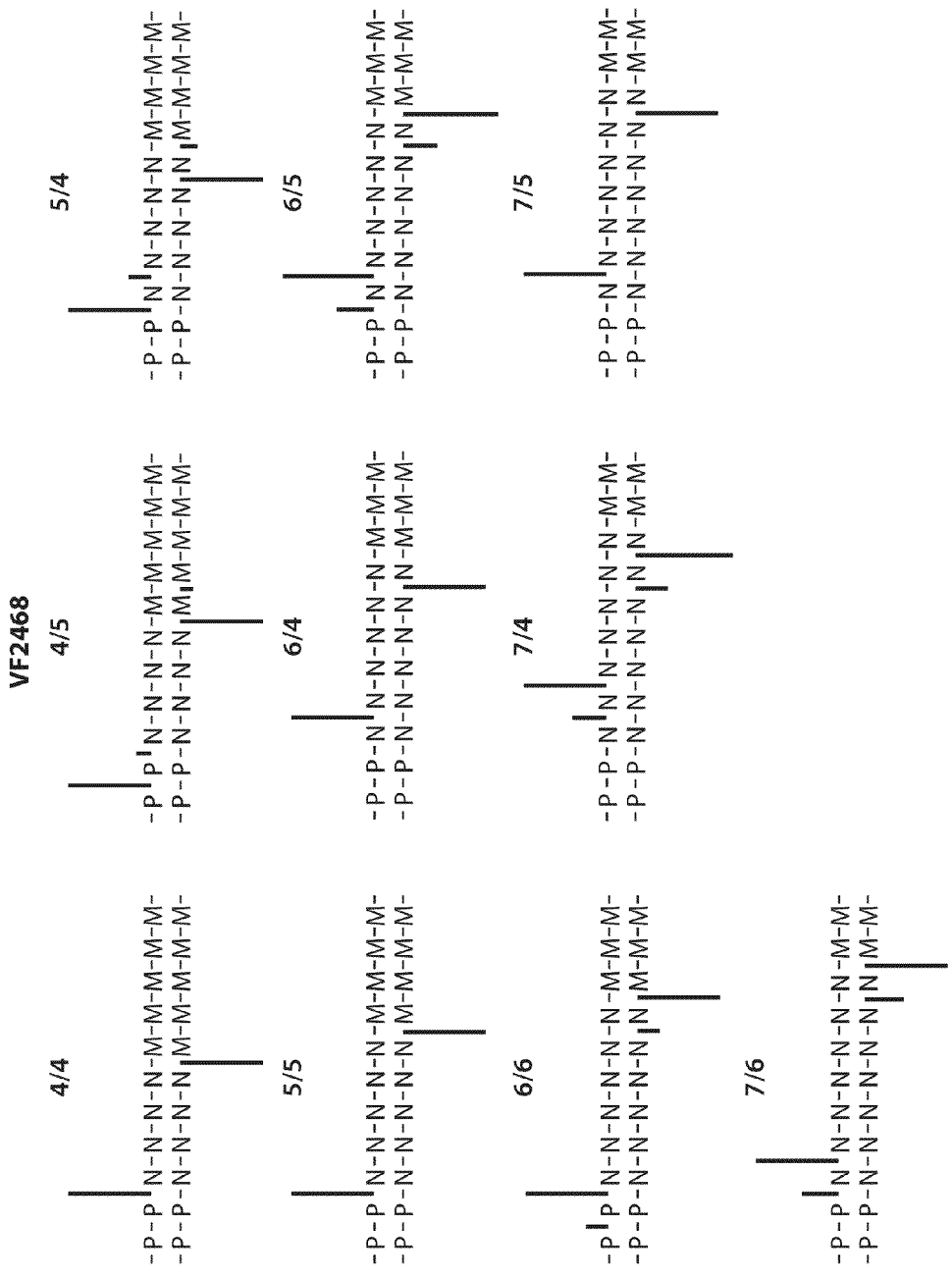
Figure 15A:
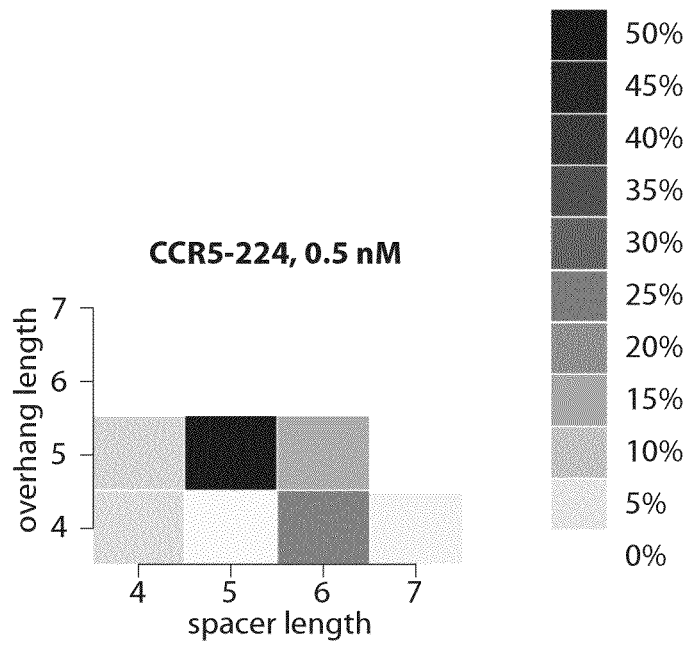
FIGS. 15A-D. CCR5-224 preferentially cleaves five- and six-base pair spacers and cleaves five-base pair spacers to leave five-nucleotide overhangs. The heat maps show the percentage of all sequences surviving each of the four CCR5-224 in vitro selections (a-d) that have the spacer and overhang lengths shown.
Figure 15B:
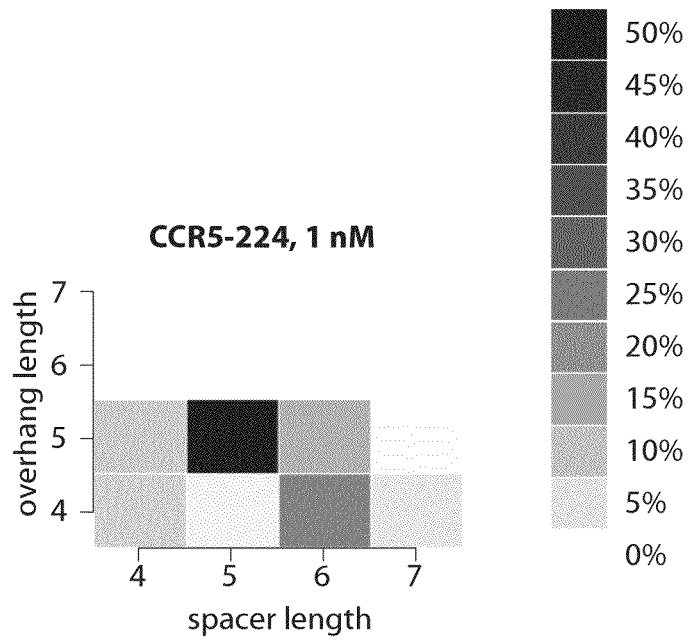
Figure 15C:
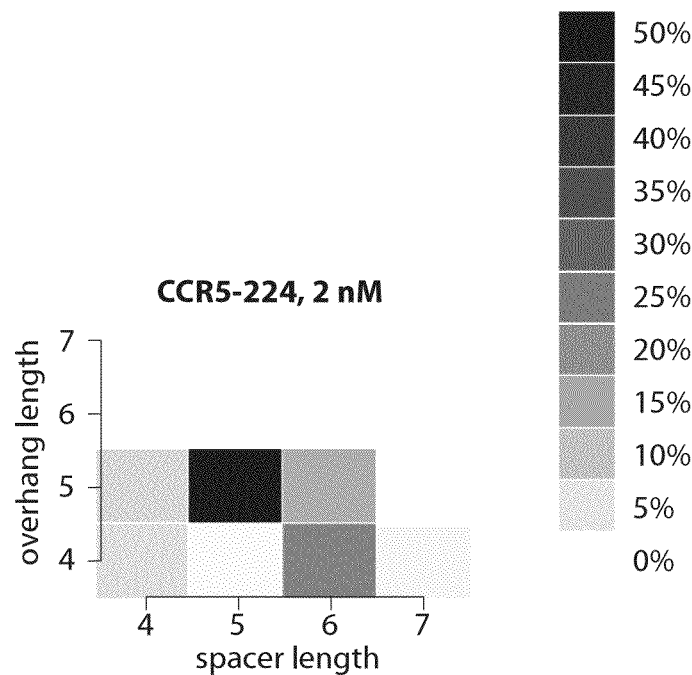
Figure 15D:
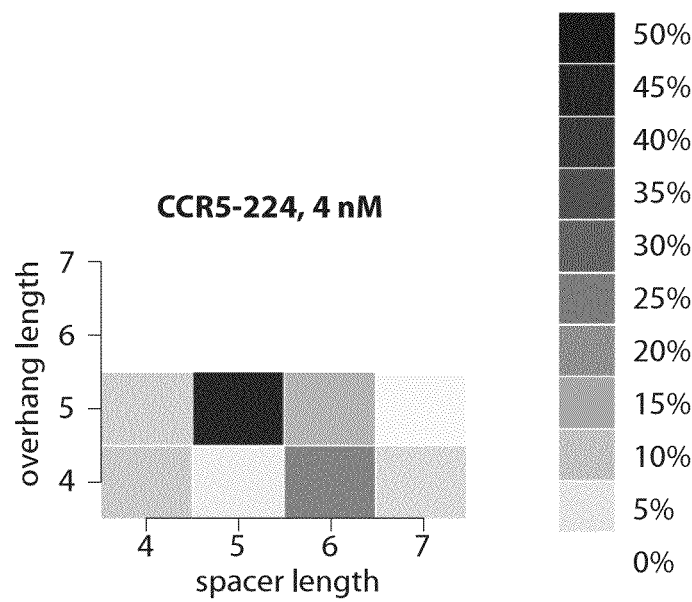
Figure 16A:
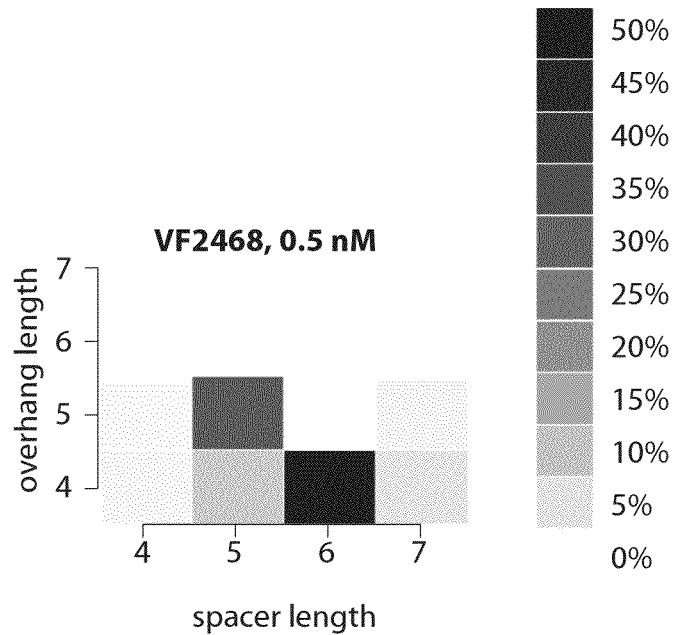
FIGS. 16A-D. VF2468 preferentially cleaves five- and six-base pair spacers, cleaves five-base pair spacers to leave five-nucleotide overhangs, and cleaves six-base pair spacers to leave four-nucleotide overhangs. The heat maps show the percentage of all sequences surviving each of the four VF2468 in vitro selections (a-d) that have the spacer and overhang lengths shown.
Figure 16B:
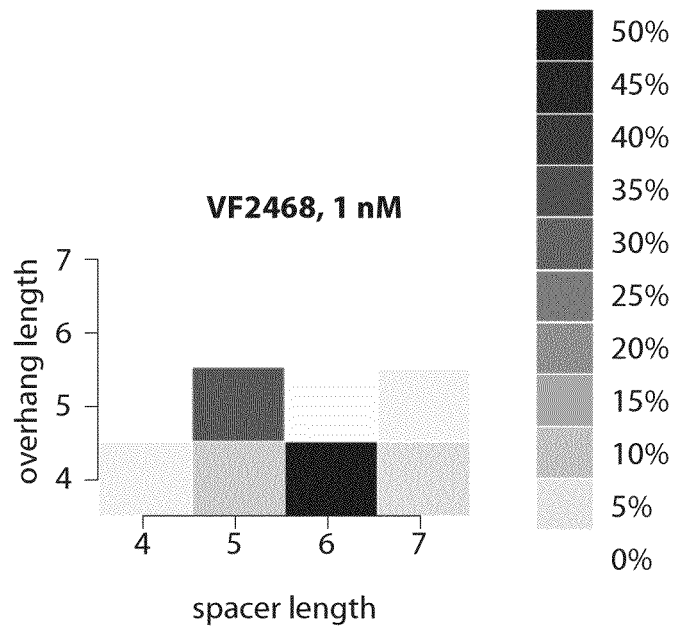
Figure 16C:
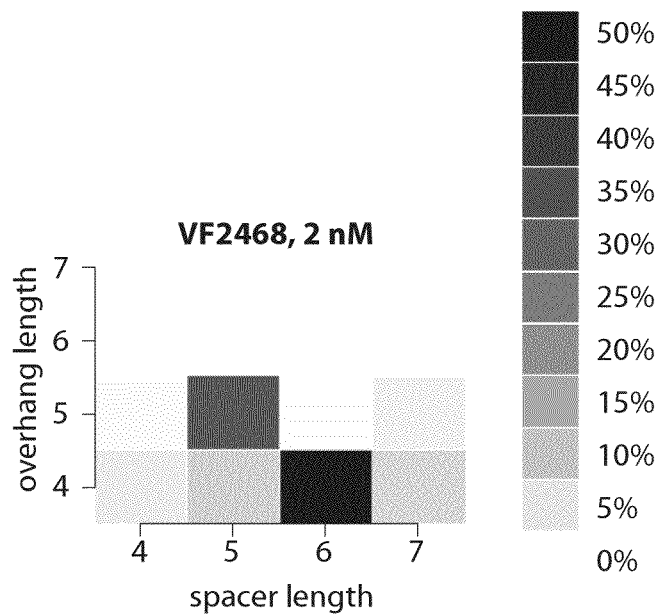
Figure 16D:
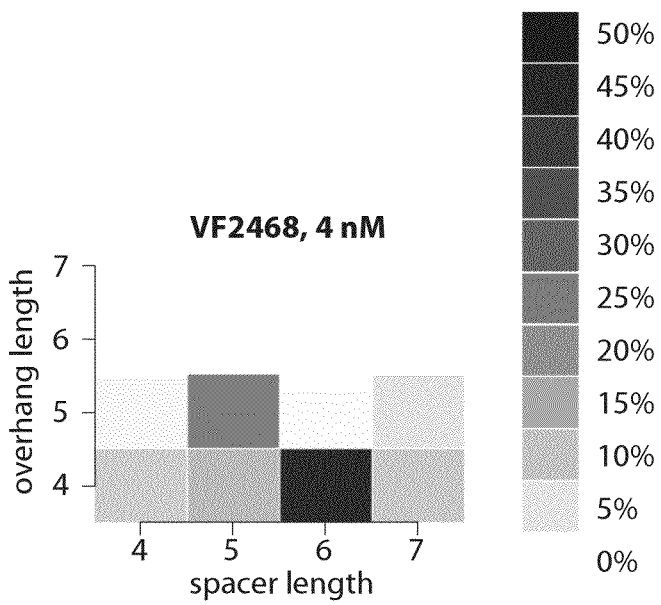
Figures 1, 17A:
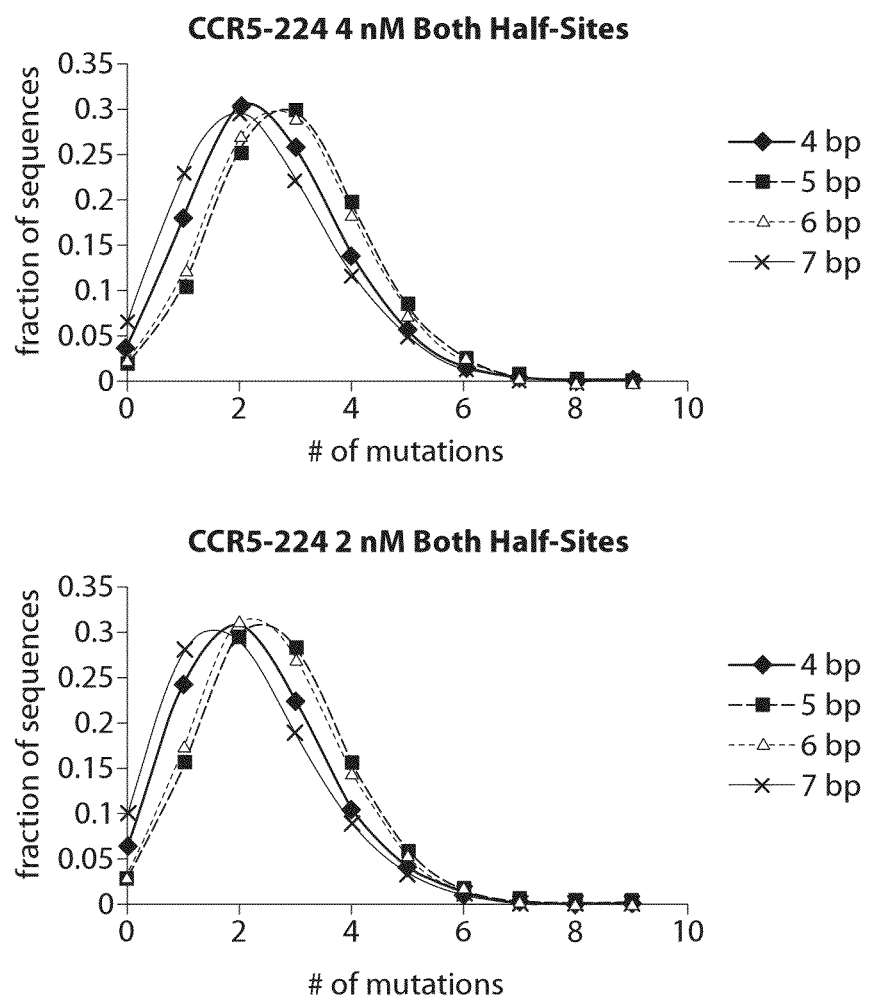
FIGS. 17A-F. ZFNs show spacer length-dependent sequence preferences. Both CCR5-224 (a-c) and VF2468 (d-f) show increased specificity for half-sites flanking four- and seven-base pair spacers than for half-sites flanking five- and six-base pair spacers. For both ZFNs, one half-site has a greater change in mutational tolerance than the other, and the change in mutational tolerance is concentration dependent.
Figures 2, 17A:
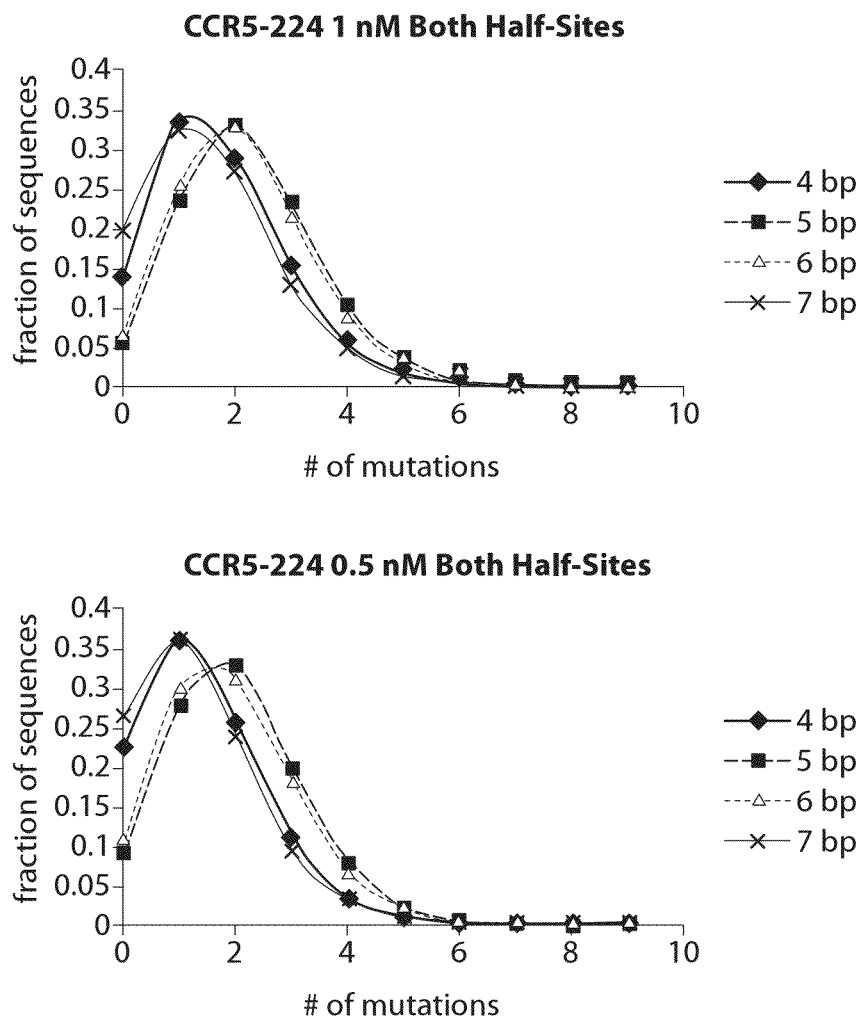
Figures 1, 17B:
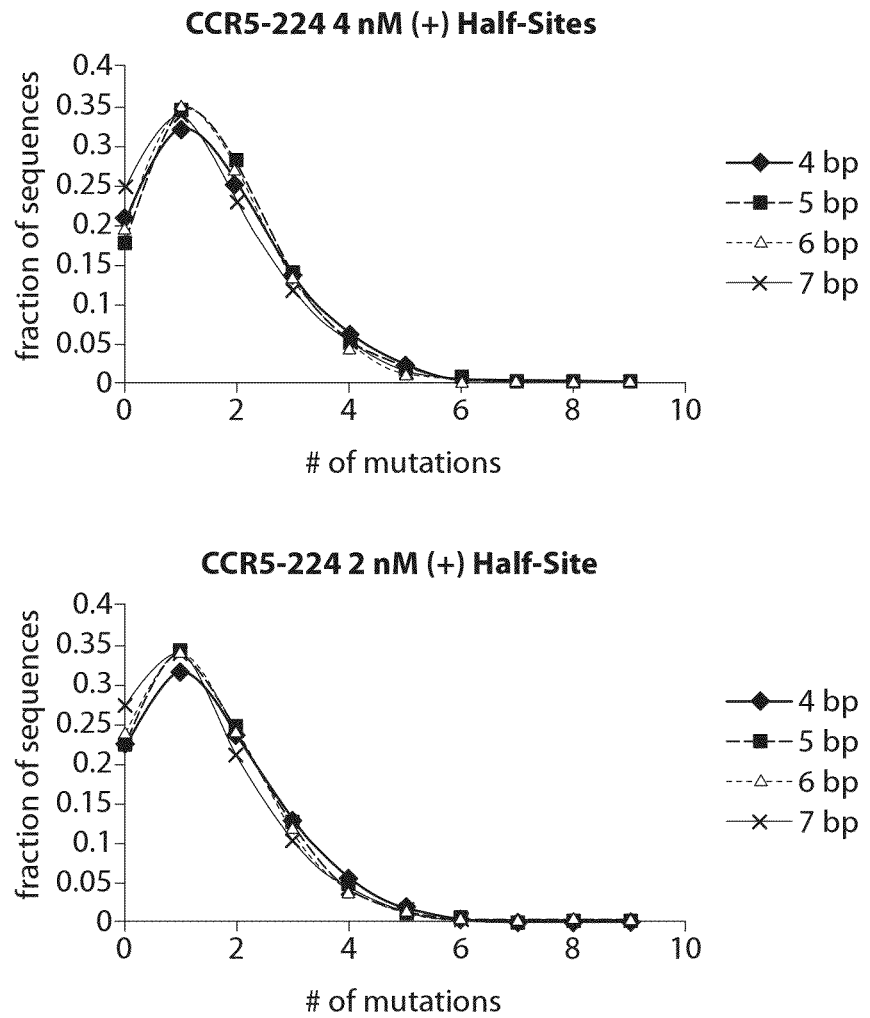
Figures 2, 17B:
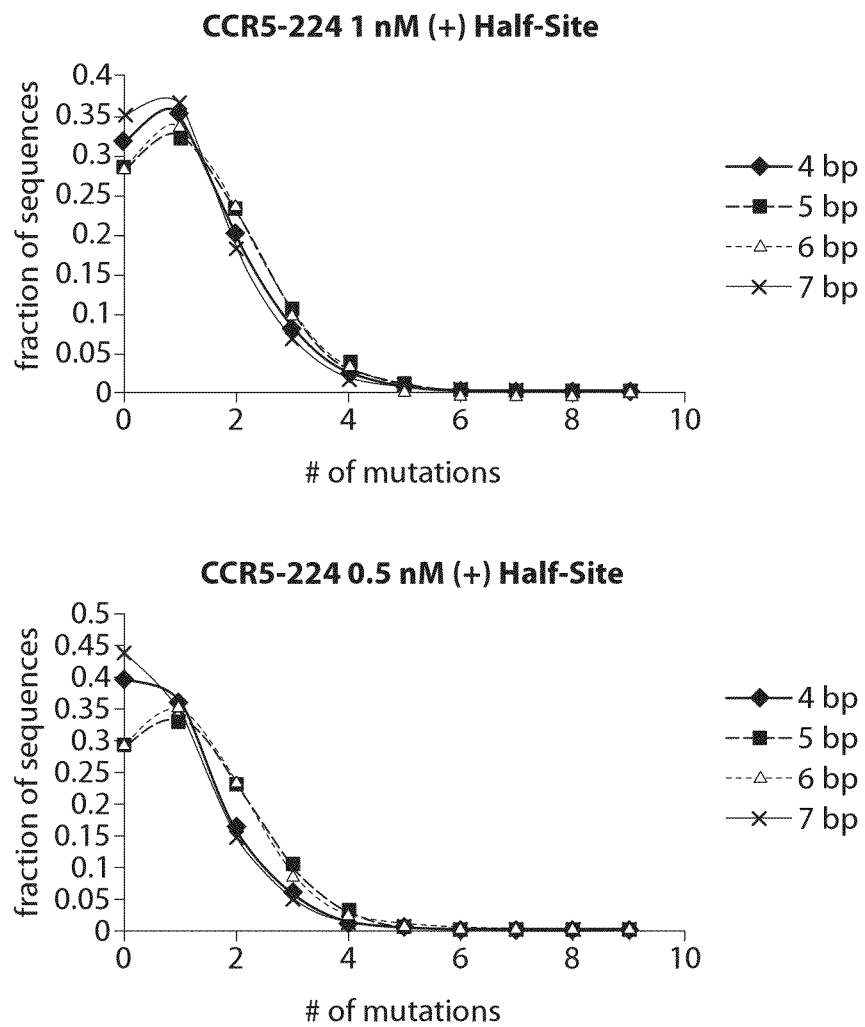
Figures 1, 17C:
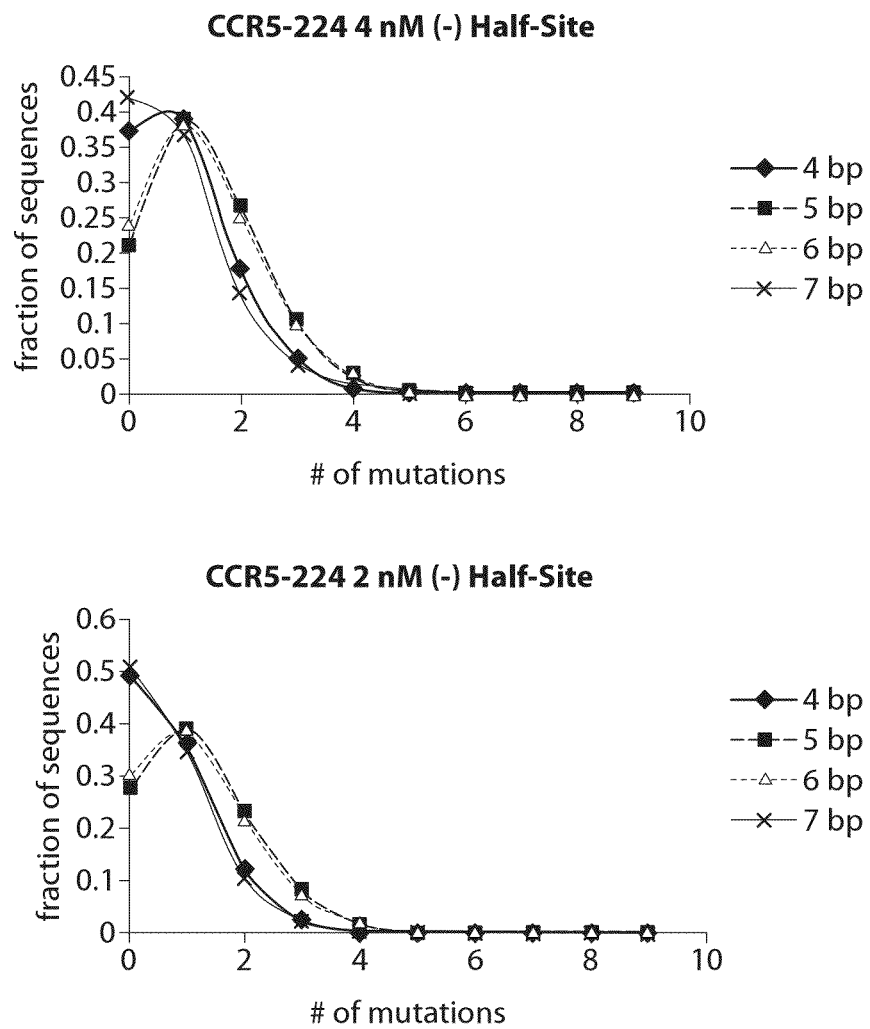
Figures 2, 17C:
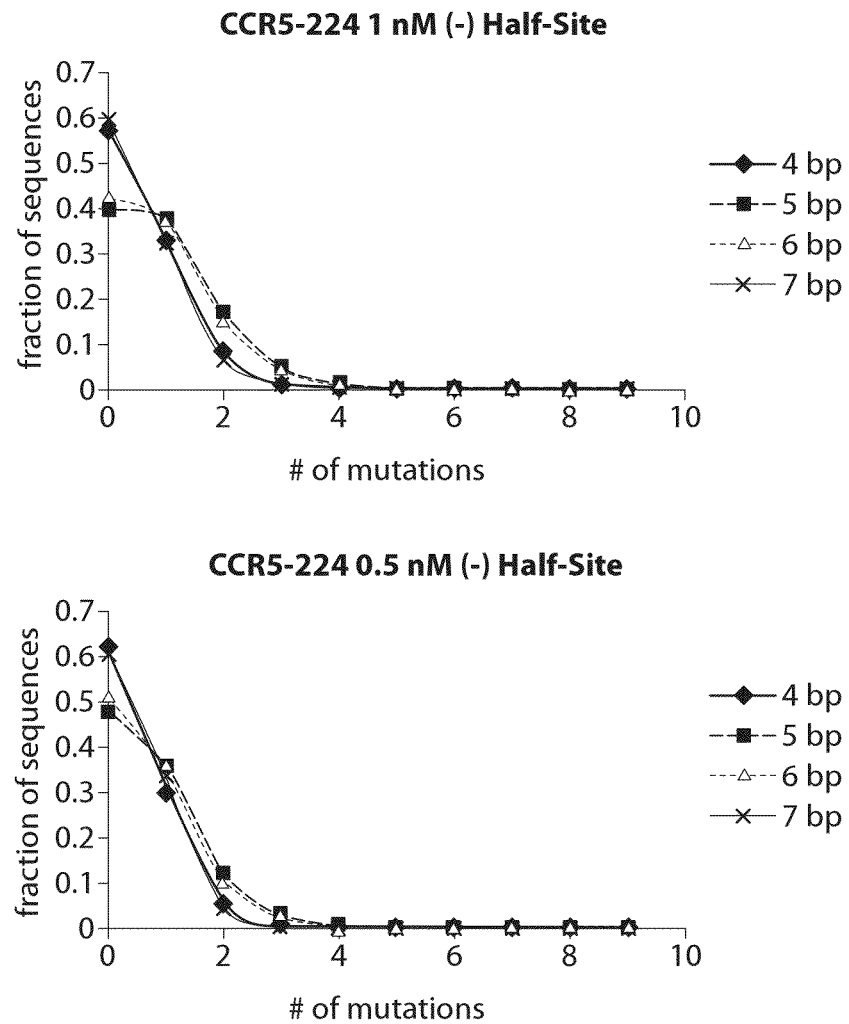
Figures 1, 17D:
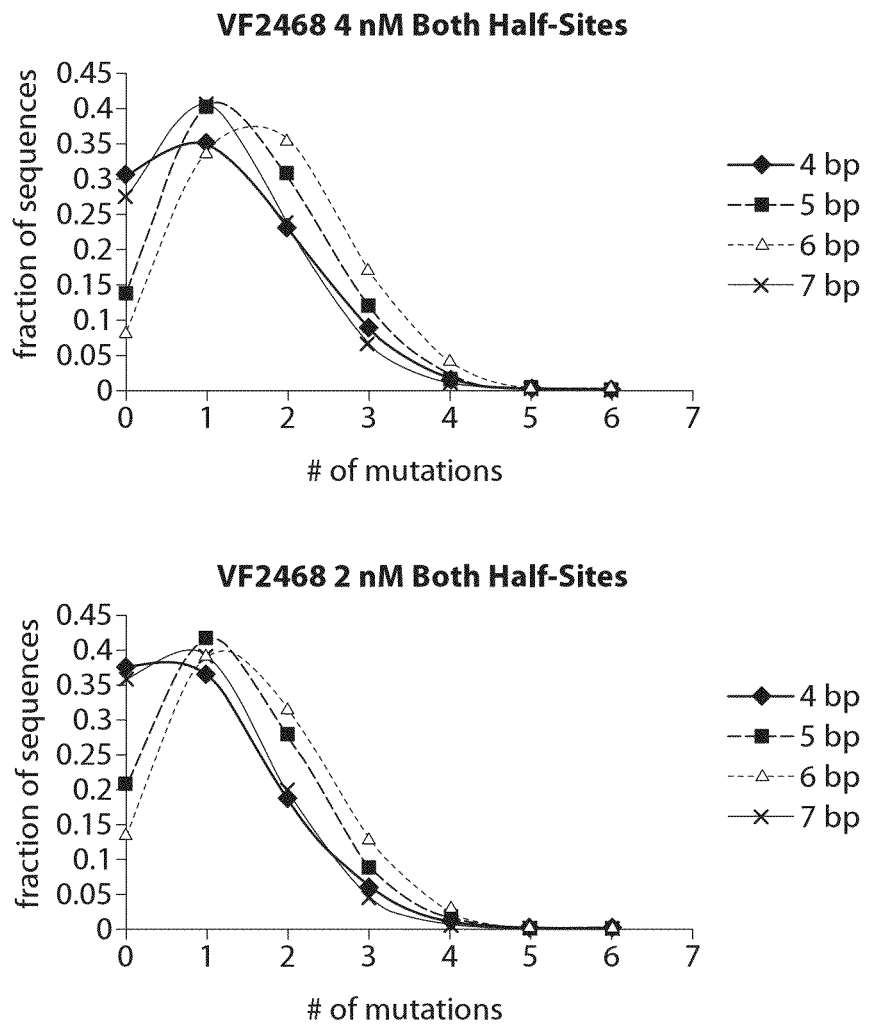
Figures 2, 17D:
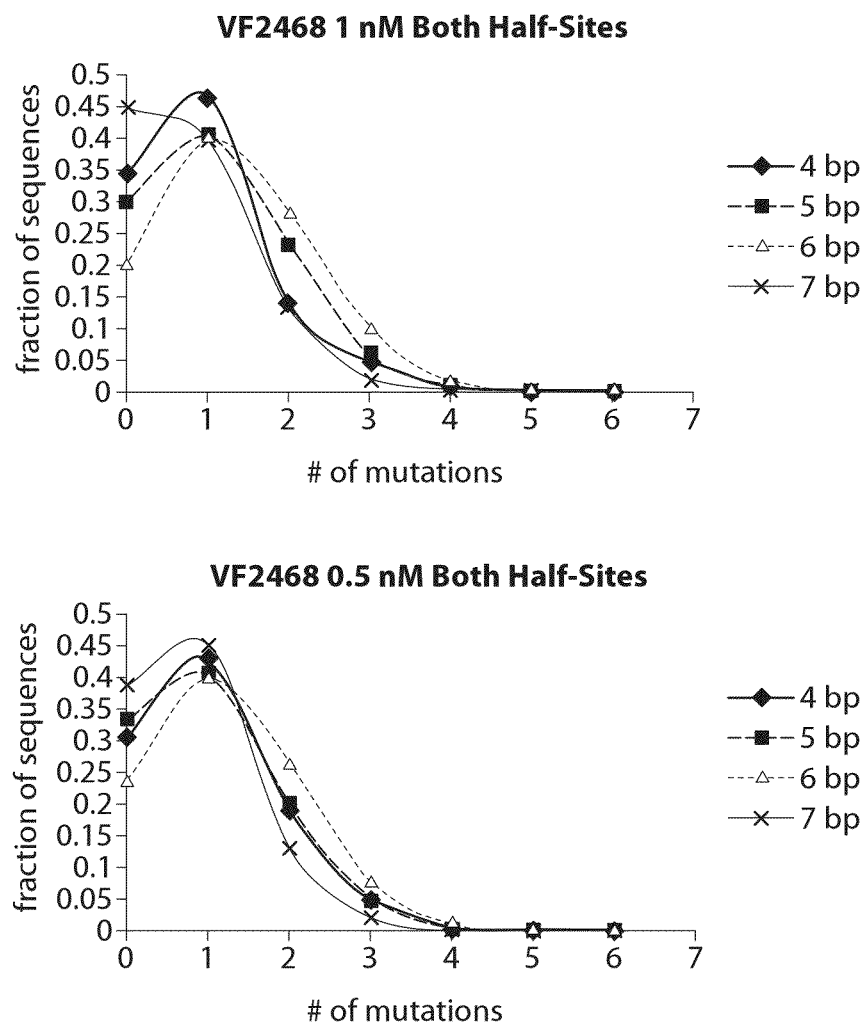
Figures 1, 17E:
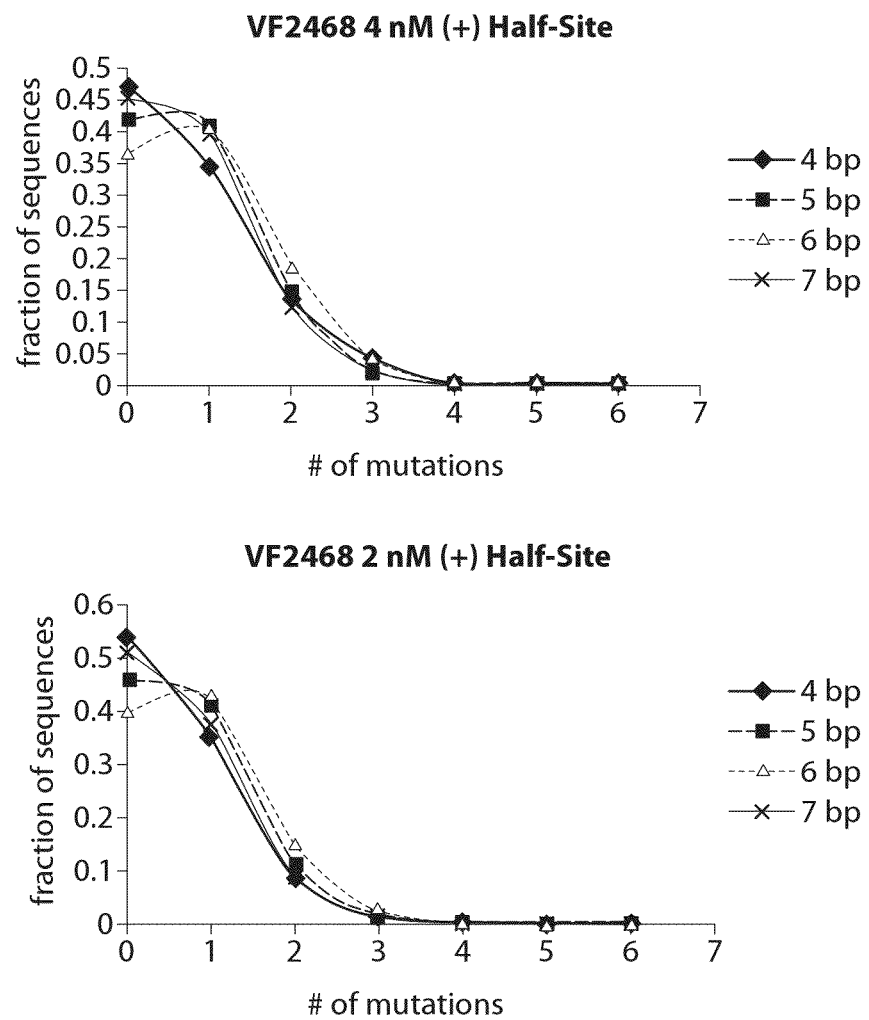
Figures 2, 17E:
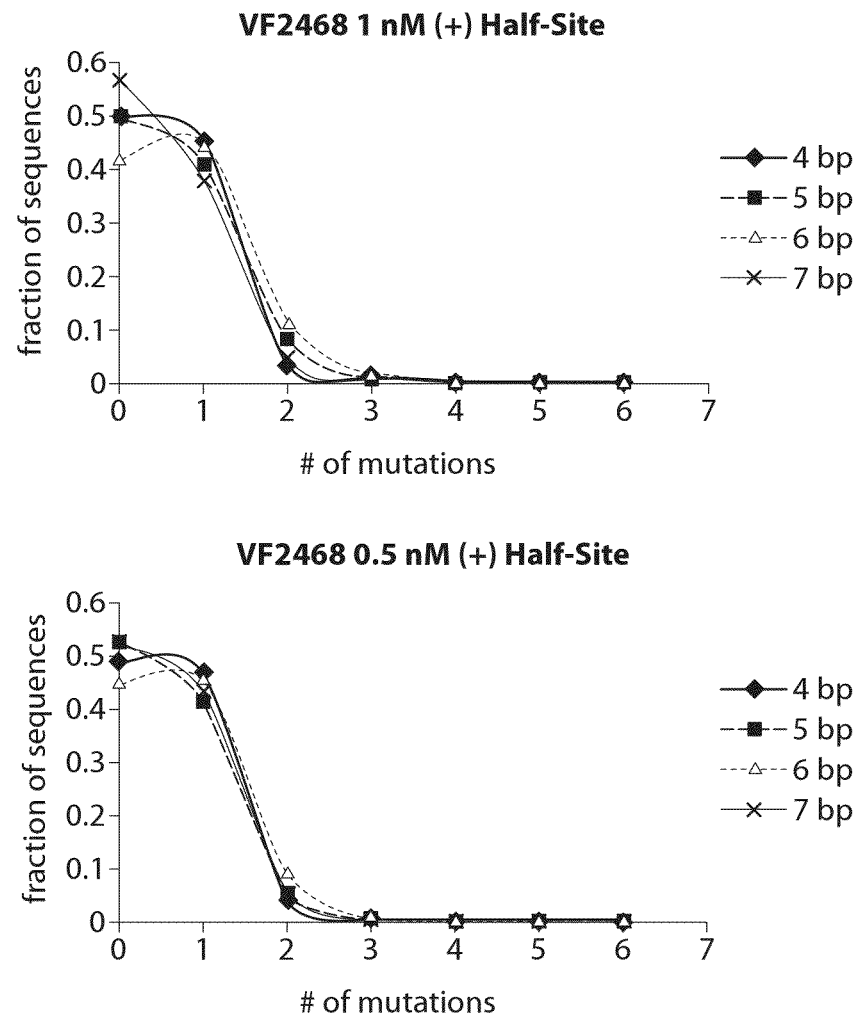
Figures 1, 17F:
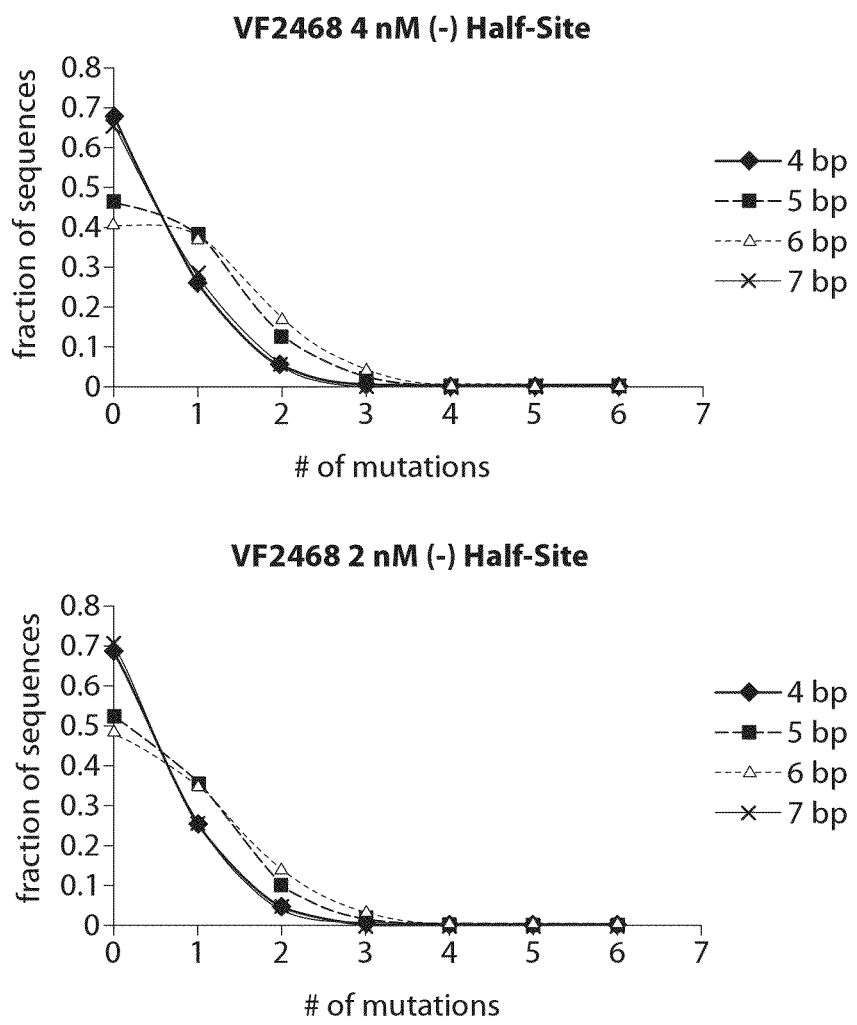
Figures 2, 17F:
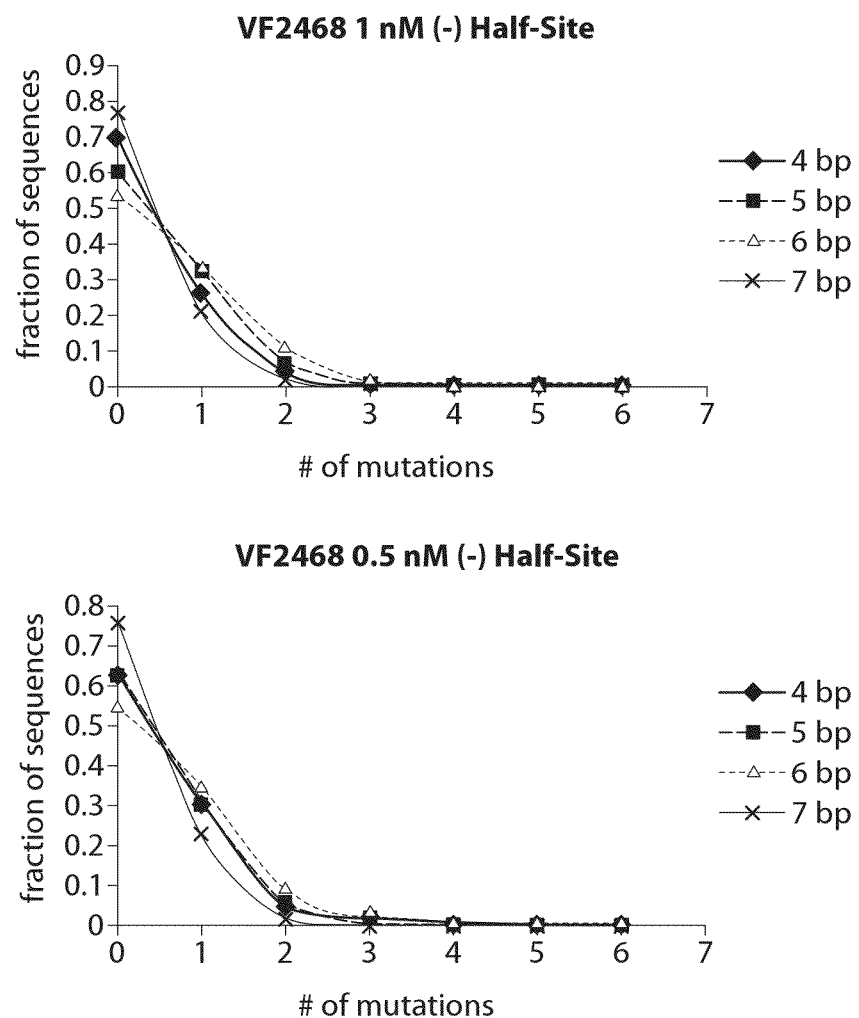
Figure 18:
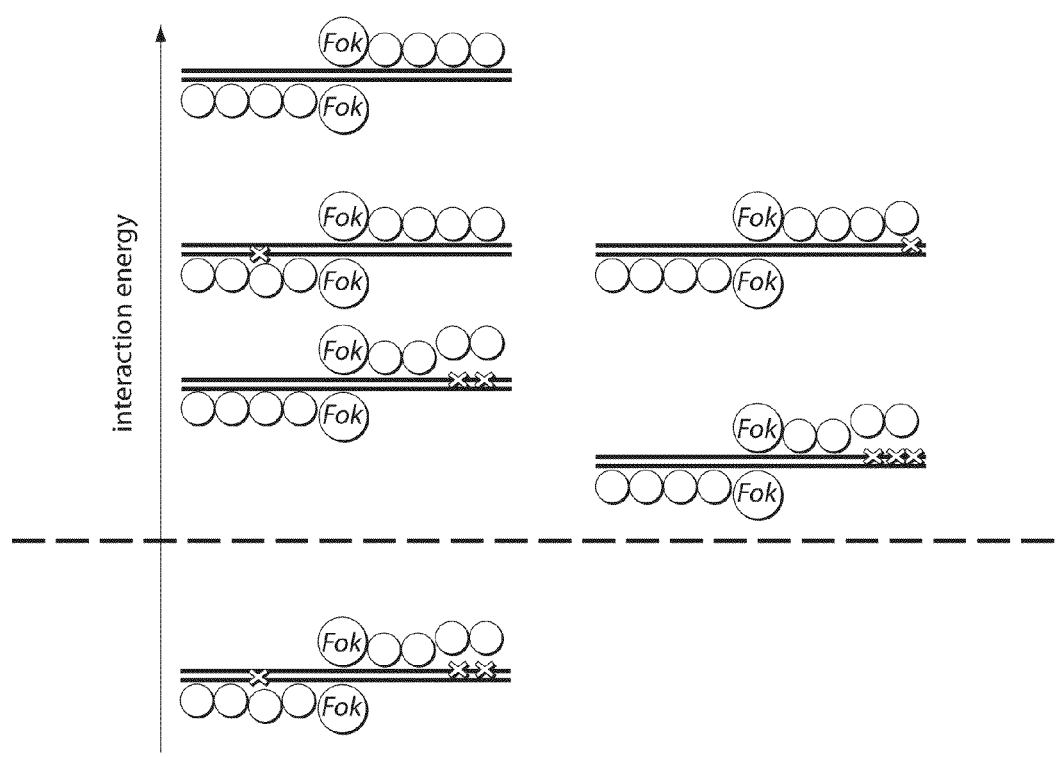
FIG. 18. Model for ZFN tolerance of off-target sequences. Our results suggest that some ZFNs recognize their intended target sites (top, black DNA strands with no Xs) with more binding energy than is required for cleavage under a given set of conditions (dotted line). Sequences with one or two mutations (one or two Xs) are generally tolerated since they do not decrease the ZFN:DNA binding energy below the threshold necessary for cleavage. Some sequences with additional mutations can still be cleaved if the additional mutations occur in regions of the zinc-finger binding interface that have already been disrupted (three Xs above the dotted line), as long as optimal interactions present at other locations in the ZFN:DNA binding interface maintain binding energies above threshold values. Additional mutations that disrupt key interactions at other locations in the ZFN:DNA interface, however, result in binding energies that fall short of the cleavage threshold.

This compensation model for ZFN site recognition applies not only to non-ideal half-sites, but also to spacers with non-ideal lengths. In general, the ZFNs cleaved at characteristic locations within the spacers (FIG. 14), and five- and six-base pair spacers were preferred over four- and seven-base pair spacers (FIGS. 15 and 16). However, cleaved sites with five- or six-base pair spacers showed greater sequence tolerance at the flanking half-sites than sites with four- or seven-base pair spacers (FIG. 17). Therefore, spacer imperfections, similar to half-site mutations, lead to more stringent in vitro recognition of other regions of the DNA substrate.

ZFNs can Cleave Many Sequences with Up to Three Mutations

Figure 4A:
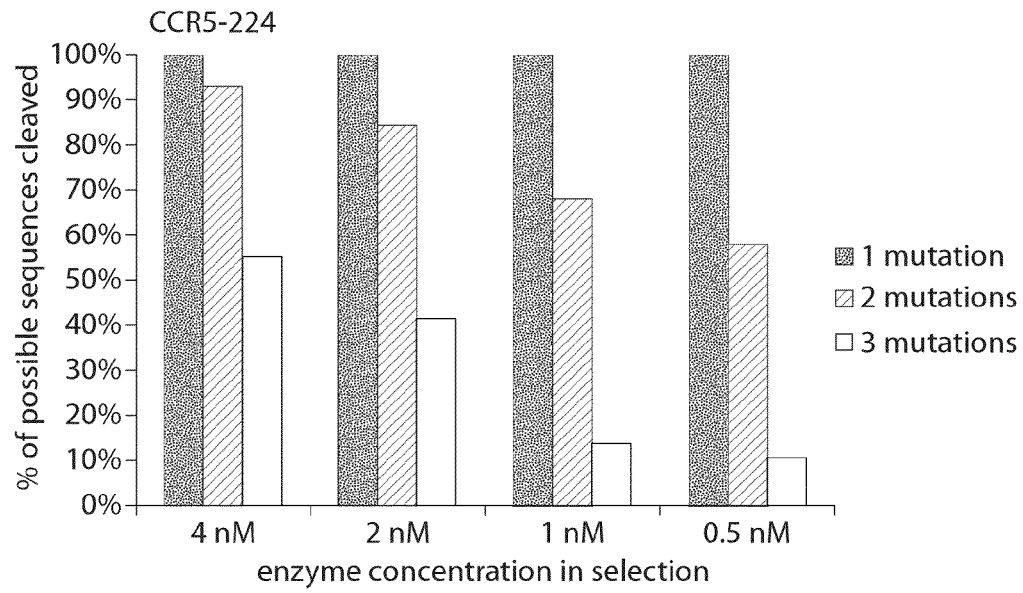
FIGS. 4A-B. ZFNs can cleave a large fraction of target sites with three or fewer mutations in vitro. The percentages of the sequences with one, two, or three mutations that are enriched for in vitro cleavage (enrichment factor>1) by the (a) CCR5-224 ZFN and (b) VF2468 ZFN are shown. Enrichment factors are calculated for each sequence identified in the selection by dividing the observed frequency of that sequence in the post-selection sequenced library by the frequency of that sequence in the pre-selection library.
Figure 4B:
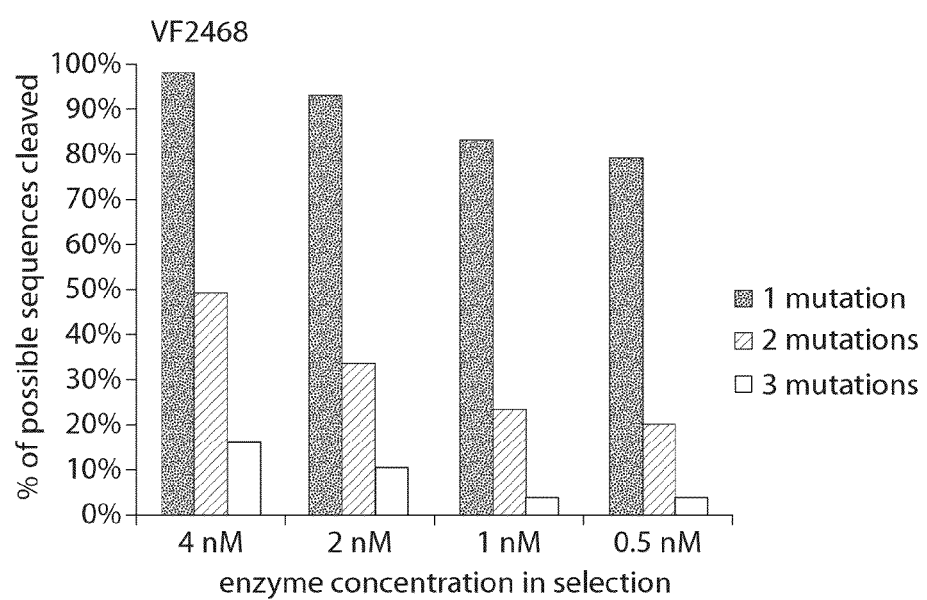

We calculated enrichment factors for all sequences containing three or fewer mutations by dividing each sequence's frequency of occurrence in the post-selection libraries by its frequency of occurrence in the pre-selection libraries. Among sequences enriched by cleavage (enrichment factor>1), CCR5-224 was capable of cleaving all unique single-mutant sequences, 93% of all unique double-mutant sequences, and half of all possible triple-mutant sequences (FIG. 4a and Table 3a) at the highest enzyme concentration used. VF2468 was capable of cleaving 98% of all unique single-mutant sequences, half of all unique double-mutant sequences, and 17% of all triple-mutant sequences (FIG. 4b and Table 3b).

Since our approach assays active ZFN dimers, it reveals the complete sequences of ZFN sites that can be cleaved. Ignoring the sequence of the spacer, the selection revealed 37 sites in the human genome with five- or six-base pair spacers that can be cleaved in vitro by CCR5-224 (Table 1 and Table 4), and 2,652 sites in the human genome that can be cleaved by VF2468 (VF2468 Data). Among the genomic sites that were cleaved in vitro by VF2468, 1,428 sites had three or fewer mutations relative to the canonical target site (excluding the spacer sequence). Despite greater discrimination against single-, double-, and triple-mutant sequences by VF2468 compared to CCR5-224 (FIG. 4 and Table 3), the larger number of in vitro-cleavable VF2468 sites reflects the difference in the number of sites in the human genome that are three or fewer mutations away from the VF2468 target site (3,450 sites) versus those that are three or fewer mutations away from the CCR5-224 target site (eight sites) (Table 5).

Identified Sites are Cleaved by ZFNs in Human Cells

We tested whether CCR5-224 could cleave at sites identified by our selections in human cells by expressing CCR5-224 in K562 cells and examining 34 potential target sites within the human genome for evidence of ZFN-induced mutations using PCR and high-throughput DNA sequencing. We defined sites with evidence of ZFN-mediated cleavage as those with insertion or deletion mutations (indels) characteristic of non-homologous end joining (NHEJ) repair (Table 6) that were significantly enriched (P<0.05) in cells expressing active CCR5-224 compared to control cells containing an empty vector. We obtained approximately 100,000 sequences or more for each site analyzed, which enabled the detection of sites that were significantly modified at frequencies of approximately 1 in 10,000. Our analysis identified ten such sites: the intended target sequence in CCR5, a previously identified sequence in CCR2, and eight other off-target sequences (Tables 1, 4, and 6), one of which lies within the promoter of the BTBD10 gene. The eight newly identified off-target sites are modified at frequencies ranging from 1 in 300 to 1 in 5,300. We also expressed VF2468 in cultured K562 cells and performed the above analysis for 90 of the most highly cleaved sites identified by in vitro selection. Out of the 90 VF2468 sites analyzed, 32 showed indels consistent with ZFN-mediated targeting in K562 cells (Table 7). We were unable to obtain site-specific PCR amplification products for three CCR5-224 sites and seven VF2468 sites and therefore could not analyze the occurrence of NHEJ at those loci. Taken together, these observations indicate that off-target sequences identified through the in vitro selection method include many DNA sequences that can be cleaved by ZFNs in human cells.

Discussion

The method presented here identified hundreds of thousands of sequences that can be cleaved by two active, dimeric ZFNs, including many that are present and can be cut in the genome of human cells. One newly identified cleavage site for the CCR5-224 ZFN is within the promoter of the BTBD10 gene. When downregulated, BTBD10 has been associated with malignancy[21] and with pancreatic beta cell apoptosis[22]. When upregulated, BTBD10 has been shown to enhance neuronal cell growth[23] and pancreatic beta cell proliferation through phosphorylation of Akt family proteins[22,23]. This potentially important off-target cleavage site as well as seven others we observed in cells were not identified in a recent study[6] that used in vitro monomer-binding data to predict potential CCR5-224 substrates.

We have previously shown that ZFNs that can cleave at sites in one cell line may not necessarily function in a different cell line[4], most likely due to local differences in chromatin structure. Therefore, it is likely that a different subset of the in vitro-cleavable off-target sites would be modified by CCR5-224 or VF2468 when expressed in different cell lines. Purely cellular studies of endonuclease specificity, such as a recent study of homing endonuclease off-target cleavage[24], may likewise be influenced by cell line choice. While our in vitro method does not account for some features of cellular DNA, it provides general, cell type-independent information about endonuclease specificity and off-target sites that can inform subsequent studies performed in cell types of interest. In addition, while our pre-selection library oversamples with at least 10-fold coverage all sequences within seven mutations of the intended ZFN target sites, the number of sequence reads obtained per selection (approximately one million) is likely insufficient to cover all cleaved sequences present in the post-selection libraries. It is therefore possible that additional off-target cleavage sites for CCR5-224 and VF2468 could be identified in the human genome as sequencing capabilities continue to improve.

Although both ZFNs we analyzed were engineered to a unique sequence in the human genome, both cleave a significant number of off-target sites in cells. This finding is particularly surprising for the four-finger CCR5-224 pair given that its theoretical specificity is 4,096-fold better than that of the three-finger VF2468 pair (CCR5-224 should recognize a 24-base pair site that is six base pairs longer than the 18-base pair VF2468 site). Examination of the CCR5-224 and VF2468 cleavage profiles (FIG. 2) and mutational tolerances of sequences with three or fewer mutations (FIG. 4) suggests different strategies may be required to engineer variants of these ZFNs with reduced off-target cleavage activities. The four-finger CCR5-224 ZFN showed a more diffuse range of positions with relaxed specificity and a higher tolerance of mutant sequences with three or fewer mutations than the three-finger VF2468 ZFN. For VF2468, re-optimization of only a subset of fingers may enable a substantial reduction in undesired cleavage events. For CCR5-224, in contrast, a more extensive re-optimization of many or all fingers may be required to eliminate off-target cleavage events.

We note that not all four- and three-finger ZFNs will necessarily be as specific as the two ZFNs tested in this study. Both CCR5-224 and VF2468 were engineered using methods designed to optimize the binding activity of the ZFNs. Previous work has shown that for both three-finger and four-finger ZFNs, the specific methodology used to engineer the ZFN pair can have a tremendous impact on the quality and specificity of nucleases[7,13,25,26].

Our findings have significant implications for the design and application of ZFNs with increased specificity. Half or more of all potential substrates with one or two site mutations could be cleaved by ZFNs, suggesting that binding affinity between ZFN and DNA substrate is sufficiently high for cleavage to occur even with suboptimal molecular interactions at mutant positions. We also observed that ZFNs presented with sites that have mutations in one half-site exhibited higher mutational tolerance at other positions within the mutated half-site and lower tolerance at positions in the other half-site. These results collectively suggest that in order to meet a minimum affinity threshold for cleavage, a shortage of binding energy from a half-site harboring an off-target base pair must be energetically compensated by excess zinc finger: DNA binding energy in the other half-site, which demands increased sequence recognition stringency at the non-mutated half-site (FIG. S18). Conversely, the relaxed stringency at other positions in mutated half-sites can be explained by the decreased contribution of that mutant half-site to overall ZFN binding energy. This hypothesis is supported by a recent study showing that reducing the number of zinc fingers in a ZFN can actually increase, rather than decrease, activity[27].

This model also explains our observation that sites with suboptimal spacer lengths, which presumably were bound less favorably by ZFNs, were recognized with higher stringency than sites with optimal spacer lengths. In vitro spacer preferences do not necessarily reflect spacer preferences in cells;[28,29] however, our results suggest that the dimeric FokI cleavage domain can influence ZFN target-site recognition. Consistent with this model, Wolfe and co-workers recently observed differences in the frequency of off-target events in zebrafish of two ZFNs with identical zinc-finger domains but different FokI domain variants.[20]

Collectively, our findings suggest that (i) ZFN specificity can be increased by avoiding the design of ZFNs with excess DNA binding energy; (ii) off-target cleavage can be minimized by designing ZFNs to target sites that do not have relatives in the genome within three mutations; and (iii) ZFNs should be used at the lowest concentrations necessary to cleave the target sequence to the desired extent. While this study focused on ZFNs, our method should be applicable to all sequence-specific endonucleases that cleave DNA in vitro, including engineered homing endonucleases and engineered transcription activator-like effector (TALE) nucleases. This approach can provide important information when choosing target sites in genomes for sequence-specific endonucleases, and when engineering these enzymes, especially for therapeutic applications.

Methods

Oligonucleotides and Sequences. All oligonucleotides were purchased from Integrated DNA Technologies or Invitrogen and are listed in Table 8. Primers with degenerate positions were synthesized by Integrated DNA Technologies using hand-mixed phosphoramidites containing 79% of the indicated base and 7% of each of the other standard DNA bases.

Sequences of ZFNs used in this study. DNA and protein sequences are shown for the ZFNs used in this study. The T7 promoter is underlined, and the start codon is in bold.

```
CCR5-224 (+) DNA sequence (SEQ ID NO: 119):
TAATACGACTCACTATAGGGAGACCCAAGCTGGCTAGCCACCATGGACTACAAAGACCATGACGGTGATTATAAA

GATCATGACATCGATTACAAGGATGACGATGACAAGATGGCCCCCAAGAAGAAGAGGAAGGTGGGCATTCACGGG

GTACCCGCCGCTATGGCTGAGAGGCCCTTCCAGTGTCGAATCTGCATGCGTAACTTCAGTGATCGCTCTAACCTG

AGTCGGCACATCCGCACCCACACAGGCGAGAAGCCTTTTGCCTGTGACATTTGTGGGAGGAAGTTTGCCATCTCC

TCCAACCTGAACTCCCATACCAAGATACACACGGGATCTCAGAAGCCCTTCCAGTGTCGAATCTGCATGCGTAAC

TTCAGTCGCTCCGACAACCTGGCCCGCCACATCCGCACCCACACAGGCGAGAAGCCTTTTGCCTGTGACATTTGT

GGGAGGAAATTTGCCACCTCCGGCAACCTGACCCGCCATACCAAGATACACCTGCGGGGATCCCAACTAGTCAAA

AGTGAACTGGAGGAGAAGAAATCTGAACTTCGTCATAAATTGAAATATGTGCCTCATGAATATATTGAATTAATT

GAAATTGCCAGAAATTCCACTCAGGATAGAATTCTTGAAATGAAGGTAATGGAATTTTTTATGAAAGTTTATGGA

TATAGAGGTAAACATTTGGGTGGATCAAGGAAACCGGACGGAGCAATTTATACTGTCGGATCTCCTATTGATTAC

GGTGTGATCGTGGATACTAAAGCTTATAGCGGAGGTTATAATCTGCCAATTGGCCAAGCAGATGAAATGCAACGA

TATGTCAAAGAAAATCAAACACGAAACAAACATATCAACCCTAATGAATGGTGGAAAGTCTATCCATCTTCTGTA

ACGGAATTTAAGTTTTTATTTGTGAGTGGTCACTTTAAAGGAAACTACAAAGCTCAGCTTACACGATTAAATCAT

AAGACTAATTGTAATGGAGCTGTTCTTAGTGTAGAAGAGCTTTTAATTGGTGGAGAAATGATTAAAGCCGGCACA

TTAACCTTAGAGGAAGTGAGACGGAAATTTAATAACGGCGAGATAAACTTTTAA

CCR5-224 (+) protein sequence (SEQ ID NO: 120):
MDYKDHDGDYKDHDIDYKDDDDKMAPKKKRKVGIHGVPAAMAERPFQCRICMRNFSDRSNLSRHIRTHTGEKPFA

CDICGRKFAISSNLNSHTKIHTGSQKPFQCRICMRNFSRSDNLARHIRTHTGEKPFACDICGRKFATSGNLTRHT

KIHLRGSQLVKSELEEKKSELRHKLKYVPHEYIELIEIARNSTQDRILEMKVMEFFMKVYGYRGKHLGGSRKPDG

AIYTVGSPIDYGVIVDTKAYSGGYNLPIGQADEMQRYVKENQTRNKHINPNEWWKVYPSSVTEFKFLFVSGHFKG

NYKAQLTRLNHKTNCNGAVLSVEELLIGGEMIKAGTLTLEEVRRKFNNGEINF

CCR5-224 (-) DNA sequence (SEQ ID NO: 121):
TAATACGACTCACTATAGGGAGACCCAAGCTGGCTAGCCACCATGGACTACAAAGACCATGACGGTGATTATAAA

GATCATGACATCGATTACAAGGATGACGATGACAAGATGGCCCCCAAGAAGAAGAGGAAGGTGGGCATTCACGGG
```

-continued

```
GTACCTGCCGCTATGGCTGAGAGGCCCTTCCAGTGTCGAATCTGCATGCGTAACTTCAGTCGCTCCGACAACCTG

TCCGTGCACATCCGCACCCACACAGGCGAGAAGCCTTTTGCCTGTGACATTTGTGGGAGGAAGTTTGCCCAGAAG

ATCAACCTGCAGGTGCATACCAAGATACACACCGGCGAGAAGCCCTTCCAGTGTCGAATCTGCATGCGTAACTTC

AGTCGCTCCGACGTGCTGTCCGAGCACATCCGCACCCACACAGGCGAGAAGCCTTTTGCCTGTGACATTTGTGGG

AGGAAATTTGCCCAGCGCAACCACCGCACCACCCATACCAAGATACACCTGCGGGGATCCCAACTAGTCAAAAGT

GAACTGGAGGAGAAGAAATCTGAACTTCGTCATAAATTGAAATATGTGCCTCATGAATATATTGAATTAATTGAA

ATTGCCAGAAATTCCACTCAGGATAGAATTCTTGAAATGAAGGTAATGGAATTTTTTATGAAAGTTTATGGATAT

AGAGGTAAACATTTGGGTGGATCAAGGAAACCGGACGGAGCAATTTATACTGTCGGATCTCCTATTGATTACGGT

GTGATCGTGGATACTAAAGCTTATAGCGGAGGTTATAATCTGCCAATTGGCCAAGCAGATGAAATGGAGCGATAT

GTCGAAGAAAATCAAACACGAAACAAACATCTCAACCCTAATGAATGGTGGAAAGTCTATCCATCTTCTGTAACG

GAATTTAAGTTTTTATTTGTGAGTGGTCACTTTAAAGGAAACTACAAAGCTCAGCTTACACGATTAAATCATATC

ACTAATTGTAATGGAGCTGTTCTTAGTGTAGAAGAGCTTTTAATTGGTGGAGAAATGATTAAAGCCGGCACATTA

ACCTTAGAGGAAGTGAGACGGAAATTTAATAACGGCGAGATAAACTTTTAA
```

CCR5-224 (-) protein sequence (SEQ ID NO: 122):
MDYKDHDGDYKDHDIDYKDDDDKMAPKKKRKVGIHGVPAAMAERPFQCRICMRNFSRSDNLSVHIR

THTGEKPFACDICGRKFAQKINLQVHTKIHTGEKPFQCRICMRNFSRSDVLSEHIRTHTGEKPFACDICG

RKFAQRNHRTTHTKIHLRGSQLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQADEMERYVEENQTRNKHL

NPNEWWKVYPSSVTEFKFLFVSGHFKGNYKAQLTRLNHITNCNGAVLSVEELLIGGEMIKAGTLTLEE

VRRKFNNGEINF

VF2468 (+) DNA sequence (SEQ ID NO: 123):
<u>TAATACGACTCACTATAGG</u>GAGACCCAAGCTGGCTAGCCACCATGGACTACAAAGACCATGACGG

```
TGATTATAAAGATCATGACATCGATTACAAGGATGACGATGACAAGATGGCCCCCAAGAAGAAGA

GGAAGGTGGGCATTCACGGGGTGCCGTCTAGACCCGGGGAGCGCCCCTTCCAGTGTCGCATTTGC

ATGCGGAACTTTTCGCGCCAGGACAGGCTTGACAGGCATACCCGTACTCATACCGGTGAAAAACC

GTTTCAGTGTCGGATCTGTATGCGAAATTTCTCCCAGAAGGAGCACTTGGCGGGCATCTACGTAC

GCACACCGGCGAGAAGCCATTCCAATGCCGAATATGCATGCGCAACTTCAGTCGCCGCGACAACC

TGAACCGGCACCTAAAAACCCACCTGAGGGGATCCCAACTAGTCAAAAGTGAACTGGAGGAGAA

GAAATCTGAACTTCGTCATAAATTGAAATATGTGCCTCATGAATATATTGAATTAATTGAAATTGC

CAGAAATTCCACTCAGGATAGAATTCTTGAAATGAAGGTAATGGAATTTTTTATGAAAGTTTATGG

ATATAGAGGTAAACATTTGGGTGGATCAAGGAAACCGGACGGAGCAATTTATACTGTCGGATCTC

CTATTGATTACGGTGTGATCGTGGATACTAAAGCTTATAGCGGAGGTTATAATCTGCCAATTGGCC

AAGCAGATGAAATGCAACGATATGTCAAAGAAAATCAAACACGAAACAAACATATCAACCCTAAT

GAATGGTGGAAAGTCTATCCATCTTCTGTAACGGAATTTAAGTTTTTATTTGTGAGTGGTCACTTTA

AAGGAAACTACAAAGCTCAGCTTACACGATTAAATCATAAGACTAATTGTAATGGAGCTGTTCTTA

GTGTAGAAGAGCTTTTAATTGGTGGAGAAATGATTAAAGCCGGCACATTAACCTTAGAGGAAGTG

AGACGGAAATTTAATAACGGCGAGATAAACTTTTAA
```

VF2468 (+) protein sequence (SEQ ID NO: 124):
MDYKDHDGDYKDHDIDYKDDDDKMAPKKKRKVGIHGVPSRPGERPFQCRICMRNFSRQDRLDRHTR

THTGEKPFQCRICMRNFSQKEHLAGHLRTHTGEKPFQCRICMRNFSRRDNLNRHLKTHLRGSQLVKSE

LEEKKSELRHKLKYVPHEYIELIEIARNSTQDRILEMKVMEFFMKVYGYRGKHLGGSRKPDGAIYTVGS

```
                                         -continued
PIDYGVIVDTKAYSGGYNLPIGQADEMQRYVKENQTRNKHINPNEWWKVYPSSVTEFKFLFVSGHFKG

NYKAQLTRLNHKTNCNGAVLSVEELLIGGEMIKAGTLTLEEVRRKFNNGEINF

VF2468 (-) DNA sequence (SEQ ID NO: 125):
TAATACGACTCACTATAGGGAGACCCAAGCTGGCTAGCCACCATGGACTACAAAGACCATGACGG

TGATTATAAAGATCATGACATCGATTACAAGGATGACGATGACAAGATGGCCCCCAAGAAGAAGA

GGAAGGTGGGCATTCACGGGGTGCCGTCTAGACCCGGGGAGCGCCCCTTCCAGTGTCGCATTTGC

ATGCGGAACTTTTCGACCGGCCAGATCCTTGACCGCCATACCCGTACTCATACCGGTGAAAAACCG

TTTCAGTGTCGGATCTGTATGCGAAATTTCTCCGTGGCGCACAGCTTGAAGAGGCATCTACGTACG

CACACCGGCGAGAAGCCATTCCAATGCCGAATATGCATGCGCAACTTCAGTGACCCCAGCAACCT

GCGGCGCCACCTAAAAACCCACCTGAGGGGATCCCAACTAGTCAAAAGTGAACTGGAGGAGAAG

AAATCTGAACTTCGTCATAAATTGAAATATGTGCCTCATGAATATATTGAATTAATTGAAATTGCC

AGAAATTCCACTCAGGATAGAATTCTTGAAATGAAGGTAATGGAATTTTTTATGAAAGTTTATGGA

TATAGAGGTAAACATTTGGGTGGATCAAGGAAACCGGACGGAGCAATTTATACTGTCGGATCTCC

TATTGATTACGGTGTGATCGTGGATACTAAAGCTTATAGCGGAGGTTATAATCTGCCAATTGGCCA

AGCAGATGAAATGGAGCGATATGTCGAAGAAAATCAAACACGAAACAAACATCTCAACCCTAATG

AATGGTGGAAAGTCTATCCATCTTCTGTAACGGAATTTAAGTTTTTATTTGTGAGTGGTCACTTTAA

AGGAAACTACAAAGCTCAGCTTACACGATTAAATCATATCACTAATTGTAATGGAGCTGTTCTTAG

TGTAGAAGAGCTTTTAATTGGTGGAGAAATGATTAAAGCCGGCACATTAACCTTAGAGGAAGTGA

GACGGAAATTTAATAACGGCGAGATAAACTTTTAA

VF2468 (-) protein sequence (SEQ ID NO: 126):
MDYKDHDGDYKDHDIDYKDDDDKMAPKKKRKVGIHGVPSRPGERPFQCRICMRNFSTGQILDRHTRT

HTGEKPFQCRICMRNFSVAHSLKRHLRTHTGEKPFQCRICMRNFSDPSNLRRHLKTHLRGSQLVKSELE

EKKSELRHKLKYVPHEYIELIEIARNSTQDRILEMKVMEFFMKVYGYRGKHLGGSRKPDGAIYTVGSPI

DYGVIVDTKAYSGGYNLPIGQADEMERYVEENQTRNKHLNPNEWWKVYPSSVTEFKFLFVSGHFKGN

YKAQLTRLNHITNCNGAVLSVEELLIGGEMIKAGTLTLEEVRRKFNNGEINF
```

Library Construction. Libraries of target sites were incorporated into double-stranded DNA by PCR with Taq DNA Polymerase (NEB) on a pUC19 starting template with primers "N5-PvuI" and "CCR5-224-N4," "CCR5-224-N5," "CCR5-224-N6," "CCR5-224-N7," "VF2468-N4," "VF2468-N5," "VF2468-N6," or "VF2468-N7," yielding an approximately 545-bp product with a PvuI restriction site adjacent to the library sequence, and purified with the Qiagen PCR Purification Kit.

Library-encoding oligonucleotides were of the form 5' backbone-PvuI site-NNNNNN-partially randomized half-site-$N_{4-7}$-partially randomized half site-N-backbone 3'. The purified oligonucleotide mixture (approximately 10 μg) was blunted and phosphorylated with a mixture of 50 units of T4 Polynucleotide Kinase and 15 units of T4 DNA polymerase (NEBNext End Repair Enzyme Mix, NEB) in 1×NEBNext End Repair Reaction Buffer (50 mM Tris-HCl, 10 mM $MgCl_2$, 10 mM dithiothreitol, 1 mM ATP, 0.4 mM dATP, 0.4 mM dCTP, 0.4 mM dGTP, 0.4 mM dTTP, pH 7.5) for 1.5 hours at room temperature. The blunt-ended and phosphorylated DNA was purified with the Qiagen PCR Purification Kit according to the manufacturer's protocol, diluted to 10 ng/μL in NEB T4 DNA Ligase Buffer (50 mM Tris-HCl, 10 mM $MgCl_2$, 10 mM dithiothreitol, 1 mM ATP, pH 7.5) and circularized by ligation with 200 units of T4 DNA ligase (NEB) for 15.5 hours at room temperature. Circular monomers were gel purified on 1% TAE-Agarose gels. 70 ng of circular monomer was used as a substrate for rolling-circle amplification at 30° C. for 20 hours in a 100 μL reaction using the Illustra TempliPhi 100 Amplification Kit (GE Healthcare). Reactions were stopped by incubation at 65° C. for 10 minutes. Target site libraries were quantified with the Quant-iT PicoGreen dsDNA Reagent (Invitrogen). Libraries with $N_4$, $N_5$, $N_6$, and $N_7$ spacer sequences between partially randomized half-sites were pooled in equimolar concentrations for both CCR5-224 and VF2468.

Zinc Finger Nuclease Expression and Characterization. 3×FLAG-tagged zinc finger proteins for CCR5-224 and VF2468 were expressed as fusions to FokI obligate heterodimers[30] in mammalian expression vectors[4] derived from pMLM290 and pMLM292. DNA and protein sequences are provided elsewhere herein. Complete vector sequences are available upon request. 2 μg of ZFN-encoding vector was transcribed and translated in vitro using the TNT Quick Coupled rabbit reticulocyte system (Promega). Zinc chloride (Sigma-Aldrich) was added at 500 μM and the transcription/translation reaction was performed for 2 hours at 30° C. Glycerol was added to a 50% final concentration. Western blots were used to visualize protein using the anti-FLAG M2 monoclonal antibody (Sigma-Aldrich). ZFN concentrations were determined by Western blot and comparison with a standard curve of N-terminal FLAG-tagged bacterial alkaline phosphatase (Sigma-Aldrich).

Test substrates for CCR5-224 and VF2468 were constructed by cloning into the HindIII/XbaI sites of pUC19. PCR with primers "test fwd" and "test rev" and Taq DNA polymerase yielded a linear 1 kb DNA that could be cleaved by the appropriate ZFN into two fragments of sizes ~300 bp and ~700 bp. Activity profiles for the zinc finger nucleases were obtained by modifying the in vitro cleavage protocols used by Miller et al.[30] and Cradick et al.[31]. 1 μg of linear 1 kb DNA was digested with varying amounts of ZFN in 1×NEBuffer 4 (50 mM potassium acetate, 20 mM Tris-acetate, 10 mM magnesium acetate, 1 mM dithiothreitol, pH 7.9) for 4 hours at 37° C. 100 μg of RNase A (Qiagen) was added to the reaction for 10 minutes at room temperature to remove RNA from the in vitro transcription/translation mixture that could interfere with purification and gel analysis. Reactions were purified with the Qiagen PCR Purification Kit and analyzed on 1% TAE-agarose gels.

In Vitro Selection. ZFNs of varying concentrations, an amount of TNT reaction mixture without any protein-encoding DNA template equivalent to the greatest amount of ZFN used ("lysate"), or 50 units PvuI (NEB) were incubated with 1 μg of rolling-circle amplified library for 4 hours at 37° C. in 1×NEBuffer 4 (50 mM potassium acetate, 20 mM Tris-acetate, 10 mM magnesium acetate, 1 mM dithiothreitol, pH 7.9). 100 μg of RNase A (Qiagen) was added to the reaction for 10 minutes at room temperature to remove RNA from the in vitro transcription/translation mixture that could interfere with purification and gel analysis. Reactions were purified with the Qiagen PCR Purification Kit. 1/10 of the reaction mixture was visualized by gel electrophoresis on a 1% TAE-agarose gel and staining with SYBR Gold Nucleic Acid Gel Stain (Invitrogen).

The purified DNA was blunted with 5 units DNA Polymerase I, Large (Klenow) Fragment (NEB) in 1×NEBuffer 2 (50 mM NaCl, 10 mM Tris-HCl, 10 mM MgCl$_2$, 1 mM dithiothreitol, pH 7.9) with 500 μM dNTP mix (Bio-Rad) for 30 minutes at room temperature. The reaction mixture was purified with the Qiagen PCR Purification Kit and incubated with 5 units of Klenow Fragment (3' exo⁻) (NEB) for 30 minutes at 37° C. in 1×NEBuffer 2 (50 mM NaCl, 10 mM Tris-HCl, 10 mM MgCl$_2$, 1 mM dithiothreitol, pH 7.9) with 240 μM dATP (Promega) in a 50 μL final volume. 10 mM Tris-HCl, pH 8.5 was added to a volume of 90 μL and the reaction was incubated for 20 minutes at 75° C. to inactivate the enzyme before cooling to 12° C. 300 fmol of "adapter1/2", barcoded according to enzyme concentration, or 6 pmol of "adapter1/2" for the PvuI digest, were added to the reaction mixture, along with 10 ul 10×NEB T4 DNA Ligase Reaction Buffer (500 mM Tris-HCl, 100 mM MgCl$_2$, 100 mM dithiothreitol, 10 mM ATP). Adapters were ligated onto the blunt DNA ends with 400 units of T4 DNA ligase at room temperature for 17.5 hours and ligated DNA was purified away from unligated adapters with Illustra Microspin S-400 HR sephacryl columns (GE Healthcare). DNA with ligated adapters were amplified by PCR with 2 units of Phusion Hot Start II DNA Polymerase (NEB) and 10 pmol each of primers "PE1" and "PE2" in 1× Phusion GC Buffer supplemented with 3% DMSO and 1.7 mM MgCl$_2$. PCR conditions were 98° C. for 3 min, followed by cycles of 98° C. for 15 s, 60° C. for 15 s, and 72° C. for 15 s, and a final 5 min extension at 72° C. The PCR was run for enough cycles (typically 20-30) to see a visible product on gel. The reactions were pooled in equimolar amounts and purified with the Qiagen PCR Purification Kit. The purified DNA was gel purified on a 1% TAE-agarose gel, and submitted to the Harvard Medical School Biopolymers Facility for Illumina 36-base paired-end sequencing.

Data Analysis. Illumina sequencing reads were analyzed using programs written in C++. Algorithms are described elsewhere herein (e.g., Protocols 1-9), and the source code is available on request. Sequences containing the same barcode on both paired sequences and no positions with a quality score of 'B' were binned by barcode. Half-site sequence, overhang and spacer sequences, and adjacent randomized positions were determined by positional relationship to constant sequences and searching for sequences similar to the designed CCR5-224 and VF2468 recognition sequences. These sequences were subjected to a computational selection step for complementary, filled-in overhang ends of at least 4 base pairs, corresponding to rolling-circle concatemers that had been cleaved at two adjacent and identical sites. Specificity scores were calculated with the formulae: positive specificity score=(frequency of base pair at position[post-selection]−frequency of base pair at position[pre-selection])/(1−frequency of base pair at position[pre-selection]) and negative specificity score=(frequency of base pair at position[post-selection]−frequency of base pair at position[pre-selection])/(frequency of base pair at position[pre-selection]).

Positive specificity scores reflect base pairs that appear with greater frequency in the post-selection library than in the starting library at a given position; negative specificity scores reflect base pairs that are less frequent in the post-selection library than in the starting library at a given position. A score of +1 indicates an absolute preference, a score of −1 indicates an absolute intolerance, and a score of 0 indicates no preference.

Assay of Genome Modification at Cleavage Sites in Human Cells. CCR5-224 ZFNs were cloned into a CMV-driven mammalian expression vector in which both ZFN monomers were translated from the same mRNA transcript in stoichiometric quantities using a self-cleaving T2A peptide sequence similar to a previously described vector[32]. This vector also expresses enhanced green fluorescent protein (eGFP) from a PGK promoter downstream of the ZFN expression cassette. An empty vector expressing only eGFP was used as a negative control.

To deliver ZFN expression plasmids into cells, 15 μg of either active CCR5-224 ZFN DNA or empty vector DNA were used to Nucleofect 2×10⁶ K562 cells in duplicate reactions following the manufacturer's instructions for Cell Line Nucleofector Kit V (Lonza). GFP-positive cells were isolated by FACS 24 hours post-transfection, expanded, and harvested five days post-transfection with the QIAamp DNA Blood Mini Kit (Qiagen).

PCR for 37 potential CCR5-224 substrates and 97 potential VF2468 substrates was performed with Phusion DNA Polymerase (NEB) and primers "[ZFN] [#] fwd" and "[ZFN] [#] rev" (Table 9) in 1× Phusion HF Buffer supplemented with 3% DMSO. Primers were designed using Primer3[33]. The amplified DNA was purified with the Qiagen PCR Purification Kit, eluted with 10 mM Tris-HCl, pH 8.5, and quantified by 1K Chip on a LabChip GX instrument (Caliper Life Sciences) and combined into separate equimolar pools for the catalytically active and empty vector control samples. PCR products were not obtained for 3 CCR5 sites and 7 VF2468 sites, which excluded these samples from further analysis. Multiplexed Illumina library preparation was performed according to the manufacturer's specifications, except that AMPure XP beads (Agencourt) were used for purification following adapter ligation and PCR enrichment steps. Illumina indices 11 ("GGCTAC") and 12 ("CTTGTA") were used for ZFN-treated libraries while indices 4 ("TGACCA") and 6 ("GCCAAT") were used for the empty vector controls. Library concentrations were quantified by KAPA Library Quantification Kit for Illumina Genome Analyzer Platform (Kapa Biosystems). Equal amounts of the barcoded libraries derived from active- and empty vector-treated cells were diluted to 10 nM and subjected to single read sequencing on an Illumina HiSeq 2000 at the Harvard University FAS Center for Systems Biology Core facility. Sequences were analyzed using Protocol 9 for active ZFN samples and empty vector controls.

Statistical Analysis. In FIG. 8, P-values were calculated for a one-sided test of the difference in the means of the number of target site mutations in all possible pairwise comparisons among pre-selection, 0.5 nM post-selection, 1 nM post-selection, 2 nM post-selection, and 4 nM post-selection libraries for CCR5-224 or VF2468. The t-statistic was calculated as $t=(x\_bar_1-x\_bar_2)/sqrt(1 \times p\_hat_1 \times (1-p\_hat_1)/n_1 + 1 \times p\_hat_2 \times (1-p\_hat_2)/n_2)$, where $x\_bar_1$ and $x\_bar_2$ are the means of the distributions being compared, 1 is the target site length (24 for CCR5-224; 18 for VF2468), $p\_hat_1$ and $p\_hat_2$ are the calculated probabilities of mutation ($x\_bar/1$) for each library, and $n_1$ and $n_2$ are the total number of sequences analyzed for each selection (Table 2). All pre- and post-selection libraries were assumed to be binomially distributed.

In Tables 4 and 7, P-values were calculated for a one-sided test of the difference in the proportions of sequences with insertions or deletions from the active ZFN sample and the empty vector control samples. The t-statistic was calculated as $t=(p\_hat_1-p\_hat_2)/sqrt((p\_hat_1 \times (1-p\_hat_1)/n_1)+(p\_hat_2 \times (1-p\_hat_2)/n_2))$, where $p\_hat_1$ and $n_1$ are the proportion and total number, respectively, of sequences from the active sample and $p\_hat_2$ and $n_2$ are the proportion and total number, respectively, of sequences from the empty vector control sample.

Plots. All heat maps were generated in the R software package with the following command: image([variable], zlim=c(−1,1), col=colorRampPalette(c("red","white", "blue"),space="Lab")(2500)

Protocol 1: Quality Score Filtering and Sequence Binning.
1) search each position of both pairs of sequencing read for quality score, reject if any position has quality score='B'
2) output to separate files all sequence reads where the first sequence in the pair start with barcodes ("AAT", "ATA", "TAA", "CAC","TCG") and count the number of sequences corresponding to each barcode Protocol 2: Filtering by ZFN ("AAT","ATA","TAA", "CAC")
For each binned file,
1) accept only sequence pairs where both sequences in the pair start with the same barcode
2) identify orientation of sequence read by searching for constant regions
   orientation 1 is identified by the constant region "CGATCGTTGG" (SEQ ID NO:127)
   orientation 2 is identified by the constant region "CAGTGAACG" (SEQ ID NO:128)
3) search sequences from position 4 (after the barcode) up to the first position in the constant region for the subsequence that has the fewest mutations compared to the CCR5-224 and VF2468 half site that corresponds to the identified constant region
   search sequences with orientation 1 for "GATGAGGATGAC" (SEQ ID NO:129) (CCR5-224(+)) and "GACGCTGCT" (SEQ ID NO:130) (VF2468(−))
   search sequences with orientation 2 for "AAACTGCAAAAG" (SEQ ID NO:131) (CCR5-224(−)) and "GAGTGAGGA" (SEQ ID NO:132) (VF2468(+))
4) bin sequences as CCR5-224 or VF2468 by testing for the fewest mutations across both half-sites
5) the positions of the half-sites and constant sequences are used to determine the overhang/spacer sequences, the flanking nucleotide sequences, and the tag sequences
   the subsequence between the half-site of orientation 1 and the constant region is the tag sequence
o if there is no tag sequence, the tag sequence is denoted by 'X'
   the overhang sequence is determined by searching for the longest reverse-complementary subsequences between the subsequences of orientation 1 and orientation 2 that start after the barcodes
   the spacer sequence is determined by concatenating the reverse complement of the subsequence in orientation 1 that is between the overhang and the half-site (if any), the overhang, and the subsequence in orientation 2 that is between the overhang and the halfsite
o if there is overlap between the overhang and half-site, only the non-overlapping subsequence present in the overhang is counted as part of the spacer
6) to remove duplicate sequences, sort each sequence pair into a tree
   each level of the tree corresponds to a position in the sequence
   each node at each level corresponds to a particular base (A, C, G, T, or X=not(A, C, G, or T)) and points to the base of the next position (A,C,G,T,X)
   the sequence pairs are encoded in the nodes and a subsequence consisting of the concatenation of the spacer sequence, flanking nucleotide sequence, and tag sequence is sorted in the tree
   at the terminal nodes of the tree, each newly entered sequence is compared to all other sequences in the node to avoid duplication
7) the contents of the tree are recursively outputted into separate files based on barcode and ZFN Protocol 3: Library Filtering ("TCG")
1) accept only sequence pairs where both sequences in the pair start with the same barcode
2) analyze the sequence pair that does not contain the sequence "TCGTTGGGAACCGGAGCTGAATGAAGCCATACCAAACGAC" (SEQ ID NO:133) (the other pair contains the library sequence)
3) search sequences for ZFN half-sites and bin by the ZFN site that has fewer mutations
   search for "GTCATCCTCATC" (SEQ ID NO:134) and "AAACTGCAAAAG" (SEQ ID NO:135) (CCR5-224) and "AGCAGCGTC" (SEQ ID NO:136) and "GAGTGAGGA" (SEQ ID NO:137) (VF2468)
4) identify the spacer, flanking nucleotide, and nucleotide tag sequences based on the locations of the half-sites
5) use the tree algorithm in step 6 under Filtering by ZFN to eliminate duplicate sequences Protocol 4: Sequence Profiles
1) analyze only sequences that contain no 'N' positions and have spacer lengths between 4 and 7
2) tabulate the total number of mutations, the spacer length, the overhang length, the nucleotide frequencies for the (+) and (−) half-sites, the nucleotide frequencies for spacers that are 4-bp, 5-bp, 6-bp, and 7-bp long, and the nucleotide frequencies for the flanking nucleotide and the tag sequence
3) repeat steps 1 and 2 for library sequences
4) calculate specificity scores at each position using positive specificity score=(frequency of base pair at position[post-selection]−frequency of base pair at position[pre-selection])/(1−frequency of base pair at position[pre-selection]) negative specificity score=(frequency of base pair at position[post-selection]−frequency of base pair at position [pre-selection])/(frequency of base pair at position[pre-selection])

Protocol 5: Genomic Matches
1) the human genome sequence was searched with 24 and 25 base windows (CCR5-224) and 18 and 19 base windows (VF2468) for all sites within nine mutations (CCR5-224) or six mutations (VF2468) of the canonical target site with all spacer sequences of five or six bases being accepted
2) each post-selection sequence was compared to the set of genomic sequences within nine and six mutations of CCR5-224 and VF2468, respectively Protocol 6: Enrichment Factors for Sequences with 0, 1, 2, or 3 Mutations
1) for each sequence, divide the frequency of occurrence in the post-selection library by the frequency of occurrence in the pre-selection library Protocol 7: Filtered Sequence Profiles
1) use the algorithm described above in Sequence profiles, except in addition, only analyze sequences with off-target bases at given positions for both pre- and post-selection data Protocol 8: Compensation Difference Map
1) use Filtered sequence profiles algorithm for mutation at every position in both half-sites
2) calculate Δ(specificity score)=filtered specificity score−non-filtered specificity score Protocol 9: NHEJ Search
1) identify the site by searching for exact flanking sequences
2) count the number of inserted or deleted bases by comparing the length of the calculated site to the length of the expected site and by searching for similarity to the unmodified target site (sequences with 5 or fewer mutations compared to the intended site were counted as unmodified)
3) inspect all sites other than CCR5, CCR2, and VEGF-A promoter by hand to identify true insertions or deletions References
1. Kim, Y. G., Cha, J. & Chandrasegaran, S. Hybrid restriction enzymes: zinc finger fusions to Fok I cleavage domain. Proc Natl Acad Sci USA 93, 1156-60 (1996).
2. Vanamee, E. S., Santagata, S. & Aggarwal, A. K. FokI requires two specific DNA sites for cleavage. J Mol Biol 309, 69-78 (2001).
3. Hockemeyer, D. et al. Efficient targeting of expressed and silent genes in human ESCs and iPSCs using zinc-finger nucleases. Nat Biotechnol 27, 851-7 (2009).
4. Maeder, M. L. et al. Rapid "open-source" engineering of customized zinc-finger nucleases for highly efficient gene modification. Mol Cell 31, 294-301 (2008).
5. Zou, J. et al. Gene targeting of a disease-related gene in human induced pluripotent stem and embryonic stem cells. Cell Stem Cell 5, 97-110 (2009).
6. Perez, E. E. et al. Establishment of HIV-1 resistance in CD4+ T cells by genome editing using zinc-finger nucleases. Nat Biotechnol 26, 808-16 (2008).
7. Urnov, F. D. et al. Highly efficient endogenous human gene correction using designed zinc-finger nucleases. Nature 435, 646-51 (2005).
8. Santiago, Y. et al. Targeted gene knockout in mammalian cells by using engineered zinc-finger nucleases. Proc Natl Acad Sci USA 105, 5809-14 (2008).
9. Cui, X. et al. Targeted integration in rat and mouse embryos with zinc-finger nucleases. Nat Biotechnol 29, 64-7 (2011).
10. Cornu, T. I. et al. DNA-binding specificity is a major determinant of the activity and toxicity of zinc-finger nucleases. Mol Ther 16, 352-8 (2008).
11. Segal, D. J., Dreier, B., Beerli, R. R. & Barbas, C. F., 3rd. Toward controlling gene expression at will: selection and design of zinc finger domains recognizing each of the 5'-GNN-3' DNA target sequences. Proc Natl Acad Sci USA 96, 2758-63 (1999).
12. Bulyk, M. L., Huang, X., Choo, Y. & Church, G. M. Exploring the DNA-binding specificities of zinc fingers with DNA microarrays. Proc Natl Acad Sci USA 98, 7158-63 (2001).
13. Meng, X., Thibodeau-Beganny, S., Jiang, T., Joung, J. K. & Wolfe, S. A. Profiling the DNA-binding specificities of engineered Cys2His2 zinc finger domains using a rapid cell-based method. Nucleic Acids Res 35, e81 (2007).
14. Wolfe, S. A., Greisman, H. A., Ramm, E. I. & Pabo, C. O. Analysis of zinc fingers optimized via phage display: evaluating the utility of a recognition code. J Mol Biol 285, 1917-34 (1999).
15. Segal, D. J. et al. Evaluation of a modular strategy for the construction of novel polydactyl zinc finger DNA-binding proteins. Biochemistry 42, 2137-48 (2003).
16. Zykovich, A., Korf, I. & Segal, D. J. Bind-n-Seq: high-throughput analysis of in vitro protein-DNA interactions using massively parallel sequencing. Nucleic Acids Res 37, e151 (2009).
17. Yanover, C. & Bradley, P. Extensive protein and DNA backbone sampling improves structure-based specificity prediction for C2H2 zinc fingers. Nucleic Acids Res (2011).
18. Beumer, K., Bhattacharyya, G., Bibikova, M., Trautman, J. K. & Carroll, D. Efficient gene targeting in Drosophila with zinc-finger nucleases. Genetics 172, 2391-403 (2006).
19. Bibikova, M., Golic, M., Golic, K. G. & Carroll, D. Targeted chromosomal cleavage and mutagenesis in Drosophila using zinc-finger nucleases. Genetics 161, 1169-75 (2002).
20. Gupta, A., Meng, X., Zhu, L. J., Lawson, N. D. & Wolfe, S. A. Zinc finger protein-dependent and -independent contributions to the in vivo off-target activity of zinc finger nucleases. Nucleic Acids Res 39, 381-92 (2011).
21. Chen, J. et al. Molecular cloning and characterization of a novel human BTB domain-containing gene, BTBD10, which is down-regulated in glioma. Gene 340, 61-9 (2004).
22. Wang, X. et al. Glucose metabolism-related protein 1 (GMRP1) regulates pancreatic beta cell proliferation and apoptosis via activation of Akt signalling pathway in rats and mice. Diabetologia 54, 852-63 (2011).
23. Nawa, M., Kanekura, K., Hashimoto, Y., Aiso, S. & Matsuoka, M. A novel Akt/PKB-interacting protein promotes cell adhesion and inhibits familial amyotrophic lateral sclerosis-linked mutant SOD1-induced neuronal death via inhibition of PP2A-mediated dephosphorylation of Akt/PKB. Cell Signal 20, 493-505 (2008).
24. Petek, L. M., Russell, D. W. & Miller, D. G. Frequent endonuclease cleavage at off-target locations in vivo. Mol Ther 18, 983-6 (2010).
25. Hurt, J. A., Thibodeau, S. A., Hirsh, A. S., Pabo, C. O. & Joung, J. K. Highly specific zinc finger proteins obtained by directed domain shuffling and cell-based selection. Proc Natl Acad Sci USA 100, 12271-6 (2003).
26. Ramirez, C. L. et al. Unexpected failure rates for modular assembly of engineered zinc fingers. Nat Methods 5, 374-5 (2008).
27. Shimizu, Y. et al. Adding Fingers to an Engineered Zinc Finger Nuclease Can Reduce Activity. Biochemistry 50, 5033-41 (2011).

28. Bibikova, M. et al. Stimulation of homologous recombination through targeted cleavage by chimeric nucleases. Mol Cell Biol 21, 289-97 (2001).
29. Handel, E. M., Alwin, S. & Cathomen, T. Expanding or restricting the target site repertoire of zinc-finger nucleases: the inter-domain linker as a major determinant of target site selectivity. Mol Ther 17, 104-11 (2009).
30. Miller, J. C. et al. An improved zinc-finger nuclease architecture for highly specific genome editing. Nat Biotechnol 25, 778-85 (2007).
31. Cradick, T. J., Keck, K., Bradshaw, S., Jamieson, A. C. & McCaffrey, A. P. Zinc-finger nucleases as a novel therapeutic strategy for targeting hepatitis B virus DNAs. Mol Ther 18, 947-54 (2010).
32. Doyon, Y. et al. Heritable targeted gene disruption in zebrafish using designed zinc-finger nucleases. Nat Biotechnol 26, 702-8 (2008).
33. Rozen, S. & Skaletsky, H. Primer3 on the WWW for general users and for biologist programmers. Methods Mol Biol 132, 365-86 (2000).

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

Example 2

TALENs

The site preferences of different TALENs were profiled in analogy to the work done for ZFN profiling described above. The experiments and results are described in FIGS. 19-49. Selection 1 included a comparison between TALENs having a +28 vs. a +63 linker. Selection 2 included a comparison of TALENs of different TAL domain length.

Figure 19:
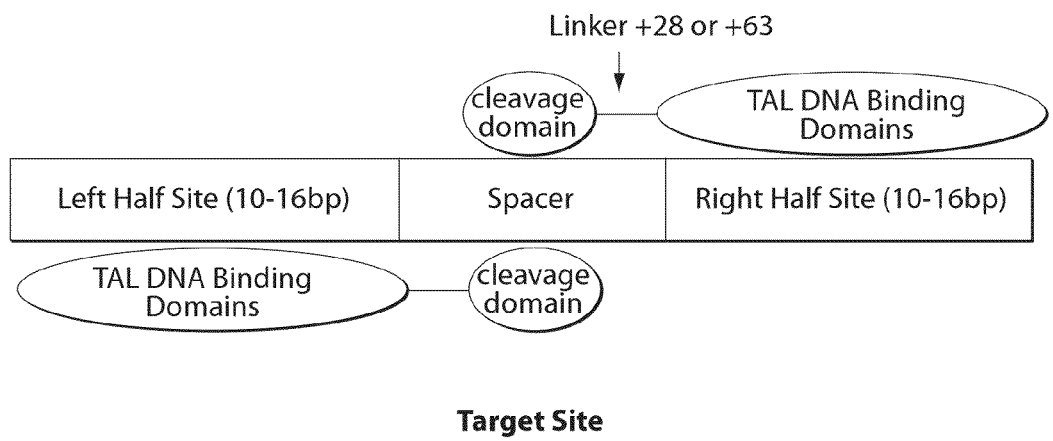
FIG. 19. Profiling The Specificity of TAL Nucleases. Selection 1: +28 vs. +63 aa Linker Between TAL DNA Binding Domain and FokI Cleavage Domain (SEQ ID NOs:42-45).
Figure 20:
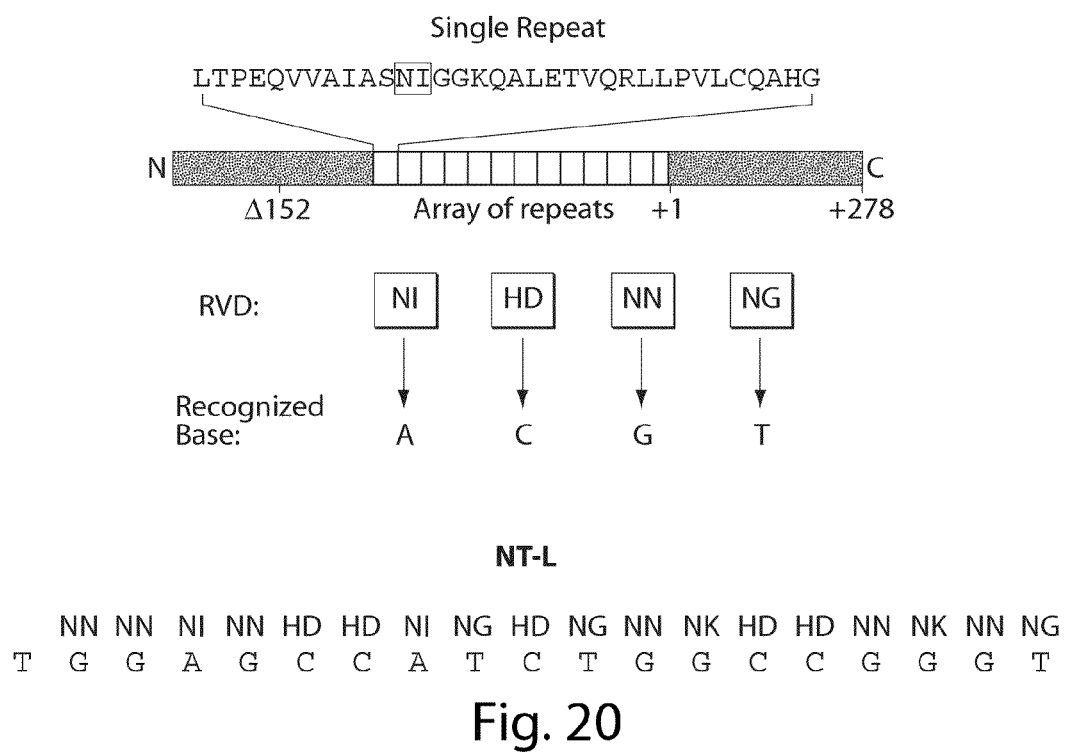
FIG. 20. Structure of TAL DNA binding domain and RVDs (SEQ ID NOs:46 and 47).
Figure 21:
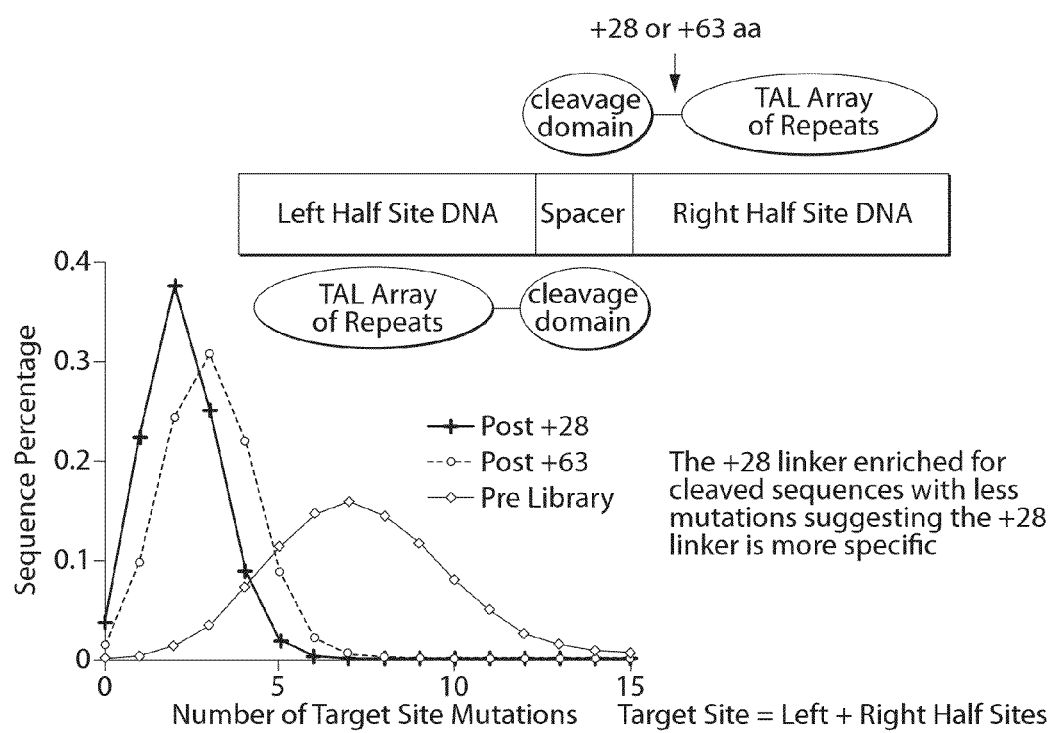
FIG. 21. Mutations in target sites from TALN selection. The +28 linker enriched for cleaved sequences with less mutations suggesting the +28 linker is more specific. There are significantly less mutations in the post-selected sequences compared to the pre-selection library sequences indicating a successful selection FIG. 22. Enrichment of Mutations in Total Target Site Between Left and Right Half Sites of Previous TALN Selection. The relatively regular (log relationship) trend between number of half sites mutations and enrichment is consistent with a single repeat binding a base pair independent of other repeat binding.
Figure 22:
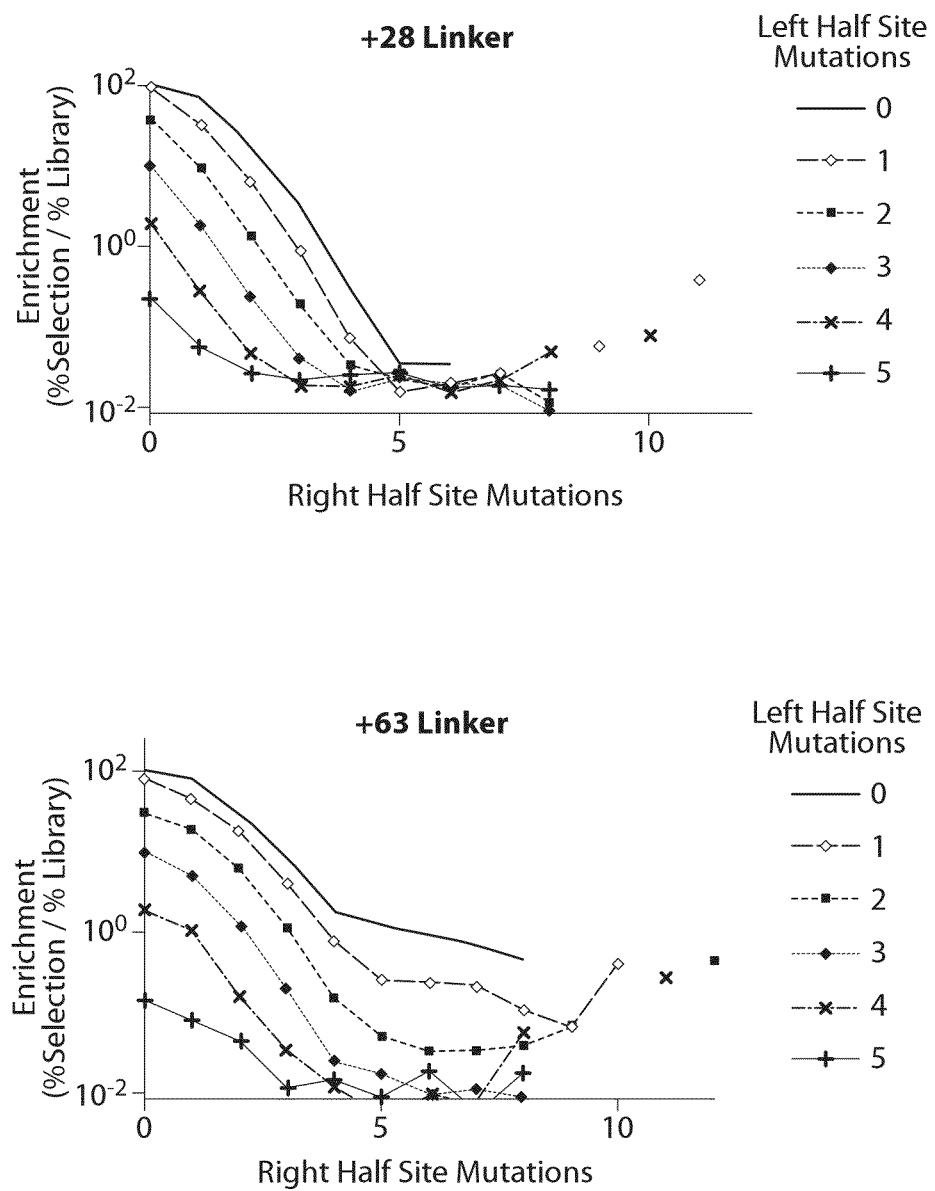
Figure 23:
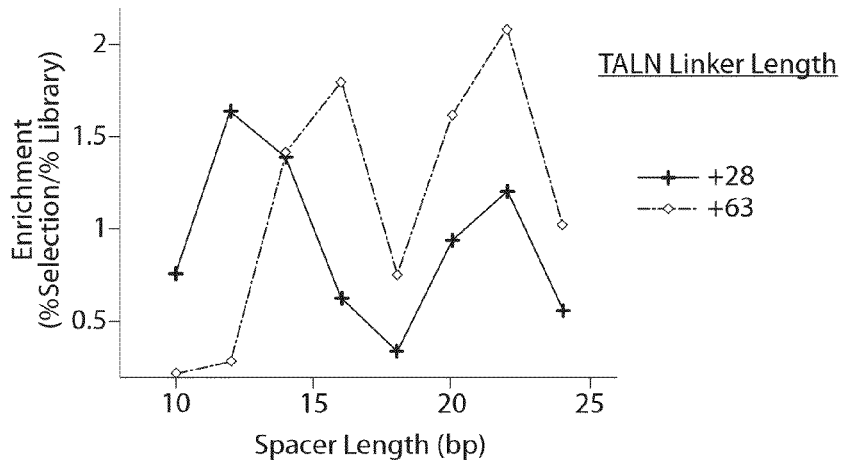
FIG. 23. TALN Cleavage Dependence on DNA Spacer Length. There is a similar preference for cut site spacer lengths in our in vitro selection compared to previous studies. In vitro, TALN cleavage. Dependence on Linker Length & Spacer Length from Mussolino (2011).
Figure 23:
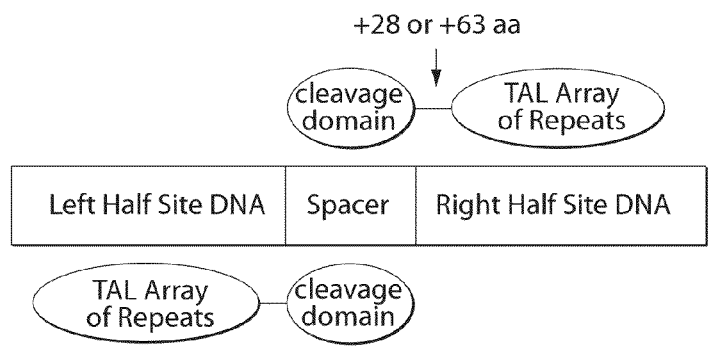
Figure 23:
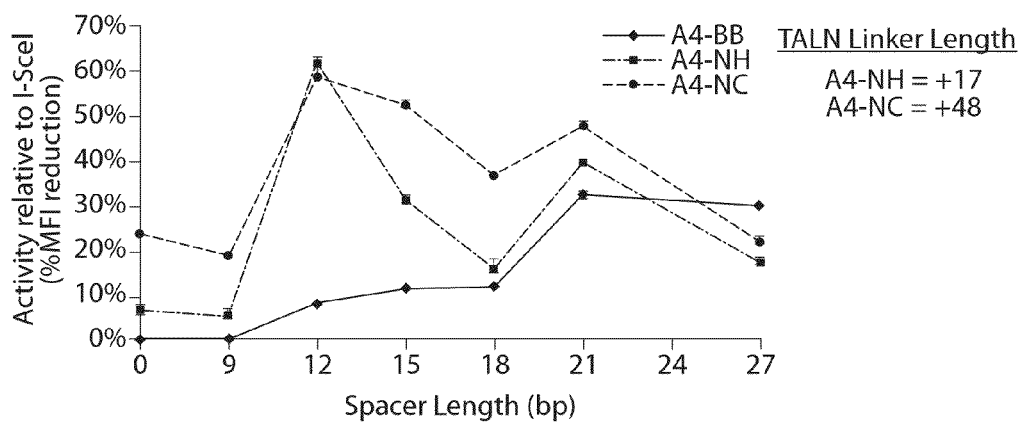
Figure 24:
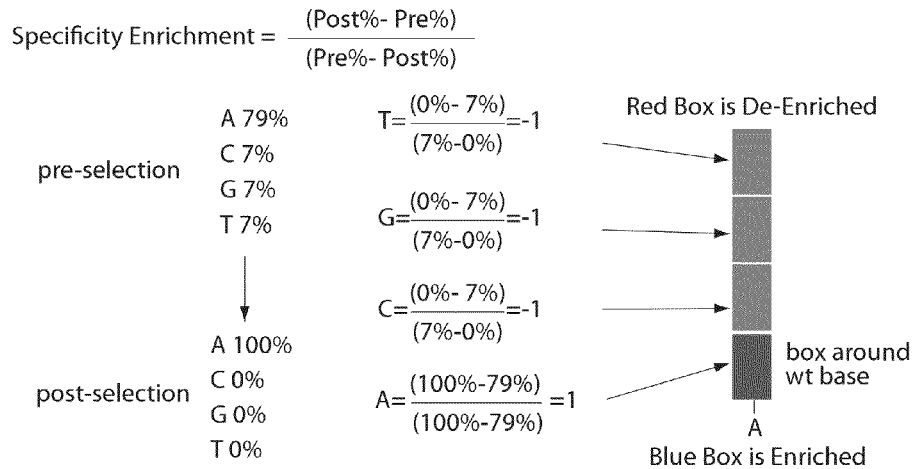
FIG. 24. Specificity score at individual bases.
Figure 25:
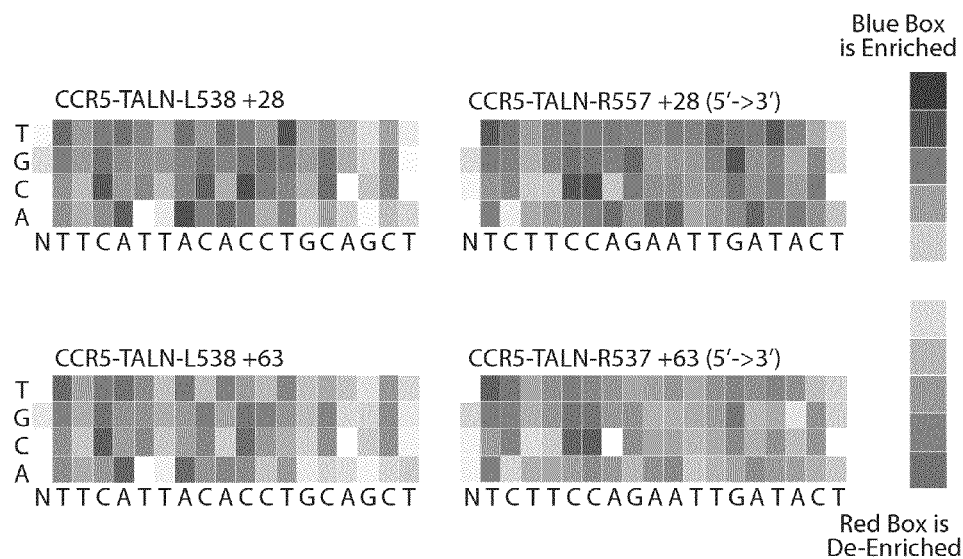
FIG. 25. Specificity score at individual bases. There is variable specificity at each individual position again with +28 linker demonstrating significantly better specificity (SEQ ID NOs:48 and 49).
Figure 26:
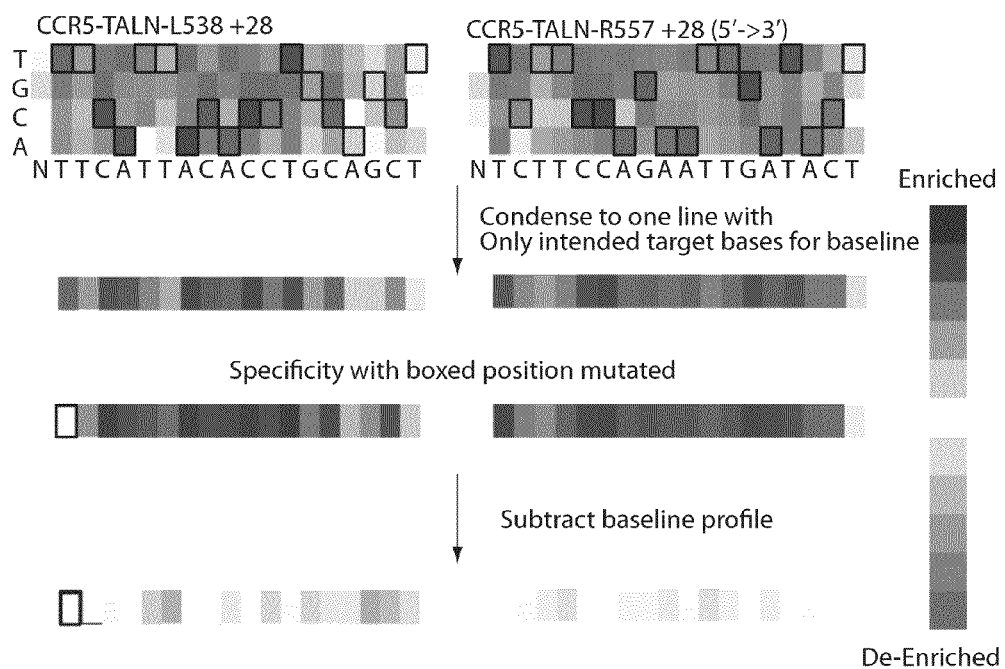
FIG. 26. Compensating Difference in Specificity of TALNs Analysis (SEQ ID NOs:50-51).
Figure 27:
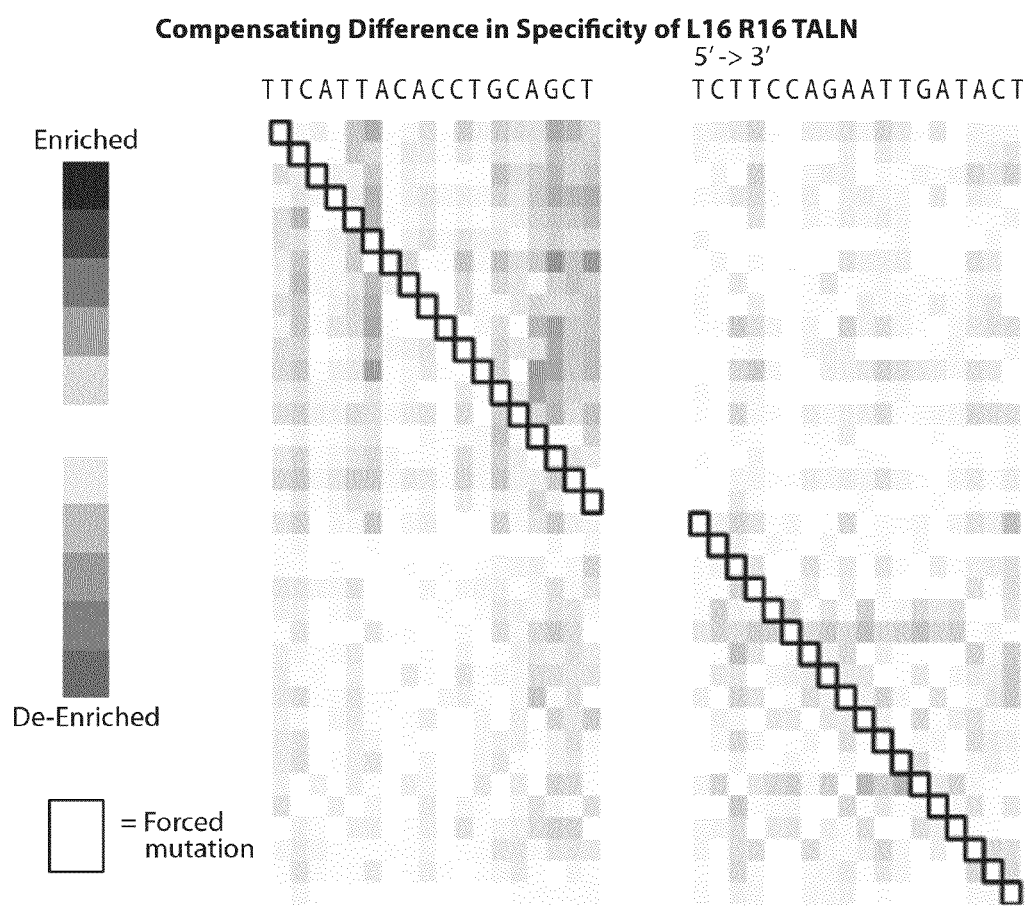
FIG. 27. Compensating Difference in Specificity of L16 R16 TALN. A single mutation in the cleavage site does not alter the distribution of other mutations suggesting that the TAL repeat domains bind independently (SEQ ID NOs:52-53).
Figure 28:
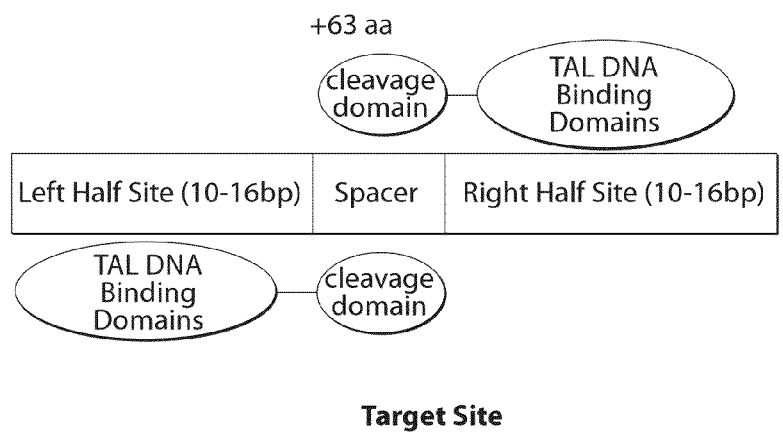
FIG. 28. Profiling the Specificity of TALNs Selection II: Varying TALN Lengths (SEQ ID NOs:54-61).
Figure 29:
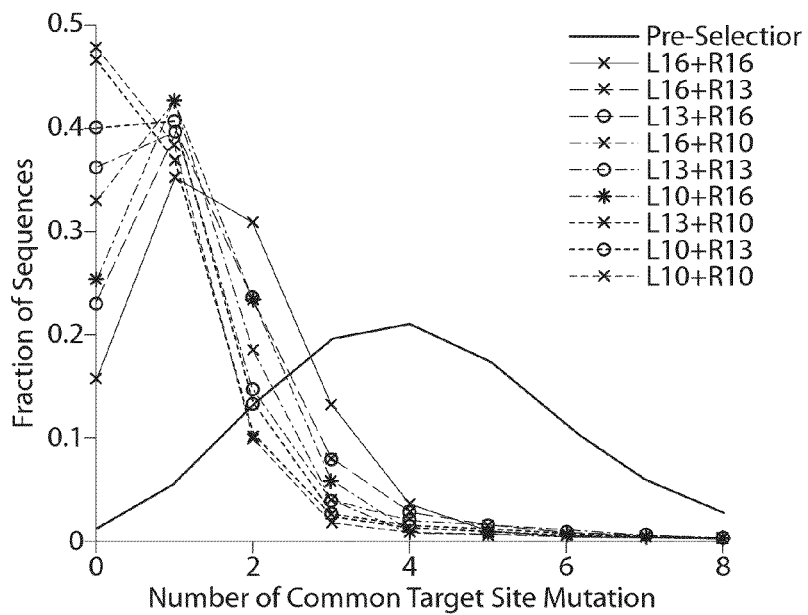
FIG. 29. Enrichment of Mutations in Common Target Site (SEQ ID NOs:62-69).
Figure 30:
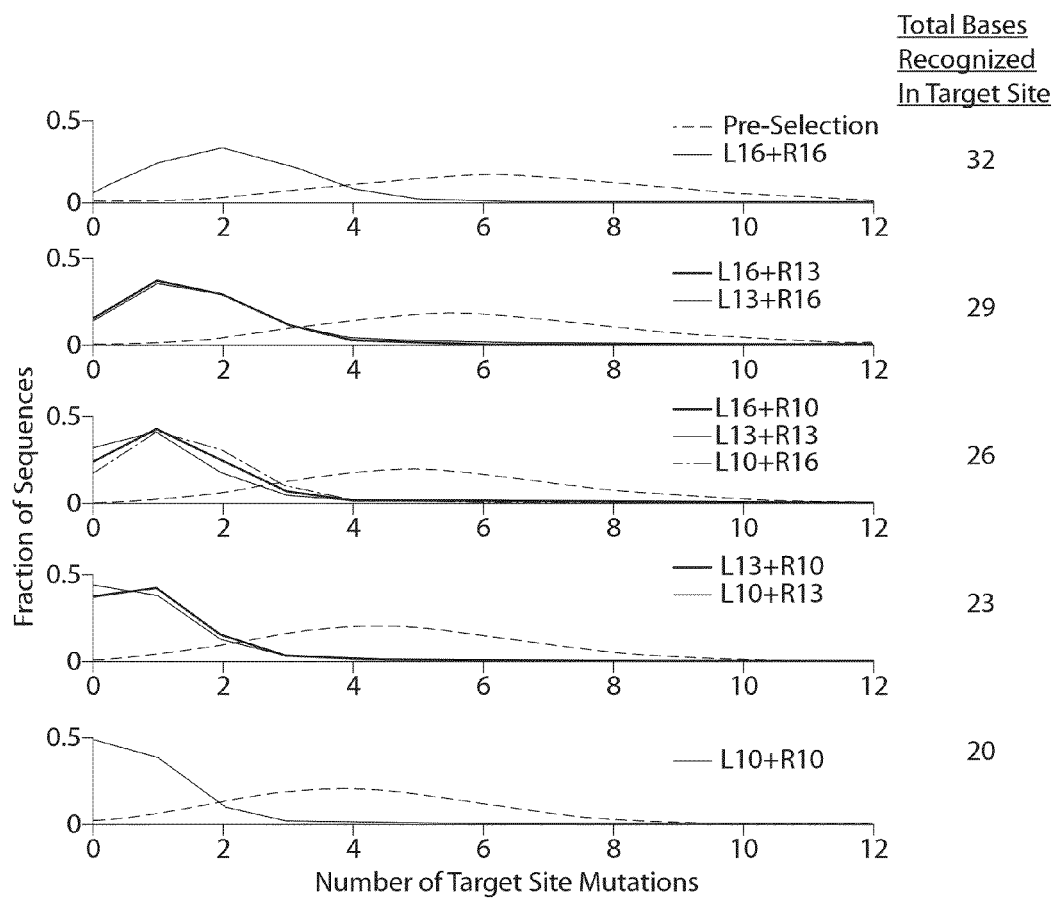
FIG. 30. Distribution of Mutations in Total Targeted Site of TALN Digestion vs. Pre-Selection Library.
Figure 31:
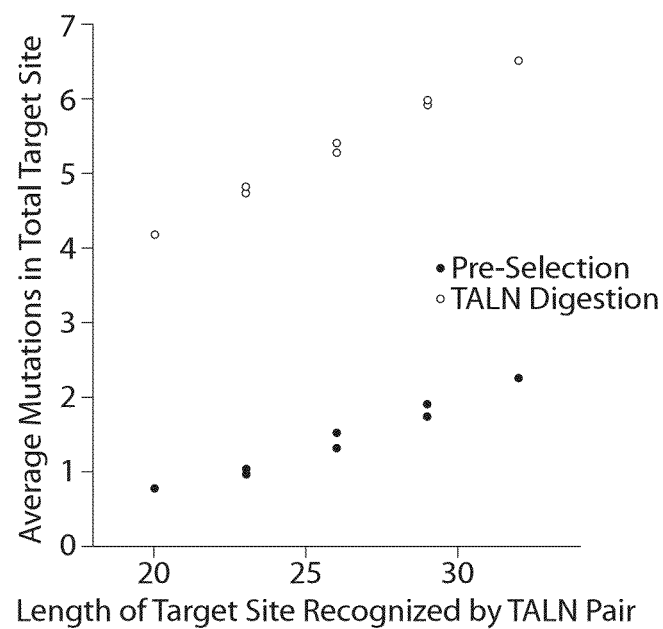
FIG. 31. Distribution of Mutations in Total Targeted Site of TALN Digestion vs. Pre-Selection Library.
Figure 32:
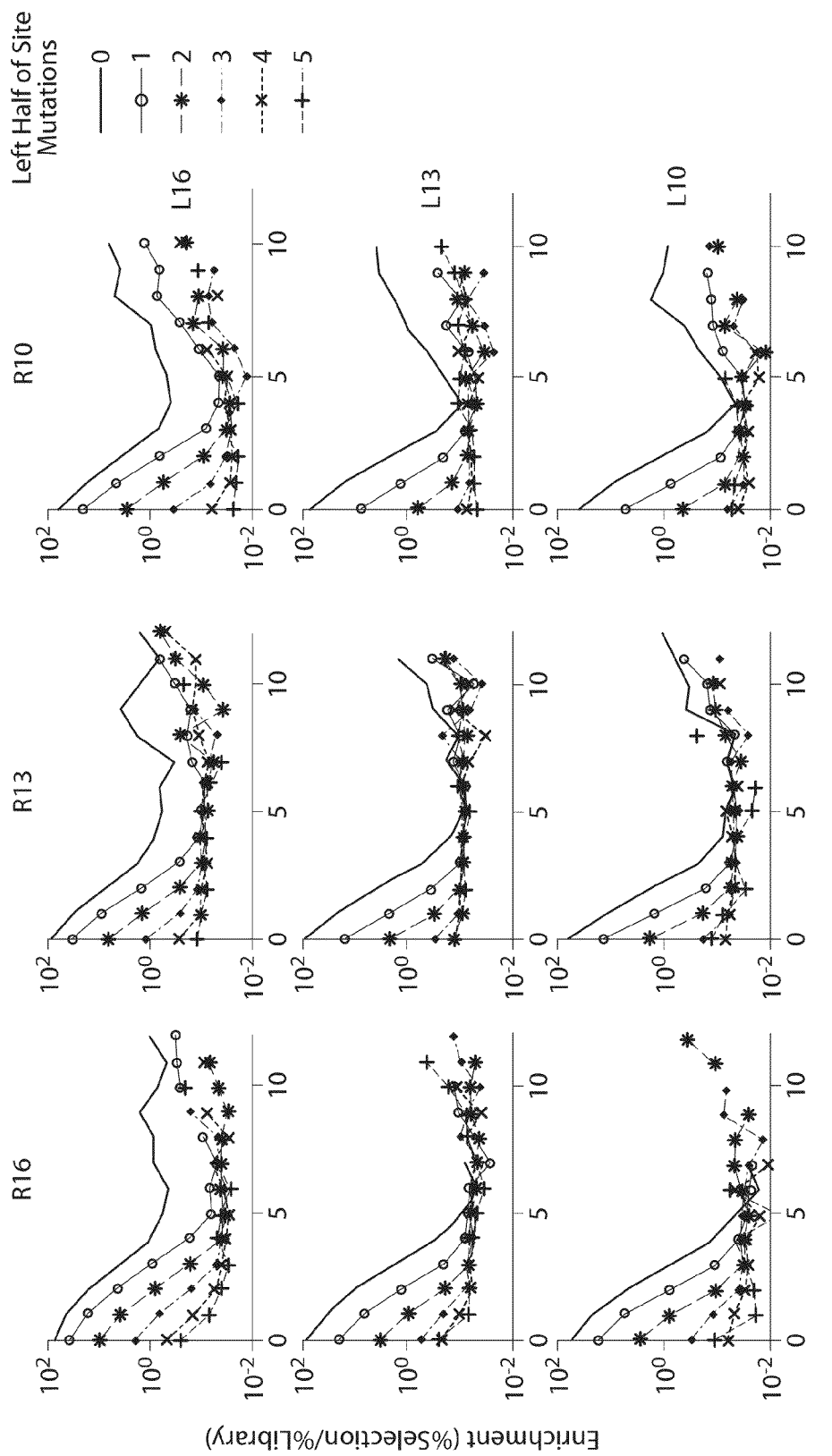
FIG. 32. Enrichment of Mutations in Total Target Site Between Right and Left Half Sites of TALN Pairs.
Figure 33:
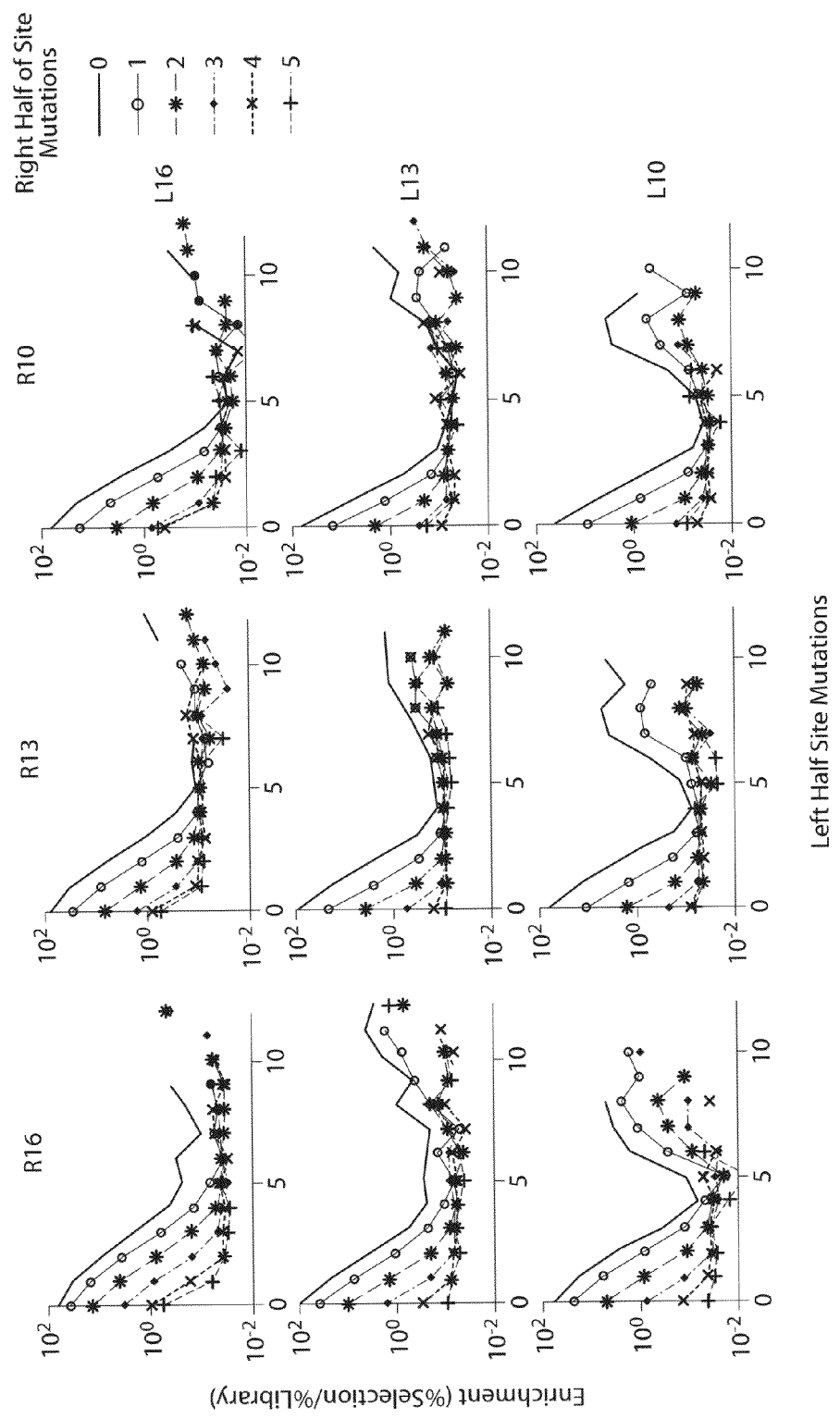
FIG. 33. Enrichment of Mutations in Total Target Site Between Right and Left Half Sites of TALN Pairs.
Figure 34:
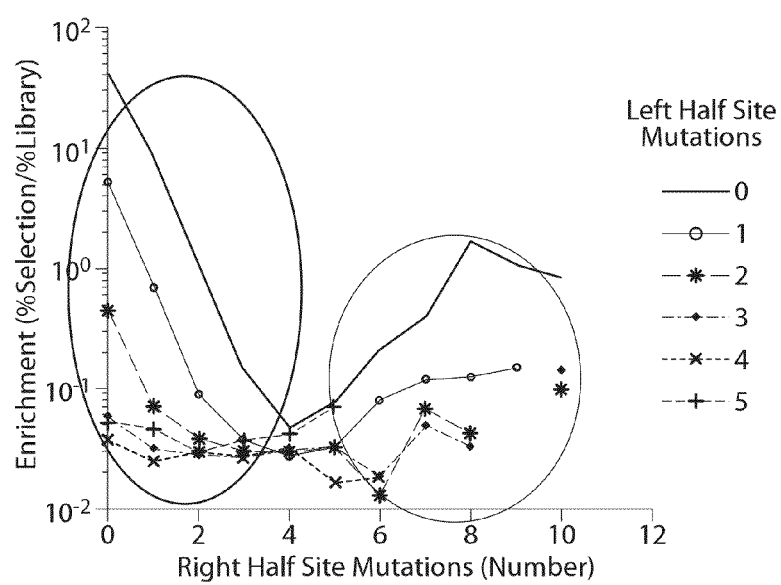
FIG. 34. Enrichment of Mutations in Total Targeted Site of TALN Digestion vs. Pre-Selection Library for L10 R10 TALN Pair.
Figure 35:
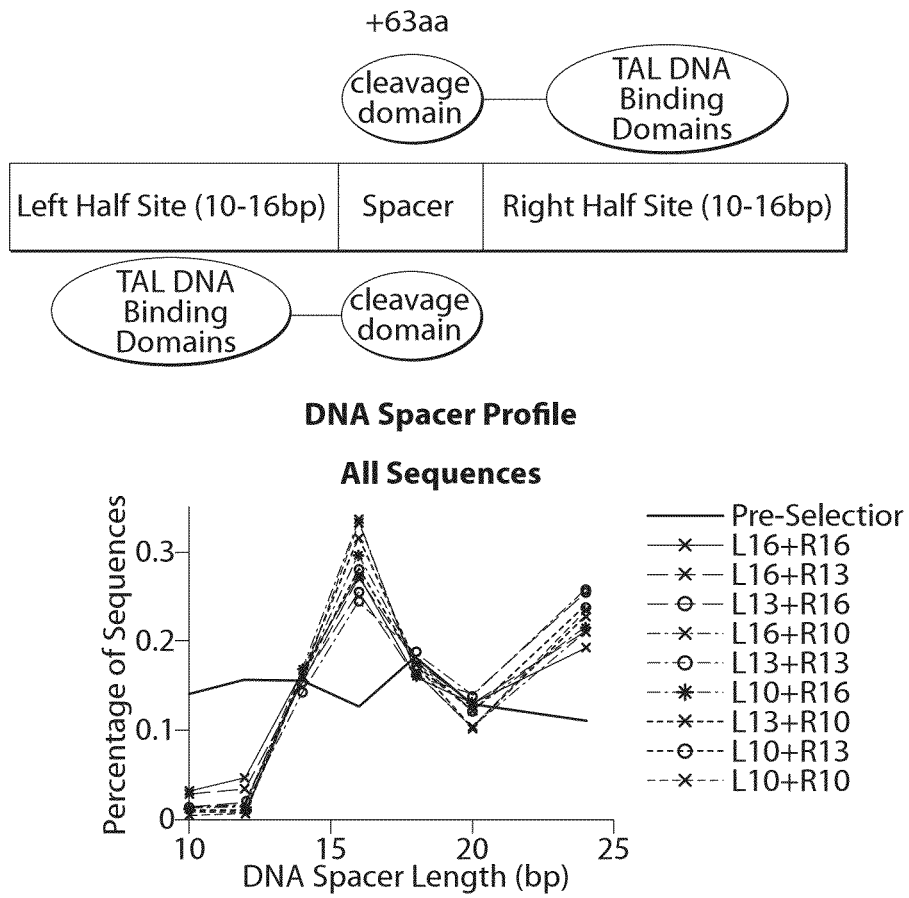
FIG. 35. DNA spacer profile. While the vast majority of sequences have a spacer preference, the highly mutant sequences have no significant spacer preference as might be expected from alternate frames changing the spacer length.
Figure 35:
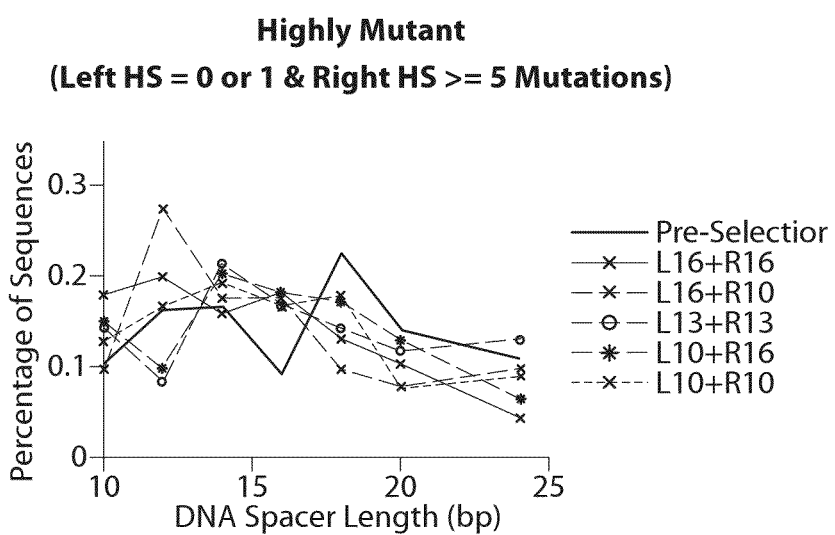
Figure 36:
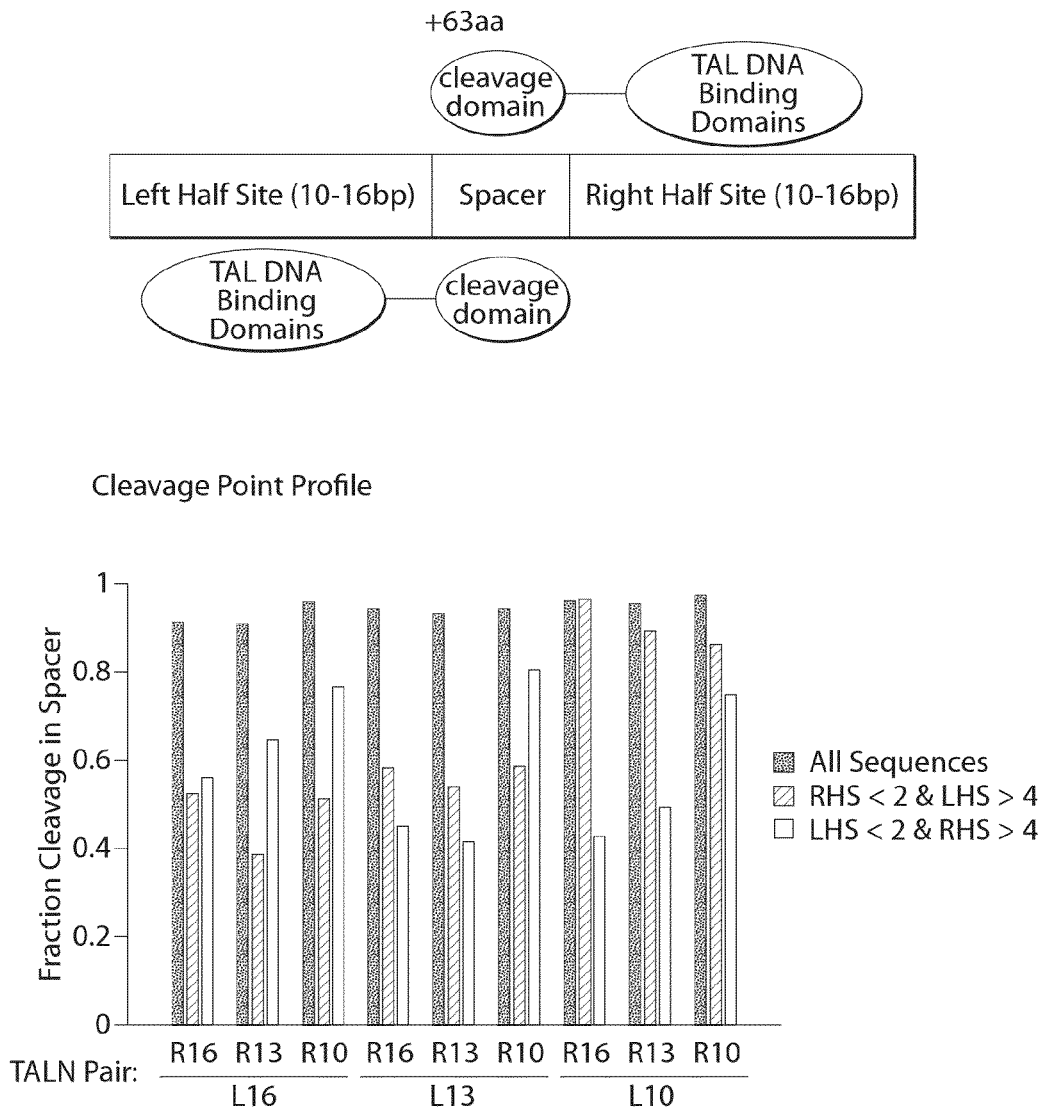
FIG. 36. Cleavage point profile. While the vast majority of sequences are cut in the spacer as expected, the R16 L16 highly mutant sequences are not predominately cut in spacer but the L10 R10 ones are cut in the spacer possibly indicative of a frame-shifted binding site leading to productive spacer cutting.
Figure 37:
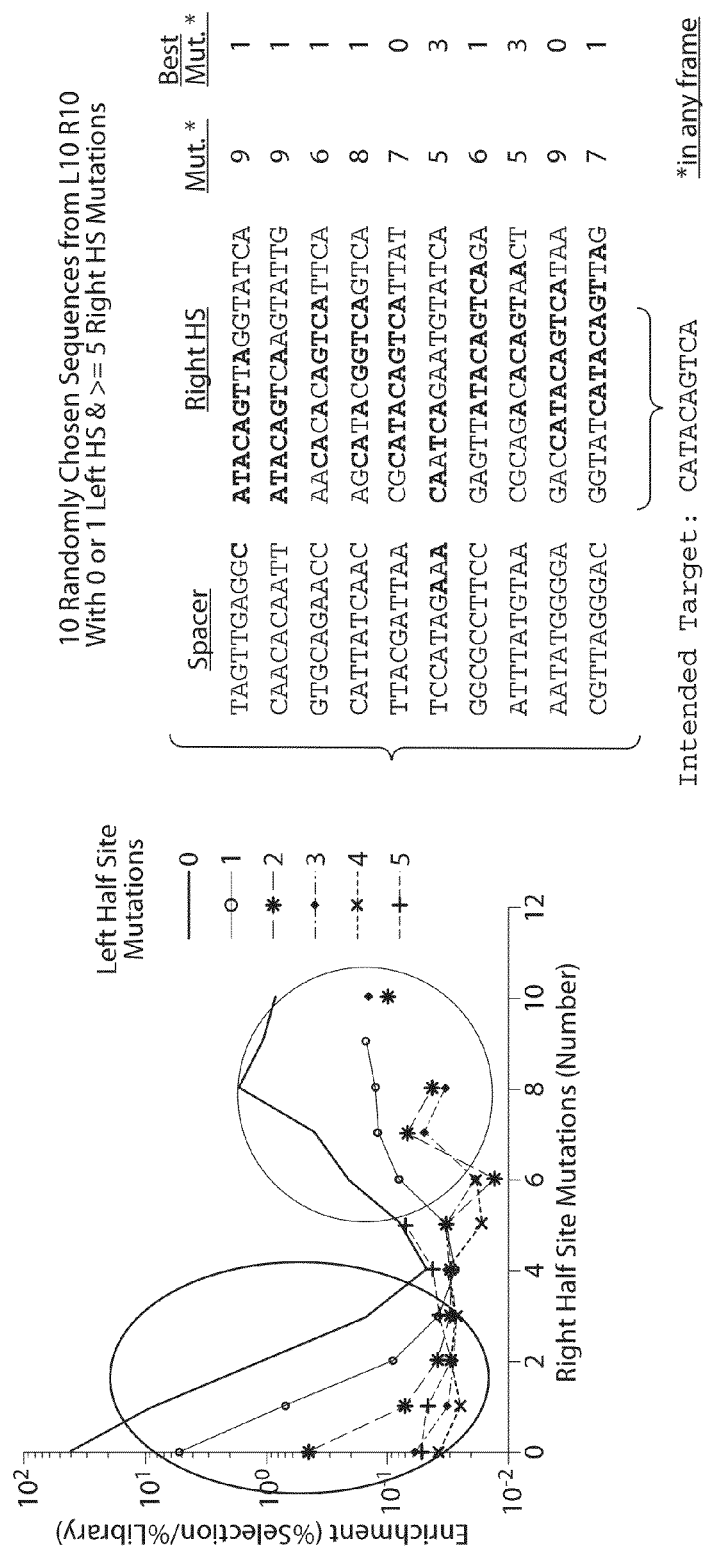
FIG. 37. Highly Mutant Half Sites in L10 R10 TALN Pair. Many potential binding sites in frames outside of the intended frame have sites more similar to the intended target (SEQ ID NOs:70-90).
Figure 38:
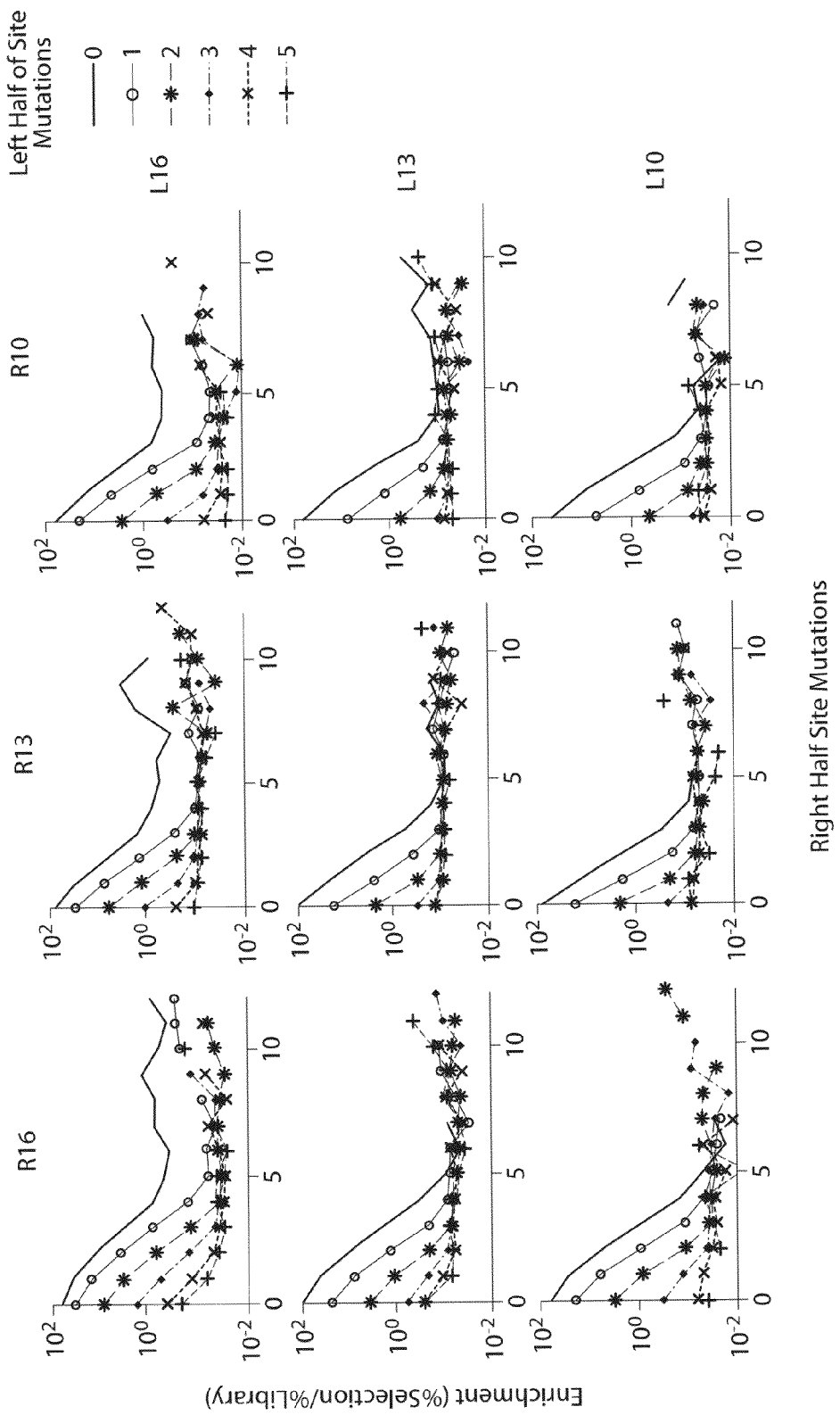
FIG. 38. Enrichment of Mutations in Total Target Site Between Left and Right Half Sites of TALN Pairs Edited for Frame-shifted Binding Sites.
Figure 39:
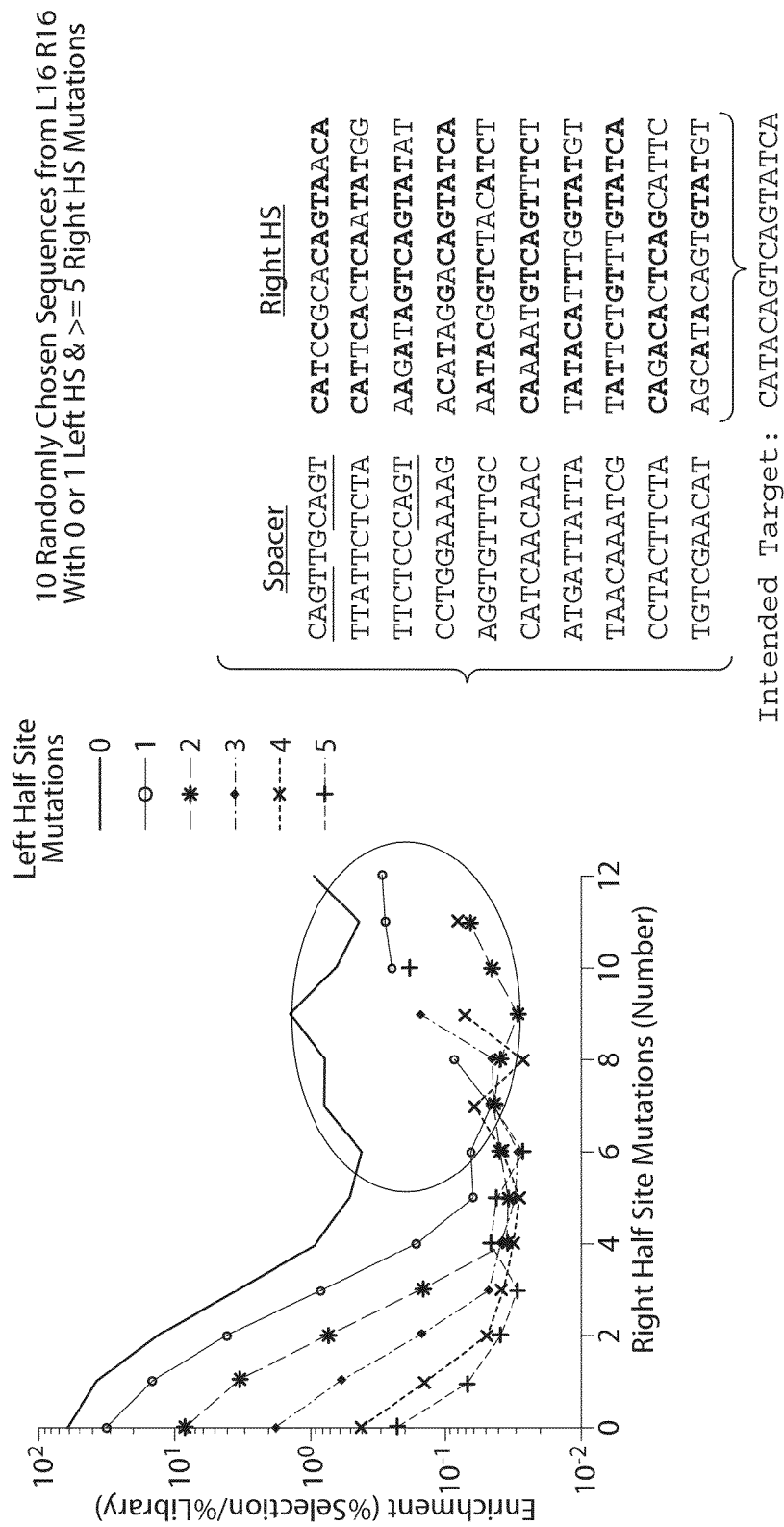
FIG. 39. Highly Mutant Half Sites in L16 R16 TALN Pair (SEQ ID NOs:91-111).
Figure 40:
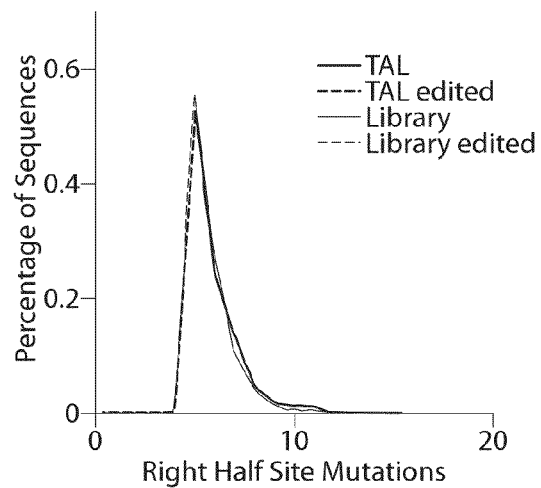
FIG. 40. Highly Mutant Half Sites in L16 R16 TALN Pair. The highly mutant sequences from L16 R16 cannot be explained by a frame-shift (left figure), have no DNA Spacer preference (see slide 11) and seem to be cutting more often outside of the DNA Spacer (right figure) indicating perhaps homodimer cleavage (even with heterodimer) or heterodimer cleavage independent of a TAL domain binding target site DNA (i.e. dimerization through the FokI cleavage domain).
Figure 40:
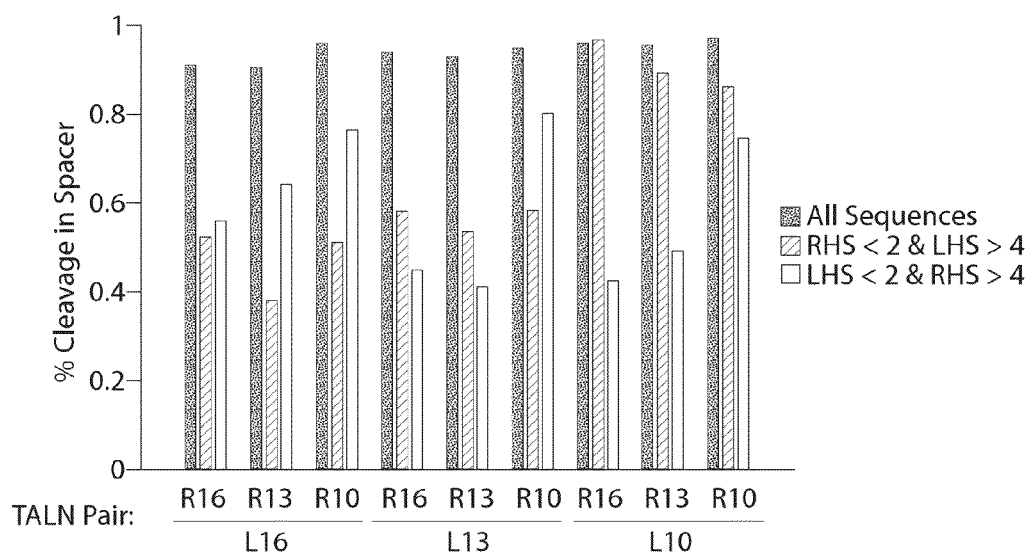
Figure 41:
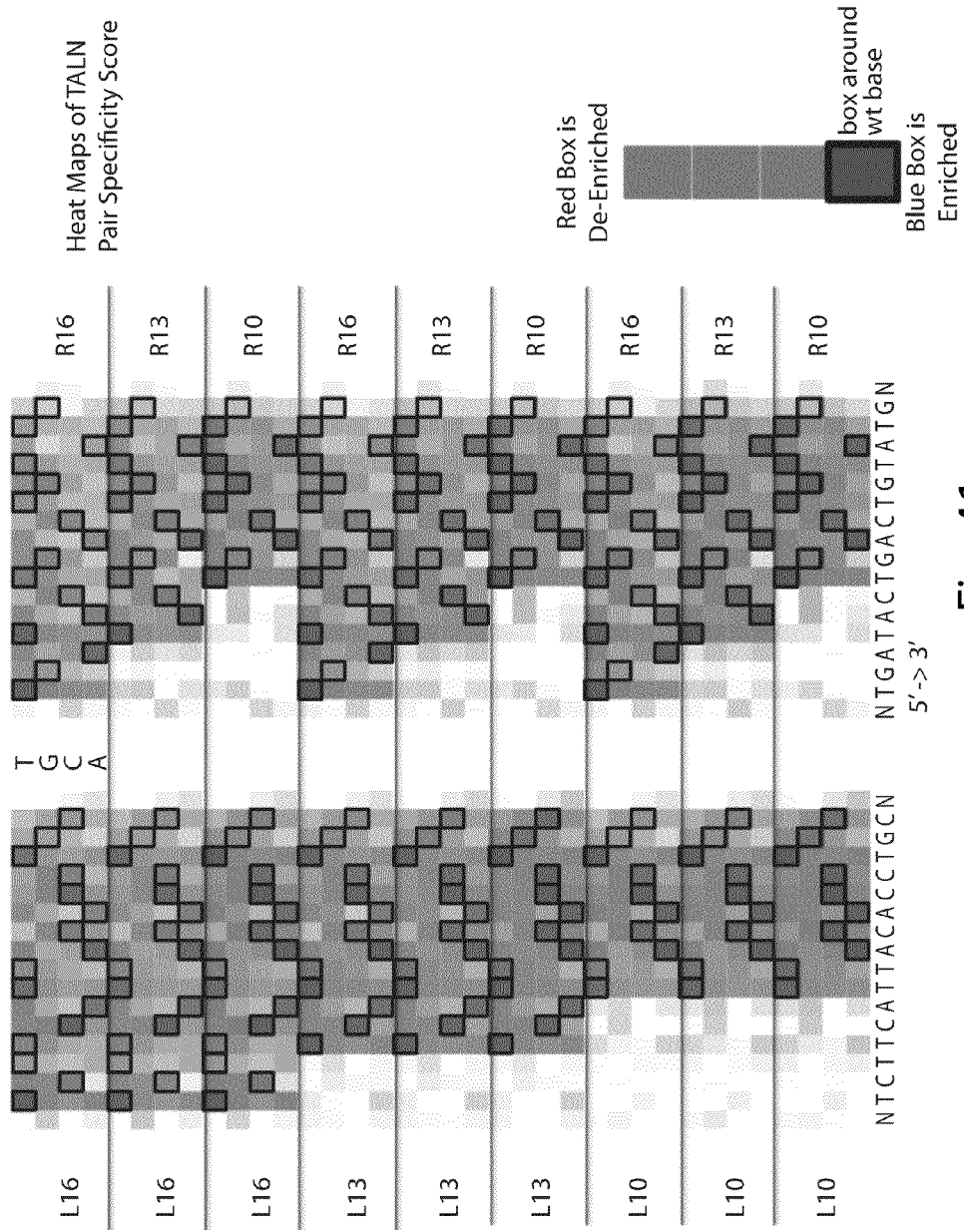
FIG. 41. Heat Maps of TALN Pair Specificity Score (SEQ ID NOs:112 and 113).
Figure 42:
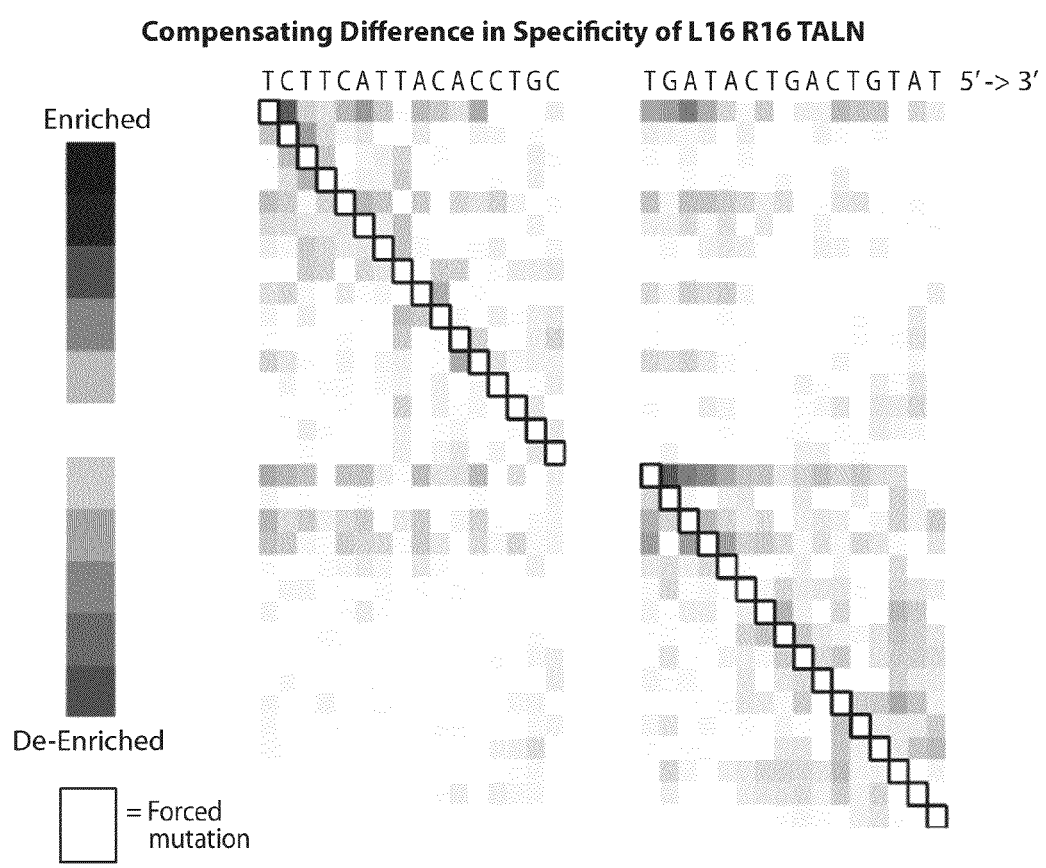
FIG. 42. Compensating Difference in Specificity of L16 R16 TALN. A single mutation in the cleavage site does not alter the distribution of other mutations suggesting that the TAL repeat domains bind independently (SEQ ID NOs:114 and 115).
Figure 43:
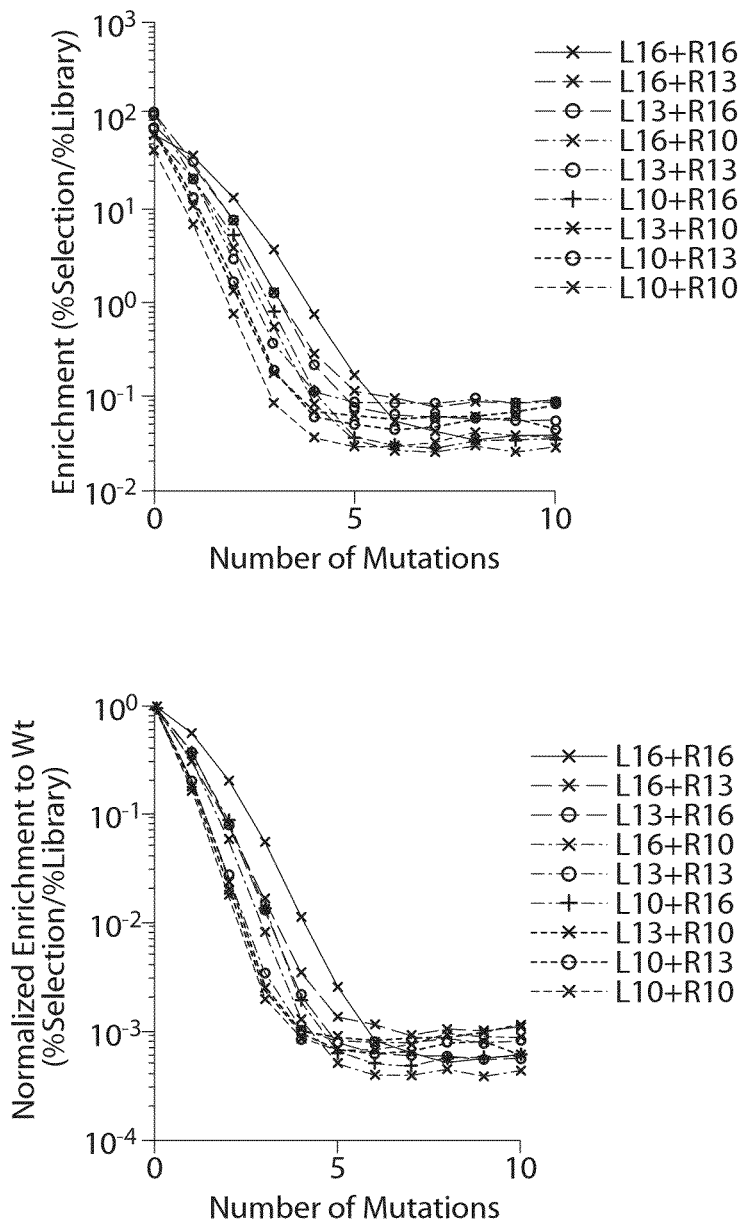
FIG. 43. Enrichment of Mutations in Full, Total Target Site of TALN Pairs. The enrichments seem to have similar log slopes in the low mutation range, the selections containing a TALN recognizing 16 bps seem to be the exceptions indicating R16 binding may be saturating for some very low mutation sites (aka R16 & L16 were near or above the Kd for the wild type site).
Figure 44:
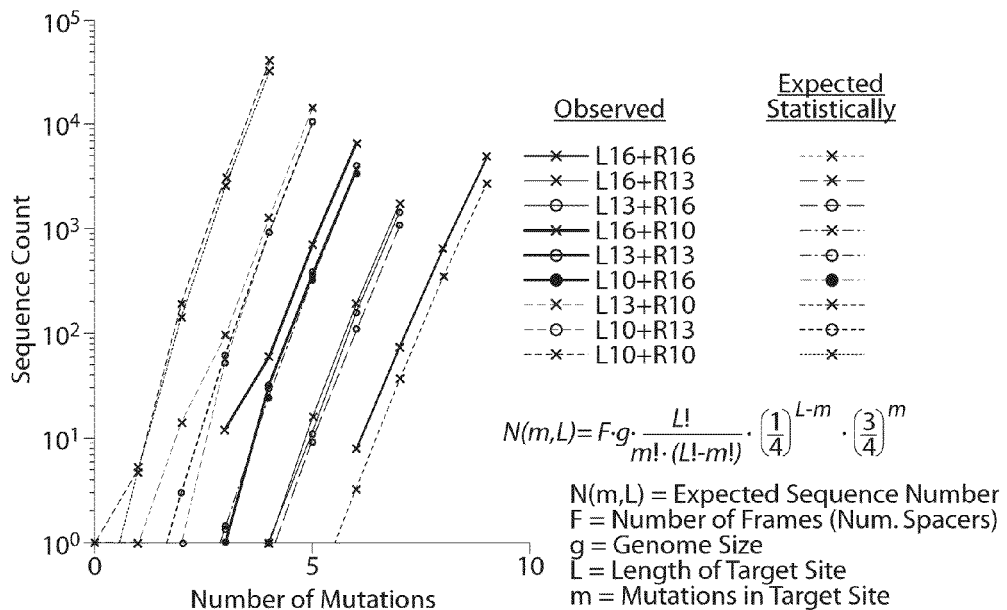
FIG. 44. TALN Off-Target Sites in the Human Genome.
Figure 45:
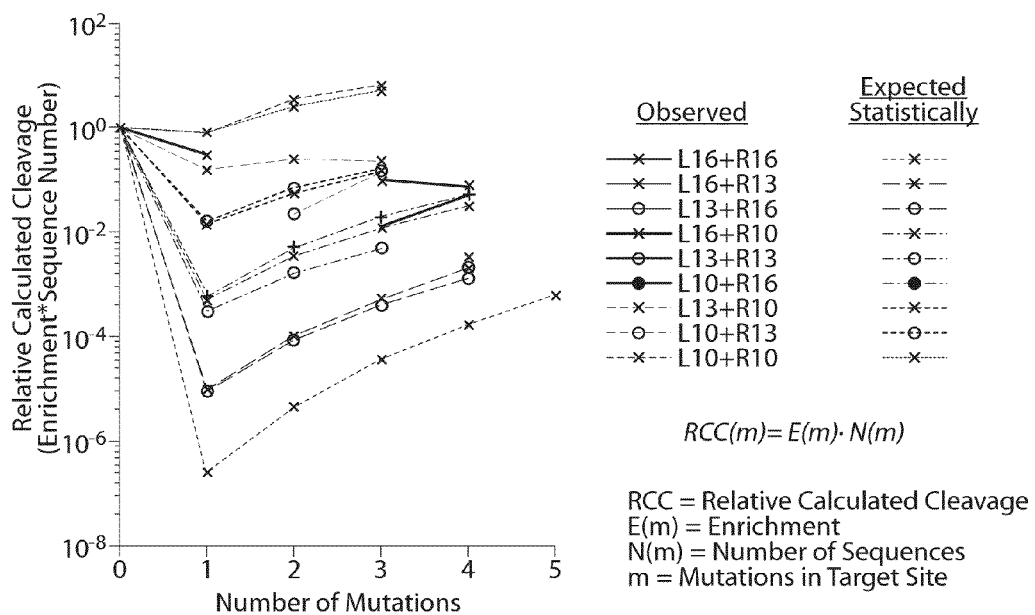
FIG. 45. TALN Off-Target Sites Predicted Cleavage.
Figure 46:
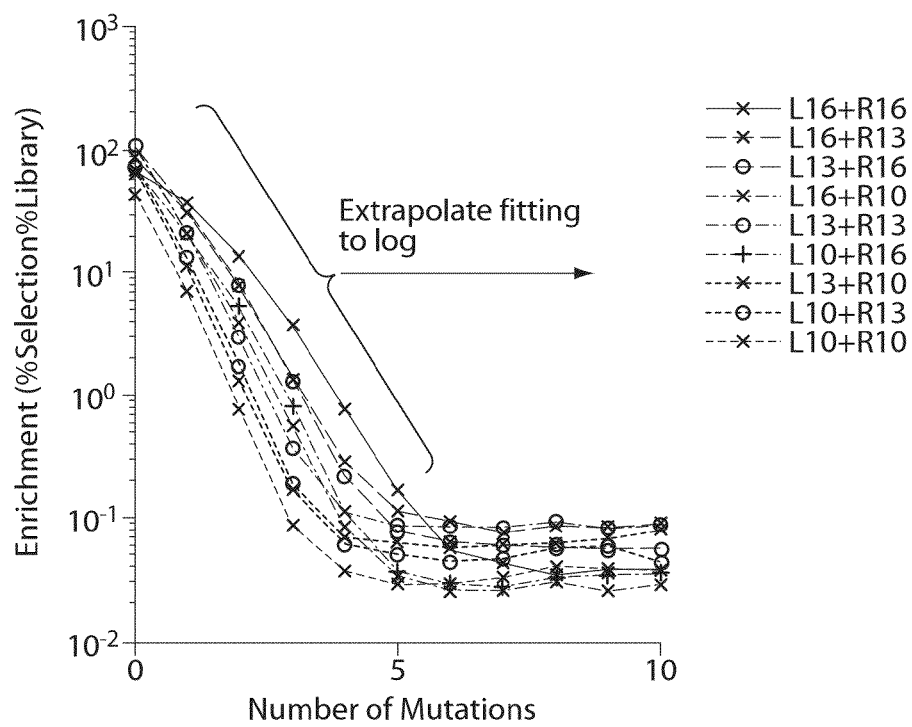
FIG. 46. TALN Off-Target Sites Predicted Cleavage For Very Mutant Target Sites below Detection Limit.
Figure 46:
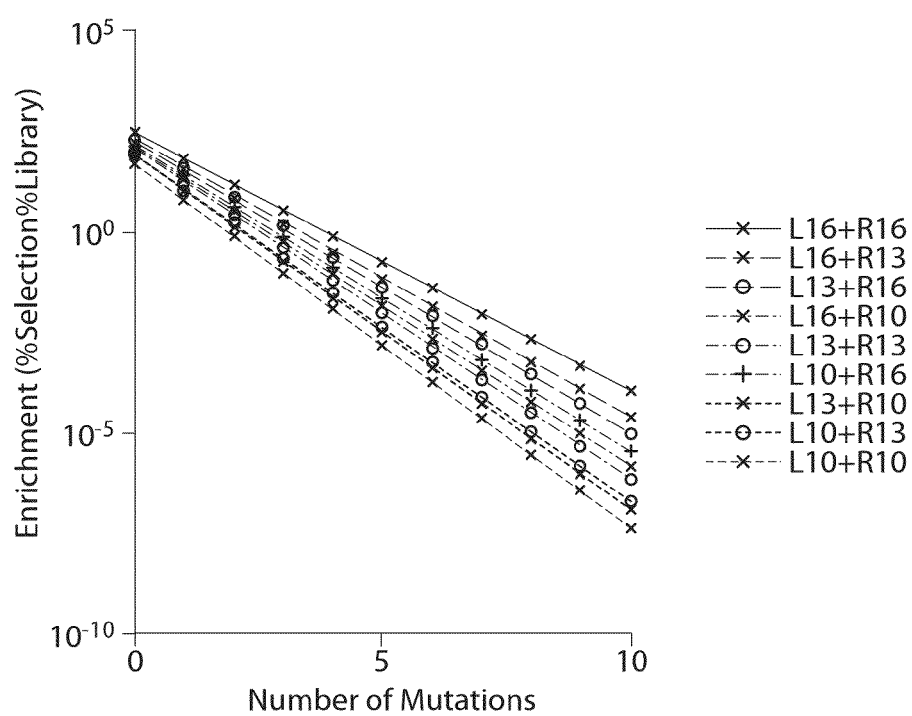
Figure 47:
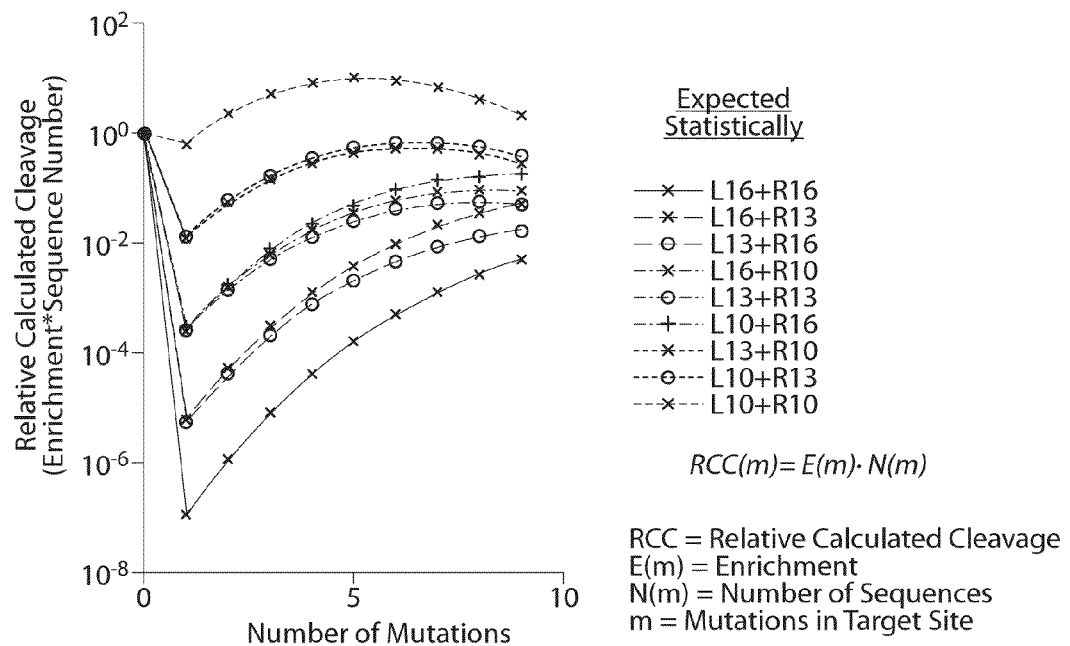
FIG. 47. TALN Off-Target Sites Predicted Cleavage For Very Mutant Target Sites below Detection Limit.
Figure 48:
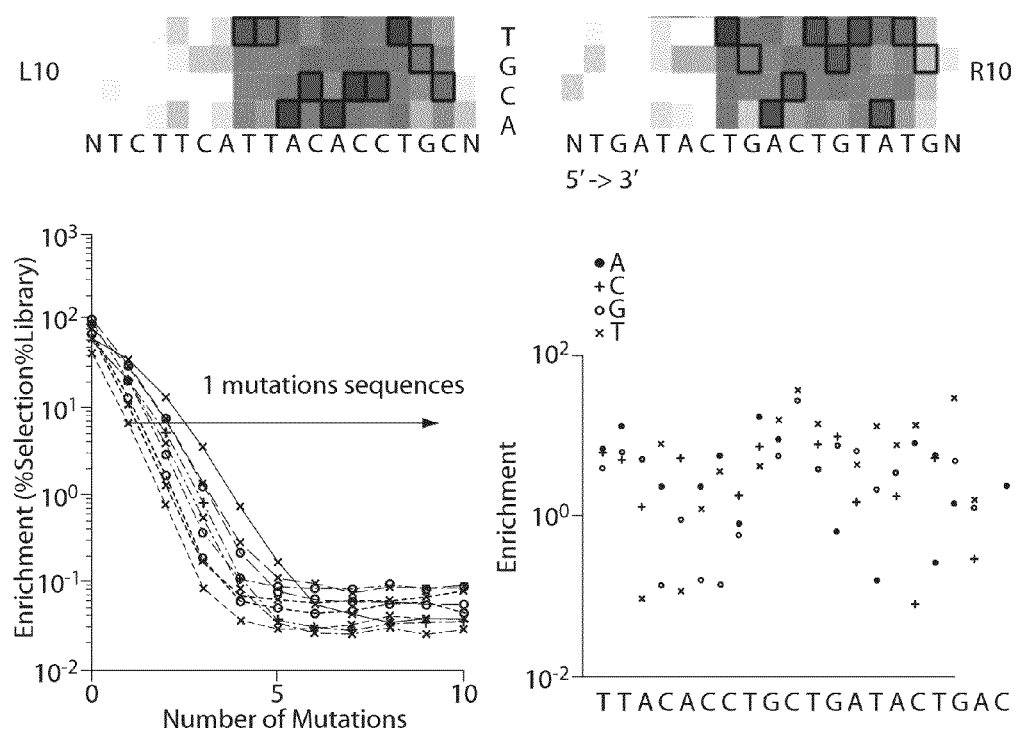
FIG. 48. TALN Off-Target Sites Predicted Cleavage For Sequences (Not just Number of Mutations). Combining the regular log decrease of cleavage efficiency (enrichment) as total target site mutations increase and the enrichment at each position we should be able to predict the off-target site cleavage of any sequence (SEQ ID NOs:116-118).
Figure 49:
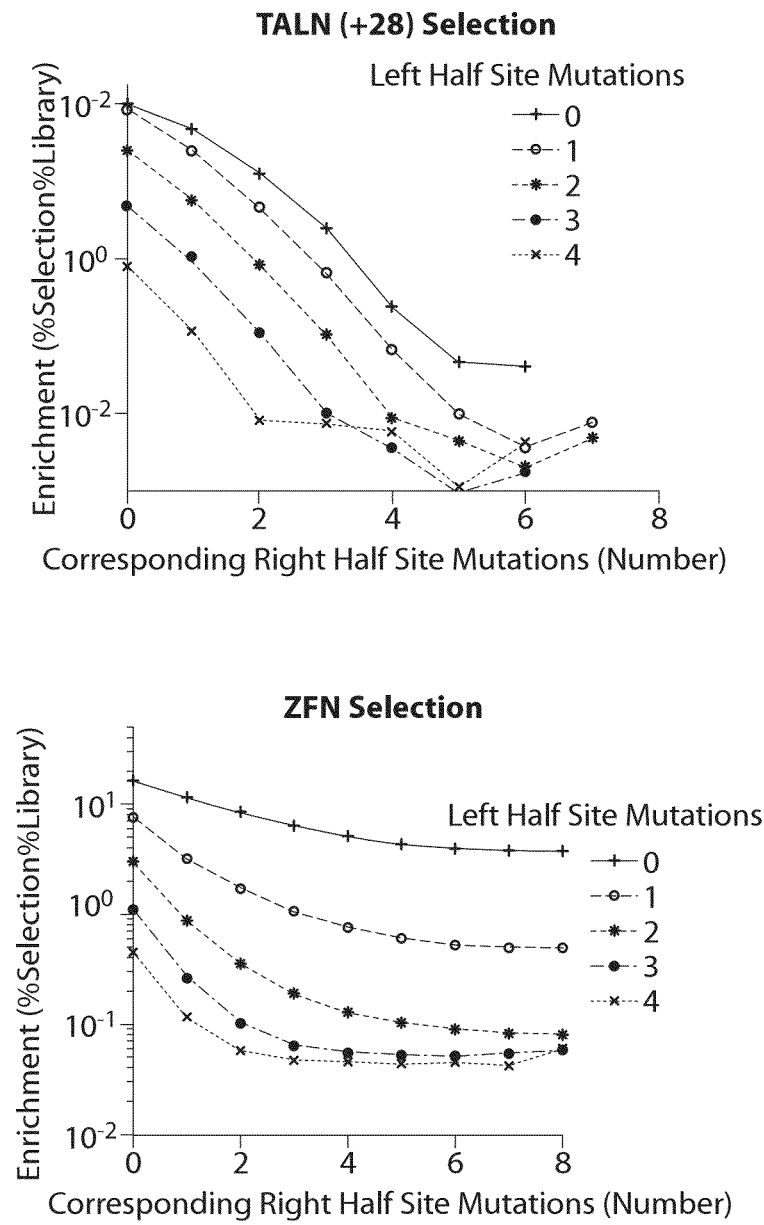
FIG. 49. Comparing TALNs vs. ZFNs. For the most part, in the TALN selection the enrichment is dependent on the total mutations in both half sites and not on the distribution of mutations between half sites like for zinc finger nucleases (ZFN). This observation combined with the context dependent binding of ZFNs potentially make ZFN far less specific than their TAL equivalents.

TAL DNA binding domains are the basis of a transformative technology to specifically modulate target DNA both in vitro and in cells. The designable TAL DNA binding domains have advantages in targetable sequence space and ease of construction compared to other DNA binding domains, for example, zinc fingers. These TAL DNA binding domains are comprised of repeats of a 34 amino acid domain with a highly variable di-amino acid (RVD) coding for recognition of a single base pair in the target DNA sequence (FIG. 20). Based on the robustness of this RVD code and the crystal structure of a TAL bound to its DNA target, it is likely that binding of a single repeat to a base pair is relatively independent of adjacent repeat binding. The TAL DNA binding domain (an array of repeats) can be linked to the monomer of a heterodimeric nuclease domain to form a TAL nuclease. Thus, two distinct TAL nucleases can bind adjacent target half sites to cleave a specific sequence resulting in genome modifications in vivo (FIGS. 19 and 20). While a number of studies have investigated the specificity of TAL DNA binding, to our knowledge no studies have profiled the specificity of TAL nucleases on a large scale. We applied the concept of high-throughput, in vitro selection for nuclease specificity outlined for ZFNs in Example 1 to TAL nucleases to both confirm the modular, independent binding of TAL repeats expected from their easy design-ability and also identify genomic off-target sequences cut by therapeutically relevant TAL nucleases.

The selection scheme for profiling the specificity of TAL nucleases via in vitro library screening was in analogy to the selection scheme described for ZFNs in Example. Detailed protocols are provided below:

Preparation of Library of Partly Randomized Target Sites
2 ul of 10 pmol TALNCCR5 Library Oligo (separate reactions for each oligo)
2 ul 10× CircLigase II 10× Reaction Buffer
1 ul 50 mM MnCl2
1 ul CircLigase II ssDNA Ligase (100 U) [Epicentre]
X ul water to 20 uL total volume
Incubate 16 hrs at 60° C. Incubate 10 min at 85° C. to inactivate.
Add 2.5 ul of each Circligase II reaction (without purification)
Add 25 ul TempliPhi™ [GE Healthcare] 100 sample buffer. Incubate 3 min at 95° C. Slow cool to 4° C.
Add 25 ul TempliPhi™ reaction buffer/1 ul enzyme mix. Incubate 16 hrs at 30° C. Heat inactive 10 min at 55° C.
Quantify amount of dsDNA using Quant-iT™ PicoGreen® dsDNA [Invitrogen]
Combine equal moles of TempliPhi™ reactions to final 2 uM with respect to number of cut sites.
TALN Expression
16 ul TnT® Quick Coupled [Promega]
0.4 ul 1 mM methionine
2 uL of 0.8 ug TALN vector expression plasmid or water for empty lysate
1.6 uL of water
Incubate at 30 for 1.5 hours and then store at 4° C. overnight.
Quantify amount of TALN in lysate via Western Blot.
TALN Digestion
25 uL of 10×NEB Buffer 3 [New England Biolabs]
10 uL of 2 uM TempliPh Library DNA
165 uL water
Add left TALN lysate to 20 nM total left TALN
Add right TALN lysate to 20 nM total right TALN
Add empty lysate to total of 50 uL lysate
Incubate 2 hrs at 37° C. Add 5 ul (50 ug) RNaseA (Qiagen). Incubate 10 min at RT. Purify with Qiagen PCR Purification Kit. Elute in 50 uL of 1 mM Tris, pH 8.0.
Adapter Ligation, PCR and Gel Purification of TALN Digestion
50 ul digested DNA
3 ul dNTP mix
6 ul NEB 2
1 ul Klenow [New England Biolabs]
Incubate 30 min at RT. Purify with Qiagen PCR Purification Kit.
50 ul eluted DNA
5.9 ul T4 DNA Ligase Buffer (NEB)
2 ul (20 pmol) heat/cooled adapter (different adapter for each selection)
1 ul T4 DNA ligase (NEB, 400 units)
Incubate at RT for 20 hrs. Purify with Qiagen PCR Purification Kit.
6 uL of TALN digested DNA
30 uL of 5× Buffer HF
1.5 uL 100 uM Illumina_fwd Primer
1.5 uL 100 uM PE_TALN_rev1 Primer
3 uL 10 mM dNTP
1.5 uL Phusion Hot Start II
106.5 uL of water
98° C. for 3 min, do 15 cycles of 98° C. for 15 s, 60° C. for 15 s, 72° C. for 1 min. Purify with Qiagen PCR Purification Kit Gel Purify on 2% Agarose gel loading 1 ug of eluted DNA in 40 uL of 10% glycerol. Run on gel at 135V for 35 min. Gel purify bands of the length corresponding to a cut half site+full half site+adapter with filter paper. Remove filter paper and collect supernatant. Purify with Qiagen PCR Purification Kit.
6 uL of TALN digested DNA (5-26-12)
30 uL of 5× Buffer HF
1.5 uL 100 uM Illumina_fwd Primer
1.5 uL 100 uM PE_TALN_rev2 Primer
3 uL 10 mM dNTP
1.5 uL Phusion Hot Start II
106.5 uL of water
98° C. for 3 min, do 6 cycles of 98° C. for 15 s, 60° C. for 15 s, 72° C. for 1 min. Purify with Qiagen PCR Purification Kit.
Preparation of Pre-selection Library
25 uL of 10×NEB Buffer 4
10 uL of 2 uM TempliPhi Library DNA
165 uL water
5 uL of Appropriate Restriction Enzyme [New England Biolabs]
210 uL of water
Incubate 1 hrs at 37° C. Purify with Qiagen PCR Purification Kit.
50 ul eluted DNA
5.9 ul T4 DNA Ligase Buffer (NEB)
2 ul (20 pmol) heat/cooled adapter (pool of 4 adapter sequences)
1 ul T4 DNA ligase (NEB, 400 units)
Incubate at RT for 20 hrs. Purify with Qiagen PCR Purification Kit.
6 uL of Restriction Enzyme Digested DNA (5-26-12)
30 uL of 5× Buffer HF
1.5 uL 100 uM Illumina_rev Primer
1.5 uL 100 uM TALNLibPCR Primer
3 uL 10 mM dNTP
1.5 uL Phusion Hot Start II
106.5 uL of water
98° C. for 3 min, 12 cycles of 98° C. for 15 s, 60° C. for 15 s, 72° C. for 1 min. Purify with Qiagen PCR Purification Kit
High-throughput Sequencing
Quantify via RT-qPCR
12.5 uL of IQ SYBR Green Supermix
1 uL of 10 uM Illumina_rev
1 uL of 10 uM Illumina_fwd
9.5 uL of water
1 uL of DNA template (both Pre-Selection Library and TALN Digestion)
95° C. for 5 min, do 30 cycles of 95° C. for 30 s, 65° C. for 30 s, 72° C. for 40 s.
Dilute DNA to 2 nM (compared to sequencing standard)
5 uL of TALN Digestion 2 nM DNA
2.5 uL of Pre-Selection Library 2 nM DNA
10 uL of 0.1N NaOH
Incubate at room temp for 5 min
Sequence via Illumina Mi-Seq
Computational Filtering
For TALN Digested sequences, find two appropriately spaced constant oligo sequences
For Pre-selection Library sequences, find appropriately spaced constant oligo sequence and library adapter sequence
Parse sequence into cut overhang, left half site, spacer, right half site
Remove sequences with poor Illumina base scores in half sites (<B=rejected)

| Primer | Sequence |
| --- | --- |
| J61TALCCR5B_10 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs:138 and 139; full sequence: SEQ ID NO: 8767) |
| J63TALCCR5B_12 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs:140 and 141; full sequence: SEQ ID NO: 8768) |
| J65TALCCR5B_14 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs:142 and 143; full sequence: SEQ ID NO: 8769) |
| J66TALCCR5B_15 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs: 144 and 145; full sequence: SEQ ID NO: 8770) |
| J67TALCCR5B_16 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNN N(N2)(N3)(N1)(N3)(N2)(N3)(N4)(N1)(N2)(N3)(N4)(N1)(N3)(N1)(N2)(N3)NCCTCGGGACT (SEQ ID NOs: 146 and 147; full sequence: SEQ ID NO: 8771) |
| J68TALCCR5B_17 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNN NN(N2)(N3)(N1)(N3)(N2)(N3)(N4)(N1)(N2)(N3)(N4)(N1)(N3)(N1)(N2)(N3)NCCTCGGGACT (SEQ ID NOs: 148 and 149; full sequence: SEQ ID NO: 8772) |

| Primer sequences | |
|---|---|
| Primer | Sequence |
| J69TALCCR5B_18 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs:150 and 151; full sequence: SEQ ID NO: 8773) |
| J71TALCCR5B_20 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs: 152 and 153; full sequence: SEQ ID NO: 8774) |
| J73TALCCR5B_22 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs: 154 and 155; full sequence: SEQ ID NO: 8775) |
| J75TALCCR5B_24 | CCACGCTN(N1: 07070779)(N2: 07790707)(N1)(N1)(N2)(N3: 79070707)(N1)(N1)(N3)(N2)(N3)(N2)(N2)(N1)(N4: 07077907)(N2)NNNNNNNNNNNNNNNNNNNNNNNN(N2)(N3)(N1)(N3)(N2)(N3)(N4)(N1)(N2)(N3)(N4)(N1)(N3)(N1)(N2)(N3)NCCTCGGGACT (SEQ ID NOs: 156 and 157; full sequence: SEQ ID NO: 8776) |
| CGTAAadapterfwd | AATGATACGGCGACCACCGAGATCTACACTCTTTCCCTACACGACGCTCTTCCGATCTCGTAA (SEQ ID NO: 158) |
| CGTAAadapterREV | TTACGAGATCGGAAGAGCGTCGTGTAGGGAAAGAGTGTAGATCTCGGTGG (SEQ ID NO: 159) |
| GTACTadapterfwd | AATGATACGGCGACCACCGAGATCTACACTCTTTCCCTACACGACGCTCTTCCGATCTGTACT (SEQ ID NO: 160) |
| GTACTadapterREV | AGTACAGATCGGAAGAGCGTCGTGTAGGGAAAGAGTGTAGATCTCGGTGG (SEQ ID NO: 161) |
| TACGAadapterfwd | AATGATACGGCGACCACCGAGATCTACACTCTTTCCCTACACGACGCTCTTCCGATCTTACGA (SEQ ID NO: 162) |
| TACGAadapterREV | TCGTAAGATCGGAAGAGCGTCGTGTAGGGAAAGAGTGTAGATCTCGGTGG (SEQ ID NO: 163) |
| ATGCTadapterfwd | AATGATACGGCGACCACCGAGATCTACACTCTTTCCCTACACGACGCTCTTCCGATCTATGCT (SEQ ID NO: 164) |
| ATGCTadapterREV | AGCATAGATCGGAAGAGCGTCGTGTAGGGAAAGAGTGTAGATCTCGGTGG (SEQ ID NO: 165) |
| TGCAAadapterfwd | AATGATACGGCGACCACCGAGATCTACACTCTTTCCCTACACGACGCTCTTCCGATCTTGCAA (SEQ ID NO: 166) |
| TGCAAadapterREV | TTGCAAGATCGGAAGAGCGTCGTGTAGGGAAAGAGTGTAGATCTCGGTGG (SEQ ID NO: 167) |
| GCATTadapterfwd | AATGATACGGCGACCACCGAGATCTACACTCTTTCCCTACACGACGCTCTTCCGATCTGCATT (SEQ ID NO: 168) |
| GCATTadapterREV | AATGCAGATCGGAAGAGCGTCGTGTAGGGAAAGAGTGTAGATCTCGGTGG (SEQ ID NO: 169) |
| GACTAadapterfwd | AATGATACGGCGACCACCGAGATCTACACTCTTTCCCTACACGACGCTCTTCCGATCTGACTA (SEQ ID NO: 170) |
| GACTAadapterREV | TAGTCAGATCGGAAGAGCGTCGTGTAGGGAAAGAGTGTAGATCTCGGTGG (SEQ ID NO: 171) |
| ACTGTadapterfwd | AATGATACGGCGACCACCGAGATCTACACTCTTTCCCTACACGACGCTCTTCCGATCTACTGT (SEQ ID NO: 172) |
| ACTGTadapterREV | ACAGTAGATCGGAAGAGCGTCGTGTAGGGAAAGAGTGTAGATCTCGGTGG (SEQ ID NO: 173) |
| CTGAAadapterfwd | AATGATACGGCGACCACCGAGATCTACACTCTTTCCCTACACGACGCTCTTCCGATCTCTGAA (SEQ ID NO: 174) |

-continued

Primer sequences

| Primer | Sequence |
| --- | --- |
| CTGAAadapterREV | TTCAGAGATCGGAAGAGCGTCGTGTAGGGAAAGAGTGTAGATCTCG GTGG (SEQ ID NO: 175) |
| PE_TALCCR5B_rev1 | CAAGCAGAAGACGGCATACGAGATCGTGATGTGACTGGAGTTCAGA CGTGTGCTCTTCCG (SEQ ID NO: 176) |
| PE_TALCCR5B_rev2 | CAGACGTGTGCTCTTCCGATCNNNNAGCGTGGAGTCCCGAGG (SEQ ID NO: 177) |
| PE_TALCCR5B_rev | CAAGCAGAAGACGGCATACGAGATACAGTCGTGACTGGAGTTCAGA CGTGTGCTCTTCCGATCNNNNAGCGTGGAGTCCCGAGG (SEQ ID NO: 178) |
| PE_TALCCR5Blib adapter1 | TCGGGAACGTGATCGGAAGAGCACACGTCTGAACTCCAGTCACCGT CTAATCTCGTATGCCGTCTTCTGCTTG (SEQ ID NO: 179) |
| PE_TALCCR5Blib adapterrev1 | GTGACTGGAGTTCAGACGTGTGCTCTTCCGATCACGTT (SEQ ID NO: 180) |
| PE_TALCCR5Blib adapter2 | TCGGGACGTAGATCGGAAGAGCACACGTCTGAACTCCAGTCACCGT CTAATCTCGTATGCCGTCTTCTGCTTG (SEQ ID NO: 181) |
| PE_TALCCR5Blib adapterrev2 | GTGACTGGAGTTCAGACGTGTGCTCTTCCGATCTACGT (SEQ ID NO: 182) |
| PE_TALCCR5Blib adapter3 | TCGGGAGTACGATCGGAAGAGCACACGTCTGAACTCCAGTCACCGT CTAATCTCGTATGCCGTCTTCTGCTTG (SEQ ID NO: 183) |
| PE_TALCCR5Blib adapterrev3 | GTGACTGGAGTTCAGACGTGTGCTCTTCCGATCGTACT (SEQ ID NO: 184) |
| PE_TALCCR5Blib adapter4 | TCGGGATACGGATCGGAAGAGCACACGTCTGAACTCCAGTCACCGT CTAATCTCGTATGCCGTCTTCTGCTTG (SEQ ID NO: 185) |
| PE_TALCCR5Blib adapterrev4 | GTGACTGGAGTTCAGACGTGTGCTCTTCCGATCCGTAT (SEQ ID NO: 186) |
| TALCCR5BlibPCR | AATGATACGGCGACCACCGAGATCTACACTCTTTCCCTACACGACG CTCTTCCGATCTNNNNCCTCGGGACTCCACGCT (SEQ ID NO: 187) |
| IlluminaFwd | AATGATACGGCGACCAC (SEQ ID NO: 188) |
| IlluminaRev | CAAGCAGAAGACGGCATACGA (SEQ ID NO: 189) |

Conclusions

The relatively regular (log relationship) trend between number of half sites mutations and enrichment is consistent with a single TAL repeat binding a base pair independent of other repeat binding. A single mutation in the cleavage site does not significantly alter the distribution of other mutations in the compensation difference analysis suggesting that the TAL repeat domains bind independently. The +28 linker is more specific than the +63 linker TALN constructs. While TALNs recognizing larger target sites are less specific in that they can tolerate more mutations, the abundance of the mutant larger sequences is less than the increase in enrichment, thus the in vitro selection data and abundance of off-target sites indicates off-target cleavage to be significantly less likely in longer TALN pairs. Combining the regular decrease of cleavage efficiency (enrichment) as total target site mutations increase and the enrichment at each position it is possible to predict the off-target site cleavage of any sequence. For the most part, in the TALN selection the enrichment was dependent on the total mutations in both half sites and not on the distribution of mutations between half sites as was observed for zinc finger nucleases (ZFN). This observation combined with the context dependent binding of ZFNs indicated that TALENs may readily be engineered to a specificity as high or higher than their ZFN equivalents.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

TABLES

| mutations T | (+) | (−) | gene | (+) half-site (SEQ ID NOs: 190-226) | spacer | (−) half-site (SEQ ID NOs: 227-263) | in vitro selection stringency (nM) 4 | 2 | 1 | 0.5 | K562 modification frequency |
|---|---|---|---|---|---|---|---|---|---|---|---|
| 0 | 0 | 0 | CCR5 (coding) | GTCATCCTCATC | CTGAT | AAACTGCAAAAG | X | X | X | X | 1 : 23 |
| 2 | 1 | 1 | CCR2 (coding) | GTCgTCCTCATC | TTAAT | AAACTGCAAAAa | X | X | X | X | 1 : 10 |
| 3 | 2 | 1 | BTBD10 (promoter) | GTttTCCTCATC | AAAGC | AAACTGCAAAAt | X | X | | | 1 : 1,400 |
| 4 | 0 | 4 | | GTCATCCTCATC | AGAGA | AAACTGgctAAt | X | X | | | n.d. |
| 4 | 3 | 1 | SLC4A8 | taaATCCTCATC | TCTATA | AAAaTGCAAAAG | X | X | | | n.d. |
| 3 | 2 | 1 | Z83955 RNA | GTCATCCcaATC | GAAGAA | AAACTGaAAAAG | X | | | X | n.d. |
| 3 | 1 | 2 | DGKK | cTCATCCTCATC | CATGC | AcAaTGCAAAAG | X | | | | n.d. |
| 3 | 1 | 2 | GALNT13 | GTCATCCTCAgC | ATGGG | AAACaGCAgAAG | X | | | | n.d. |
| 3 | 1 | 2 | | GTCATCtTCATC | AAAAG | gAACTGCAAAAc | X | | | | 1 : 2,800 |
| 4 | 0 | 4 | | GTCATCCTCATC | CAATA | AAAgaaCAAAgG | X | | | | n.d. |
| 4 | 1 | 3 | TACR3 | GTCATCtTCATC | AGCAT | AAACTGtAAAgt | X | | | | 1 : 300 |

-continued

| mutations T | (+) | (−) | gene | (+) half-site (SEQ ID NOs: 190-226) | spacer | (−) half-site (SEQ ID NOs: 227-263) | in vitro selection stringency (nM) 4 | 2 | 1 | 0.5 | K562 modification frequency |
|---|---|---|---|---|---|---|---|---|---|---|---|
| 4 | 1 | 3 | PIWIL2 | GTCATCCTCATa | CATAA | AAACTGCcttAG | X | | | | |
| 4 | 1 | 3 | | aTCATCCTCATC | CATCC | AAtgTtCAAAAG | X | | | | n.d. |
| 4 | 3 | 1 | | GTCcTgCTCAgC | AAAAG | AAACTGaAAAAG | X | | | | 1 : 4,000 |
| 4 | 3 | 1 | KCNB2 | aTgtTCCTCATC | TCCCG | AAACTGCAAAtG | X | | | | 1 : 1,400 |
| 4 | 3 | 1 | | GTCtTCCTgATg | CTACC | AAACTGgAAAAG | X | | | | 1 : 5,300 |
| 4 | 3 | 1 | | aaCATCCaCATC | ATGAA | AAACTGCAAAAa | X | | | | n.d. |
| 6 | 3 | 3 | | aTCtTCCTCATt | ACAGG | AAAaTGtAAtAG | X | | | | n.d. |
| 6 | 4 | 2 | CUBN | GgCtTCCTgAcC | CACGG | AAACTGtAAAtG | X | | | | |
| 6 | 5 | 1 | NID1 | GTttTgCaCATt | TCAAT | tAACTGCAAAAG | X | | | | n.d. |
| 3 | 2 | 1 | | GTCAaCCTCAaC | ACCTAC | AgACTGCAAAAG | X | | | | 1 : 1,700 |
| 4 | 1 | 3 | WWOX | GTCATCCTCcTC | CAACTC | cAAtTGCtAAAG | X | | | | n.d. |
| 4 | 2 | 2 | AMBRA1 | GTCtTCCTCcTC | TGCACA | tcACTGCAAAAG | X | | | | n.d. |
| 4 | 2 | 2 | | GTgATaCTCATC | ATCAGC | AAtCTGCAtAAG | X | | | | n.d. |
| 4 | 2 | 2 | WBSCR17 | GTtATCCTCAgC | AAACTA | AAACTGgAAcAG | X | | | | 1 : 860 |
| 4 | 2 | 2 | ITSN | cTCATgCTCATC | ATTTGT | tAACTGCAAAAt | X | | | | n.d. |
| 4 | 4 | 0 | | GcCAgtCTCAgC | ATGGTG | AAACTGCAAAAG | X | | | | n.d. |
| 4 | 4 | 0 | | cTCATtCTgtTC | ATGAAA | AAACTGCAAAAG | X | | | | n.d. |
| 5 | 3 | 2 | | GaagTCCTCATC | CCGAAG | AAACTGaAAgAG | X | | | | n.d. |
| 5 | 3 | 2 | ZNF462 | GTCtTCCTCtTt | CACATA | AAACcGCAAAtG | X | | | | n.d. |
| 5 | 4 | 1 | | aTaATCCTtttC | TGTTTA | AAACaGCAAAAG | X | | | | n.d. |
| 5 | 4 | 1 | | GaCATCCaaATt | ACATGG | AAACTGaAAAAG | X | | | | n.d. |
| 5 | 5 | 0 | SDK1 | GTCtTgCTgtTg | CACCTC | AAACTGCAAAAG | X | | | | n.d. |
| 4 | 1 | 3 | SPTB(coding) | GTCATCCgCATC | GCCCTG | gAACTGgAAAAa | | X | | | n.d. |
| 4 | 2 | 2 | | aTCATCCTCAaC | AAACTA | AAACaGgAAAAG | | X | | | |
| 4 | 4 | 0 | KIAA1680 | GgaATgCcCATC | ACCACA | AAACTGCAAAAG | | X | | | n.d. |
| 5 | 5 | 0 | | GTttTgCTCcTg | TACTTC | AAACTGCAAAAG | | X | | | n.d. |

Table 1. CCR5-224 off-target sites in the genome of human K562 cells. Lower case letters indicate mutations compared to the target site. Sites marked with an 'X' were found in the corresponding in vitro selection dataset. 'T' refers to the total number of mutations in the site, and '(+)' and '(−)' to the number of mutations in the (+) and (−) half-sites, respectively. The sequences of the sites are listed as 5' (+) half-site/spacer/(−) half-site 3', therefore the (+) half-site is listed in the reverse sense as it is in the sequence profiles. K562 modification frequency is the frequency of observed sequences showing significant evidence of non-homologous end joining repair (see Methods) in cells expressing active ZFN compared to cells expressing empty vector. Sites that did not show statistically significant evidence of modifications are listed as not detected (n.d.), and K562 modification frequency is left blank for the three sites that were not analyzed due to non-specific PCR amplification from the genome. Table 4 shows the sequence counts and P-values for the tested sites used to determine K562 modification frequency, and Table 6 shows the modified sequences obtained for each site.

|  | Total Sequences | Analyzed Sequences | Rejected Sequences | | |
|---|---|---|---|---|---|
|  |  |  | Incompatible Overhangs | Repeated Sequences | Uncalled Bases in Half-Sites |
| CCR5-224 Pre-Selection | 1,426,442 | 1,392,576 | 0 | 33,660 | 206 |
| CCR5-224 0.5 nM | 649,348 | 52,552 | 209,442 | 387,299 | 55 |
| CCR5-224 1 nM | 488,798 | 55,618 | 89,672 | 343,442 | 66 |
| CCR5-224 2 nM | 1,184,523 | 303,462 | 170,700 | 710,212 | 149 |
| CCR5-224 4 nM | 1,339,631 | 815,634 | 352,888 | 170,700 | 159 |
| Total | 5,088,742 | 2,619,842 | 822,702 | 1,645,563 | 635 |
| VF2468 Pre-Selection | 1,431,372 | 1,393,153 | 0 | 38,128 | 91 |
| VF2468 0.5 nM | 297,650 | 25,851 | 79,113 | 192,671 | 15 |
| VF2468 1 nM | 148,556 | 24,735 | 19,276 | 104,541 | 4 |
| VF2468 2 nM | 1,362,058 | 339,076 | 217,475 | 805,433 | 74 |
| VF2468 4 nM | 1,055,972 | 397,573 | 376,364 | 281,991 | 44 |
| Total | 4,295,608 | 2,180,388 | 692,228 | 1,422,764 | 228 |

Table 2: Sequencing statistics. The total number of interpretable sequences ("total sequences") and the number of analyzed sequences for each in vitro selection condition are shown. Analyzed sequences are non-repeated sequences containing no ambiguous nucleotides that, for post-selection sequences, contained reverse complementary overhang sequences of at least four bases, a signature used in this study as a hallmark of ZFN-mediated cleavage. "Incompatible overhangs" refer to sequences that did not contain reverse complementary overhang sequences of at least four bases. The high abundance of repeated sequences in the 0.5 nM, 1 nM, and 2 nM selections indicate that the number of sequencing reads obtained in those selections, before repeat sequences were removed, was larger than the number of individual DNA sequences that survived all experimental selection steps.

Table 3: Both ZFNs tested have the ability to cleave a large fraction of target sites with three or fewer mutations. The percentage of the set of sequences with 1, 2, or 3 mutations (muts) that can be cleaved by (a) the CCR5-224 ZFN and (b) the VF2468 ZFN is shown. Enrichment factors (EFs) were calculated for each sequence identified in the selection by dividing the observed frequency of that sequence in the post-selection sequenced library by the observed frequency of that sequence in the preselection library. The enrichment factors for the wild-type sequence (wt EFs) calculated for each in vitro selection stringency are shown in the first row of the table.

a

| CCR5-224 | 4 nM (wt EF = 5.48) | | | 2 nM (wt EF = 8.11) | | | 1 nM (wt EF = 16.6) | | | 0.5 nM (wt EF = 24.9) | | |
|---|---|---|---|---|---|---|---|---|---|---|---|---|
|  | 1 mut | 2 muts | 3 muts | 1 mut | 2 muts | 3 muts | 1 mut | 2 muts | 3 muts | 1 mut | 2 muts | 3 muts |
| EF > 0 | 100% | 99.98% | 76% | 100% | 99% | 49% | 100% | 83% | 14% | 100% | 75% | 11% |
| EF > 1 | 100% | 93% | 55% | 100% | 84% | 42% | 100% | 68% | 14% | 100% | 58% | 11% |
| EF > 2 | 100% | 78% | 37% | 100% | 70% | 31% | 99% | 55% | 14% | 96% | 46% | 11% |
| EF > (.5 × wt EF) | 100% | 63% | 28% | 93% | 40% | 17% | 51% | 15% | 8% | 31% | 8% | 4% |
| EF > wt EF | 14% | 9% | 10% | 8% | 6% | 6% | 3% | 2% | 3% | 6% | 1% | 2% | b

| VF2468 | 4 nM (wt EF = 16.7) | | | 2 nM (wt EF = 22.5) | | | 1 nM (wt EF = 30.2) | | | 0.5 nM (wt EF = 33.1) | | |
|---|---|---|---|---|---|---|---|---|---|---|---|---|
|  | 1 mut | 2 muts | 3 muts | 1 mut | 2 muts | 3 muts | 1 mut | 2 muts | 3 muts | 1 mut | 2 muts | 3 muts |
| EF > 0 | 100% | 95% | 38% | 100% | 92% | 26% | 100% | 47% | 5% | 100% | 44% | 4% |
| EF > 1 | 98% | 49% | 17% | 93% | 34% | 11% | 83% | 24% | 5% | 80% | 21% | 4% |
| EF > 2 | 89% | 31% | 10% | 83% | 23% | 7% | 74% | 17% | 5% | 61% | 14% | 4% |
| EF > (.5 × wt EF) | 57% | 15% | 4% | 30% | 10% | 2% | 11% | 6% | 1% | 9% | 5% | 1% |
| EF > wt EF | 7% | 1% | 1% | 7% | 1% | 0.4% | 7% | 1% | 0.4% | 7% | 1% | 0.3% |

| | mutations T (+) (−) | | | gene | build 36 coordinates | (+) half-site | spacer | (−) half-site |
|---|---|---|---|---|---|---|---|---|
| CCR5-224 1 | 0 | 0 | 0 | CCR5 (coding) | chr3: 48399548-46389578 | GTCATCCTCATC | CIGAT | AAACTGCAAAAG |
| CCR5-224 2 | 2 | 1 | 1 | CCR2 (coding) | chr3: 46374209-46374237 | GTCgTCCTCATC | TTAAT | AAACTGCAAAAA |
| CCR5-224 3 | 3 | 2 | 1 | BTBD10 (promoter) | chr11: 13441738-13441766 | GTttTCCTCTATC AAAGC | | AAACTGCAAAAt |
| CCR5-224 4 | 4 | 0 | 4 | | chr10: 29604352-29604380 | GTCATCCTCATC | AGAGA | AAACTGgctAAt |
| CCR5-224 5 | 4 | 3 | 1 | SILC4A8 | chr12: 50186653-50186682 | taaATCCTCATC | TCTATA | AAAaTGCAAAAG |
| CCR5-224 6 | 3 | 2 | 1 | Z83955 RNA | chr12: 33484433-33484462 | GTCATCCcaATC | GAAGAA | AAACTGaAAAAG |
| CCR5-224 7 | 3 | 1 | 2 | DGKK | chrX: 50149961-50149989 | cTCATCCTCATC | CATGC | AcAaTGCAAAAG |
| CCR5-224 8 | 3 | 1 | 2 | GALNT13 | chr2: 154567664-154567692 | GTCATCCTCAgC | ATGGG | AAACaGCAgAAG |
| CCR5-224 9 | 3 | 1 | 2 | | chr17: 61624429-51624457 | GTCATCtTCATC | AAAAG | gAACTGCAAAAc |
| CCR5-224 10 | 4 | 0 | 4 | | chrX: 145275453-145275481 | GTCATCCTCATC | CAATA | AAAgaaCAAAgG |
| CCR5-224 11 | 4 | 1 | 3 | TACR3 | chr4: 104775175-104775203 | GTCATCtTCATC | AGCAT | AAACTGtAAAgt |
| CCR5-224 12 | 4 | 1 | 3 | PIWIL2 | chr8: 22191670-22191698 | GTCATCCTCATa | CATAA | AAACTGCcttAG |
| CCR5-224 13 | 4 | 1 | 3 | | chr9: 76194351-76194379 | aTCATCCTCATC | CATCC | AAtgTtCAAAAG |
| CCR5-224 14 | 4 | 3 | 1 | | chr8: 52114315-52114343 | GTCcTgCTCAgC | AAAAC | AAACTGaAAAAG |
| CCR5-224 15 | 4 | 3 | 1 | KCNB2 | chr8: 73399370-73899398 | aTgtTCCTCATC | TCCCG | AAACTGCAAAtG |
| CCR5-224 16 | 4 | 3 | 1 | | chr8: 4865886-4865914 | GTCtTCCTgATg | CTACC | AAACTGgAAAAG |
| CCR5-224 17 | 4 | 3 | 1 | | chr9: 14931072-14931100 | aaCATCCaCATC | ATGAA | AAACTGCAAAAa |
| CCR5-224 18 | 6 | 3 | 3 | | chr13: 65537258-65537286 | aTCtTCCTCATt | ACAGG | AAAaTGtAAtAG |
| CCR5-224 19 | 6 | 4 | 2 | CUBN | chr10: 17044849-17044877 | GgCtTCCTgAcC | CACGG | AAACTGtAAAtG |
| CCR5-224 20 | 6 | 5 | 1 | NID1 | chr1: 234244827-234244855 | GTtttTgCaCATt | TCAAT | tAACTGCAAAAG |
| CCR5-224 21 | 3 | 2 | 1 | | chr9: 80584200-80584229 | GTCAaCCTCAaC | ACCTAC | AgACTGCAAAAG |
| CCR5-224 22 | 4 | 1 | 3 | WWOX | chr16: 77185306-77185335 | GTCATCCTCcTC | CAACTC | cAAtGCtAAAG |
| CCR5-224 23 | 4 | 2 | 2 | AMBRA1 | chr11: 46422800-46422829 | GTCtTCCTCcTC | TGCACA | tcACTGCAAAAG |
| CCR5-224 24 | 4 | 2 | 2 | | chr1: 99456616-99456645 | GTgATaCTCATC | ATCAGC | AAtCTGCAtAAG |
| CCR5-224 25 | 4 | 2 | 2 | WBSCR17 | chr7: 70557254-70557283 | GTtATCCTCAgC | AAACTA | AAACTGgAAcAG |
| CCR5-224 25 | 4 | 2 | 2 | ITSN | chr21: 34098210-341398239 | cTCATgCTCATC | ATTTGT | tAACTGCAAAAt |
| CCR5-224 27 | 4 | 4 | 0 | | chr9: 106457399-106457428 | GcCAgtCTCAgC | ATGGTG | AAACTGCAAAAG |
| CCR5-224 28 | 4 | 4 | 0 | | chr17: 49929141-49929170 | cTCATtCTgtTC | ATGAAA | AAACTGCAAAAG |
| CCR5-224 29 | 5 | 3 | 2 | | chr15: 96714952-96714981 | GaagTCCTCATC | CCGAAG | AAACTGaAAgAG |
| CCR5-224 30 | 5 | 3 | 2 | ZNF462 | chr9: 108684858-108684887 | GTCtTCCTCtTt | CACATA | AAAcCGCAAAtG |
| CCR5-224 31 | 5 | 4 | 1 | | chr5: 101113644-101113673 | aTaATCCTttTC | TGTTTA | AAACaGCAAAAG |
| CCR5-224 32 | 5 | 4 | 1 | | chr17: 43908810-43908839 | GaCATCCaaATt | ACATGG | AAACTGaAAAAG |
| CCR5-224 33 | 5 | 5 | 0 | SDK1 | chr7: 3446932-3446961 | GTCtTgCTgtTg | CACCTC | AAACTGCAAAAG |
| CCR5-224 34 | 4 | 1 | 3 | SPTB(coding) | chr14: 64329872-64329901 | GTCATCCgCATC | GCCCTG | gAACTGgAAAAG |
| CCR5-224 35 | 4 | 2 | 2 | | chr10: 54268729-54268758 | aTCATCCTCAaC | AAACTA | AAACaGgAAAAG |
| CCR5-224 36 | 4 | 4 | 0 | KIAA1680 | chr4: 92322851-92322880 | GgaATgCcCATC | ACCACA | AAACTGCAAAAG |
| CCR5-224 37 | 5 | 5 | 0 | | chr5: 114708142-114708171 | GTttTgCTCcTg | TACTTC | AAACTGCAAAAG |

Table 4. Continued below; (+) half-sites SEQ ID NOs:190-226 descending; (−) half sites SEQ ID NOs:227-263 descending; full sequence with spacer descending SEQ ID NOs:264-300.

products. Indels and totals are not shown for those sites that were not tested. P-values shown are for the one-sided alternative hypothesis that the indel frequency is greater for active ZFN treated cells than for cells not expressing ZFN.

| in vitro selection stringency | | | | empty vector | | | active CCR5-224 | | | |
|---|---|---|---|---|---|---|---|---|---|---|
| 4 nM | 2 nM | 1 nM | 0.5 nM | indels | total | mutation frequency | indels | total | mutation frequency | p-value |
| X | X | X | X | 1 | 226676 | 0.00044% | 105639 | 240966 | 44% | 0 |
| X | X | X | X | 0 | 114904 | | 12856 | 130496 | 10% | 0 |
| X | X | | | 1 | 283015 | 0.00035% | 155 | 224000 | 0.070% | 0 |
| X | X | | | 2 | 297084 | 0.00067% | 3 | 245078 | 0.0012% | 0.26 |
| X | X | | | 0 | 147246 | | 0 | 136979 | | |
| X | | | X | 0 | 147157 | | 1 | 146283 | 0.00068% | 0.16 |
| X | | | | 0 | 316468 | | 0 | 313981 | | |
| X | | | | 0 | 136684 | | 0 | 94657 | | |
| X | | | | 0 | 178692 | | 52 | 146525 | 0.035% | 2.7E−13 |
| X | | | | 0 | 296730 | | 0 | 276961 | | |
| X | | | | 0 | 273436 | | 1045 | 308726 | 0.34% | 0 |
| X | | | | | | | | | | |
| X | | | | 0 | 168244 | | 1 | 171618 | 0.00058% | 0.16 |
| X | | | | 0 | 66317 | | 35 | 138728 | 0.025% | 1.6E−09 |
| X | | | | 1 | 427161 | 0.00023% | 280 | 393899 | 0.071% | 0 |
| X | | | | 0 | 190993 | | 32 | 171160 | 0.019% | 7.7E−09 |
| X | | | | 0 | 163704 | | 0 | 146176 | | |
| X | | | | 0 | 109939 | | 0 | 100948 | | |
| X | | | | | | | | | | |
| X | | | | 0 | 114743 | | 0 | 120169 | | |
| X | | | | 0 | 188149 | | 127 | 213248 | 0.060% | 0 |
| X | | | | 0 | 366156 | | 0 | 354878 | | |
| X | | | | 0 | 237240 | | 0 | 227568 | | |
| X | | | | 0 | 129468 | | 0 | 144274 | | |
| X | | | | 0 | 172543 | | 486 | 417198 | 0.12% | 0 |
| X | | | | 0 | 267772 | | 0 | 308093 | | |
| X | | | | 0 | 350592 | | 0 | 335281 | | |
| X | | | | 0 | 105012 | | 0 | 99968 | | |
| X | | | | 0 | 355674 | | 0 | 338910 | | |
| X | | | | 0 | 173646 | | 1 | 152744 | 0.00065% | 0.16 |
| X | | | | 1 | 245650 | 0.00041% | 0 | 185572 | | 0.84 |
| X | | | | 0 | 482635 | | 2 | 413317 | 0.00048% | 0.079 |
| X | | | | 0 | 237791 | | 0 | 200398 | | |
| | X | | | 0 | 180783 | | 0 | 167885 | | |
| | X | | | | | | | | | |
| | X | | | 0 | 165657 | | 2 | 153995 | 0.0013% | 0.079 |
| | X | | | 0 | 152083 | | 0 | 183305 | | |

Table 5. Potential CCR5-224 genomic off-target sites. The human genome was searched for DNA sequences surviving in vitro selection for CCR5-224 cleavage. Sites marked with an 'X' were found in the in vitro selection dataset. 'T' refers to the total number of mutations in the site, and '(+)' and '(−)' to the number of mutations in the (+) and (−) half-sites, respectively. Chromosomal coordinates from build 36 of the human genome are listed. Mutation frequency for each site is the percentage of sequences with insertions or deletions (indels) in the sequenced DNA from cultured K562 cells expressing active CCR5-224. Bolded red sites have significantly enriched indel percentages in the active nuclease sample compared to cells containing empty vector. The sequences of the sites are listed as 5' (+) halfsite/spacer/(−) half-site 3', therefore the (+) half-site is listed in the reverse sense as it is in the sequence profiles. Three sites were not tested since they did not yield site-specific PCR amplification

| CCR5-224 | | VF2468 | |
|---|---|---|---|
| # of mutations | # of sites in genome | # of mutations | # of sites in genome |
| 0 | 1 | 0 | 1 |
| 1 | 0 | 1 | 3 |
| 2 | 1 | 2 | 245 |
| 3 | 6 | 3 | 3,201 |
| 4 | 99 | 4 | 35,995 |
| 5 | 964 | 5 | 316,213 |
| 6 | 9,671 | 6 | 2,025,878 |
| 7 | 65,449 | | |
| 8 | 372,801 | | |
| 9 | 1,854,317 | | |

Table 6: There are many more potential genomic VF2468 target sites than CCR5-224 target sites. The human genome was computationally searched for sites up to nine mutations away from the canonical CCR5-224 target site and up to six mutations away from the canonical VF2468 target site. The number of occurrences of sites containing five or six base pair spacers in the genome, including repeated sequences, is listed in the table.

|  | # of sequences |
|---|---|
| BTBD10 (promoter) | |
| ATTTTGCAGTTT GCTTT GATGAGGAAAAC | |
| ATTTTGCAGTTT GCTTT GATGAGGAAAAC | 63 |
| ATTTTGCAGTTT GCTTTGCTTT GATGAGGAAAAC | 86 |
| ATTTTGCAGTTT GgTTTGCTTT GATGAGGAAAAC | 1 |
| ATTTTGCAGTTT GCTTTGGTTT GgTGAGGAAAAC | 1 |
| gTTTTGCAGTTT GCTTTGCTTT GATGAGGAAAAC | 1 |
| cTTTTGCAGgTT GCTTTGCTTT GATGAGGAAAAC | 1 |
| ATTTTGCAGTTT GCTTTGCTTT GATGtGGAAAAC | 1 |
| ATTTTGCAGTTT GCTTT GATGAGGAAAAC | 1 |
| chr17: 61624429-61624457 | |
| GTTTTGCAGTTC CTTTT GATGAAGATGAC | |
| GTTTTGCAGTTC CTTTT GATGAAGATGAC | 51 |
| GTTTTGGAGgTC CTTTT GATGAAGATGAC | 1 |
| TACR3 | |
| ACTTTACAGTTT ATGCT GATGAAGATGAC | |
| AGTTTACAGTTT ATGCT GATGAAGATGAC | 5 |
| ACTTTAGAGTTT ATGCT GATGAAGATGAC | 169 |
| gCTTTACAGTTT ATGCT GATGAAGATGAC | 1 |
| ACTTTACAGTTT ATGCT GATGAAGAatAC | 1 |
| ACTTTACAGTTT ATGCT GATGAAGATGtt | 1 |
| ACTTTACAGTTT ATGCT GATGAAGATGAC | 34 |
| ACTTTACgGTTT ATGCT GATGAAGATGAC | 1 |
| ACTTTACAGTTT ATGCT GATGAAGATGAC | 180 |
| ACTTTACAGTTT ATGCT GATGAAGATGcC | 1 |
| ACTTTACAGTTT ATGCTATGCT GATGAAGATGAC | 507 |
| gCTTTACAGTTT ATGCTATGCT GATGAAGATGAC | 1 |
| ACTTTACgGTTT ATGCTATGCT GATGAAGATGAC | 1 |
| ACTTTACAGTTT ATGCTATGCT GATGAtGATGAC | 1 |
| ACgTTACAGTTT ATGCTATGCT GATGAAGATGAC | 1 |
| ACTTTACAGTTT ATGCT GATGAAGATGAC | 140 |
| ACTTTACAGTTT ATGCT GATGAAGATGtC | 1 |
| WBSCR17 | |
| GTTATCCTCAGC AAACTA AAACTGGAACAG | |
| GTTATCCTCAGC AAACTAACTA AAACTGGAACAG | 128 |
| GTTATCCTCAGC AAACTA AAACTGGAACAG | 118 |
| GTTATCCTCAGC AAACTA AAACTGGgACAG | 1 |
| GTTATCCTCAGC AAACTA AAACTGGAcCAG | 1 |
| GTTATaCTCAGC AAACTA AAACTGGAACAG | 1 |
| GTTATCCTCAGC AAACTA AAAGTGGAACAG | 116 |
| aTTATCCTCAGC AAACTA AAACTGGAACAG | 1 |

|  | # of sequences |
|---|---|
| GTTATCCTtAGC AAACTA AAACTGGAACAG | 1 |
| GTTATCCTCAGC AAACTA AAACTGGAACAG | 118 |
| GaTATCCTCAGC AAACTA AAACTGGAACAG | 1 |
| chr6: 52114315-52114343 | |
| CTTTTTCAGTTT CTTTT GCTGAGCAGGAC | |
| CTTTTTCAGTTT CTTTT GCTGAGCAGGAC | 35 |
| KCNB2 | |
| CATTTGCAGTTT CGGGA GATGAGGAACAT | |
| CATTTGGAGTTT CGGGAGA GATGAGGAACAT | 15a |
| CATTTGCAGTTa CGGGAGA GATGAGGAACAT | 1 |
| CATTTGGAGTTT CGGGAGA GATGAGGgACAT | 1 |
| CATTTGacGcTT CGGGAGA GgTGAGGgACAT | 1 |
| CATTTGGAGTTT CGGGCGGGA GATGAGGAACAT | 109 |
| CATTTGCAGTTT CGGGCGGGA GATGcGGAACAT | 1 |
| CATTTGGAGTTT CGGGCGGGc GATGAGGAACAT | 1 |
| CATTTGCAGTTT CGGGCGGGA GgTGAGGAACAT | 1 |
| CgTTTGCAGTTT CGGGCGGGA GATGAGGAACAT | 2 |
| CATTTGCtGTTT CGGGCGGGA GATGAGGAACAT | 1 |
| CATTTGCAGTTT CGGGCGGGA GATGAGGAcCAT | 1 |
| CATTTGGAGTTT CGGGCGGGA GgTGAGGAAGAT | 1 |
| CcTTTGCAGTTT CGGGCGGGA GATGAGGAACAT | 1 |
| CATTTGCAGTTg CGGGCGGGA GATGAGGAACAT | 1 |
| chr8: 4865886-4865914 | |
| GTCTTCCTGATG CTACC AAACTGGAAAAG | |
| GTCTTCCTGATG CTACC AAACTGGAAAAG | 30 |
| GTCTTCCTGATG CTACC AAACTtGAAAAG | 1 |
| GTCTTCaTGATG CTACC AAACTGGAAAAG | 1 |
| chr9: 80584200-80584229 | |
| CTTTTGCAGTCT GTAGGT GTTGAGGTTGAC | |
| CTTTTGCAGTCT GTAGGT GTTGAGGTTGAC | 125 |
| CTTTTGCAGTCT GTAGGT GTTGAGGTTGAC | 1 |
| CTTTTGGAGICT GTAGGT GTTGAGGTTGAC | 1 |

Table 7: Sequences of CCR5-224-mediated genomic DNA modifications identified in cultured human K562 cells (SEQ ID NOs:301-365, descending, then left to right). Sequences with insertions (blue) and deletions (red) identified after sequencing potential CCR5-224 off-target sites from cultured K562 cells expressing CCR5-224 are shown. The numbers of occurrences are shown to the right of each sequence. Other mutations are indicated with lowercase letters and likely reflect mutations that arose during PCR or sequencing. The unmodified site is listed under the gene name or coordinates (build 36), and the spacer sequence is underlined.

| | muta-tions | | | | build 36 coordinates | (+) half-site | spacer | (−) half-site | In vitro selection frequency | | | | empty vector | | | active VF2468 | | | |
|---|---|---|---|---|---|---|---|---|---|---|---|---|---|---|---|---|---|---|---|
| | T | (+) | (−) | gene | | | | | 4 nM | 2 nM | 1 nM | 0.5 nM | indels | total | mutation frequency | indels | total | mutation frequency | p-value |
| VF2468 1 | 0 | 0 | 0 | VEGF-a (promoter) | chr8:43,846,383-43,845,415 | AGCAGCGTC | TTCGA | GAGTGAGGA | X | X | X | X | 125 | 147187 | 0.086% | 27067 | 188786 | 1.4% | 0 |
| VF2468 2 | 1 | 1 | 0 | | chr1:168,832,550-168,832,672 | AGCAGCGTC | AATAC | GAGTGAaGA | X | X | X | X | ☐ | 57855 | | 1 | 62196 | 0.0016% | 0.16 |
| VF2468 3 | 1 | 1 | 0 | | chr1:242,574,122-242,574,144 | AGCAGCctC | TGCTT | GAGTGAGGA | X | X | X | X | ☐ | 167447 | | 0 | 147340 | 0 | 0 |
| VF2468 4 | 1 | 1 | 0 | ZNF683 | chr1:26,989,668-26,569,690 | AGCAGCGTt | GGGAG | GAGTGAGGA | X | X | X | X | ☐ | 111340 | | 0 | 109365 | 0 | 0 |
| VF2468 5 | 2 | 0 | 2 | GSG1L | chr16:27,853,984-27,854,006 | AGCAGCGTC | AAAAA | cAGTGAGcA | X | X | X | X | ☐ | 80047 | | 0 | 69080 | 0 | 0 |
| VF2468 6 | 2 | 0 | 2 | C5orF98 | chr9:134,636,934-134,636,956 | AGCAGCGTC | GTGTG | GtGTGAGGt | X | X | X | X | | | | | | | |
| VF2468 7 | 2 | 0 | 2 | EFHD1 | chr2:233,205,384-233,205,477 | AGCAGCGTC | GTTCTC | cAGTGgGGA | X | X | X | X | ☐ | 202694 | | 0 | 204809 | 0 | 0 |
| VF2468 8 | 2 | 0 | 2 | | chr20:30,234,845-30,234,968 | AGCAGCGTC | TAGCA | GAGgGAaGA | X | X | X | X | ☐ | 160769 | | 1 | 158886 | 0.00063% | 0.16 |
| VF2468 9 | 2 | 0 | 2 | KIAA0841 (exon-intron) | chr18:40,800,787-40,800,820 | AGCAGCGTC | TAGGGG | GAcgGAGGG | X | X | X | X | 1 | 81184 | 0.0012% | 446 | 79138 | 0.58% | 0 |
| VF2468 10 | 2 | 0 | 2 | CE37 | chr16:54,501,918-54,501,941 | AGCAGCGTC | TCAAAA | GAGTGtGcA | X | X | X | X | 1 | 168501 | 0.00059% | 0 | 144701 | 0 | 0.84 |
| VF2468 11 | 2 | 0 | 2 | PTK2B | chr8:27,338,866-27,229,978 | AGCAGCGTC | TCCCTT | GAGTGAtCg | X | X | X | X | 0 | 178602 | | 58 | 138849 | 0.040% | 3.8E-14 |
| VF2468 12 | 2 | 0 | 2 | | chr8:137,316,488-137,316,621 | AGCAGCGTC | TGAAA | GAGTGAaaA | X | X | X | X | 0 | 286630 | | 186 | 254714 | 0.086% | 0 |
| VF2468 13 | 2 | 1 | 1 | | chr20:7,985,471-7,985,493 | AGCAGCGTC | ATCGA | GAGTGAGGt | X | X | X | X | ☐ | 166914 | | 0 | 148547 | 0 | 0 |
| VF2468 14 | 2 | 1 | 1 | | chrY:8,461,018-8,461,041 | AGCaGCGTC | AGATAG | GgGTGAGGG | X | X | X | X | | | | | | | |
| VF2468 15 | 2 | 1 | 1 | | chr1:63,720,888-63,720,480 | AGCaGCGTC | ATATT | cAGTGAGGA | X | X | X | X | 0 | 328680 | | 146 | 290700 | 0.060% | 0 |

-continued

| | muta-tions T (+) (-) | gene | build 36 coordinates | (+) half-site | spacer | (-) half-site | In vitro selection frequency 4nM 2nM 1nM 0.5nM | empty vector indels | total | mutation frequency | active VF2468 indels | total | mutation frequency | p-value |
|---|---|---|---|---|---|---|---|---|---|---|---|---|---|---|
| VF2468 16 | 2 1 1 | | chrX:122,132,519-122,132,541 | AGCAGCGTC | GTAGT | GAtTGAGGA | X X X X | □ | 157651 | | 0 | 136373 | 0 | |
| VF2468 17 | 2 1 1 | F4HA1 | chr10:74,506,346-74,506,368 | AGCAcCGTC | TTTTC | tAGTGAGGA | X X X X | | | | | | | |
| VF2468 18 | 2 1 1 | DFKZp488L07201 | chrX:58,830,910-68,830,833 | AGCAGaGTC | AGACTT | GAGTGAGGt | X X X X | 0 | 13880 | | 13 | 12338 | 0.10% | 0.00016 |
| VF2468 19 | 2 1 1 | TTC4 | chr1:64,881,886-64,831,917 | AGCAGaGTC | TCTGA | GAGTGAGGc | X X X X | 0 | 176808 | | 183 | 191327 | 0.086% | 0 |
| VF2468 20 | 2 1 1 | | chr1:175,647,668-175,647,690 | AGCAGCaTC | AGTGA | GAGTGAGGc | X X X X | 1 | 286818 | 0.00035% | 3 | 343497 | 0.00087% | 0.20 |
| VF2468 21 | 2 1 1 | | chr1:50,490,333-50,490,356 | GAGTGAGGc | TCCAAA | GAGTGAGGc | X X X X | □ | 168032 | | 0 | 183289 | 0 | |
| VF2468 22 | 2 1 1 | | chr4:128,244,847-128,244,870 | AGCAGCcTC | TGCATC | GAGTGAGGt | X X X X | □ | 86347 | | 0 | 87663 | 0 | |
| VF2468 23 | 2 1 1 | | chr13:27,399,187-27,399,210 | AGCAGCGaC | GCCTGG | GAGTGAGGt | X X X X | 0 | 23198 | | 384 | 34466 | 1.1% | 0 |
| VF2468 24 | 2 1 1 | | chr18:82,803,202-82,803,328 | AGCAGCGTa | TCACAT | GAGTGAGGg | X X X X | 0 | 57001 | | 283 | 83341 | 0.44% | 0 |
| VF2468 25 | 2 1 1 | | chr11:69,063,501-69,063,523 | AGCAGCGTg | CCCAA | GAGTGAGGc | X X X X | □ | 181022 | | 0 | 221989 | 0 | |
| VF2468 26 | 2 1 1 | TNR | chr1:173,885,442-172,885,465 | AGCAGCtTC | AGGGGA | GtGTGAGGA | X X X X | □ | 132693 | | 0 | 139071 | 0 | |
| VF2468 27 | 2 1 1 | PTPRM | chr18:8,320,310-6,320,332 | AGCAGCtTC | CTTTT | GAGTGAGGA | X X X X | □ | 73084 | | 0 | 100249 | 0 | |
| VF2468 28 | 2 1 1 | | chr12:26,724,684-26,724,688 | AGCAGCtTC | TCCTTGG | GAGTGAGGg | X X X X | 0 | 323231 | | 1116 | 353441 | 0.32% | 0 |
| VF2468 29 | 2 1 1 | | chr13:82,039,140-82,039,183 | AGCAGgGTC | AGGGCT | GAGTGAGGc | X X X X | 0 | 168241 | | 439 | 188937 | 0.28% | 0 |
| VF2468 30 | 2 1 1 | | chr3:131,201,886-131,201,818 | AGCAGtGTC | AGGCTG | GtGTGAGGA | X X X X | 0 | 77427 | | 1980 | 82791 | 2.1% | 0 |

-continued

| | muta-tions T (+) (−) | gene | build 36 coordinates | (+) half-site | spacer | (−) half-site | In vitro selection frequency 4 nM | 2 nM | 1 nM | 0.5 nM | empty vector indels | total | mutation frequency | active VF2468 indels | total | mutation frequency | p-value |
|---|---|---|---|---|---|---|---|---|---|---|---|---|---|---|---|---|---|
| VF2468 31 | 2 1 1 | | chr3:76,708,387-76,709,410 | AGCAgtGTC | AGGCTG | GtGTGAGGA | X | X | X | X | 0 | 34408 | | 114 | 33070 | 0.34% | 0 |
| VF2468 32 | 2 1 1 | | chr11:3,668,299-3,668,322 | AGCAgtGTC | AGGCTG | GtGTGAGGA | X | X | X | X | 0 | 19830 | | 19 | 17408 | 0.11% | 8.6E-08 |
| VF2468 33 | 2 1 1 | | chr3:128,870,762-128,870,786 | AGCAgtGTC | AGGCTG | GtGTGAGGA | X | X | X | X | 0 | 89879 | | 2570 | 90901 | 2.8% | 0 |
| VF2468 34 | 2 1 1 | | chr11:71,030,884-71,030,907 | AGCAgtGTC | AGGCTG | GtGTGAGGA | X | X | X | X | 0 | 112449 | | 231 | 150276 | 0.16% | 0 |
| VF2468 35 | 2 1 1 | 8BF2/U80788 | chr11:8,884,211-8,884,234 | AGCAgtGTC | CTAAGG | GgGTGAGGA | X | X | X | X | 0 | 418083 | | 885 | 532186 | 0.13% | 0 |
| VF2468 36 | 2 1 0 | KRI1 (coding) | chr19:10,534,492-10,534,515 | AGCAtCGTC | ATCAGA | cAGTGAGGA | X | X | X | X | | 141739 | | 0 | 1393668 | | |
| VF2468 37 | 2 1 0 | | chr8:112,421,478-112,421,498 | AGCAtCGTC | TGAAGT | GAGTGAGGA | X | X | X | X | 0 | 153887 | | 1174 | 178569 | 0.88% | 0 |
| VF2468 38 | 2 1 0 | MICAL3/KIAA1384 | chr22:18,713,914-18,713,837 | AGCAtCGTC | TTCTGT | GAGTGAGtA | X | X | X | X | 0 | 287706 | | 176 | 283796 | 0.82% | 0 |
| VF2468 39 | 2 1 0 | MUC16 (exon-intron) | chr19:8,894,218-8,894,241 | AGgAGCGTC | TCACCT | GAGTGAGGc | X | X | X | X | | 212038 | | 0 | 219913 | | |
| VF2468 40 | 2 2 0 | | chr8:6,638,000-6,628,023 | AaCAGcTTC | ATCTCG | GAGTGAGGA | X | X | X | X | | 132803 | | 0 | 147070 | | |
| VF2468 41 | 2 2 0 | PREX1 | chr20:46,733,644-36,733,667 | AaCAGcTTC | TCGGGA | GAGTGAGGA | X | X | X | X | | 204408 | | 0 | 227091 | | |
| VF2468 42 | 2 2 0 | CDH20 | chr18:57,303,454-57,303,477 | AaCAGcTTC | TCTGAG | GAGTGAGGA | X | X | X | X | 1 | 313747 | 0.00032% | 1 | 403382 | 0.00025% | 0.57 |
| VF2468 43 | 2 2 0 | | chr20:6,213,500-6,213,522 | AGCAaaGTC | AAACA | GAGTGAGGA | X | X | X | X | 1 | 154154 | 0.00065% | 0 | 183644 | | 0.84 |
| VF2468 44 | 2 2 0 | | chr5:85,841,208-65,841,331 | AGCAGcGTC | TGGAA | GAGTGAGGA | X | X | X | X | | | | | | | |
| VF2468 45 | 2 2 0 | | chr8:20,481,270-20,481,292 | AGCAaCTTC | AATTG | GAGTGAGGA | X | X | X | X | | 250890 | | 0 | 297104 | | |

-continued

| | muta-tions | | | | | (+) half-site | spacer | (-) half-site | In vitro selection frequency | | | | empty vector | | | active VF2468 | | |
|---|---|---|---|---|---|---|---|---|---|---|---|---|---|---|---|---|---|---|
| | T | (+) | (-) | gene | build 36 coordinates | | | | 4 nM | 2 nM | 1 nM | 0.5 nM | indels total | mutation frequency | | indels total | mutation frequency | p-value |
| VF2468 46 | 2 | 2 | 0 | | chr5:95,417,045-96,417,068 | AGCAcCaTC | ATAGCA | GAGTGAGGA | X | X | X | X | ☐ | 274402 | | 1 | 319493 | 0.00031% | |
| VF2468 47 | 2 | 2 | 0 | RCRA | chr15:59,165,302-59,165,325 | AGCAGCaTa | GATATG | GAGTGAGGA | X | X | X | X | ☐ | 270263 | | 1 | 358704 | 0.00028% | 0.16 |
| VF2468 48 | 2 | 2 | 0 | | chr6:24,504,489-24,504,511 | AGCAGCaTa | TCAGG | GAGTGAGGA | X | X | X | X | ☐ | 103878 | | 0 | 176333 | | |
| VF2468 49 | 2 | 2 | 0 | | chr3:31,085,287-31,085,309 | AGCAGCGag | AAAGA | GAGTGAGGA | X | X | X | X | ☐ | 542052 | | 0 | 708517 | | |
| VF2468 50 | 2 | 2 | 0 | | chr6:27,579,690-27,579,712 | AGCAGCGgt | CTTAG | GAGTGAGGA | X | X | X | X | ☐ | 177732 | | 1 | 212250 | 0.00047% | 0.16 |
| VF2468 51 | 2 | 2 | 0 | | chr12:113,410,592-113,410,615 | AGCAGgGTt | CTTCAA | GAGTGAGGA | X | X | X | X | ☐ | 294783 | | 0 | 302167 | | |
| VF2468 52 | 2 | 2 | 0 | | chr11:11,399,534-11,399,556 | AGCtGaGTC | CTAAA | GAGTGAGGA | X | X | X | X | ☐ | 482765 | | 1 | 402831 | 0.00025% | 0.16 |
| VF2468 53 | 2 | 2 | 0 | MCTP1 | chr5:94,590,016-94,590,038 | AGCtGaGTC | TTAAG | GAGTGAGGA | X | X | X | X | ☐ | 183510 | | 1 | 202083 | 0.00049% | 0.16 |
| VF2468 54 | 2 | 2 | 0 | | chr1:13,394,902-13,394,924 | AGCtGgGTC | ATGAG | GAGTGAGGA | X | X | X | X | ☐ | 88944 | | 0 | 105879 | | |
| VF2468 55 | 2 | 2 | 0 | PRAMEF20 | chr1:13,615,741-13,615,763 | AGCtGgGTC | ATGAG | GAGTGAGGA | X | X | X | X | | | | | | | |
| VF2468 56 | 2 | 2 | 0 | | chr20:59,154,784-59,154,806 | AGCtGtGTC | CACAG | GAGTGAGGA | X | X | X | X | ☐ | 360710 | | 0 | 351215 | | |
| VF2468 57 | 2 | 2 | 0 | | chr14:100,903,675-100,903,697 | AGCtGtGTC | TTGGA | GAGTGAGGA | X | X | X | X | ☐ | 140671 | | 0 | 157922 | | |
| VF2468 58 | 2 | 2 | 0 | | chrX:141,701,170-141,701,192 | AGtAGcGgC | AAATT | GAGTGAGGA | X | X | X | X | ☐ | 196624 | | 0 | 209781 | | |
| VF2468 59 | 2 | 2 | 0 | GTF3C1 | chr16:27,452,953-27,452,975 | AGtgGCGTC | CCAGT | GAGTGAGGA | X | X | X | X | ☐ | 223714 | | 0 | 246196 | | |
| VF2468 60 | 2 | 2 | 0 | DNMBP/AKD89111 | chr10:101,688,961-101,688,983 | gGcAGaGTC | CTAGA | GAGTGAGGA | X | X | X | X | ☐ | 302495 | | 0 | 383303 | | |

-continued

| muta-tions T (+) (-) | gene | build 36 coordinates | (+) half-site | spacer | (-) half-site | In vitro selection frequency 4nM 2nM 1nM 0.5nM | empty vector indels | empty vector total | empty vector mutation frequency | active VF2468 indels | active VF2468 total | active VF2468 mutation frequency | p-value |
|---|---|---|---|---|---|---|---|---|---|---|---|---|---|
| VF2468 61  3  2  0 |  | chr6:137,852,455-137,852,478 | tcCAGCGTC | CTCCCA | GAGTGAGGA | X X X X | □ | 84153 |  | 0 | 113996 |  |  |
| VF2468 62  3  2  0 | 3ARDH | chr9:136,682,239-136,692,282 | tGCAGCGgC | GTAGGG | GAGTGAGGA | X X X X |  | 191187 |  | 138 | 212086 | 0.086% | 0 |
| VF2468 63  3  2  0 |  | chr7:19,683,400-19,683,423 | tGCAGCGTt | AAAATA | GAGTGAGGA | X X X X | 1 | 372808 | 0.00027% | 2 | 438355 | 0.00046% | 0.33 |
| VF2468 64  3  2  0 | ZNF62B | chr19:60,683,246-60,683,269 | tGCAGgGTC | GGGCAG | GAGTGAGGA | X X X X | □ | 167551 |  | 0 | 185442 |  |  |
| VF2468 65  3  2  0 |  | chr3:130,430,426-130,430,448 | tGCAgtGTC | CACAA | GAGTGAGGA | X X X X |  |  |  |  |  |  |  |
| VF2468 66  3  1  2 | GBF1 | chr10:104,073,889-104,074,012 | AGCAaCGTC | CATAGT | GtGTGAGaA | X X X X | 4 | 646643 | 0.00073% | 3768 | 687393 | 0.84% | 0 |
| VF2468 67  3  1  2 |  | chr14:96,561,728-96,561,751 | AGCAaCGTC | TAACCC | GAGTGttGA | X X X X | □ | 171147 |  | 0 | 203860 |  |  |
| VF2468 68  3  1  2 | PDE9A | chr21:42,882,083-42,932,106 | AGCAcCGTC | CCCCT | cAGTGAGGc | X X X X | 0 | 88878 |  | 381 | 137234 | 0.28% | 0 |
| VF2468 69  3  1  2 | MTX2 | chr2:178,842,448-176,842,470 | AGCAGCGgC | GGCTG | cAGTGAGGc | X X X X | 0 | 38342 |  | 153 | 60273 | 0.30% | 0 |
| VF2468 70  3  1  2 |  | chr6:104,071,040-104,071,063 | AGCAGCCgC | TTAAGG | GgGTGAGGt | X X X X | □ | 252020 |  | 0 | 277262 |  |  |
| VF2468 71  3  1  2 |  | chr3:32,220,862-32,220,885 | AGCAgtGTC | TAAAAG | GAGTGAGat | X X X X | □ | 178243 |  | 0 | 225921 |  |  |
| VF2468 72  3  1  1 |  | chr2:11,428,186-11,428,218 | AGaAaCGTC | GTGGAG | GAGTGAGGg | X X X X | 0 | 138844 |  | 84 | 221878 | 0.042% | 0 |
| VF2468 73  3  1  1 | OPH6 | chr8:47,881,416-47,891,438 | AGCAaaGTC | TGTACT | GAGTGAGGg | X X X X | 0 | 182686 |  | 2808 | 212729 | 1.3% | 0 |
| VF2468 74  3  1  1 |  | chr2:195,362,417-195,362,439 | AGCAaCaTC | ATCTT | GAGTGAGGg | X X X X | □ | 103739 |  | 1 | 130605 | 0.00077% | 0.16 |
| VF2468 75  3  1  1 | MPOL1 | chr14:36,952,701-36,952,724 | AGCAaCaTC | TGGTG | GAGTGAGGg | X X X X | 1 | 300572 | 0.00033% | 0 | 355283 |  | 0.84 |

-continued

| | muta-tions | | | build 36 coordinates | (+) half-site | spacer | (−) half-site | In vitro selection frequency | | | | empty vector | | | active VF2468 | | |
|---|---|---|---|---|---|---|---|---|---|---|---|---|---|---|---|---|---|
| T | (+) | (−) | gene | | | | | 4 nM | 2 nM | 1 nM | 0.5 nM | indels | total | mutation frequency | indels | total | mutation frequency | p-value |
| VF2468 76 | 3 | 2 | 1 | | chr4:138,603,959-138,603,981 | AGCAaCtTC | ATCTT | GAGTGAGg | X | X | X | X | ☐ | 185773 | | 0 | 185094 | |
| VF2468 77 | 3 | 2 | 1 | LRCH1 | chr13:46,079,921-46,079,943 | ATCAaCtTC | CTGGC | GAGTGAGg | X | X | X | X | 1 | 131239 | 0.00076% | 0 | 133319 | 0.84 |
| VF2468 78 | 3 | 2 | 1 | KIAA0888 | chr11:116,282,384-116,282,408 | AGCAatGTC | AAAA | GAGTGAGc | X | X | X | X | 0 | 212883 | | 243 | 167434 | 0.16% 0 |
| VF2468 79 | 3 | 2 | 1 | | chr12:13,363,829-13,363,861 | AGCAcCGTg | GCTTC | GAGTGAGc | X | X | X | X | 0 | 112164 | | 34 | 118886 | 0.029% 2.7E-09 |
| VF2468 80 | 3 | 2 | 1 | PLMXMA4 (coding) | chr7:131,503,708-131,603,730 | AGCAcgGTC | ATGAT | GAGTGAGc | X | X | X | X | 0 | 186677 | | 77 | 188336 | 0.041% 0 |
| VF2468 81 | 3 | 2 | 1 | TSPEAR | chr21:44,817,259-44,817,282 | AGCAGCggc | CCACAG | GAGTGAGg | X | X | X | X | 1 | 151845 | 0.00066% | 0 | 144107 | 0.84 |
| VF2468 82 | 3 | 2 | 1 | | chr18:74,634,790-74,634,812 | AGCAGCagC | TAGGG | GAGTGAGg | X | X | X | X | | | | | | |
| VF2468 83 | 3 | 2 | 1 | | chr10:33,904,306-33,9-4,328 | AGCAGCtcC | TCTCC | GAGTGAGt | X | X | X | X | ☐ | 240952 | | 1 | 233954 | 0.00043% 0.16 |
| VF2468 84 | 3 | 2 | 1 | | chr6:170,226,156-170,226,178 | AGCAGgGTg | GCGTG | GAGTGAGc | X | X | X | X | ☐ | 191108 | | 0 | 167663 | |
| VF2468 85 | 3 | 2 | 1 | | chr3:118,684,878-118,684,901 | AGCAtaGTC | TAGGCC | GAGTGAGc | X | X | X | X | 0 | 406843 | | 209 | 366897 | 0.068% 0 |
| VF2468 86 | 3 | 2 | 1 | HRA3L3 | chr3:194,462,126-184,462,147 | AGCAtgGTC | CAAG | GAGTGAGg | X | X | X | X | 0 | 212842 | | 383 | 247078 | 0.18% 0 |
| VF2468 87 | 3 | 2 | 1 | | chr17:18,434,608-19,434,531 | AGCAttGTC | TCATGT | GAGTGAGt | X | X | X | X | 0 | 4171 | | 18 | 3024 | 0.60% 1.0E-06 |
| VF2468 88 | 3 | 2 | 1 | | chr8:126,882,679-126,932,801 | AGCAttGTC | TCCTG | GAGTGAGg | X | X | X | X | 0 | 116887 | | 58 | 116268 | 0.061% 7.8E-16 |
| VF2468 89 | 3 | 2 | 1 | UHRF1BP1L | chr12:99,011,715-99,011,737 | AGtAGCGTt | TTTAG | GAGTGAGt | X | X | X | X | 1 | 171873 | 0.00058% | 0 | 207336 | 0.84 |
| VF2468 90 | 3 | 2 | 1 | | chr14:762,405-14,762,427 | AtCAGaGTC | TCTGG | GAGTGAGc | X | X | X | X | 2 | 193447 | 0.0010% | 1 | 196665 | 0.00051% 0.72 |

-continued

| | muta-tions | | | | build 36 coordinates | (+) half-site | spacer | (−) half-site | In vitro selection frequency | | | | empty vector | | | active VF2468 | | |
|---|---|---|---|---|---|---|---|---|---|---|---|---|---|---|---|---|---|---|
| | T | (+) | (−) | gene | | | | | 4 nM | 2 nM | 1 nM | 0.5 nM | indels | total | mutation frequency | indels | total | mutation frequency p-value |
| VF2468 91 | 3 | 2 | 1 | LAMB3 (promoter) | chr1:207,894,357-207,894,382 | AtCAGtGTC | CCTCAG | GAGTGAGGc | X | X | X | X | ☐ | 107549 | | 0 | 109933 | |
| VF2468 92 | 3 | 2 | 1 | BRUNOL4 | chr18:33,160,009-33,160,032 | gGCAGaGTC | AGGGCT | GAGTGAGGc | X | X | X | X | ☐ | 71298 | | 0 | 77229 | |
| VF2468 93 | 3 | 2 | 1 | | chr16:84,004,297-84,004,320 | gGCAGCGgC | CGCTGT | GAGTGAGGt | X | X | X | X | ☐ | 99279 | | 0 | 121284 | |
| VF2468 94 | 3 | 2 | 1 | DFKZp586E1619/ BRD1 | chr22:48,558,064-48,558,086 | tGCAGCtTC | ATGGT | GAGTGAGGc | X | X | X | X | ☐ | 152551 | | 0 | 206428 | |
| VF2468 95 | 3 | 3 | 0 | | chr7:22,054,784-22,054,907 | AGCAtaGTt | ACCTGG | GAGTGAGGA | X | X | X | X | ☐ | 91338 | | 0 | 134004 | |
| VF2468 96 | 3 | 3 | 0 | | chr14:25,876,126-25,876,149 | AGtAaaGTC | TAAGTA | GAGTGAGGA | X | X | X | X | ☐ | 245402 | | 0 | 345728 | |
| VF2468 97 | 4 | 3 | 1 | CNNM2 | chr10:104,716,593-104,716,615 | tGCAGctTC | CTTGG | GAGTGAGGt | X | X | X | X | ☐ | 76762 | | 0 | 92742 | |

Table 8: Potential VF2468 genomic off-target sites. DNA for 90 out of 97 potential VF2468 genomic target sites were amplified by PCR from cultured K562 cells expressing active VF2468 ZFN or from cells containing empty expression vector (SEQ ID NOs: 366-653). Mutation frequency for each site is the percentage of sequences with insertions or deletions (indels) in the sequenced DNA from cultured K562 cells expressing active VF2468. Bolded red sites have significantly enriched indel percentages in the active nuclease sample compared to cells not expressing nuclease. The sequences of the sites are listed as 5' (+) halfsite (SEQ ID NOs: 366-461)/spacer/(−) half-site 3' (SEQ ID NOs:462-557) (Full sequences are SEQ ID NOs: 558-653), therefore the (+) half-site is listed in the reverse sense as it is in the sequence profiles. Seven sites were not tested since they did not yield site-specific PCR amplification products. Indels and totals are not shown for those sites that were not tested. P-values shown are for the one-sided alternative hypothesis that the indel frequency is greater for active ZFN treated cells than for cells not expressing ZFN.

| oligonucleotide name | oligonucleotide sequence (5'→3') |
| --- | --- |
| N5-PvuI | NNNNNCGATCGTTGGGAACCGGA |
| CCR5-224-N4 | NG*T*C*A*T*C*C*T*C*A*T*C*NNNNA*A*A*C*T*G*C*A*A*A*A*G*NCAGTGGAACGAA |
| CCR5-224-N5 | NG*T*C*A*T*C*C*T*C*A*T*C*NNNNNA*A*A*C*T*G*C*A*A*A*A*G*NCAGTGGAACGAAAACTCACG |
| CCR5-224-N6 | NG*T*C*A*T*C*C*T*C*A*T*C*NNNNNNA*A*A*C*T*G*C*A*A*A*A*G*NCAGTGGAACGAAAACTCACG |
| CCR5-224-N7 | NG*T*C*A*T*C*C*T*C*A*T*C*NNNNNNNA*A*A*C*T*G*C*A*A*A*A*G*NCAGTGGAACGAAAACTCACG |
| VF2468-N4 | NA*G*C*A*G*C*G*T*C*NNNNG*A*G*T*G*A*G*G*A*NCAGTGGAACGAAAACTCACG |
| VF2468-N5 | NA*G*C*A*G*C*G*T*C*NNNNNG*A*G*T*G*A*G*G*A*NCAGTGGAACGAAAACTCACG |
| VF2468-N6 | NA*G*C*A*G*C*G*T*C*NNNNNNG*A*G*T*G*A*G*G*A*NCAGTGGAACGAAAACTCACG |
| VF2468-N7 | NA*G*C*A*G*C*G*T*C*NNNNNNNG*A*G*T*G*A*G*G*A*NCAGTGGAACGAAAACTCACG |
| test fwd | GCGACACGGAAATGTTGAATACTCAT |
| test rev | CAGCGAGTCAGTGAGCGA |
| adapter1 | ACACTCTTTCCCTACACGACGCTCTTCCGATCTT |
| adapter1(AAT) | ACACTCTTTCCCTACACGACGCTCTTCCGATCTAATT |
| adapter1(ATA) | ACACTCTTTCCCTACACGACGCTCTTCCGATCTATAT |
| adapter1(TAA) | ACACTCTTTCCCTACACGACGCTCTTCCGATCTTAAT |
| adapter1(CAC) | ACACTCTTTCCCTACACGACGCTCTTCCGATCTCACT |
| adapter2 | /5Phos/AGATCGGAAGAGCGGTTCAGCAGGAATGCCGAG |
| adapter2(AAT) | /5Phos/ATTAGATCGGAAGAGCGGTTCAGCAGGAATGCCGAG |
| adapter2(ATA) | /5Phos/TATAGATCGGAAGAGCGGTTCAGCAGGAATGCCGAG |
| adapter2(TAA) | /5Phos/TTAAGATCGGAAGAGCGGTTCAGCAGGAATGCCGAG |
| adapter2(CAC) | /5Phos/GTGAGATCGGAAGAGCGGTTCAGCAGGAATGCCGAG |
| PE1 | CAAGCAGAAGACGGCATACGAGATCGGTCTCGGCATTCCTGCTGAACCGCTCTTCCGATC |
| PE2 | AATGATACGGCGACCACCGAGATCTACACTCTTTCCCTACACGACGCTCTTCCGATCT |
| CCR5-224 1 fwd | ATACATCGGAGCCCTGCCAA |
| CCR5-224 1 rev | GGAAAAACAGGTCAGAGATGGC |
| CCR5-224 2 fwd | TCCTGCCTCCGCTCTACTCG |
| CCR5-224 2 rev | ACCCCAAAGGTGACCGTCCT |
| CCR5-224 3 fwd | TCCCACGTTTTCCCCTTGAC |
| CCR5-224 3 rev | GTCCCTCACGACGACCGACT |
| CCR5-224 4 fwd | GCACTGCCCCCAGAAATATTGGTT |
| CCR5-224 4 rev | TGGTTTGTTGGGGGATCAGG |
| CCR5-224 5 fwd | ATGCCACCCCTGCCAGATAA |
| CCR5-224 5 rev | GCCTACCTCAATGCAGGCAAA |

-continued

| oligonucleotide name | oligonucleotide sequence (5'→3') |
|---|---|
| CCR5-224 6 fwd | TCTGCTTCTGCCCTTCTGGA |
| CCR5-224 6 rev | GGAGGATCGCCAAGACCTGA |
| CCR5-224 7 fwd | CCCCAGTGCTTAACATAGTTCTTGG |
| CCR5-224 7 rev | ACTCCCAGACAAACCCCGCT |
| CCR5-224 8 fwd | GGCACCAGAACTTACTCACTGCC |
| CCR5-224 8 rev | TGTGAAGGCCCAAAACCCTG |
| CCR5-224 9 fwd | GTTTTGGGGGTCATGGCAAA |
| CCR5-224 9 rev | TGGGCAGCCCTAGGTCCTTT |
| CCR5-224 10 fwd | TTTCCCTGGTGATGCACTCCT |
| CCR5-224 10 rev | TGATGAGTAACTTGGGCGAAAA |
| CCR5-224 11 fwd | TTGGGGGAATGAGATTGGGA |
| CCR5-224 11 rev | GGAAAATCCAGCAAGGTGAAA |
| CCR5-224 13 fwd | CCTTCCCATGGTCACAGAGG |
| CCR5-224 13 rev | CAACTCTCTAACAGCAAAGTGGCA |
| CCR5-224 14 fwd | TCCTCCCGTTGAGGAAGCAC |
| CCR5-224 14 rev | GCCTCAAAAGCATAAACAGCA |
| CCR5-224 15 fwd | CAGACCGCTGCTGCTGAGAC |
| CCR5-224 15 rev | AGGGCGGACTCATTGCTTTG |
| CCR5-224 16 fwd | TGGGTTCCTCGGGTTCTCTG |
| CCR5-224 16 rev | GAAACCAGAAGTTCACAACAATGCTT |
| CCR5-224 17 fwd | AGGCATAAGCCACTGCACCC |
| CCR5-224 17 rev | TGGCAATGCCTAATCAGACCA |
| CCR5-224 18 fwd | GAGGATATTTTATTGCTGGCTCTTGC |
| CCR5-224 18 rev | GAGTTTGGGGAAAAGCCACTT |
| CCR5-224 20 fwd | GCTGAGGCCCACCTTTCCTT |
| CCR5-224 20 rev | TGCTCTGCCAACTGTGAGGG |
| CCR5-224 21 fwd | TGTTTTGGGTGCATGTGGGT |
| CCR5-224 21 rev | TCCAGGGAGTGAGGTGAAGACA |
| CCR5-224 22 fwd | CTGGGTCAGCTGGGCCATAC |
| CCR5-224 22 rev | TCACATCTCCGCCTCACGAT |
| CCR5-224 23 fwd | CCAGCCTTGGAAAAATGGACA |
| CCR5-224 23 rev | CTGACACAGTGGCCAGCAGC |
| CCR5-224 24 fwd | CATGGATGTAATGGGTTGTATCTGC |
| CCR5-224 24 rev | GAGGGCAGAAGGGGGTGAGT |
| CCR5-224 25 fwd | AGGATGCATTGTCCCCCAGA |
| CCR5-224 25 rev | TGGAGTGACATGTATGAAGCCA |
| CCR5-224 26 fwd | CGTTGGCTTGCAGAAGGGAC |
| CCR5-224 26 rev | TRGAACCCCGGATTTTTCAACC |

-continued

| oligonucleotide name | oligonucleotide sequence (5'→3') |
|---|---|
| CCR5-224 27 fwd | TGACCCAACTAAGTCTGTGACCC |
| CCR5-224 27 rev | TTGGGAAAGCTTTGATGCTGG |
| CCR5-224 28 fwd | TGGGTTGTGTTTTTGACTGACAGA |
| CCR5-224 28 rev | CCCTAGGGGTCACTGGAGCA |
| CCR5-224 29 fwd | CACCCCCATGCAGGAAAATG |
| CCR5-224 29 rev | TTGGCTGCTGGCATTTGGTA |
| CCR5-224 30 fwd | GGCCATTGGTTCTGGAGGAA |
| CCR5-224 30 rev | TCCGTTGCTTCATCCTTCCAA |
| CCR5-224 31 fwd | AGTCAGCAATGCCCCAGAGC |
| CCR5-224 31 rev | TGGAGAGGGTTTACTTTCCCAGA |
| CCR5-224 32 fwd | CCTGGGAGGGTGACTAGTTGGA |
| CCR5-224 32 rev | GCTCAGGGCCTGGCTTACAG |
| CCR5-224 33 fwd | TGGCAATTAGGATGTGCCAG |
| CCR5-224 33 rev | TCCACTCACAAATTTACCTTTCCAC |
| CCR5-224 34 fwd | TGCCCCACATCTTCACCAGA |
| CCR5-224 34 rev | CCGCATAAAGGAGGTGTCGG |
| CCR5-224 36 fwd | GTTGCATCTGCGGTCTTCCA |
| CCR5-224 36 rev | GGAGAGTCTTCCGCCTGTGTT |
| CCR5-224 37 fwd | TAGTGGCCCCAACATGCAAA |
| CCR5-224 37 rev | GCACATATCATGCACTGTGACTGTAA |
| VF2468 1 fwd | CCTTTCCAAAGCCCATTCCC |
| VF2468 1 rev | CAACCCCACACGCACAC |
| VF2468 2 fwd | TTCACTGCCTTCAGGCCTCC |
| VF2468 2 rev | AATGGCCAGAAAATTCCCAAA |
| VF2468 3 fwd | CACAGGGACCCAGGACTGCT |
| VF2468 3 rev | TGACTGGAACCGTGCAGCAT |
| VF2468 4 fwd | GCACCAGGCTTCTCTGCCAT |
| VF2468 4 rev | TCGGGGGTCCATGGTATTTG |
| VF2468 5 fwd | CCAAGGCGAGGACATTGAGG |
| VF2468 5 rev | CCCCAAGTCAGACCCTGCAT |
| VF2468 7 fwd | ACCATAGTCCAGCGGGGTCA |
| VF2468 7 rev | TTCTCCCCAAGGAAGGCTGA |
| VF2468 8 fwd | AGAAAGGGTGGTCGGGGAAG |
| VF2468 8 rev | GCCACCATGCCCAGTCTACA |
| VF2468 9 fwd | TTCCCATGGGGTCTCAGCTC |
| VF2468 9 rev | ATGGCCTTCCCCAACTGTGA |
| VF2468 10 fwd | CAGCAAGGATGCCCTTCACC |
| VF2468 10 rev | CGTTGTGATTGAGGAGACGAGG |

-continued

| oligonucleotide name | oligonucleotide sequence (5'→3') |
|---|---|
| VF2468 11 fwd | GGCTTGAGCTGGAAGGACCA |
| VF2468 11 rev | TGGAGCAACTGAACATCTTGGG |
| VF2468 12 fwd | AACCGAGTTTGCACCGTCGT |
| VF2468 12 rev | CATAACCACCAGGACATCCGC |
| VF2468 13 fwd | TATCCTCCCCTTTCCCCTGA |
| VF2468 13 rev | TGTTGCCAGAAGTATCAGGTCCC |
| VF2468 15 fwd | AGAACCCGGAATCCCTTTGC |
| VF2468 15 rev | GCAGAGAAGGCAGCAGCACA |
| VF2468 16 fwd | GGTCTCTGCCATGCCCAACT |
| VF2468 16 rev | TGGAGGAAGCAGGAAAGGCAT |
| VF2468 18 fwd | CCCCTTGGGATCCTTGTCCT |
| VF2468 18 rev | TCAACAGGCAGCTACAGGGC |
| VF2468 19 fwd | CTAGGCCTGTGGGCTGAGGA |
| VF2468 19 rev | CAAATGTTGGGGTGTGGGTG |
| VF2468 20 fwd | TACCTGAAACCCCTGGCCCT |
| VF2468 20 rev | CAAGCTGGATGTGGATGCAGAG |
| VF2468 21 fwd | CGGGGGCCTGACATTAGTGA |
| VF2468 21 rev | GCCTGAAGATGCATTTGCCC |
| VF2468 22 fwd | TGCATTGGCTCAAGAATTGGG |
| VF2468 22 rev | TCACACAGTGGTAATGGACAGGAA |
| VF2468 23 fwd | GCGCTCCCTGTGTTCAGTACC |
| VF2468 23 rev | GCGCAAGTTCCCCTTTCTGA |
| VF2468 24 fwd | TGTTTGGGTTATGGGGCAG |
| VF2468 24 rev | TCCAGCATCTGCTCCTGGTG |
| VF2468 25 fwd | AAGGAGACTTCTCAGGCCCCA |
| VF2468 25 rev | TGAAGGGAAGCCACAGCTCC |
| VF2468 26 fwd | CTTGGGGCAGACAGCATCT |
| VF2468 26 rev | GCCATGGGATGGCAGTTAGG |
| VF2468 27 fwd | TGGCCTCAAGCAATCCTCCT |
| VF2468 27 rev | TTCCATGGCAGTGAAGGGTG |
| VF2468 28 fwd | CCAAAGAGCCTGGAGGAGCA |
| VF2468 28 rev | CAGAGGGTGTGGTGGTGTCG |
| VF2468 29 fwd | CCAGCCTGTGAAGCTGGAAGTAA |
| VF2468 29 rev | CCAGTGGGCTGAGTGGATGA |
| VF2468 30 fwd | CATCTGAATGCCCATGCTGC |
| VF2468 30 rev | CCGCCACACCCATTCCTC |
| VF2468 31 fwd | CCTCAAAGAAACGGCTGCTGA |
| VF2468 31 rev | GCCGCTCGAAAAGAGGGAAT |

| oligonucleotide name | oligonucleotide sequence (5'→3') |
|---|---|
| VF2468 32 fwd | CGGGCTCTCCTCCTCAAAGA |
| VF2468 32 rev | GGCCCCTTGAAAAGAGGGAA |
| VF2468 33 fwd | GGAATCGCATGACCTGAGGC |
| VF2468 33 rev | CGGGCTCTCCTCCTCAAAGA |
| VF2468 34 fwd | CCCGCCAGACACATTCCTCT |
| VF2468 34 rev | CATCTGAATGCCCATGCTGC |
| VF2468 35 fwd | CCGCACCTTTTTCCTATGTGGT |
| VF2468 35 rev | TCAGATGTGCTAGGACACAGATGAC |
| VF2468 36 fwd | GGTACATGGGCCGCACTTTC |
| VF2468 36 rev | GGACAGCTGGGAATTGGTGG |
| VF2468 37 fwd | TTACACCTGCTGGCAGGCAA |
| VF2468 37 rev | GCTGGTGTGAGCAAGAGGCA |
| VF2468 38 fwd | TGGCCAAGCCTGCCTAACTC |
| VF2468 38 rev | TGATCAGTTAGCCCTGGGGG |
| VF2468 39 fwd | CCCCTTCTGCTCCTGCTTCA |
| VF2468 39 rev | CCTTCCTTGCAGCTCAAACCC |
| VF2468 40 fwd | TGATTTTCAGCGTGGAGGGC |
| VF2468 40 rev | ACGGCAAAGCCAGAGCAAAG |
| VF2468 41 fwd | AAGCTGGCAGCCACTCTTCA |
| VF2468 41 rev | TCTCAGGGCTTCTGTGTGCG |
| VF2468 42 fwd | TCGATTCTCCATACACCATCAAT |
| VF2468 42 rev | GCAACCAACTCCCAACAGGG |
| VF2468 43 fwd | AGGTCCTGGCATTGTCTGGG |
| VF2468 43 rev | TGGTTGCCTGTTTCACACCC |
| VF2468 45 fwd | CTGGGAGGCAGCCAGTCAAG |
| VF2468 45 rev | GCCCTGTAAGCTGAAGCTGGA |
| VF2468 46 fwd | CAGGTGTGCATTTTGTTGCCA |
| VF2468 46 rev | GCCTGCCAGGTATTTCCTGTGT |
| VF2468 47 fwd | TGGCCCTGGTCATGTGAAAA |
| VF2468 47 rev | AACTGCAAGTGGCCTCCCAG |
| VF2468 48 fwd | TTGATAAGGGCGGTGCCACT |
| VF2468 48 rev | TAGAGGGAGGTGCTTGCCCA |
| VF2468 49 fwd | CATCCCCTTGACCAACAGGC |
| VF2468 49 rev | GCTTGGGCACTGATCCTGCT |
| VF2468 50 fwd | ACTGCCAATGGACCCTCTCG |
| VF2468 50 rev | GAGTTGCCCAGGTCAGCCAT |
| VF2468 51 fwd | GGGGAGCTAGAATGGTGGGC |
| VF2468 51 rev | CAAGGTACACAGCTGCCCAGG |

-continued

| oligonucleotide name | oligonucleotide sequence (5'→3') |
|---|---|
| VF2468 52 fwd | CCCATGCTGGTCCTGCTGTT |
| VF2468 52 rev | GGAGGCTCAGCGGAGAGGAT |
| VF2468 53 fwd | GGGGTCACCAGGGAAGGTTT |
| VF2468 53 rev | AGTTGCGGGGAGGTGCTACA |
| VF2468 54 fwd | TGCCCAGAGACCTTCCAAGC |
| VF2468 54 rev | TGGCCAAGGCCTCTCTAAGC |
| VF2468 56 fwd | GCCAATGTGCAATCGAGACG |
| VF2468 56 rev | TGCATGCCTCTGACTGATGCT |
| VF2468 57 fwd | TGACTTGAACTGGGTCCCCC |
| VF2468 57 rev | CTGGGGCTACAGCCCTCCTT |
| VF2468 58 fwd | CCCAATCCAGACACCACACG |
| VF2468 58 rev | TGCAGATTTTAGGGGTTGCCA |
| VF2468 59 fwd | GGTGAGGAAGGATGGGGGTT |
| VF2468 59 rev | GTAGGCTCTGCCACGCCAGT |
| VF2468 60 fwd | TGCCCATGTTGTTGCTCCAC |
| VF2468 60 rev | GACAAGTTAGACCATCCTAGCCCTCA |
| VF2468 61 fwd | TCACAGCTCCCCTTTCTCGG |
| VF2468 61 rev | TGTGCCTCCACTGACGCATT |
| VF2468 62 fwd | CCTAGGCACAGTGGGGGATG |
| VF2468 62 rev | GGGCTGACACACTGAGGGCT |
| VF2468 63 fwd | CCATGAGCACAATTGCCAAAA |
| VF2468 63 rev | TGAGTTATTTCGAAAGAGGAAACAGTG |
| VF2468 64 fwd | CTGCCAAGAACAGGAGGGGA |
| VF2468 64 rev | AGCCCATCTACCATCCAGCG |
| VF2468 66 fwd | ATCGGGGCAGGGCTAGAGTC |
| VF2468 66 rev | CCCCTGGCATTCCCTACACA |
| VF2468 67 fwd | GCCGTTAGTGCATTTGCCTG |
| VF2468 67 rev | TCCCTTCAACCCCTGTAGTGC |
| VF2468 68 fwd | GTTCCTCCCAGAGTGGGGCT |
| VF2468 68 rev | ACTGAGGGAGGCAGCACTGG |
| VF2468 69 fwd | AGGCCTGGCGGTAACCTTG |
| VF2468 69 rev | AAGCTCCAGCCCTGTACCCC |
| VF2468 70 fwd | GGGATCCTACAGGATGGGACAA |
| VF2468 70 rev | CAGCCCAGGACAAGGGTAGC |
| VF2468 71 fwd | GCCACCAATGTCCACTGGTT |
| VF2468 71 rev | TTCCCCAAGCAGTCCAGCTC |
| VF2468 72 fwd | GCACCAGCCTCTTCGATGGT |
| VF2468 72 rev | CCTTTGGCAGACTGTGGCCT |

| oligonucleotide name | oligonucleotide sequence (5'→3') |
|---|---|
| VF2468 73 fwd | AATGGGGCAAAAGGCAAGAAA |
| VF2468 73 rev | CAGACCTCGTGGTGCATGTG |
| VF2468 74 fwd | TGGCGAGATAGGCTCTGCTACA |
| VF2468 74 rev | TGGACAGGGAATTACTCAGACCAG |
| VF2468 75 fwd | TGTGGGCATGAGACCACAGG |
| VF2468 75 rev | TTTGACTCCCCCGCATTGTT |
| VF2468 76 fwd | TCCTATTTTCAGATGCACTCGAACC |
| VF2468 76 rev | GTGCTCACTGAAGCCCACCA |
| VF2468 77 fwd | GGACCTTCTTGCCCTCATGATTC |
| VF2468 77 rev | GGGAACTGTGCCTTTGCGTC |
| VF2468 78 fwd | CCTTGCAAAGGCTTGCCTAAA |
| VF2468 78 rev | GGCAGGCACCTGTAGTCCCA |
| VF2468 79 fwd | TGGCTTGCAGAGGAGGTGAG |
| VF2468 79 rev | CAGGGAAGGGTGTTGGCTTG |
| VF2468 80 fwd | GCTTCAGCACATCAGTGGCG |
| VF2468 80 rev | TTCGCCCAGCTCATCAACAA |
| VF2468 81 fwd | GGTGAGGCCACTGTAAGCCAA |
| VF2468 81 rev | TGGGCTGCCATGACAAACAG |
| VF2468 83 fwd | GAGTTGAGCTGTCAGCGGGG |
| VF2468 83 rev | GAAGCCAACTGCCTTGTGAGC |
| VF2468 84 fwd | TGTTTTCTGCAGTTTTGCAGGG |
| VF2468 84 rev | GGCTCAGGGAGTTTGAGCCA |
| VF2468 85 fwd | GCTCTGGCACCAGGCACACT |
| VF2468 85 rev | GGGAGAGAACCATGAATTTCCCA |
| VF2468 86 fwd | GCCAAACCCTTTCCAGGGAG |
| VF2468 86 rev | CCCACCCTATGCACAGAGCC |
| VF2468 87 fwd | CCTCAGCCAGTTGGAATCGG |
| VF2468 87 rev | CAACGGTTTAGTTTAGTTCCGGTTT |
| VF2468 88 fwd | TGGGTGGTGAAAATGGGGTT |
| VF2468 88 rev | GGTGGGGTATGCACTGGTCA |
| VF2468 89 fwd | GGAATGTGTGGAACTCAATTTCTTT |
| VF2468 89 rev | TTGCTTGCAGGGTGTGGAAA |
| VF2468 90 fwd | CCACAAGGGTCATCTGGGGA |
| VF2468 90 rev | CGGAGGCATCATCCACTGAG |
| VF2468 91 fwd | CCTGGAGTGGTTTGGCTTCG |
| VF2468 91 rev | TGGAGCCCTGGAGTTCTTGG |
| VF2468 92 fwd | GGCTCCTGGGGTCATTTCC |
| VF2468 92 rev | TGTGCTCCATCCTCCTCCCT |

| oligonucleotide name | oligonucleotide sequence (5'→3') |
|---|---|
| VF2468 93 fwd | GTGTGTTTCCGCACACCCTG |
| VF2468 93 rev | GCTCTTGGCTTCCCAACCCT |
| VF2468 94 fwd | CCATCGCCGTGTCTGAGTGT |
| VF2468 94 rev | CAGCAGGAACATCATCCCCC |
| VF2468 95 fwd | AGGCAATGGCACCAAAATGG |
| VF2468 95 rev | GCAGCCTTCACCATACCTGTGA |
| VF2468 96 fwd | TTTTGACTTTGAGAACCCCCTGA |
| VF2468 96 rev | CCTTGTCCTTTCTCAGTTAGACACA |
| VF2468 97 fwd | GCTGAGTGCAAAGCTCAGGGA |
| VF2468 97 rev | GGCAACACAGCAAGACCCCT |

Table 9: Oligonucleotides used in this study. Oligonucleotides "[ZFN] [#] fwd/rev" were ordered from Invitrogen. All other oligonucleotides were ordered from Integrated DNA Technologies. 'N' refers to machine mixed incorporation of 'A', 'C', 'G', or 'T.' An asterisk indicates that the preceding nucleotide was incorporated as a mixture containing 79 mol % of that nucleotide and 7 mol % each of the other canonical nucleotides. "/5Phos/" denotes a 5' phosphate group installed during synthesis. Sequences correspond, from top left to bottom right, to SEQ ID NOs:654-924.

VF2468 Data

Potential VF2468 genomic off-target sites. The human genome was searched for DNA sequences surviving in vitro selection for VF2468 cleavage. Sites marked with an 'X' were found in the in vitro selection dataset. 'T' refers to the total number of mutations in the site, and '(+)' and '(−)' to the number of mutations in the (+) and (−) half-sites, respectively. The sequences of the sites are listed as they appear in the genome, therefore the (−) half-site is listed in the reverse sense as it is in the sequence profiles. Sequence (+) half-sites correspond, from top to bottom, to SEQ ID NOs:925-3538; sequence (−) half-sites correspond, from top to bottom, to SEQ ID NOs:3539-6152; full sequences with spacers correspond, from top to bottom, to SEQ ID NOs: 6153-8766.

| # of mutations | | | | | | VF2468 concentration | | | |
|---|---|---|---|---|---|---|---|---|---|
| T | (−) | (+) | (−) site | spacer | (+) site | 4 nM | 2 nM | 10.5 nM | nM |
| 2 | 1 | 1 | AGCAGCTTC | CTTTT | GAGTGAGAA | X | X | X | X |
| 2 | 1 | 1 | AGCATCGTC | ATCAGA | CAGTGAGGA | X | X | X | X |
| 2 | 1 | 1 | AGCAACGTC | GTAGT | GATTGAGGA | X | X | X | X |
| 2 | 2 | 0 | AGCTGGGTC | ATGAG | GAGTGAGGA | X | X | X | X |
| 2 | 2 | 0 | AGCTGGGTC | ATGAG | GAGTGAGGA | X | X | X | X |
| 2 | 2 | 0 | AGCAACTTC | TGGAAA | GAGTGAGGA | X | X | X | X |
| 2 | 2 | 0 | AGCTGAGTC | TTAAG | GAGTGAGGA | X | X | X | X |
| 2 | 2 | 0 | TCCAGCGTC | CTCCCA | GAGTGAGGA | X | X | X | X |
| 2 | 2 | 0 | TGCAGCGTT | AAAATA | GAGTGAGGA | X | X | X | X |
| 2 | 2 | 0 | AGCACCTTC | AATTG | GAGTGAGGA | X | X | X | X |
| 2 | 2 | 0 | TGCAGCGGC | GTAGGG | GAGTGAGGA | X | X | X | X |
| 2 | 2 | 0 | AGCAGGGTT | CTTCAA | GAGTGAGGA | X | X | X | X |
| 2 | 2 | 0 | AGCAGCATA | GATATG | GAGTGAGGA | X | X | X | X |
| 2 | 2 | 0 | AACAGCTTC | TCTGAG | GAGTGAGGA | X | X | X | X |
| 2 | 2 | 0 | TGCAGGGTC | GGGCAG | GAGTGAGGA | X | X | X | X |
| 2 | 2 | 0 | AGCAAAGTC | AAACA | GAGTGAGGA | X | X | X | X |
| 2 | 2 | 0 | AACAGCTTC | TCGGGA | GAGTGAGGA | X | X | X | X |
| 2 | 2 | 0 | AGTAGCGGC | AAATT | GAGTGAGGA | X | X | X | X |
| 2 | 2 | 0 | AGCTGAGTC | CTAAA | GAGTGAGGA | X | X | X | X |
| 2 | 2 | 0 | AGCAGCGAG | AAAGA | GAGTGAGGA | X | X | X | X |
| 2 | 2 | 0 | TGCAGTGTC | CACAA | GAGTGAGGA | X | X | X | X |
| 2 | 2 | 0 | AGCAGCATA | ATAGCA | GAGTGAGGA | X | X | X | X |
| 2 | 2 | 0 | AGCAGCATA | TCAGG | GAGTGAGGA | X | X | X | X |
| 2 | 2 | 0 | AGCAGCGGT | CTTAG | GAGTGAGGA | X | X | X | X |
| 2 | 2 | 0 | AACAGCTTC | ATCTCG | GAGTGAGGA | X | X | X | X |
| 2 | 2 | 0 | GGCAGAGTC | CTAGA | GAGTGAGGA | X | X | X | X |
| 2 | 2 | 0 | AGCTGTGTC | TTGGA | GAGTGAGGA | X | X | X | X |

| # of mutations T | (-) | (+) | (-) site | spacer | (+) site | VF2468 concentration 4 nM | 2 nM | 10.5 nM | nM |
|---|---|---|---|---|---|---|---|---|---|
| 2 | 2 | 0 | AGTGGCGTC | CCAGT | GAGTGAGGA | X | X | X | X |
| 2 | 2 | 0 | AGCTGTGTC | CACAG | GAGTGAGGA | X | X | X | X |
| 3 | 1 | 2 | AGCAGCGGC | TTAAGG | GGGTGAGGT | X | X | X | X |
| 3 | 1 | 2 | AGCAACGTC | TAACCC | GAGTGTTGA | X | X | X | X |
| 3 | 1 | 2 | AGCACCGTC | CCCCT | CAGTGAGGC | X | X | X | X |
| 3 | 1 | 2 | AGCAGCGGC | GGCTG | CAGTGAGGC | X | X | X | X |
| 3 | 1 | 2 | AGCAGTGTC | TAAAAG | GAGTGAGAT | X | X | X | X |
| 3 | 1 | 2 | AGCAACGTC | CATAGT | GTGTGAGAA | X | X | X | X |
| 3 | 2 | 1 | AGAAACGTC | GTGGAG | GAGTGAGGG | X | X | X | X |
| 3 | 2 | 1 | AGCATAGTC | TAGGCC | GAGTGAGGC | X | X | X | X |
| 3 | 2 | 1 | AGCAACTTC | ATCTT | GAGTGAGGG | X | X | X | X |
| 3 | 2 | 1 | AGCAGGGTG | GCGTG | GAGTGAGGC | X | X | X | X |
| 3 | 2 | 1 | AGCACGGTC | ATGAT | GAGTGAGGC | X | X | X | X |
| 3 | 2 | 1 | AGCATTGTC | TCCTG | GAGTGAGGG | X | X | X | X |
| 3 | 2 | 1 | AGCACCGTG | GCTTC | GAGTGAGGC | X | X | X | X |
| 3 | 2 | 1 | AGCAACTTC | CTGGC | GAGTGAGGG | X | X | X | X |
| 3 | 2 | 1 | AGCAACATC | TGGTTG | GAGTGAGGG | X | X | X | X |
| 3 | 2 | 1 | GGCAGCGGC | CGCTGT | GAGTGAGGT | X | X | X | X |
| 3 | 2 | 1 | AGCATTGTC | TCATGT | GAGTGAGGT | X | X | X | X |
| 3 | 2 | 1 | AGCAGCAGC | TAGGG | GAGTGAGGG | X | X | X | X |
| 3 | 2 | 1 | AGCAGCAGC | CCACAG | GAGTGAGGG | X | X | X | X |
| 3 | 2 | 1 | ATCAGAGTC | TCTGG | GAGTGAGGG | X | X | X | X |
| 3 | 2 | 1 | ATCAGTGTC | CCTCAG | GAGTGAGGG | X | X | X | X |
| 3 | 2 | 1 | AGCAACATC | ATCTT | GAGTGAGGG | X | X | X | X |
| 3 | 2 | 1 | AGCATGGTC | CCAAG | GAGTGAGGG | X | X | X | X |
| 3 | 2 | 1 | AGCAAAGTC | TGTACT | GAGTGAGGG | X | X | X | X |
| 3 | 2 | 1 | AGCAGCTCC | TCTCC | GAGTGAGGT | X | X | X | X |
| 3 | 2 | 1 | AGCAATGTC | AAAAA | GAGTGAGGG | X | X | X | X |
| 3 | 2 | 1 | AGTAGCGTT | TTTAG | GAGTGAGGT | X | X | X | X |
| 3 | 2 | 1 | GGCAGAGTC | AGGGCT | GAGTGAGGC | X | X | X | X |
| 3 | 2 | 1 | TGCAGCTTC | ATGGT | GAGTGAGGT | X | X | X | X |
| 3 | 3 | 0 | AGCATAGTT | ACCTGG | GAGTGAGGA | X | X | X | X |
| 3 | 3 | 0 | AGTAAAGTC | TAAGTA | GAGTGAGGA | X | X | X | X |
| 3 | 3 | 0 | AGCATTGTT | CTGCG | GAGTGAGGA | X | X | X | X |
| 4 | 3 | 1 | TGCAGTCTC | CTTGG | GAGTGAGGT | X | X | X | X |
| 2 | 0 | 2 | AGCAGCGTC | CACTTC | CAGAGAGGA | X | X | X |  |
| 2 | 1 | 1 | AGCAGCGTG | GACCCA | GAGTGAGCA | X | X | X |  |
| 2 | 1 | 1 | AGCAGCGCC | AATCC | GAGTGAGAA | X | X | X |  |
| 2 | 1 | 1 | AGCAGCGGC | AGGCT | GAGAGAGGA | X | X | X |  |
| 2 | 1 | 1 | AGCAGCTTC | TGCCTT | GAGTGAGTA | X | X | X |  |
| 2 | 1 | 1 | AGCAGCTTC | ACTGT | CAGTGAGGA | X | X | X |  |
| 2 | 1 | 1 | ATCAGCGTC | TTCAG | AAGTGAGGA | X | X | X |  |
| 2 | 1 | 1 | AGCAGCGTG | GACCCA | GAGTGAGCA | X | X | X |  |
| 2 | 1 | 1 | AGCAGGGTC | AAGAAA | GAGTGAGTA | X | X | X |  |
| 2 | 1 | 1 | AGCAGCGTT | ACACA | GAGTGGGGA | X | X | X |  |
| 2 | 1 | 1 | AGCAGCGGC | AAGAGA | GAATGAGGA | X | X | X |  |
| 2 | 1 | 1 | AGCAGAGTC | CAGGC | AAGTGAGGA | X | X | X |  |
| 2 | 1 | 1 | AGCAGAGTC | CAGGC | AAGTGAGGA | X | X | X |  |
| 2 | 1 | 1 | AGCAGGGTC | TGGGTA | GAGTGATGA | X | X | X |  |
| 2 | 1 | 1 | AGCAGCGTG | GACCCA | GAGTGAGCA | X | X | X |  |
| 2 | 2 | 0 | AGCAGCAGC | TAGCTA | GAGTGAGGA | X | X | X |  |
| 2 | 2 | 0 | AGGAGCTTC | ACTAA | GAGTGAGGA | X | X | X |  |
| 2 | 2 | 0 | AGCAGCCTG | CAATA | GAGTGAGGA | X | X | X |  |
| 2 | 2 | 0 | ACCAGTGTC | TGAGCT | GAGTGAGGA | X | X | X |  |
| 2 | 2 | 0 | AACAGAGTC | CCCAT | GAGTGAGGA | X | X | X |  |
| 2 | 2 | 0 | AGCAGCCTG | GCCAGG | GAGTGAGGA | X | X | X |  |
| 2 | 2 | 0 | AGCAGCAGC | AGTGA | GAGTGAGGA | X | X | X |  |
| 2 | 2 | 0 | ATCAGAGTC | TTAGG | GAGTGAGGA | X | X | X |  |
| 2 | 2 | 0 | AGCGGGGTC | TAGGGG | GAGTGAGGA | X | X | X |  |
| 2 | 2 | 0 | AGCAGCGGA | CAAGT | GAGTGAGGA | X | X | X |  |
| 3 | 0 | 3 | AGCAGCGTC | CCTGCC | TAGGGAGGG | X | X | X |  |
| 3 | 0 | 3 | AGCAGCGTC | TTTTCT | ATGTGAGGC | X | X | X |  |
| 3 | 0 | 3 | AGCAGCGTC | ACCTCT | GTGTGGGGC | X | X | X |  |
| 3 | 0 | 3 | AGCAGCGTC | TAAGG | GAGGGGGT | X | X | X |  |
| 3 | 0 | 3 | AGCAGCGTC | TTGGG | GTGTGGGGC | X | X | X |  |
| 3 | 0 | 3 | AGCAGCGTC | TAGAG | TAGAGAGGT | X | X | X |  |
| 3 | 1 | 2 | AGCAGGGTC | TCCCAG | GAGTGTGAA | X | X | X |  |
| 3 | 1 | 2 | AGCAGTGTC | TATTT | CAGTGAGGG | X | X | X |  |
| 3 | 1 | 2 | AGCAGGGTC | AGCCCA | GAGTGGGGG | X | X | X |  |
| 3 | 1 | 2 | AGCAGGGTC | AGGCA | CAGTGAGGC | X | X | X |  |
| 3 | 1 | 2 | AGCAGGGTC | CTCTG | GAGTGGGGG | X | X | X |  |

| # of mutations T | (−) | (+) | (−) site | spacer | (+) site | 4 nM | 2 nM | 10.5 nM |
|---|---|---|---|---|---|---|---|---|
| 3 | 1 | 2 | GGCAGCGTC | CGGAG | GAGTGAAGG | X | X | X |
| 3 | 1 | 2 | GGCAGCGTC | ACTCCA | GAGTTAGGT | X | X | X |
| 3 | 1 | 2 | AGCAGGGTC | ATTCAT | CAGTGAGGC | X | X | X |
| 3 | 1 | 2 | AGCAGAGTC | CTGTCA | GAGGGAGGC | X | X | X |
| 3 | 1 | 2 | AGCAGCATC | TTCTG | GAGTGAGAC | X | X | X |
| 3 | 1 | 2 | AGCATCGTC | TTTCT | GTGTGAGGC | X | X | X |
| 3 | 1 | 2 | AGCAGTGTC | TCACAG | GAGGGAGGG | X | X | X |
| 3 | 1 | 2 | GGCAGCGTC | CAGGA | GAGAGAGGT | X | X | X |
| 3 | 1 | 2 | AGCAGCGGC | CCCGG | GAGTTAGGT | X | X | X |
| 3 | 1 | 2 | AGCAGCGGC | GGGTGG | GAGTGGGGG | X | X | X |
| 3 | 1 | 2 | AGCAGTGTC | CAGAC | GAGGGAGGT | X | X | X |
| 3 | 1 | 2 | AGCAGTGTC | TATGA | GAGGGAGGG | X | X | X |
| 3 | 1 | 2 | AGCAGTGTC | AGCCAT | GAGGGAGGG | X | X | X |
| 3 | 1 | 2 | AGCAGTGTC | CCTGTG | GAGGGAGGT | X | X | X |
| 3 | 1 | 2 | AGCACCGTC | TGCCA | GAGTGGGCA | X | X | X |
| 3 | 2 | 1 | AGCCACGTC | CACACT | AGTGAGGA | X | X | X |
| 3 | 2 | 1 | AGTAGCGCC | AAAAG | GAGTGAGGT | X | X | X |
| 3 | 2 | 1 | AACAGGGTC | TTTGAC | GAGTGAGGC | X | X | X |
| 3 | 2 | 1 | GGCAGGGTC | TCAAT | GAGTGAGGG | X | X | X |
| 3 | 2 | 1 | AACAGGGTC | CCTGA | GAGTGAGGG | X | X | X |
| 3 | 2 | 1 | AGGAGAGTC | CAGGT | GAGTGAGGG | X | X | X |
| 3 | 2 | 1 | AGCAGCCGC | CAACA | GAGTGAGGG | X | X | X |
| 3 | 2 | 1 | GGCAGAGTC | AGTGTT | GAGTGAGGG | X | X | X |
| 3 | 2 | 1 | AGCAGTGTG | TGAGCT | GAGTGAGGC | X | X | X |
| 3 | 2 | 1 | AGCATCTTC | CAGTG | GAGTGAGGG | X | X | X |
| 3 | 2 | 1 | AGCAGAGTG | GTTGA | GAGTGAGGT | X | X | X |
| 3 | 2 | 1 | ATCAGTGTC | CCAGA | GAGTGAGGG | X | X | X |
| 3 | 2 | 1 | TTCAGCGTC | CAAGAA | GAGTGAGGT | X | X | X |
| 3 | 2 | 1 | AGCAACTTC | CGGACA | GAGTAAGGA | X | X | X |
| 3 | 2 | 1 | AGCAGCGGG | AGATG | GAGTGAGGC | X | X | X |
| 3 | 2 | 1 | AGTAGCGTG | GAGAG | GAGTGAGGT | X | X | X |
| 3 | 2 | 1 | AGCTGCATC | TTTGG | GAGTGAGGT | X | X | X |
| 3 | 2 | 1 | ATCAGAGTC | AAAGAA | GAGTGAGGT | X | X | X |
| 3 | 2 | 1 | AGCAGGATC | TGAAAT | GAGTGAGGT | X | X | X |
| 3 | 2 | 1 | AGCCACGTC | CAGTTT | TAGTGAGGA | X | X | X |
| 3 | 2 | 1 | AGCAATGTC | TCAAAT | CAGTGAGGA | X | X | X |
| 3 | 2 | 1 | AGCAATGTC | TGAAA | CAGTGAGGA | X | X | X |
| 3 | 2 | 1 | GGCTGCGTC | ATCGG | GAGTGAGGT | X | X | X |
| 3 | 2 | 1 | GGCAGAGTC | AAAAT | GAGTGAGGT | X | X | X |
| 3 | 2 | 1 | AGCAGTGTG | CATGT | GAGTGAGGT | X | X | X |
| 3 | 3 | 0 | GGCAACATC | AAACAG | GAGTGAGGA | X | X | X |
| 3 | 3 | 0 | CCCAGCGGC | TGGCAG | GAGTGAGGA | X | X | X |
| 3 | 3 | 0 | AGCCTGGTC | GGAGAG | GAGTGAGGA | X | X | X |
| 3 | 3 | 0 | TGCAGTCTC | TATGG | GAGTGAGGA | X | X | X |
| 3 | 3 | 0 | AGCATTGTA | GAGGC | GAGTGAGGA | X | X | X |
| 3 | 3 | 0 | AGCCTGGTC | TCACA | GAGTGAGGA | X | X | X |
| 3 | 3 | 0 | AGCATAGTG | AATAT | GAGTGAGGA | X | X | X |
| 3 | 3 | 0 | AGCAAAGGC | ACCAG | GAGTGAGGA | X | X | X |
| 3 | 3 | 0 | AACATGGTC | CACGT | GAGTGAGGA | X | X | X |
| 3 | 3 | 0 | AGCTTTGTC | AACCTA | GAGTGAGGA | X | X | X |
| 3 | 3 | 0 | AGCAAAGGC | AAAAA | GAGTGAGGA | X | X | X |
| 3 | 3 | 0 | ATCAAGGTC | TTTTG | GAGTGAGGA | X | X | X |
| 3 | 3 | 0 | GCCAGTGTC | TCGTCT | GAGTGAGGA | X | X | X |
| 3 | 3 | 0 | TGCAAAGTC | AGATCT | GAGTGAGGA | X | X | X |
| 4 | 1 | 3 | AGCAACGTC | TACAG | GAGGAAGGT | X | X | X |
| 4 | 1 | 3 | AGCAACGTC | CCAGGA | AAGTGAAGG | X | X | X |
| 4 | 2 | 2 | GGCAGTGTC | CAGTAG | GAGTGAGAT | X | X | X |
| 4 | 2 | 2 | AGCAAAGTC | TCACA | AAGTGAGGT | X | X | X |
| 4 | 3 | 1 | TGCTGTGTC | AAACCC | GAGTGAGGT | X | X | X |
| 4 | 3 | 1 | GGCAAGGTC | TCTGTG | GAGTGAGGG | X | X | X |
| 4 | 3 | 1 | ATCAACGTG | TCTCA | GAGTGAGGC | X | X | X |
| 2 | 0 | 2 | AGCAGCGTC | TGAGGC | GGGTGAGAA | X | X | X |
| 2 | 0 | 2 | AGCAGCGTC | TGCATG | GTGTGGGGA | X | X | X |
| 2 | 1 | 1 | AGCAGAGTC | AGGCA | GAGTGAGAA | X | X | X |
| 2 | 1 | 1 | AGCAGCTTC | ATTTAT | GAGTGAGCA | X | X | X |
| 2 | 1 | 1 | GGCAGCGTC | CTTCT | GAGTGAGCA | X | X | X |
| 2 | 1 | 1 | AGCAGTGTC | GTGAA | GAGTCAGGA | X | X | X |
| 2 | 1 | 1 | AGCAGCTTC | CGGGGA | GAGAGAGGA | X | X | X |
| 2 | 2 | 0 | AGCAGCTGC | GGACC | GAGTGAGGA | X | X | X |
| 2 | 2 | 0 | AGCAGTGGC | ATTAA | GAGTGAGGA | X | X | X |
| 2 | 2 | 0 | AGCAGCATG | CACAT | GAGTGAGGA | X | X | X |

| # of mutations T | (−) | (+) | (−) site | spacer | (+) site | VF2468 concentration 4 nM | 2 nM | 10.5 nM |
|---|---|---|---|---|---|---|---|---|
| 2 | 2 | 0 | AGCAGCATG | ACCAA | GAGTGAGGA | X | X | X |
| 2 | 2 | 0 | ACCAGGGTC | TGTGGG | GAGTGAGGA | X | X | X |
| 2 | 2 | 0 | AGCAGCATG | AAAAGG | GAGTGAGGA | X | X | X |
| 2 | 2 | 0 | AGCAGGGTG | ATGGA | GAGTGAGGA | X | X | X |
| 2 | 2 | 0 | AGCAGTGAC | CGAAG | GAGTGAGGA | X | X | X |
| 2 | 2 | 0 | AGCAGATTC | CTCAG | GAGTGAGGA | X | X | X |
| 2 | 2 | 0 | ATCAGCGTG | GCCAT | GAGTGAGGA | X | X | X |
| 2 | 2 | 0 | AGCAGGGGC | AAGAGA | GAGTGAGGA | X | X | X |
| 2 | 2 | 0 | AGCGCCGTC | CACAGG | GAGTGAGGA | X | X | X |
| 3 | 0 | 3 | AGCAGCGTC | CCCTG | GAGTGGCCA | X | X | X |
| 3 | 0 | 3 | AGCAGCGTC | CAGTGG | GAGTGGGCC | X | X | X |
| 3 | 0 | 3 | AGCAGCGTC | CTTCCT | CAGTGAGAC | X | X | X |
| 3 | 1 | 2 | AGCAGCGGC | GGCGGG | GAGGGAGGC | X | X | X |
| 3 | 1 | 2 | AGCAGAGTC | TGTTGA | GAGTGAGAC | X | X | X |
| 3 | 1 | 2 | TGCAGCGTC | AGAAG | GTGTGAGGC | X | X | X |
| 3 | 1 | 2 | AGCAGCGTG | CCTCT | GGGTGAGGC | X | X | X |
| 3 | 1 | 2 | AGCAGCTTC | CATCTG | GAGTGAGTC | X | X | X |
| 3 | 1 | 2 | AGCAGCATC | TGCTCT | TAGTGAGGC | X | X | X |
| 3 | 1 | 2 | AGCAACGTC | CTGCA | GAGGGAGAA | X | X | X |
| 3 | 1 | 2 | AGCAGCGGC | CCGCA | GAGGGAGGC | X | X | X |
| 3 | 1 | 2 | AGCAACGTC | AGCAA | CAGTGAGAA | X | X | X |
| 3 | 1 | 2 | AGTAGCGTC | TCGAA | GAGAGAGGC | X | X | X |
| 3 | 1 | 2 | AGCAGCGTT | TTCAG | GAGGGAGGG | X | X | X |
| 3 | 1 | 2 | AGCAGCGGC | ACCCT | GGGTGAGGC | X | X | X |
| 3 | 2 | 1 | AGCAAGGTC | AACTCA | GAGTGAGAA | X | X | X |
| 3 | 2 | 1 | AGCATGGTC | AGTTTC | TAGTGAGGA | X | X | X |
| 3 | 2 | 1 | AGTAGGGTC | ACGCCA | GAGTGAGGC | X | X | X |
| 3 | 2 | 1 | ATCAGGGTC | CTGTT | GAGTGAGGG | X | X | X |
| 3 | 2 | 1 | AGCATGGTC | TTTTTC | TAGTGAGGA | X | X | X |
| 3 | 2 | 1 | AGCAGGGTA | AGAGGG | GAGTGAGGG | X | X | X |
| 3 | 2 | 1 | GGCAACGTC | AACTCA | GAGTGAGAA | X | X | X |
| 3 | 2 | 1 | GCCAGCGTC | TTGGGT | GAGTGAGGT | X | X | X |
| 3 | 2 | 1 | AGCAGCTTT | CTGCT | GAGTGAGGC | X | X | X |
| 3 | 2 | 1 | AGCAGTGGC | TGCGG | GAGTGAGGC | X | X | X |
| 3 | 2 | 1 | GGCAGCATC | TGGGC | GAGTGAGGC | X | X | X |
| 3 | 2 | 1 | GGCAGCATC | TGAAT | GAGTGAGGC | X | X | X |
| 3 | 2 | 1 | AGCAGTGTA | TGTGG | GAGTGAGGT | X | X | X |
| 3 | 2 | 1 | AGGAGAGTC | CCTGG | GAGTGAGGC | X | X | X |
| 3 | 2 | 1 | AGCATGGTC | AGATTC | TAGTGAGGA | X | X | X |
| 3 | 2 | 1 | ATCAGGGTC | TTGAGG | GAGTGAGGT | X | X | X |
| 3 | 2 | 1 | AACAGCGTG | CTGTA | GAGTGAGGT | X | X | X |
| 3 | 2 | 1 | AGTAGCTTC | TGTGG | GAGTGAGGC | X | X | X |
| 3 | 2 | 1 | AGCAACTTC | TTGAT | GAGTGAGAA | X | X | X |
| 3 | 2 | 1 | AGCATGGTC | AGGTTC | TAGTGAGGA | X | X | X |
| 3 | 2 | 1 | AGAAGTGTC | AGAGTA | GAGTGAGGC | X | X | X |
| 3 | 2 | 1 | AACAGCGGC | ATGGG | GAGTGAGGC | X | X | X |
| 3 | 2 | 1 | AGCAGTGGC | ATCTAG | GAGTGAGGC | X | X | X |
| 3 | 3 | 0 | AAAAGTGTC | ATATAG | GAGTGAGGA | X | X | X |
| 3 | 3 | 0 | AGCAATGGC | TGGAT | GAGTGAGGA | X | X | X |
| 3 | 3 | 0 | GCCACCGTC | GGTGAG | GAGTGAGGA | X | X | X |
| 3 | 3 | 0 | AAAAGTGTC | AGTAGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | AACATTGTC | TAGTGG | GAGTGAGGA | X | X | X |
| 3 | 3 | 0 | AACATTGTC | TAGTGA | GAGTGAGGA | X | X | X |
| 3 | 3 | 0 | ATCAACTTC | TTCAGG | GAGTGAGGA | X | X | X |
| 3 | 3 | 0 | AGCATGGTG | ATTAA | GAGTGAGGA | X | X | X |
| 4 | 3 | 1 | AGTAGTCTC | TGGCT | GAGTGAGGT | X | X | X |
| 4 | 3 | 1 | AGCATTGTT | TCTCA | GAGTGAGGT | X | X | X |
| 4 | 3 | 1 | AGCAAGGTT | AGGCT | GAGTGAGGG | X | X | X |
| 4 | 3 | 1 | AGCAGTCTT | CCACCA | GAGTGAGGC | X | X | X |

| # of mutations T (−) (+) (−) | site | spacer | (+) site | VF2468 concentration 4 nM | 2 nM | 10.5 nM |
|---|---|---|---|---|---|---|
| 4 3 1 | AGCATTGTT | TGAGT | GAGTGAGGT | X | X | X |
| 2 0 2 | AGCAGCGTC | CGCAGC | AAGTTAGGA | X | X | |
| 2 0 2 | AGCAGCGTC | ACTACA | GAGGCAGGA | X | X | |
| 2 1 1 | GGCAGCGTC | TCTCTG | GGGTGAGGA | X | X | |
| 2 1 1 | AGCAGAGTC | TTGAA | GAGTGAGTA | X | X | |
| 2 1 1 | AGCAGCATC | TATGC | CAGTGAGGA | X | X | |
| 2 1 1 | AGCAGAGTC | TGGCA | GAGAGAGGA | X | X | |
| 2 1 1 | AGCAGTGTC | CCTCA | GAGTGTGGA | X | X | |
| 2 1 1 | AGCAGCATC | TTGGA | GTGTGAGGA | X | X | |
| 2 1 1 | AGCTGCGTC | TTCTG | GAGGGAGGA | X | X | |
| 2 1 1 | AGCAGCTTC | AGAAGA | GAATGAGGA | X | X | |
| 2 1 1 | AGCAGGGTC | GAGGG | GAGGGAGGA | X | X | |
| 2 1 1 | AGCAGGGTC | TGGTG | CAGTGAGGA | X | X | |
| 2 1 1 | AGCAGCATC | CATGT | CAGTGAGGA | X | X | |
| 2 1 1 | AGCAGAGTC | CCAAG | GGGTGAGGA | X | X | |
| 2 1 1 | AGCAGCCTC | TGAAC | AAGTGAGGA | X | X | |
| 2 1 1 | AGCAGCCTC | TAGGT | AAGTGAGGA | X | X | |
| 2 1 1 | AGCAGCTTC | AGATTT | GAGTTAGGA | X | X | |
| 2 1 1 | AGCAGCCTC | ACAGG | CAGTGAGGA | X | X | |
| 2 1 1 | AGCAGCATC | AACAC | CAGTGAGGA | X | X | |
| 2 1 1 | AGCAGCGTG | TCAGCT | GTGTGAGGA | X | X | |
| 2 1 1 | AGCAGCATC | TATGC | CAGTGAGGA | X | X | |
| 2 1 1 | AGCAGCATC | AATAAT | AAGTGAGGA | X | X | |
| 2 1 1 | AGCAGAGTC | ACACA | GTGTGAGGA | X | X | |
| 2 1 1 | GGCAGCGTC | TGGGAG | GAGTTAGGA | X | X | |
| 2 1 1 | AGCAGCGCC | ATCTT | GAGCGAGGA | X | X | |
| 2 1 1 | AGCTGCGTC | GTGAG | AAGTGAGGA | X | X | |
| 2 1 1 | AGCAGGGTC | ACACA | GGGTGAGGA | X | X | |
| 2 1 1 | AGCAGAGTC | AGAGAG | GAGAGAGGA | X | X | |
| 2 1 1 | AGCAGAGTC | ACTGAC | CAGTGAGGA | X | X | |
| 2 1 1 | AGCAGTGTC | TCCCA | GAGTGTGGA | X | X | |
| 2 1 1 | AGCAGTGTC | TGAGTA | GAGTGTGGA | X | X | |
| 2 1 1 | AGCAGCATC | CCGGG | GAGTGAAGA | X | X | |
| 2 1 1 | AACAGCGTC | AAGGCA | GAGTGAAGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCGCC | ATCTT | GAGCGAGGA | X | X | |
| 2 1 1 | AGCAGCATC | CATGT | CAGTGAGGA | X | X | |
| 2 1 1 | AGCAGAGTC | AGGGAG | GAGTGAAGA | X | X | |
| 2 1 1 | AGCAGCCTC | ATGGTC | AAGTGAGGA | X | X | |
| 2 1 1 | AGCAGCATC | GTGAGT | GAGTGTGGA | X | X | |
| 2 1 1 | AGCAGTGTC | TAGCAC | GAATGAGGA | X | X | |
| 2 1 1 | AGCAGAGTC | ACAGAA | GAGAGAGGA | X | X | |
| 2 1 1 | AGCAGCGTG | GTTAA | GAGTCAGGA | X | X | |
| 2 1 1 | ACCAGCGTC | TGGTGA | GAGTGGGGA | X | X | |
| 2 1 1 | AGCAGTGTC | TTGCT | GAGAGAGGA | X | X | |
| 2 1 1 | AGCAGCGAC | CTGGGC | GAGTGAGAA | X | X | |
| 2 1 1 | AGCAGTGTC | TGCCGT | GAGTGGGGA | X | X | |
| 2 1 1 | AGCAGCGTA | ATACA | CAGTGAGGA | X | X | |
| 2 1 1 | AGCAGCCTC | TAGAGA | AAGTGAGGA | X | X | |
| 2 1 1 | AGCAGAGTC | ACGGGT | GTGTGAGGA | X | X | |
| 2 1 1 | TGCAGCGTC | ATCAA | GAGTGTGGA | X | X | |
| 2 2 0 | AGCAGGGAC | CAGGTG | GAGTGAGGA | X | X | |
| 2 2 0 | AGCAGGCTC | TAAAAT | GAGTGAGGA | X | X | |
| 2 2 0 | AGCAGCCTA | GGAAT | GAGTGAGGA | X | X | |
| 2 2 0 | AGCATCCTC | CAGGAG | GAGTGAGGA | X | X | |
| 2 2 0 | AGCAGAGTA | CTCAGT | GAGTGAGGA | X | X | |
| 2 2 0 | AGCAGGGTA | GAAGA | GAGTGAGGA | X | X | |
| 2 2 0 | AGCAGAGAC | CTGAGG | GAGTGAGGA | X | X | |
| 2 2 0 | AGCAGAGTG | GGCAA | GAGTGAGGA | X | X | |
| 2 2 0 | AGCTGCCTC | GGTGGG | GAGTGAGGA | X | X | |
| 2 2 0 | AGGAGGGTC | CTGGAT | GAGTGAGGA | X | X | |
| 2 2 0 | AGCAGACTC | CTTGAT | GAGTGAGGA | X | X | |
| 2 2 0 | AGCAGAGTA | TTTGG | GAGTGAGGA | X | X | |
| 2 2 0 | AGCAGAGTT | GCCAG | GAGTGAGGA | X | X | |
| 2 2 0 | AGCAGCACC | AAAATG | GAGTGAGGA | X | X | |

| # of mutations T (−) (+) (−) | site | spacer | (+) site | VF2468 concentration 4 nM | 2 nM | 10.5 nM |
|---|---|---|---|---|---|---|
| 2 2 0 | AGCAGGATC | AGGTTA | GAGTGAGGA | X | X | |
| 2 2 0 | TGCAGCATC | CTTCAG | GAGTGAGGA | X | X | |
| 2 2 0 | AGCAGAGTG | TGGTG | GAGTGAGGA | X | X | |
| 2 2 0 | AGCAGTGCC | TACCA | GAGTGAGGA | X | X | |
| 2 2 0 | AGCAGAGTA | CCCAT | GAGTGAGGA | X | X | |
| 2 2 0 | AGCAGAGTG | AAAGGA | GAGTGAGGA | X | X | |
| 2 2 0 | AGCAGGATC | AAGAAA | GAGTGAGGA | X | X | |
| 2 2 0 | AGCAGCTTG | TGTCAT | GAGTGAGGA | X | X | |
| 2 2 0 | AGCAGAGTA | GGTTGT | GAGTGAGGA | X | X | |
| 3 0 3 | AGCAGCGTC | TGCAGT | TTGTGGGA | X | X | |
| 3 0 3 | AGCAGCGTC | AGGGGA | TTGTGGGA | X | X | |
| 3 0 3 | AGCAGCGTC | CAAGA | GAGTTACAA | X | X | |
| 3 0 3 | AGCAGCGTC | AAAGT | TTGAGAGGA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | TTTTT | GAGAGAAGG | X | X | |
| 3 0 3 | AGCAGCGTC | GGGGA | GAGTTGGGG | X | X | |
| 3 0 3 | AGCAGCGTC | TCCAG | GAACGTGGA | X | X | |
| 3 0 3 | AGCAGCGTC | CTTGGG | GAGTTTGGG | X | X | |
| 3 0 3 | AGCAGCGTC | GTCAC | AGGGGAGGA | X | X | |
| 3 0 3 | AGCAGCGTC | CAAAA | GGCTGAGGG | X | X | |
| 3 0 3 | AGCAGCGTC | CGTCG | CAGTGGGGC | X | X | |
| 3 0 3 | AGCAGCGTC | CGCACT | GAGGGGGCA | X | X | |
| 3 0 3 | AGCAGCGTC | TCTGC | GGGAGAGGC | X | X | |
| 3 0 3 | AGCAGCGTC | ATCTT | GAGTGGAGC | X | X | |
| 3 0 3 | AGCAGCGTC | AGCGA | CAGAGAGGC | X | X | |
| 3 0 3 | AGCAGCGTC | TGTAT | GTGTCAGAA | X | X | |
| 3 0 3 | AGCAGCGTC | ATTAGG | GCATGAGCA | X | X | |
| 3 0 3 | AGCAGCGTC | GATGGA | AAGGGAAGA | X | X | |
| 3 0 3 | AGCAGCGTC | AGGAA | GAGTTGTGA | X | X | |
| 3 0 3 | AGCAGCGTC | TACCGT | GAGTGCTCA | X | X | |
| 3 0 3 | AGCAGCGTC | AGGGT | TTGAGAGGA | X | X | |
| 3 0 3 | AGCAGCGTC | ATGAGT | GTGTAATGA | X | X | |
| 3 0 3 | AGCAGCGTC | TCTTTA | GAGTGGGTT | X | X | |
| 3 0 3 | AGCAGCGTC | CTGTG | GAGGCAGAA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | AGGCTT | CAGTGTGAA | X | X | |
| 3 0 3 | AGCAGCGTC | AGGGT | TTGAGAGGA | X | X | |
| 3 0 3 | AGCAGCGTC | ACACTC | TACTGAGGT | X | X | |
| 3 0 3 | AGCAGCGTC | ACATGC | CAGCGAGGT | X | X | |
| 3 0 3 | AGCAGCGTC | CATGGT | GACAGAGGT | X | X | |
| 3 0 3 | AGCAGCGTC | TTCCCT | GAGAGAGCT | X | X | |
| 3 0 3 | AGCAGCGTC | CAGGA | GAGGAAGGC | X | X | |
| 3 0 3 | AGCAGCGTC | ATACA | GGCTGAGGT | X | X | |
| 3 0 3 | AGCAGCGTC | TGCAT | GAAGGAGGT | X | X | |
| 3 0 3 | AGCAGCGTC | CCAGT | GAGCGATGG | X | X | |
| 3 0 3 | AGCAGCGTC | TTGCA | AAGGGAGAA | X | X | |
| 3 0 3 | AGCAGCGTC | AGGGT | TTGAGAGGA | X | X | |
| 3 0 3 | AGCAGCGTC | CACGT | GTGTGCGGT | X | X | |
| 3 0 3 | AGCAGCGTC | AGCCTC | TAGAGGGGA | X | X | |
| 3 0 3 | AGCAGCGTC | CGCAG | GAGGTAGGG | X | X | |
| 3 0 3 | AGCAGCGTC | CAAGA | GTGTTACGA | X | X | |
| 3 0 3 | AGCAGCGTC | CTAGC | CTGTGAGGG | X | X | |
| 3 0 3 | AGCAGCGTC | CTCCTG | GAGGGAGAG | X | X | |
| 3 0 3 | AGCAGCGTC | AGGGAG | GAGGGGAGA | X | X | |
| 3 0 3 | AGCAGCGTC | CCCCCG | CAGTGATGG | X | X | |
| 3 0 3 | AGCAGCGTC | TCCTGA | GAGAGAAGG | X | X | |
| 3 0 3 | AGCAGCGTC | TGTCCT | GAGTCCAGA | X | X | |
| 3 0 3 | AGCAGCGTC | AAGGAT | TAGAGAGTA | X | X | |
| 3 0 3 | AGCAGCGTC | TCCTGA | GAGAGAAGG | X | X | |
| 3 1 2 | AGTAGCGTC | CTAAT | GAGTGTGAA | X | X | |
| 3 1 2 | AGCAGCTTC | TCCATG | GAGTGAGAC | X | X | |
| 3 1 2 | AGCAGGGTC | GGGGA | GAGGGAGGG | X | X | |
| 3 1 2 | AGCAGCATC | CAGACT | CAGTGAGGT | X | X | |
| 3 1 2 | AGCAGGGTC | AGCTAA | GAGGGAGGC | X | X | |
| 3 1 2 | AGCAGCGGC | AGCGA | GAGTGATGT | X | X | |

| # of mutations | | | | | | VF2468 concentration | | |
|---|---|---|---|---|---|---|---|---|
| T | (−) | (+) | (−) site | spacer | (+) site | 4 nM | 2 nM | 10.5 nM |
| 3 | 1 | 2 | GGCAGCGTC | TGACG | GAGTGAGTG | X | X | |
| 3 | 1 | 2 | AGCAGTGTC | AGGTAG | GAGAGAGGC | X | X | |
| 3 | 1 | 2 | AGCAGGGTC | TGAGTG | GAGTAAGGT | X | X | |
| 3 | 1 | 2 | AGCAGTGTC | AGCTGG | TAGTGAGAA | X | X | |
| 3 | 1 | 2 | AGCACCGTC | TGGGG | GAGGGAAGA | X | X | |
| 3 | 1 | 2 | AGCAGCATC | AGCATG | GAGGGAGGC | X | X | |
| 3 | 1 | 2 | AGCAGCCTC | GGTCAA | GAGTGAGAG | X | X | |
| 3 | 1 | 2 | GGCAGCGTC | AATAA | AAGTGAGGG | X | X | |
| 3 | 1 | 2 | AGCAACGTC | GGCAG | CAGTGGGGA | X | X | |
| 3 | 1 | 2 | AGCAACGTC | AGCAAA | GTCTGAGGA | X | X | |
| 3 | 1 | 2 | AGCAGGGTC | AGTGTC | TAGTGAGAA | X | X | |
| 3 | 1 | 2 | AGCAGGGTC | AGGATG | GAGTGGGGT | X | X | |
| 3 | 1 | 2 | AGCAGTGTC | AGTGAA | CAGTGAGGT | X | X | |
| 3 | 1 | 2 | AGCAGGGTC | AGTGCC | TAGTGAGGG | X | X | |
| 3 | 1 | 2 | AGCAGCGTA | CGGACT | GAGTGAGCC | X | X | |
| 3 | 1 | 2 | AGCAGCTTC | CCCAGT | AAGTGAGAA | X | X | |
| 3 | 1 | 2 | AGCAGCGGC | ACCTC | GAGAGAGAA | X | X | |
| 3 | 1 | 2 | AGCAGTGTC | CTCAC | CAGTAAGGA | X | X | |
| 3 | 1 | 2 | AGCAGGGTC | TGTTA | GAGTGAGTG | X | X | |
| 3 | 1 | 2 | AGCAGCTTC | ACCTG | GAGGGAGGG | X | X | |
| 3 | 1 | 2 | AGCACCGTC | ATCTAA | GGGTGAGGC | X | X | |
| 3 | 1 | 2 | AGCATCGTC | CTGTG | GAGCGAGGG | X | X | |
| 3 | 1 | 2 | AGCAGGGTC | CTTACT | CAGTGAGGT | X | X | |
| 3 | 1 | 2 | AGCAGAGTC | TGAGA | GTGTGAGGT | X | X | |
| 3 | 1 | 2 | AGCAGCGTG | CAGTGA | CAGTGAGGC | X | X | |
| 3 | 1 | 2 | AGCACCGTC | ATTGGA | GAGGGAGAA | X | X | |
| 3 | 1 | 2 | AGCAGCTTC | ACCTG | GAGGGAGGG | X | X | |
| 3 | 1 | 2 | AGCAGAGTC | GCTGCA | GAGTGAGCC | X | X | |
| 3 | 1 | 2 | AGCAGCTTC | ACCTG | GAGGGAGGG | X | X | |
| 3 | 1 | 2 | AGCAGCTTC | ACCTG | GAGGGAGGG | X | X | |
| 3 | 1 | 2 | AGCAGCTTC | ACCTG | GAGGGAGGG | X | X | |
| 3 | 1 | 2 | AGCAGCTTC | ACCTG | GAGGGAGGG | X | X | |
| 3 | 1 | 2 | AGCAGCTTC | ACCTG | GAGGGAGGG | X | X | |
| 3 | 1 | 2 | AGCAGAGTC | CTTGG | GAGGGAGGG | X | X | |
| 3 | 1 | 2 | AGCAGCTTC | ACCTG | GAGGGAGGG | X | X | |
| 3 | 1 | 2 | AGCAGCGTA | TGCATA | CAGTGAGGG | X | X | |
| 3 | 1 | 2 | AGCAGTGTC | AGGCTG | GTGTGAGAA | X | X | |
| 3 | 1 | 2 | AGCAGAGTC | GGCGTC | TAGTGAGGG | X | X | |
| 3 | 1 | 2 | AGCAGCGTG | GGCCGG | GAGGGAGGT | X | X | |
| 3 | 1 | 2 | GGCAGCGTC | CGATT | CAGTGAGGG | X | X | |
| 3 | 1 | 2 | AGCAGCTTC | ACTGAA | GAGGGAGGC | X | X | |
| 3 | 1 | 2 | ATCAGCGTC | TCTGG | GAGTGGGGC | X | X | |
| 3 | 1 | 2 | AGCAGCGGC | AGGCGA | GAGTGACAA | X | X | |
| 3 | 1 | 2 | AGCAGCTTC | AACGT | GAGTGATGT | X | X | |
| 3 | 1 | 2 | AGCAGCTTC | CTGGG | GAGTGAGTT | X | X | |
| 3 | 1 | 2 | AGCAGCATC | TCGTG | GAGGGAGGC | X | X | |
| 3 | 1 | 2 | AGCAGAGTC | TTCAG | GAGAGAGGC | X | X | |
| 3 | 1 | 2 | AGCAGGGTC | AAGTTC | CAGTGAGGG | X | X | |
| 3 | 1 | 2 | AGCAGAGTC | AGTCTT | GAGTGAGTT | X | X | |
| 3 | 1 | 2 | AGCAGAGTC | AGACTT | GAGTGAGTT | X | X | |
| 3 | 1 | 2 | TGCAGCGTC | CAGAT | GAGGGAGGT | X | X | |
| 3 | 1 | 2 | AGCATCGTC | AGAAT | GGGTGAGGG | X | X | |
| 3 | 1 | 2 | AGCAGTGTC | CAGCTC | CAGTGAGGC | X | X | |
| 3 | 1 | 2 | AGCAGCTTC | TAAAAG | GAGAGAGGT | X | X | |
| 3 | 1 | 2 | AGCAGGGTC | CATGAG | GAGTGAGCC | X | X | |
| 3 | 1 | 2 | AGCAGTGTC | ACCACA | GAGTGAAGG | X | X | |
| 3 | 1 | 2 | AGCAGGGTC | AGGTTT | TAGTGAGGG | X | X | |
| 3 | 1 | 2 | AGCAGCATC | AATGTC | TAGTGAGGG | X | X | |
| 3 | 1 | 2 | AGCAGTGTC | CCGCAC | GAGGAAGGA | X | X | |
| 3 | 1 | 2 | AGCAGCTTC | TTGTGA | GAGAGAGGT | X | X | |
| 3 | 1 | 2 | AGCAGAGTC | CTAAGC | GGGTGAGGG | X | X | |
| 3 | 1 | 2 | AGCAGTGTC | AAGTA | GAGTGAAGG | X | X | |
| 3 | 1 | 2 | AGCATCGTC | AAGTTC | TGGTGAGGA | X | X | |
| 3 | 1 | 2 | AGCAGGGTC | CCTGCT | GAGAGAGGG | X | X | |
| 3 | 1 | 2 | AGCAGAGTC | AAGTCA | GAGAGAGGC | X | X | |
| 3 | 1 | 2 | AGCAGCGGC | TGATG | GACTGAGGC | X | X | |
| 3 | 1 | 2 | AGCAGAGTC | CAGTGG | GTGTGAGGC | X | X | |
| 3 | 1 | 2 | AGCAGCGGC | TGATG | GACTGAGGC | X | X | |
| 3 | 1 | 2 | AGCAGCGGC | AGCCGA | GAGAGAGGG | X | X | |
| 3 | 1 | 2 | AGCAGCGGC | TGATG | GACTGAGGC | X | X | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 3 | 1 | 2 AGCAGCGGC | TGATG | GACTGAGGC | | X | X | |
| 3 | 1 | 2 AGCAGCGGC | TGATG | GACTGAGGC | | X | X | |
| 3 | 1 | 2 AGCAGCGGC | TGATG | GACTGAGGC | | X | X | |
| 3 | 1 | 2 AGCAGCGGC | TGATG | GACTGAGGC | | X | X | |
| 3 | 1 | 2 AGCAGCGGC | AGCCGA | GAGAGAGGG | | X | X | |
| 3 | 1 | 2 AGCAGCGGC | TGATG | GACTGAGGC | | X | X | |
| 3 | 1 | 2 TGCAGCGTC | TTGTT | TAGTGAGGC | | X | X | |
| 3 | 1 | 2 AGCAGTGTC | AGGCTG | GTGTGAGAA | | X | X | |
| 3 | 1 | 2 AGCAGCGTA | GAGTGG | GAATGAGGG | | X | X | |
| 3 | 1 | 2 AGCATCGTC | ACAGGA | GGGTGAGGT | | X | X | |
| 3 | 1 | 2 AGCAGCGGC | ACCCA | GAATGAGGG | | X | X | |
| 3 | 1 | 2 AGCAGCGTT | ATTTCA | GAGTGTGGT | | X | X | |
| 3 | 1 | 2 AGCAGAGTC | GCTCCA | GAGTGAGCC | | X | X | |
| 3 | 1 | 2 AGCAGTGTC | ATCTTT | GAGTGGGAA | | X | X | |
| 3 | 1 | 2 AGCAGCATC | TCCTAG | CAGTGAGGG | | X | X | |
| 3 | 1 | 2 AGCAACGTC | AGTGG | GACTGAGGG | | X | X | |
| 3 | 1 | 2 AGCACCGTC | ATCTT | GAGTGAGCT | | X | X | |
| 3 | 1 | 2 AGCAGGGTC | CTGAG | GGGAGAGGA | | X | X | |
| 3 | 1 | 2 GGCAGCGTC | AGGAGA | GAGTGATGT | | X | X | |
| 3 | 1 | 2 AGCATCGTC | GGGGAG | GAGTGGGAA | | X | X | |
| 3 | 1 | 2 AGCAGTGTC | TGTGCT | CAGTGAGGT | | X | X | |
| 3 | 1 | 2 AGCAGTGTC | AGTCCT | GAGAGAGCA | | X | X | |
| 3 | 1 | 2 AGCAGCGTT | GCTTTC | TAGTGAGGT | | X | X | |
| 3 | 1 | 2 AGCAGCGGC | GACAGG | GAGAGAGGG | | X | X | |
| 3 | 1 | 2 AGCACCGTC | CTGAAA | CAGTGAGTA | | X | X | |
| 3 | 1 | 2 AGCAGTGTC | TGCTGG | GAGGGTGGA | | X | X | |
| 3 | 1 | 2 AGCAGCGCC | CTGTGG | GAGGGAGGT | | X | X | |
| 3 | 1 | 2 AGCAGAGTC | AGAAA | GAGTAAGGC | | X | X | |
| 3 | 1 | 2 AGCAGCTTC | TCTAAG | GAGTGGGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ATCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | ACCTG | GAGGGAGGG | | X | X | |
| 3 | 1 | 2 AGCAGCTTC | CTGCTC | CAGTGAGGG | | X | X | |
| 3 | 1 | 2 AGCAGCTTC | ACCTG | GAGGGAGGG | | X | X | |
| 3 | 1 | 2 AGCAGAGTC | AAGAGG | GTGTGAGGG | | X | X | |
| 3 | 1 | 2 AGCAGGGTC | CTGAAG | GAGGGAGGG | | X | X | |
| 3 | 1 | 2 AGCAGGGTC | AGCCCA | GAGGGAGGC | | X | X | |
| 3 | 1 | 2 GGCAGCGTC | ATTTT | GAGTGGGGG | | X | X | |
| 3 | 1 | 2 AGCAGCGTG | TGGCA | GAGAGAGGG | | X | X | |
| 3 | 1 | 2 AGCACCGTC | CCCGAG | GTGGGAGGA | | X | X | |
| 3 | 1 | 2 AGCAGCTTC | CCATC | GGGTGAGGG | | X | X | |
| 3 | 1 | 2 AGCAGCATC | TGTGGA | CAGTGAGGT | | X | X | |
| 3 | 1 | 2 AGCAGCGTG | CTGGAT | GAGTGTGGT | | X | X | |
| 3 | 1 | 2 AGCAGCGGC | AGGCAC | CAGTGAGGG | | X | X | |
| 3 | 1 | 2 AGCAGGGTC | AGGGGT | GAGTGGGGT | | X | X | |
| 3 | 1 | 2 AGCAGCGGC | GAACA | GAGCGGGGA | | X | X | |
| 3 | 1 | 2 AGCTGCGTC | TCTGGG | AAGTGAGGG | | X | X | |
| 3 | 1 | 2 AGCAGGGTC | ATGACA | GAGAGAGGG | | X | X | |
| 3 | 1 | 2 AGCAGCATC | TGGCA | GAGTAAGGG | | X | X | |
| 3 | 1 | 2 AGCAGTGTC | CACCT | GAGTTAGGT | | X | X | |
| 3 | 1 | 2 AGCAGCGAC | GGCGG | GTGTGAGGC | | X | X | |
| 3 | 1 | 2 AGCAGGGTC | ACACTA | AAGTGAGGC | | X | X | |
| 3 | 2 | 1 AGCTGTGTC | ATGAC | AAGTGAGGA | | X | X | |
| 3 | 2 | 1 AGCTGGGTC | ATGTG | AAGTGAGGA | | X | X | |
| 3 | 2 | 1 AGCTGGGTC | ATGTG | AAGTGAGGA | | X | X | |
| 3 | 2 | 1 GGCAGCGGC | CGGAAA | AAGTGAGGA | | X | X | |
| 3 | 2 | 1 AGCATGGTC | AATGA | CAGTGAGGA | | X | X | |
| 3 | 2 | 1 ATCAGCCTC | TTGTAG | GAGTGAGGG | | X | X | |
| 3 | 2 | 1 AGCATGGTC | ATGAA | CAGTGAGGA | | X | X | |
| 3 | 2 | 1 AGCAGGGGC | ATGAGA | GAGTGAGGT | | X | X | |
| 3 | 2 | 1 AACAGCGTG | GCGGA | GAGTGAGGG | | X | X | |
| 3 | 2 | 1 AACAGAGTC | CAGGAA | GAGTGAGGT | | X | X | |
| 3 | 2 | 1 AACAGCATC | AGCTCT | GAGTGAGGC | | X | X | |

| # of mutations | | | (−) site | spacer | (+) site | VF2468 concentration | | |
|---|---|---|---|---|---|---|---|---|
| T (−) | (+) | (−) | | | | 4 nM | 2 nM | 10.5 nM |
| 3 | 2 | 1 | ATCAGTGTC | AGTGAG | CAGTGAGGA | X | X | |
| 3 | 2 | 1 | AGCAGCTGC | ATGAT | GAGTGAGGT | X | X | |
| 3 | 2 | 1 | AGCAGGGTT | GATCA | GAGGGAGGA | X | X | |
| 3 | 2 | 1 | AGCATAGTC | CAGAT | TAGTGAGGA | X | X | |
| 3 | 2 | 1 | AGCAGCAAC | CTTAA | GAGTGAGGG | X | X | |
| 3 | 2 | 1 | AGCTACGTC | TAAGG | GAGAGAGGA | X | X | |
| 3 | 2 | 1 | AGCAGCATT | GGTCCT | GAGTGAGGT | X | X | |
| 3 | 2 | 1 | AGCATTGTC | ATGAA | GAGGGAGGA | X | X | |
| 3 | 2 | 1 | AGCAGCACC | TGGCCT | GAGTGAGGG | X | X | |
| 3 | 2 | 1 | AGCAGGGTT | GGGCA | GAGGGAGGA | X | X | |
| 3 | 2 | 1 | AGTAGAGTC | TGACTA | AAGTGAGGA | X | X | |
| 3 | 2 | 1 | AGCAACGTG | AGTGT | GAGCGAGGA | X | X | |
| 3 | 2 | 1 | AGCAAGGTC | CCACT | CAGTGAGGA | X | X | |
| 3 | 2 | 1 | AGCAGCCAC | AAGGT | GAGTGAGGG | X | X | |
| 3 | 2 | 1 | AGCAATGTC | AGGGA | AAGTGAGGA | X | X | |
| 3 | 2 | 1 | AGCAGCTAC | TCCAGA | GAGTGAGGT | X | X | |
| 3 | 2 | 1 | AGCAGCTGC | AGCAG | GGGTGAGGA | X | X | |
| 3 | 2 | 1 | AGCAGGGGC | AGCAT | GAGTGAGGT | X | X | |
| 3 | 2 | 1 | AGCAACGTG | ACCTAC | TAGTGAGGA | X | X | |
| 3 | 2 | 1 | AACAGCGTA | AGTAC | AAGTGAGGA | X | X | |
| 3 | 2 | 1 | TGCACCGTC | AGTAA | CAGTGAGGA | X | X | |
| 3 | 2 | 1 | AGCAGTGTG | TCCCAA | GAGTGAGGG | X | X | |
| 3 | 2 | 1 | AGCAGCTGC | AATTAT | GAGAGAGGA | X | X | |
| 3 | 2 | 1 | AGCACCTTC | TAGCTA | GAGTGAGCA | X | X | |
| 3 | 2 | 1 | AGCAAGGTC | AGAAG | GAGTAAGGA | X | X | |
| 3 | 2 | 1 | AGCTGCGTG | GGAGCA | GAGTGAGGC | X | X | |
| 3 | 2 | 1 | AGCAAGGTC | CTAGT | GAGTGAAGA | X | X | |
| 3 | 2 | 1 | AGCAGATTC | AGAAG | GAGTGAGGG | X | X | |
| 3 | 2 | 1 | AGCAAAGTC | ATTAGA | GAGTAAGGA | X | X | |
| 3 | 2 | 1 | TGCAGGGTC | TTCCC | GAGTGAGGG | X | X | |
| 3 | 2 | 1 | AGCAGAATC | TTCTGG | GAGTGAGGT | X | X | |
| 3 | 2 | 1 | AGCTGAGTC | CCTAGA | GAGGGAGGA | X | X | |
| 3 | 2 | 1 | AGCATTGTC | CAGAAA | CAGTGAGGA | X | X | |
| 3 | 2 | 1 | TGCAGGGTC | CCAGC | GAGTGAGGG | X | X | |
| 3 | 2 | 1 | AGCAACTTC | ATGTAT | GAGTGTGGA | X | X | |
| 3 | 2 | 1 | AGCAGCTGC | CTGCTG | GAGTGAGGG | X | X | |
| 3 | 2 | 1 | AGCAGGGTT | GGGGA | GAGGGAGGA | X | X | |
| 3 | 2 | 1 | AGCAAGGTC | ACTGA | GAGTAAGGA | X | X | |
| 3 | 2 | 1 | AGCTGTGTC | AAAGG | AAGTGAGGA | X | X | |
| 3 | 2 | 1 | AACAGCATC | TTAGGG | GAGTGAGGG | X | X | |
| 3 | 2 | 1 | AGAAGCTTC | TAGGCT | GAGTGAGGC | X | X | |
| 3 | 2 | 1 | AGCAGAGTT | TGGGGT | GAGTGAGAA | X | X | |
| 3 | 2 | 1 | AGCAGAGTT | TGCTTT | GAGTGAGTA | X | X | |
| 3 | 2 | 1 | AGGAGGGTC | TGAAGA | GAGTGAGGG | X | X | |
| 3 | 2 | 1 | AGCAACTTC | AGCAAA | GTGTGAGGA | X | X | |
| 3 | 2 | 1 | AGCAGCTCC | CTGGA | GAGTGAGGG | X | X | |
| 3 | 2 | 1 | AGCAAAGTC | TGGGAG | AAGTGAGGA | X | X | |
| 3 | 2 | 1 | AGCAACGTG | ACCCCT | GAGTGGGGA | X | X | |
| 3 | 2 | 1 | AGCAGGGTG | TATAA | GAGTGAGGG | X | X | |
| 3 | 2 | 1 | AGCAGGTTC | TTGGGA | GAGTGAGGT | X | X | |
| 3 | 2 | 1 | AGCAGCTTG | TTTCT | GAGTGAGGG | X | X | |
| 3 | 2 | 1 | AGCAGTGTT | GCATTA | AAGTGAGGA | X | X | |
| 3 | 2 | 1 | AGAGGCGTC | TGAGCA | GAGTGAGGG | X | X | |
| 3 | 2 | 1 | AGCAGTGAC | TTAGGA | AAGTGAGGA | X | X | |
| 3 | 2 | 1 | AGCACCTTC | CGAGT | GAGTGAGCA | X | X | |
| 3 | 2 | 1 | ATCAGTGTC | TCCTC | CAGTGAGGA | X | X | |
| 3 | 2 | 1 | AGCAGCAGC | AGGAA | GAGTGAGGC | X | X | |
| 3 | 2 | 1 | AGCAGTGAC | ACCTG | AAGTGAGGA | X | X | |
| 3 | 2 | 1 | AGCAGGGTT | CACAGG | GAGGGAGGA | X | X | |
| 3 | 2 | 1 | AGCTGCGGC | AGGCCC | GAGTGAGGC | X | X | |
| 3 | 2 | 1 | AGCAACATC | TGCTA | CAGTGAGGA | X | X | |
| 3 | 2 | 1 | AGCAACGTA | TAATC | TAGTGAGGA | X | X | |
| 3 | 2 | 1 | AGCAGGATC | GCCTGT | GAGTGAGGG | X | X | |
| 3 | 2 | 1 | AGCAGCAAC | ATGGGA | GAGTGAGGT | X | X | |
| 3 | 2 | 1 | AGTAGCGGC | TTCACA | GAGTGAGAA | X | X | |
| 3 | 2 | 1 | AGCAGCCAC | ATCCT | GAGTGAGGG | X | X | |
| 3 | 2 | 1 | AGCAGCTGC | CAGAA | GAGAGAGGA | X | X | |
| 3 | 2 | 1 | AGCACCGTT | GTTAG | AAGTGAGGA | X | X | |
| 3 | 2 | 1 | AGCAGGGTG | GTTAA | GAGTGAGGG | X | X | |
| 3 | 2 | 1 | AGCTGGGTC | TTGGGA | AAGTGAGGA | X | X | |
| 3 | 2 | 1 | ACCACCGTC | GCGGA | AAGTGAGGA | X | X | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 3 | 2 | 1 AGAAGCTTC | AGTTG | GAGTGAGGT | | X | X | |
| 3 | 2 | 1 AGCAGAGGC | ACCTTT | GAGTGAGGT | | X | X | |
| 3 | 2 | 1 AGCATCGTT | GAGCT | CAGTGAGGA | | X | X | |
| 3 | 2 | 1 AGAAGCGTG | TGCTG | GAGTGAGGC | | X | X | |
| 3 | 2 | 1 GACAGCGTC | TGGGAG | GTGTGAGGA | | X | X | |
| 3 | 2 | 1 AGCAGAGAC | CTGCAT | GAGTGAGGG | | X | X | |
| 3 | 2 | 1 AGCAAAGTC | CTAAGG | AAGTGAGGA | | X | X | |
| 3 | 2 | 1 AGCATTGTC | TCTAGA | GAATGAGGA | | X | X | |
| 3 | 2 | 1 AGCAAAGTC | TTGAGA | GAGCGAGGA | | X | X | |
| 3 | 2 | 1 AGCACAGTC | CCCGTT | GAGAGAGGA | | X | X | |
| 3 | 2 | 1 AGCAGCAGC | ACTGA | GAGTGAGGC | | X | X | |
| 3 | 2 | 1 AGCAGGGTG | GGGTGT | GAGTGAGGT | | X | X | |
| 3 | 2 | 1 AGGAGCATC | GCGCAG | GAGTGAGGC | | X | X | |
| 3 | 2 | 1 AGCTGGGTC | ATGTG | AAGTGAGGA | | X | X | |
| 3 | 2 | 1 AGCTGTGTC | ATGAC | AAGTGAGGA | | X | X | |
| 3 | 2 | 1 AGCTGTGTC | ATGAC | AAGTGAGGA | | X | X | |
| 3 | 2 | 1 AGGAGCGTA | TCTTCT | GAGTGAGGC | | X | X | |
| 3 | 2 | 1 AGCAGCCAC | AGCCA | GAGTGAGGG | | X | X | |
| 3 | 2 | 1 AGCAGCATG | TGCAGG | GAGTGAGGC | | X | X | |
| 3 | 2 | 1 AGCATTGTC | TTTTGA | GAGTGAGAA | | X | X | |
| 3 | 2 | 1 AGCAGCCTG | GACGT | GAGTGAGGT | | X | X | |
| 3 | 2 | 1 AGCAGCTCC | AGCGA | GAGTGAGGG | | X | X | |
| 3 | 2 | 1 AGCAGCAGC | TAGGGA | GAGTGAGGC | | X | X | |
| 3 | 2 | 1 AGCAACTTC | AATCAG | GAGTGTGGA | | X | X | |
| 3 | 2 | 1 AGCAGAGTA | GCTTT | GAGTGAGGG | | X | X | |
| 3 | 2 | 1 AGCAGCCTT | GTGTG | GAGTGAGGT | | X | X | |
| 3 | 2 | 1 AGCAGTGTT | TCTGA | AAGTGAGGA | | X | X | |
| 3 | 2 | 1 AGAAGCATC | TGTAT | GAGTGAGGG | | X | X | |
| 3 | 2 | 1 AGCAGGGTA | AACAAA | GAGTGAGGT | | X | X | |
| 3 | 2 | 1 AGCAGAGTT | AGGAGA | GAGTGAGGG | | X | X | |
| 3 | 2 | 1 AGCAGAGGC | TGGGGA | GAGTGAGGG | | X | X | |
| 3 | 2 | 1 AGCAACATC | TTATA | GAGTGAGCA | | X | X | |
| 3 | 2 | 1 AGCAGAGTA | TGTCA | GAGTGAGGT | | X | X | |
| 3 | 2 | 1 AGCATCGTT | GAGCT | GAGTGAAGA | | X | X | |
| 3 | 2 | 1 AGAAGCTTC | CAGAAT | GAGTGAGGC | | X | X | |
| 3 | 2 | 1 ATCAGCGGC | AGATGG | CAGTGAGGA | | X | X | |
| 3 | 2 | 1 AGCAGAATC | TCTGG | GAGTGAGGC | | X | X | |
| 3 | 2 | 1 AGCTACGTC | ACCTT | GAGGGAGGA | | X | X | |
| 3 | 2 | 1 AGCAATGTC | AACAA | GAGTGAGAA | | X | X | |
| 3 | 2 | 1 AGCATTGTC | ATGGTG | GAGGGAGGA | | X | X | |
| 3 | 2 | 1 AGCACCGCC | GGGAA | AAGTGAGGA | | X | X | |
| 3 | 2 | 1 AGCACGGTC | GGGTAC | TAGTGAGGA | | X | X | |
| 3 | 2 | 1 AGCAACATC | TATAT | GAGTGAGCA | | X | X | |
| 3 | 2 | 1 AGCAGGGTT | GGAGT | GAGGGAGGA | | X | X | |
| 3 | 2 | 1 AGCAGCTGC | AGCACC | GAGTGAGGG | | X | X | |
| 3 | 2 | 1 AGCAGTGTG | TGGGAG | GAGTGAGGG | | X | X | |
| 3 | 2 | 1 AACAGAGTC | TGGTT | GAGTGAGGC | | X | X | |
| 3 | 2 | 1 GGCAGTGTC | TGGCA | AAGTGAGGA | | X | X | |
| 3 | 2 | 1 AGCAGTGTG | TGGGAG | GAGTGAGGG | | X | X | |
| 3 | 2 | 1 AGCAAGGTC | CAGACA | AAGTGAGGA | | X | X | |
| 3 | 2 | 1 AGCAGTGTG | TGGGAG | GAGTGAGGG | | X | X | |
| 3 | 2 | 1 AGCAGTGTG | TGGGAG | GAGTGAGGG | | X | X | |
| 3 | 2 | 1 AGCAGTGTG | TGGGAG | GAGTGAGGG | | X | X | |
| 3 | 2 | 1 AGCAGTGTG | TGGGAG | GAGTGAGGG | | X | X | |
| 3 | 2 | 1 AGCAGCATG | AGAGG | GAGTGAGGG | | X | X | |
| 3 | 2 | 1 AGCACTGTC | ATTAT | AAGTGAGGA | | X | X | |
| 3 | 2 | 1 GGCAGTGTC | TGGAAA | AAGTGAGGA | | X | X | |
| 3 | 2 | 1 CACAGCGTC | ATCCTG | GAGTGAGAA | | X | X | |
| 3 | 2 | 1 AGCACCTTC | CTGGCT | GAGTGAGGG | | X | X | |
| 3 | 2 | 1 AGCACAGTC | CCAAAT | GAGTGAGAA | | X | X | |
| 3 | 2 | 1 AGCAGATTC | TGGTA | GAGTGAGGG | | X | X | |
| 3 | 2 | 1 AGGAGGGTC | AGCCT | GAGTGAGGG | | X | X | |
| 3 | 2 | 1 AGCAACGTG | GCGGG | AAGTGAGGA | | X | X | |
| 3 | 2 | 1 AGCGGCGTT | GAGCTT | GAGTGAGGC | | X | X | |
| 3 | 2 | 1 AGGAGTGTC | TGGGT | GAGTGAGGT | | X | X | |
| 3 | 2 | 1 AGCTGCTTC | ACTGAT | GAGTGAGGC | | X | X | |
| 3 | 2 | 1 AGCAACATC | CACTG | CAGTGAGGA | | X | X | |
| 3 | 2 | 1 AGCATAGTC | GGACAA | TAGTGAGGA | | X | X | |
| 3 | 2 | 1 AGCAACATC | AAACCT | GAGAGAGGA | | X | X | |
| 3 | 2 | 1 GGCAGCGCC | CATCT | GAGTGAGGG | | X | X | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 3 | 2 | 1 AGCAGAGTG | TCCAA | GAGTGAGGG | | X | X | |
| 3 | 2 | 1 AGCAAAGTC | CTAGAT | GAGGGAGGA | | X | X | |
| 3 | 2 | 1 GACAGCGTC | ACACA | CAGTGAGGA | | X | X | |
| 3 | 2 | 1 AGCGGCGGC | TGGAT | GAGTGAGGG | | X | X | |
| 3 | 2 | 1 AGCCGCATC | ATCAA | GAGTGAGGC | | X | X | |
| 3 | 2 | 1 AGCAAAGTC | CCCAG | GAGGGAGGA | | X | X | |
| 3 | 2 | 1 AGCAGGTTC | TAAGA | GAGTGAGGT | | X | X | |
| 3 | 2 | 1 AGCTGGGTC | ACACG | AAGTGAGGA | | X | X | |
| 3 | 2 | 1 AGCAGAGAC | TGAATG | GAGTGAGGG | | X | X | |
| 3 | 2 | 1 AGCAGAGGC | TTAAAG | GAGTGAGGG | | X | X | |
| 3 | 2 | 1 AGCTGAGTC | TAGCCA | AAGTGAGGA | | X | X | |
| 3 | 2 | 1 AGTAGAGTC | TTCCA | GAGTGAGAA | | X | X | |
| 3 | 2 | 1 TGCAGCGAC | AACAG | GAGTGAGGT | | X | X | |
| 3 | 2 | 1 AGCAGCTGC | CTCCG | GAGAGAGGA | | X | X | |
| 3 | 2 | 1 AGCAGCATG | GCCCT | GAGTGAGGG | | X | X | |
| 3 | 2 | 1 AGCTGAGTC | CCAAA | GAGTGAGAA | | X | X | |
| 3 | 2 | 1 AGCAACATC | TGCTA | CAGTGAGGA | | X | X | |
| 3 | 2 | 1 AGCAACATC | TGCTA | CAGTGAGGA | | X | X | |
| 3 | 2 | 1 ACCAGCTTC | CTGCT | GAGTGAGGT | | X | X | |
| 3 | 2 | 1 AGCAGCATT | ATTCT | GAGTGAGGG | | X | X | |
| 3 | 2 | 1 AGGAGTGTC | GACAAG | GAGTGAGGG | | X | X | |
| 3 | 2 | 1 AGAAGCGGC | TGCAG | GAGTGAGGG | | X | X | |
| 3 | 2 | 1 AGCAGCCAC | AGACTA | GAGTGAGGC | | X | X | |
| 3 | 2 | 1 AGCAGCAGC | AGCAG | GAGTGAGGC | | X | X | |
| 3 | 2 | 1 AGCACAGTC | CGCAGG | GAGGGAGGA | | X | X | |
| 3 | 2 | 1 AGCTGCGGC | GAATGA | GAGTGAGGG | | X | X | |
| 3 | 2 | 1 AGCAAGGTC | TTATA | GGGTGAGGA | | X | X | |
| 3 | 2 | 1 AGCACCTTC | TCCAT | GAGTGGGGA | | X | X | |
| 3 | 2 | 1 AGCAGCATG | ATCCTG | GAGTGAGGC | | X | X | |
| 3 | 2 | 1 AGCAAGGTC | AAGAGA | GAGTGAGCA | | X | X | |
| 3 | 2 | 1 AGCATGGTC | AAAGCT | GAGTGAGAA | | X | X | |
| 3 | 2 | 1 AGCAGCATG | ATCTTG | GAGTGAGGC | | X | X | |
| 3 | 2 | 1 AGCAGGGTG | GGGTGT | GAGTGAGGT | | X | X | |
| 3 | 3 | 0 AGAGGTGTC | GCCAT | GAGTGAGGA | | X | X | |
| 3 | 3 | 0 GTCAGGGTC | ATCAG | GAGTGAGGA | | X | X | |
| 3 | 3 | 0 TGCACTGTC | TCTCCC | GAGTGAGGA | | X | X | |
| 3 | 3 | 0 TGCGGAGTC | GAGGGT | GAGTGAGGA | | X | X | |
| 3 | 3 | 0 AGAAACGTT | CTTGCT | GAGTGAGGA | | X | X | |
| 3 | 3 | 0 AGGAGCAAC | ATGCT | GAGTGAGGA | | X | X | |
| 3 | 3 | 0 CGCTGTGTC | CCCGGG | GAGTGAGGA | | X | X | |
| 3 | 3 | 0 AGCGTGGTC | ACTAGG | GAGTGAGGA | | X | X | |
| 3 | 3 | 0 AGCAGGTCC | TTGAA | GAGTGAGGA | | X | X | |
| 3 | 3 | 0 GGCTGTGTC | ATTCAG | GAGTGAGGA | | X | X | |
| 3 | 3 | 0 TGCAGAGTT | AGAGGT | GAGTGAGGA | | X | X | |
| 3 | 3 | 0 ATCATGGTC | AGAAAA | GAGTGAGGA | | X | X | |
| 3 | 3 | 0 AGCAACGCG | GTGAGG | GAGTGAGGA | | X | X | |
| 3 | 3 | 0 TGAAGTGTC | AGCTC | GAGTGAGGA | | X | X | |
| 3 | 3 | 0 AGCAACTCC | GTCTT | GAGTGAGGA | | X | X | |
| 3 | 3 | 0 AGAAATGTC | TTCCAG | GAGTGAGGA | | X | X | |
| 3 | 3 | 0 GGCAGGGTA | TCACAG | GAGTGAGGA | | X | X | |
| 3 | 3 | 0 AGCAACATG | GAGTT | GAGTGAGGA | | X | X | |
| 3 | 3 | 0 GACAGCGTG | GCCAGT | GAGTGAGGA | | X | X | |
| 3 | 3 | 0 GGCTGAGTC | ACTCT | GAGTGAGGA | | X | X | |
| 3 | 3 | 0 TGCAGAGTT | TTGTG | GAGTGAGGA | | X | X | |
| 3 | 3 | 0 AGCTGAGTG | CTGGAT | GAGTGAGGA | | X | X | |
| 3 | 3 | 0 AACTGAGTC | TCTGA | GAGTGAGGA | | X | X | |
| 3 | 3 | 0 AACATAGTC | TGTACA | GAGTGAGGA | | X | X | |
| 3 | 3 | 0 AGCTGGGTG | ACAGT | GAGTGAGGA | | X | X | |
| 3 | 3 | 0 AGCACCATA | TGGCT | GAGTGAGGA | | X | X | |
| 3 | 3 | 0 ATCAGGTTC | CTTCT | GAGTGAGGA | | X | X | |
| 3 | 3 | 0 ACCACGGTC | AGGTCT | GAGTGAGGA | | X | X | |
| 3 | 3 | 0 ACCACGGTC | AGGTCT | GAGTGAGGA | | X | X | |
| 3 | 3 | 0 ACCACGGTC | AGGTCT | GAGTGAGGA | | X | X | |
| 3 | 3 | 0 ACCACGGTC | AGGTCT | GAGTGAGGA | | X | X | |
| 3 | 3 | 0 ACCATGGTC | AAGTCT | GAGTGAGGA | | X | X | |
| 3 | 3 | 0 AGAAACTTC | CTCTC | GAGTGAGGA | | X | X | |
| 3 | 3 | 0 CACAGCTTC | TCACAG | GAGTGAGGA | | X | X | |
| 3 | 3 | 0 ATCATGGTC | TTAGA | GAGTGAGGA | | X | X | |
| 3 | 3 | 0 AGCAGTGAT | TGAGG | GAGTGAGGA | | X | X | |
| 3 | 3 | 0 ACCAAGGTC | ACACT | GAGTGAGGA | | X | X | |
| 3 | 3 | 0 AGCCCCTTC | CTAGAG | GAGTGAGGA | | X | X | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 3 | 3 | 0 | CTCAGTGTC | TAAGCA | GAGTGAGGA | X | X | |
| 3 | 3 | 0 | AGTTGCTTC | CTGAG | GAGTGAGGA | X | X | |
| 3 | 3 | 0 | AAGAGAGTC | TGAAA | GAGTGAGGA | X | X | |
| 3 | 3 | 0 | GGCAGTGTG | GTCACC | GAGTGAGGA | X | X | |
| 3 | 3 | 0 | TGCAGAGTT | GGGTCA | GAGTGAGGA | X | X | |
| 3 | 3 | 0 | AGCCTCGTT | GCCAGA | GAGTGAGGA | X | X | |
| 3 | 3 | 0 | ATCATCTTC | AAGTAA | GAGTGAGGA | X | X | |
| 3 | 3 | 0 | AGTAGTGTG | TGAAGG | GAGTGAGGA | X | X | |
| 3 | 3 | 0 | AGCCTCGTG | TCCTCA | GAGTGAGGA | X | X | |
| 3 | 3 | 0 | AAAAGCGTT | TGGGAA | GAGTGAGGA | X | X | |
| 3 | 3 | 0 | ACTAGAGTC | CCCCAA | GAGTGAGGA | X | X | |
| 3 | 3 | 0 | GGCGGCGGC | GAAGG | GAGTGAGGA | X | X | |
| 3 | 3 | 0 | ATGAGAGTC | CTGGG | GAGTGAGGA | X | X | |
| 3 | 3 | 0 | AGCACAGTG | GCCTGA | GAGTGAGGA | X | X | |
| 3 | 3 | 0 | TACAGGGTC | CTCGGT | GAGTGAGGA | X | X | |
| 3 | 3 | 0 | AGCAGAGGT | GCTGA | GAGTGAGGA | X | X | |
| 3 | 3 | 0 | GGAAGAGTC | CAGGG | GAGTGAGGA | X | X | |
| 3 | 3 | 0 | GGAAGAGTC | CAGGG | GAGTGAGGA | X | X | |
| 3 | 3 | 0 | AGTGGGGTC | TGTTGG | GAGTGAGGA | X | X | |
| 3 | 3 | 0 | ATGAGGGTC | ACTGAG | GAGTGAGGA | X | X | |
| 3 | 3 | 0 | GTCAGAGTC | CTAGG | GAGTGAGGA | X | X | |
| 3 | 3 | 0 | GCCAGGGTC | TGGGAG | GAGTGAGGA | X | X | |
| 3 | 3 | 0 | AGCAACTCC | ATCTT | GAGTGAGGA | X | X | |
| 3 | 3 | 0 | AGGGGAGTC | GACAG | GAGTGAGGA | X | X | |
| 3 | 3 | 0 | GTCAGGGTC | ATCAG | GAGTGAGGA | X | X | |
| 3 | 3 | 0 | GTCAGGGTC | ATCAG | GAGTGAGGA | X | X | |
| 3 | 3 | 0 | AGCATAGTA | GTTAA | GAGTGAGGA | X | X | |
| 3 | 3 | 0 | GTCAGAGTC | CAAAA | GAGTGAGGA | X | X | |
| 3 | 3 | 0 | GGCAGTGTT | ACAAA | GAGTGAGGA | X | X | |
| 3 | 3 | 0 | GCCATCGTC | ACCCA | GAGTGAGGA | X | X | |
| 3 | 3 | 0 | CTCAGTGTC | GAGAGA | GAGTGAGGA | X | X | |
| 3 | 3 | 0 | GGAAGAGTC | AAGGA | GAGTGAGGA | X | X | |
| 3 | 3 | 0 | AGCAACTCC | AGAAGA | GAGTGAGGA | X | X | |
| 3 | 3 | 0 | AGCCTCGGC | GGCCCT | GAGTGAGGA | X | X | |
| 3 | 3 | 0 | GACAGGGTC | ACTTTA | GAGTGAGGA | X | X | |
| 3 | 3 | 0 | AGAATAGTC | CTGGG | GAGTGAGGA | X | X | |
| 3 | 3 | 0 | AGTAGAGTA | GTAAAG | GAGTGAGGA | X | X | |
| 3 | 3 | 0 | GGGAGGGTC | GGTCAG | GAGTGAGGA | X | X | |
| 3 | 3 | 0 | AACAGGGTT | ATCCA | GAGTGAGGA | X | X | |
| 3 | 3 | 0 | GCCAGGGTC | ACCCA | GAGTGAGGA | X | X | |
| 3 | 3 | 0 | GGAAGAGTC | TTACCT | GAGTGAGGA | X | X | |
| 3 | 3 | 0 | AGTGGAGTC | ACCGTA | GAGTGAGGA | X | X | |
| 3 | 3 | 0 | GCCAGAGTC | ACCCTT | GAGTGAGGA | X | X | |
| 3 | 3 | 0 | GGCAGTGTA | ACTTAA | GAGTGAGGA | X | X | |
| 3 | 3 | 0 | CTCAGTGTC | GTTGT | GAGTGAGGA | X | X | |
| 3 | 3 | 0 | AGATGGGTC | TACAGA | GAGTGAGGA | X | X | |
| 3 | 3 | 0 | GCCAGAGTC | TGAGTG | GAGTGAGGA | X | X | |
| 3 | 3 | 0 | AGTAGGGTT | TGAAT | GAGTGAGGA | X | X | |
| 3 | 3 | 0 | CACTGCGTC | CTTGGT | GAGTGAGGA | X | X | |
| 3 | 3 | 0 | AACTGGGTC | CCTGAG | GAGTGAGGA | X | X | |
| 3 | 3 | 0 | AGTAACATC | AGTAGT | GAGTGAGGA | X | X | |
| 3 | 3 | 0 | GACAGAGTC | CACAGA | GAGTGAGGA | X | X | |
| 3 | 3 | 0 | ATCAGGTTC | CAATA | GAGTGAGGA | X | X | |
| 3 | 3 | 0 | AGCATGGTA | GTGGG | GAGTGAGGA | X | X | |
| 3 | 3 | 0 | AGCAACTGC | CCTTCT | GAGTGAGGA | X | X | |
| 3 | 3 | 0 | GGCTGAGTC | TTGCAG | GAGTGAGGA | X | X | |
| 3 | 3 | 0 | AGCAGCCCA | GGGGT | GAGTGAGGA | X | X | |
| 3 | 3 | 0 | AGCAAAGTG | TCAAT | GAGTGAGGA | X | X | |
| 3 | 3 | 0 | AGAAAAGTC | CACAGG | GAGTGAGGA | X | X | |
| 3 | 3 | 0 | AACAACTTC | TCCTG | GAGTGAGGA | X | X | |
| 3 | 3 | 0 | TGCGGAGTC | CCTGGG | GAGTGAGGA | X | X | |
| 3 | 3 | 0 | AGAATGGTC | TCTGAT | GAGTGAGGA | X | X | |
| 3 | 3 | 0 | AGCAGCAGA | ACAACT | GAGTGAGGA | X | X | |
| 3 | 3 | 0 | AGCAGCAGA | TATTG | GAGTGAGGA | X | X | |
| 3 | 3 | 0 | AGTTGCTTC | TTCTAA | GAGTGAGGA | X | X | |
| 3 | 3 | 0 | GACAGGGTC | CTGGA | GAGTGAGGA | X | X | |
| 3 | 3 | 0 | GGAAGAGTC | CGGGG | GAGTGAGGA | X | X | |
| 3 | 3 | 0 | GGAAGAGTC | CAAAG | GAGTGAGGA | X | X | |
| 3 | 3 | 0 | AGGGGGGTC | AAGAGT | GAGTGAGGA | X | X | |
| 3 | 3 | 0 | AACAACTTC | CATGT | GAGTGAGGA | X | X | |
| 3 | 3 | 0 | ACCAAGGTC | AGCAGG | GAGTGAGGA | X | X | |

| # of mutations T (−) (+) (−) | site | spacer | (+) site | VF2468 concentration 4 nM | 2 nM | 10.5 nM |
|---|---|---|---|---|---|---|
| 3 3 0 | GGCCACGTC | GCACAG | GAGTGAGGA | X | X | |
| 3 3 0 | AGCAAGGTT | AGGAAG | GAGTGAGGA | X | X | |
| 3 3 0 | AGTAGGGTT | GGAGGG | GAGTGAGGA | X | X | |
| 4 0 4 | AGCAGCGTC | ACAAAA | TAGCAAGGT | X | X | |
| 4 0 4 | AGCAGCGTC | AAGGG | GAGACAAGT | X | X | |
| 4 0 4 | AGCAGCGTC | CGTCCC | GAGAGGCGC | X | X | |
| 4 1 3 | AGCAGCGGC | CTAGC | GGGTGAGTC | X | X | |
| 4 1 3 | AGCAGCGTT | GCTAT | GAGAAAGGT | X | X | |
| 4 1 3 | AGCAACGTC | ATGTGC | TGGGGAGGA | X | X | |
| 4 1 3 | AGCAGCGGC | CGGAG | AAGTGTGGG | X | X | |
| 4 1 3 | AGCAACGTC | TGTTT | GTGTAAGGC | X | X | |
| 4 1 3 | AGCAACGTC | ACCTG | GAGTCACGC | X | X | |
| 4 1 3 | AGCAGTGTC | ATGATG | GTGTGTGAA | X | X | |
| 4 1 3 | AGCAGCGGC | CACATA | GTGTGTGAA | X | X | |
| 4 1 3 | AGCAACGTC | CAGTCC | AAGTGTGGC | X | X | |
| 4 1 3 | AGCAACGTC | GGATGC | AGGTGAGCA | X | X | |
| 4 1 3 | ATCAGCGTC | CAGATG | GTGTGAGTC | X | X | |
| 4 1 3 | AGCAACGTC | CTTAC | TAGTGAATA | X | X | |
| 4 1 3 | AGCAACGTC | GTGAC | GTGCGATGA | X | X | |
| 4 1 3 | AGCAGTGTC | TGTCTG | GAGTGTTGC | X | X | |
| 4 1 3 | AGCAGCGTT | GTTTTG | ATGTGAGGC | X | X | |
| 4 1 3 | AGCAACGTC | TGTGT | GAGTGACAG | X | X | |
| 4 1 3 | AGCACCGTC | TGCCG | GTGTGCGGT | X | X | |
| 4 1 3 | AGCAACGTC | CAGTCC | AAGTGTGGC | X | X | |
| 4 2 2 | AGCATTGTC | TTGTGG | GAGTAAGGC | X | X | |
| 4 2 2 | AGCAGCGAT | GGGGTT | GAGTGAGAC | X | X | |
| 4 2 2 | AGCTGTGTC | ATCCAT | GAGTGAGTC | X | X | |
| 4 2 2 | AGCATGGTC | AAGTTC | TAGTGAGGG | X | X | |
| 4 2 2 | AGCATGGTC | AAGTTC | TAGTGAGGG | X | X | |
| 4 2 2 | AGCATCTTC | ATATG | GAGTGAGAG | X | X | |
| 4 2 2 | AGCATGGTC | AGGTTC | TAGTGAGGG | X | X | |
| 4 2 2 | AGCATAGTC | AAGGG | GAGTGAGAG | X | X | |
| 4 2 2 | AGCATGGTC | TCTTTC | TAGTGAGGG | X | X | |
| 4 2 2 | AGCATGGTC | AGGTTC | TAGTGAGGG | X | X | |
| 4 2 2 | AGCATAGTC | TTTATT | GAGTGAGAG | X | X | |
| 4 2 2 | AGCAAAGTC | CTGAAG | GAGTGAGAG | X | X | |
| 4 2 2 | AGCAGCGCA | AAGCAC | GTGTGAGGC | X | X | |
| 4 2 2 | ATCAACGTC | TGGAC | TAGTGAGGG | X | X | |
| 4 2 2 | AGTAGTGTC | CACAG | AAGTGAGGG | X | X | |
| 4 2 2 | AGCAAAGTC | CCTTG | GAGTGAGTG | X | X | |
| 4 2 2 | AGCCACGTC | TATGCT | TTGTGAGGA | X | X | |
| 4 2 2 | AGCATGGTC | GGGTTC | TAGTGAGGG | X | X | |
| 4 2 2 | AGCAGAGTT | GGGAAA | AAGTGAGGG | X | X | |
| 4 2 2 | AGCATTGTC | ACTGT | GAGTGAGAG | X | X | |
| 4 2 2 | AGCATGGTC | AGGTTC | TAGTGAGGG | X | X | |
| 4 2 2 | AGCATGGTC | AGGTTC | TAGTGAGGG | X | X | |
| 4 2 2 | AGCATGGTC | TAGCA | GAGTGAGTC | X | X | |
| 4 2 2 | AGCTGTGTC | ATCCAT | GAGTGAGTC | X | X | |
| 4 2 2 | AGTAGAGTC | TGGGTG | GAGTGAGAC | X | X | |
| 4 2 2 | AGCATGGTC | AGGTTC | TAGTGAGGG | X | X | |
| 4 2 2 | AGCTGTGTC | CAGGAG | GAGTGAGTC | X | X | |
| 4 2 2 | AGCAACTTC | TGATC | TAGTGAGGT | X | X | |
| 4 2 2 | AGCTGAGTC | AACCT | GAGTAAGGG | X | X | |
| 4 2 2 | AGTAGGGTC | ATCAG | AAGTGAGGT | X | X | |
| 4 2 2 | AGCTGTGTC | ACCTT | GAGTGAGTC | X | X | |
| 4 2 2 | AGCAACATC | TGGAA | GAGTGAGAG | X | X | |
| 4 2 2 | AGCATCGTG | TTTGA | AAGTGAGGC | X | X | |
| 4 2 2 | AGCATGGTC | AGGTTC | TAGTGAGGG | X | X | |
| 4 2 2 | AGCAACTTC | AGGGG | AAGTGAGGG | X | X | |
| 4 2 2 | AGCATGGTC | AGATTA | TAGTGAGGG | X | X | |
| 4 2 2 | AGCATGGTC | CGTGTC | TAGTGAGGG | X | X | |
| 4 2 2 | AGCAAGGTC | ACCTGA | GAGTGAGAG | X | X | |
| 4 2 2 | AGCATGGTC | AAGTTC | TAGTGAGGG | X | X | |
| 4 2 2 | AGCAGGGTA | TAGGG | GAGTGAGAT | X | X | |
| 4 2 2 | GGCAGAGTC | CAAGCA | GAGTGAGAG | X | X | |
| 4 2 2 | AGTAACGTC | AAAGGT | GAGTGAAAA | X | X | |
| 4 2 2 | AGCATGGTC | AATTTC | TAGTGAGGG | X | X | |
| 4 2 2 | AGCAGTGTG | GAGTG | GAGTGAGAG | X | X | |
| 4 2 2 | AGCACCATC | CCCAT | GAGTGAGTC | X | X | |
| 4 2 2 | AGCAACGTG | AGACAG | TAGTGAGAA | X | X | |
| 4 2 2 | AGCAACGGC | CCTGGG | CAGTGAGGG | X | X | |

| # of mutations T | # of mutations (+) | # of mutations (−) | (−) site | spacer | (+) site | VF2468 concentration 4 nM | VF2468 concentration 2 nM | VF2468 concentration 10.5 nM |
|---|---|---|---|---|---|---|---|---|
| 4 | 2 | 2 | AGTAGAGTC | ATGGA | GAGTGAGAG | X | X | |
| 4 | 2 | 2 | GGCACCGTC | GCTGA | GAGTGAGTC | X | X | |
| 4 | 2 | 2 | AGCATGGTC | AGGTTC | TAGTGAGGG | X | X | |
| 4 | 2 | 2 | AGCATAGTC | AGGTTC | TAGTGAGGG | X | X | |
| 4 | 2 | 2 | AGTAACGTC | TCCCT | GAGTGTGGG | X | X | |
| 4 | 3 | 1 | AGCATAGTG | GTTAG | GAGTGAGGG | X | X | |
| 4 | 3 | 1 | ATCAGGGTG | GGTAG | GAGTGAGGC | X | X | |
| 4 | 3 | 1 | TACAGAGTC | TCCAG | GAGTGAGGG | X | X | |
| 4 | 3 | 1 | ATGAGGGTC | TCATA | GAGTGAGGT | X | X | |
| 4 | 3 | 1 | AGCAAATTC | TTCAG | GAGTGAGGT | X | X | |
| 4 | 3 | 1 | AGCAAAGTG | CTCAAA | GAGTGAGGC | X | X | |
| 4 | 3 | 1 | ATAAGTGTC | ATTGAA | GAGTGAGGC | X | X | |
| 4 | 3 | 1 | AGTAGTCTC | TTGAT | GAGTGAGGG | X | X | |
| 4 | 3 | 1 | CGCAGCAAC | AGCGGT | GAGTGAGGG | X | X | |
| 4 | 3 | 1 | AGCAATGTG | TGCTT | GAGTGAGGC | X | X | |
| 4 | 3 | 1 | ACCAAAGTC | TTTGAT | GAGTGAGGG | X | X | |
| 4 | 3 | 1 | AGTAGTGTT | TCAAGA | GAGTGAGGC | X | X | |
| 4 | 3 | 1 | AGCATAGTG | GGGTAG | GAGTGAGGG | X | X | |
| 4 | 3 | 1 | ATCACCATC | CTAAGT | GAGTGAGGG | X | X | |
| 4 | 3 | 1 | AGAATCGTT | TGAAA | GAGTGAGGG | X | X | |
| 4 | 3 | 1 | AGTAACATC | GGAAAA | GAGTGAGGT | X | X | |
| 4 | 3 | 1 | AGGACAGTC | AGTTG | GAGTGAGGT | X | X | |
| 4 | 3 | 1 | GGCAGTGTT | GACAG | GAGTGAGGC | X | X | |
| 4 | 3 | 1 | AGTTGTGTC | GTTTT | GAGTGAGGT | X | X | |
| 4 | 3 | 1 | CCCACCGTC | CCGCCC | GAGTGAGGG | X | X | |
| 4 | 3 | 1 | AGTACCGGC | TTCACA | GAGTGAGGT | X | X | |
| 4 | 3 | 1 | AGCAACTTT | GGAATG | GAGTGAGGG | X | X | |
| 4 | 3 | 1 | AGCAAGGGC | AGTGA | GAGTGAGGG | X | X | |
| 4 | 3 | 1 | GTCAGGGTC | ATAAGA | GAGTGAGGT | X | X | |
| 4 | 3 | 1 | AGGAAAGTC | TAACA | GAGTGAGGT | X | X | |
| 4 | 3 | 1 | CACAGTGTC | AGGCT | GAGTGAGGT | X | X | |
| 4 | 3 | 1 | GTCAGTGTC | CAAGAA | GAGTGAGGT | X | X | |
| 4 | 3 | 1 | ATCACCATC | CAGAGA | GAGTGAGGG | X | X | |
| 4 | 3 | 1 | ATCAACATC | TTTGG | GAGTGAGGC | X | X | |
| 4 | 3 | 1 | CCGAGCGTC | TGAAA | GAGTGAGGT | X | X | |
| 4 | 3 | 1 | AGCACAGTG | AGCACT | GAGTGAGGG | X | X | |
| 4 | 3 | 1 | AACATTGTC | TAAGG | GAGTGAGGT | X | X | |
| 4 | 3 | 1 | AACATTGTC | TAAGG | GAGTGAGGT | X | X | |
| 4 | 3 | 1 | AACATTGTC | TAAGG | GAGTGAGGT | X | X | |
| 4 | 3 | 1 | AGTACCGGC | ATCCAT | GAGTGAGGT | X | X | |
| 4 | 3 | 1 | AGTACAGTC | TCTGTT | GAGTGAGAA | X | X | |
| 4 | 3 | 1 | AACAACATC | ACGGG | GAGTGAGGT | X | X | |
| 4 | 3 | 1 | TCCCGCGTC | CGGGAA | GAGTGAGGT | X | X | |
| 4 | 3 | 1 | AGGGGAGTC | AGATGC | GAGTGAGGG | X | X | |
| 4 | 3 | 1 | AGTAGCTGC | GGCCA | GAGTGAGGC | X | X | |
| 4 | 3 | 1 | GGAAGGGTC | AGTGC | GAGTGAGGG | X | X | |
| 4 | 3 | 1 | GGAAGGGTC | AGTGC | GAGTGAGGG | X | X | |
| 4 | 3 | 1 | GGAAGGGTC | AGTGC | GAGTGAGGG | X | X | |
| 4 | 3 | 1 | GGAAGGGTC | AGTGC | GAGTGAGGG | X | X | |
| 4 | 3 | 1 | GGAAGGGTC | AGTGC | GAGTGAGGG | X | X | |
| 4 | 3 | 1 | CTCAGTGTC | TCCCA | GAGTGAGGC | X | X | |
| 4 | 3 | 1 | AGTAAAGTC | ACAAG | GAGTGAGGT | X | X | |
| 4 | 3 | 1 | AACGGGGTC | TGGGA | GAGTGAGGT | X | X | |
| 4 | 3 | 1 | GGGAGGGTC | CCCAT | GAGTGAGGG | X | X | |
| 4 | 3 | 1 | GGCAGGGTT | AAGATT | GAGTGAGGC | X | X | |
| 4 | 3 | 1 | AGGGGAGTC | TGAGGG | GAGTGAGGG | X | X | |
| 4 | 3 | 1 | AACAATGTC | ATGTT | GAGTGAGGG | X | X | |
| 4 | 3 | 1 | AGCTTGGTC | TGGCT | GAGTGAGGT | X | X | |
| 4 | 3 | 1 | ATGAGGGTC | TCATA | GAGTGAGGT | X | X | |
| 4 | 3 | 1 | GCCAGTGTC | TCTTAG | GAGTGAGGT | X | X | |
| 4 | 3 | 1 | ATCACAGTC | TCTGG | GAGTGAGGC | X | X | |
| 4 | 3 | 1 | GACAGGGTC | TTAAT | GAGTGAGGC | X | X | |
| 4 | 3 | 1 | AGCCTTGTC | GTAACT | GAGTGAGGT | X | X | |
| 4 | 3 | 1 | GGCAGCGGT | GTTCA | GAGTGAGGG | X | X | |
| 4 | 3 | 1 | TCCAGTGTC | TATGG | GAGTGAGGC | X | X | |
| 4 | 3 | 1 | AGCAGCTGT | GATGT | GAGTGAGGG | X | X | |
| 4 | 3 | 1 | AGCAGCTCA | CATGG | GAGTGAGGT | X | X | |
| 4 | 3 | 1 | GGCAACGGC | ACACA | GAGGGAGGA | X | X | |
| 4 | 3 | 1 | AGCTGAGTT | AAGCA | GAGTGAGGT | X | X | |
| 4 | 3 | 1 | AGCAGCACA | AAGCTG | GAGTGAGGG | X | X | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 4 | 3 | 1 | AGCAACCTT | GAGAT | GAGTGAGGC | X | X | |
| 4 | 3 | 1 | AGCAAATTC | GGGCCC | GAGTGAGGT | X | X | |
| 4 | 3 | 1 | AGACGGGTC | GGCCC | GAGTGAGGT | X | X | |
| 4 | 3 | 1 | GCCAGAGTC | TGCACA | GAGTGAGGG | X | X | |
| 4 | 3 | 1 | AGCAACAGC | ATTTGG | GAGTGAGGG | X | X | |
| 4 | 3 | 1 | AACCGAGTC | ACTCAA | GAGTGAGGG | X | X | |
| 4 | 3 | 1 | AGCAGCTCA | CCAGCA | GAGTGAGGT | X | X | |
| 4 | 3 | 1 | GGAAGGGTC | CTGTGT | GAGTGAGGG | X | X | |
| 4 | 3 | 1 | AGAACGGTC | CAGCA | GAGTGAGGC | X | X | |
| 4 | 3 | 1 | AGCAAGGTA | AGGAA | AAGTGAGGA | X | X | |
| 4 | 3 | 1 | AGAATGGTC | AGTGGG | GAGTGAGGG | X | X | |
| 4 | 3 | 1 | AGAATGGTC | CAAAT | GAGTGAGGG | X | X | |
| 4 | 3 | 1 | AGCAAGGGC | TCCGT | GAGTGAGGG | X | X | |
| 4 | 3 | 1 | TGCTGAGTC | TCCATG | GAGTGAGGG | X | X | |
| 4 | 3 | 1 | AGCATTGTT | TCTGGG | GAGTGAGGG | X | X | |
| 4 | 3 | 1 | AGCATTGTG | GTGAG | GAGTGAGGG | X | X | |
| 4 | 3 | 1 | GCTAGCGTC | CATGG | GAGTGAGGC | X | X | |
| 4 | 3 | 1 | AGCAACTTT | CCACTG | GAGTGAGGC | X | X | |
| 4 | 3 | 1 | AGTAGGGTT | GGTGG | GAGTGAGGG | X | X | |
| 4 | 3 | 1 | GGCAGTGTT | TCCCAG | GAGTGAGGC | X | X | |
| 4 | 3 | 1 | AACTGAGTC | TCTGG | GAGTGAGGT | X | X | |
| 4 | 3 | 1 | AGCATTGTG | ATGAG | GAGTGAGGG | X | X | |
| 4 | 3 | 1 | AGCAAGGTT | TATGT | GAGTGAGCA | X | X | |
| 4 | 3 | 1 | GGCAACGTT | TGTAT | GAGTGAGGT | X | X | |
| 4 | 3 | 1 | AACAACCTC | GCCTAT | GAGTGAGGG | X | X | |
| 4 | 3 | 1 | AGGGACGTC | CAAGG | GAGTGAGGG | X | X | |
| 4 | 3 | 1 | TCCAGTGTC | ACATCA | GAGTGAGGC | X | X | |
| 4 | 3 | 1 | AGCATGGTT | GGAGTA | GAGTGAGGG | X | X | |
| 4 | 3 | 1 | AATAGGGTC | AAAAT | GAGTGAGGT | X | X | |
| 4 | 3 | 1 | AGTATAGTC | TTTAGG | GAGTGAGGC | X | X | |
| 4 | 3 | 1 | TGCAATGTC | CTTGG | GAGTGAGGG | X | X | |
| 4 | 3 | 1 | AGCTACATC | TACAGG | GAGTGAGGG | X | X | |
| 4 | 3 | 1 | AGCAAAGTA | AAGAGA | GAGTGAGGG | X | X | |
| 4 | 4 | 0 | CACCCCGTC | TACCTG | GAGTGAGGA | X | X | |
| 4 | 4 | 0 | AGGCACGTT | AGGCA | GAGTGAGGA | X | X | |
| 4 | 4 | 0 | CACCCCGTC | GACGTC | GAGTGAGGA | X | X | |
| 4 | 4 | 0 | GCAAGAGTC | TGGCT | GAGTGAGGA | X | X | |
| 4 | 4 | 0 | AGTGCAGTC | CCTTA | GAGTGAGGA | X | X | |
| 4 | 4 | 0 | ATCCACGTT | ATGCTG | GAGTGAGGA | X | X | |
| 4 | 4 | 0 | ATCCACGTT | TTGGG | GAGTGAGGA | X | X | |
| 3 | 1 | 2 | AGCAGCTTC | TGCCAT | GAGTGAAGT | X | | X |
| 3 | 1 | 2 | AGCAGGGTC | TGCAGT | GAGAGAGGC | X | | X |
| 3 | 1 | 2 | AGCAGCTTC | CAGGA | GAGTGAAGT | X | | X |
| 3 | 1 | 2 | AGCAGGGTC | TGTTTT | GAGTGAGTT | X | | X |
| 4 | 3 | 1 | AGCAACTGC | ATTTT | GAGTGAGGG | X | | X |
| 4 | 3 | 1 | AGCAACTGC | ATCTT | GAGTGAGGG | X | | X |
| 3 | 1 | 2 | AGCAGCTTC | CCAAAA | ATGTGAGGA | X | | X |
| 3 | 3 | 0 | AGGTGCCTC | CCCATG | GAGTGAGGA | X | | X |
| 5 | 3 | 2 | AGCTCAGTC | CACAG | GAGTGAGTC | X | | X |
| 2 | 1 | 1 | AGCAGCGTG | CAGAA | GAGAGAGGA | X | | |
| 2 | 1 | 1 | AGCAGCGTG | GATGGA | GAGAGAGGA | X | | |
| 2 | 1 | 1 | AGCAGCGTG | GATGGA | GAGAGAGGA | X | | |
| 2 | 1 | 1 | AGCAGCGTG | GATGGA | GAGAGAGGA | X | | |
| 2 | 1 | 1 | AGCAGCCTC | TGCCAG | GGGTGAGGA | X | | |
| 2 | 1 | 1 | AGCAGCCTC | CCATA | GAGGGAGGA | X | | |
| 2 | 1 | 1 | AGGAGCGTC | CCTTGG | GAGTGATGA | X | | |
| 2 | 1 | 1 | AGCAGCGAC | AGCCA | GAGTGACGA | X | | |
| 2 | 1 | 1 | AGCTGCGTC | CTGTA | GCGTGAGGA | X | | |
| 2 | 1 | 1 | AGCAGGGTC | TGCCT | GAGTCAGGA | X | | |
| 2 | 1 | 1 | AGCAGCATC | TGGGA | GAATGAGGA | X | | |
| 2 | 1 | 1 | AGGAGCGTC | CAGTGC | GACTGAGGA | X | | |
| 2 | 1 | 1 | AGCAGCGTG | GATGGA | GAGAGAGGA | X | | |
| 2 | 1 | 1 | AGCAGCGTG | GATGGA | GAGAGAGGA | X | | |
| 2 | 1 | 1 | AGCAGCATC | ACAGAC | GCGTGAGGA | X | | |
| 2 | 1 | 1 | ACCAGCGTC | TGCTTT | GGGTGAGGA | X | | |
| 2 | 1 | 1 | AGCAGGGTC | ATTGA | GAATGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |

| # of mutations T | (−) | (+) | (−) site | spacer | (+) site | 4 nM | 2 nM | 10.5 nM |
|---|---|---|---|---|---|---|---|---|
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AGGAGCGAC | GGGGG | GAGTGAGGA | X | | |
| 2 | 2 | 0 | AACAGCCTC | CTTCC | GAGTGAGGA | X | | |
| 2 | 2 | 0 | AGAAGCATC | CGAAGG | GAGTGAGGA | X | | |
| 2 | 2 | 0 | AGAAGCCTC | CATTCC | GAGTGAGGA | X | | |
| 3 | 0 | 3 | AGCAGCGTC | AGGGG | AAATTAGGA | X | | |
| 3 | 0 | 3 | AGCAGCGTC | TTGGAA | GACCGAGGT | X | | |
| 3 | 0 | 3 | AGCAGCGTC | CTGTG | GCGTGGCGA | X | | |
| 3 | 0 | 3 | AGCAGCGTC | TCAGCG | GGTGGAGGA | X | | |
| 3 | 0 | 3 | AGCAGCGTC | CGCCGA | GAGTCAGCC | X | | |
| 3 | 0 | 3 | AGCAGCGTC | AGGGAG | AAGTCAGGT | X | | |
| 3 | 0 | 3 | AGCAGCGTC | AACAGT | GCCTGATGA | X | | |
| 3 | 0 | 3 | AGCAGCGTC | AGTAGA | GACAGAGAA | X | | |
| 3 | 0 | 3 | AGCAGCGTC | GGGTGG | GTTTGGGA | X | | |
| 3 | 0 | 3 | AGCAGCGTC | TCCGAA | GAGACAGCA | X | | |
| 3 | 0 | 3 | AGCAGCGTC | CCGAG | GAGCTGGGA | X | | |
| 3 | 0 | 3 | AGCAGCGTC | CGGCC | GCGGCAGGA | X | | |
| 3 | 0 | 3 | AGCAGCGTC | CGGCC | GCGGCAGGA | X | | |
| 3 | 0 | 3 | AGCAGCGTC | ACTCCC | AAGCGAGTA | X | | |
| 3 | 0 | 3 | AGCAGCGTC | CCCTG | CAGAGAGCA | X | | |
| 3 | 0 | 3 | AGCAGCGTC | TCTCTG | GGCTGGGGA | X | | |
| 3 | 0 | 3 | AGCAGCGTC | CAGGAG | GGCTGGGGA | X | | |
| 3 | 0 | 3 | AGCAGCGTC | AGGGTG | GAGTCATGT | X | | |
| 3 | 0 | 3 | AGCAGCGTC | TGATTG | GCGGGGGA | X | | |
| 3 | 0 | 3 | AGCAGCGTC | TGGGG | AATTGGGA | X | | |
| 3 | 0 | 3 | AGCAGCGTC | CGCCGA | GAGTCAGCC | X | | |
| 3 | 1 | 2 | AGCAGTGTC | AGTTG | GCGGGAGGA | X | | |
| 3 | 1 | 2 | AGCAGAGTC | CAAAAG | GGGTGAGGC | X | | |
| 3 | 1 | 2 | ATCAGCGTC | CAGAG | GAGTGAACA | X | | |
| 3 | 1 | 2 | AGCAGAGTC | TCAGAG | GAGTGAAGC | X | | |
| 3 | 1 | 2 | AACAGCGTC | CTGGGA | GAGTGTGCA | X | | |
| 3 | 1 | 2 | TGCAGCGTC | TTCTT | TAGTGAGCA | X | | |
| 3 | 1 | 2 | AGCAGCTTC | CAACAA | TAGTAAGGA | X | | |
| 3 | 1 | 2 | AGCAGTGTC | CCCTAT | AAGTGAGAA | X | | |
| 3 | 1 | 2 | AGCAGCATC | AATCT | GAGTGTGGG | X | | |
| 3 | 1 | 2 | AGCAGTGTC | AACAT | CAGTGAGAA | X | | |
| 3 | 1 | 2 | AGCAGCTTC | TCCCA | GGGTGAGGC | X | | |
| 3 | 1 | 2 | AGCAGAGTC | AGGCA | GGGTGAGGC | X | | |
| 3 | 1 | 2 | AGCAGGGTC | TGCAGG | GAGTGTGGT | X | | |
| 3 | 1 | 2 | AGCTGCGTC | CTCTA | GAGGGAGGG | X | | |
| 3 | 1 | 2 | AGCAGCGTA | CCTGG | GTGTGAGAA | X | | |
| 3 | 1 | 2 | AGCAGCCTC | AGAAAT | AGGTGAGGA | X | | |
| 3 | 1 | 2 | AGCAGCGTT | CCTCT | CAGTGATGA | X | | |
| 3 | 1 | 2 | AGCAGCCTC | TGGAGG | GAGGGAGGG | X | | |

| # of mutations | | | (−) site | spacer | (+) site | VF2468 concentration | | |
|---|---|---|---|---|---|---|---|---|
| T | (+) | (−) | | | | 4 nM | 2 nM | 10.5 nM |
| 3 | 1 | 2 | AGCAGTGTC | AGATGG | TGGTGAGGA | X | | |
| 3 | 1 | 2 | AGCAGTGTC | TTGTTA | AAGTGAAGA | X | | |
| 3 | 1 | 2 | AGCAGCATC | TGGGTA | GAGTGAAGG | X | | |
| 3 | 1 | 2 | AGCAGCATC | CTCCT | GGGTAAGGA | X | | |
| 3 | 1 | 2 | AGCAGGGTC | CCTCT | GAGTGGGGC | X | | |
| 3 | 1 | 2 | ATCAGCGTC | TTTCTT | GAGTGATAA | X | | |
| 3 | 1 | 2 | AGCAGCATC | CTCCT | GGGTAAGGA | X | | |
| 3 | 1 | 2 | AGCAGCATC | CTCCT | GGGTAAGGA | X | | |
| 3 | 1 | 2 | AGCAGCATC | CTCCT | GGGTAAGGA | X | | |
| 3 | 1 | 2 | AGCAGCATC | CTCCT | GGGTAAGGA | X | | |
| 3 | 1 | 2 | AGCAGTGTC | TTAGGG | GAATGAGGC | X | | |
| 3 | 1 | 2 | AGCAGCTTC | CAGGCA | GAGGGAGAA | X | | |
| 3 | 1 | 2 | AGCAGCGTG | CTGCGA | GAGTGTGAA | X | | |
| 3 | 1 | 2 | AGTAGCGTC | CTTGG | GATTGAAGA | X | | |
| 3 | 1 | 2 | AGCAGCTTC | CAGACT | GAGGGAGAA | X | | |
| 3 | 1 | 2 | AGCAGCGTG | GAGGA | GAGAGAGGC | X | | |
| 3 | 1 | 2 | ATCAGCGTC | ATCCA | GAAGGAGGA | X | | |
| 3 | 1 | 2 | AGCAGCATC | AAAGAG | GAGAGAGGG | X | | |
| 3 | 1 | 2 | AGCAGTGTC | TTCCAT | GAGTGGGTA | X | | |
| 3 | 1 | 2 | AGCAGCGAC | TGTAG | AAATGAGGA | X | | |
| 3 | 1 | 2 | AGCAGTGTC | GATACA | TGGTGAGGA | X | | |
| 3 | 1 | 2 | AGCAGCGTG | GAGAG | GAGGAAGGA | X | | |
| 3 | 1 | 2 | AGCAGCTTC | ACTGT | GACTGAAGA | X | | |
| 3 | 1 | 2 | AGCAGAGTC | CTCTT | TTGTGAGGA | X | | |
| 3 | 1 | 2 | AGCAGCTTC | TCCAG | CAGTGATGA | X | | |
| 3 | 1 | 2 | AGCAGTGTC | ATACT | AAGGGAGGA | X | | |
| 3 | 1 | 2 | AGCCGCGTC | TCCAA | GAGTCAGTA | X | | |
| 3 | 1 | 2 | TGCAGCGTC | AAATTG | GAGTAAGGG | X | | |
| 3 | 1 | 2 | AGCAGCATC | AGAGGT | GTGTGAGAA | X | | |
| 3 | 1 | 2 | AGCAGCGTG | TTCATG | GAGTGCGGC | X | | |
| 3 | 1 | 2 | AGCAGTGTC | CTTTG | CAGTGAGAA | X | | |
| 3 | 1 | 2 | AGCAGCGCC | TCTCA | GAGTGAACA | X | | |
| 3 | 1 | 2 | AGCAGCATC | TTGGG | AACTGAGGA | X | | |
| 3 | 1 | 2 | AGCAGCCTC | TTTTTG | GAGGGAGGG | X | | |
| 3 | 1 | 2 | GGCAGCGTC | GCAGG | GAGTGGGAA | X | | |
| 3 | 1 | 2 | AGCAGCCTC | GGAAAC | AAGTGAGGG | X | | |
| 3 | 1 | 2 | AGCAGAGTC | TGATAT | GAGTGAGCT | X | | |
| 3 | 1 | 2 | TGCAGCGTC | AGCAT | GAGTGGGGC | X | | |
| 3 | 1 | 2 | AGCAGGGTC | TGGAGG | GAGACAGGA | X | | |
| 3 | 1 | 2 | AGCAGAGTC | ACGAGA | GAATGGGGA | X | | |
| 3 | 1 | 2 | AGCAGGGTC | CTGCA | GGGTGAGGC | X | | |
| 3 | 1 | 2 | AGCAGCCTC | AGGGAT | GAGGGAGGT | X | | |
| 3 | 1 | 2 | AGCAGCGGC | ATCGG | GGGCGAGGA | X | | |
| 3 | 1 | 2 | AGCAGGGTC | ATCACA | GAGGGAAGA | X | | |
| 3 | 1 | 2 | AGCAGTGTC | TGGTGT | GAGGGAGCA | X | | |
| 3 | 1 | 2 | AGCAGCGGC | TGGGGG | GAGGCAGGA | X | | |
| 3 | 1 | 2 | AGCAGCATC | CCTGGA | GAGGGAGAA | X | | |
| 3 | 1 | 2 | AGCAGGGTC | GGTGTC | TGGTGAGGA | X | | |
| 3 | 1 | 2 | AGCAGGGTC | CAGGT | AAGAGAGGA | X | | |
| 3 | 1 | 2 | AGCAGTGTC | ATCTCT | GAGTGGAGA | X | | |
| 3 | 1 | 2 | AGCAGCCTC | CGTCTA | GAGGGAGGT | X | | |
| 3 | 1 | 2 | AGCAGCGCC | AGCCTC | AAGTGAGGG | X | | |
| 3 | 1 | 2 | AGCAGCGAC | ATTGT | GAGTAAGCA | X | | |
| 3 | 1 | 2 | AGCAGCTTC | CGGTG | TAGTGATGA | X | | |
| 3 | 1 | 2 | AGCAGGGTC | CCAGCA | GAGAAAGGA | X | | |
| 3 | 1 | 2 | AGCAGCGAC | TCCGG | GAGTGCAGA | X | | |
| 3 | 1 | 2 | AGCAGCGTG | GGAAA | GAGGAAGGA | X | | |
| 3 | 1 | 2 | GGCAGCGTC | TATGGA | GAATGAGAA | X | | |
| 3 | 1 | 2 | AGCAGCCTC | CACACT | GAGGGAGGT | X | | |
| 3 | 1 | 2 | AGCAGCCTC | CCTCTT | GTGTGAGGG | X | | |
| 3 | 1 | 2 | TGCAGCGTC | GCTGA | AAGTGAGAA | X | | |
| 3 | 1 | 2 | AGCAGTGTC | TTGTAT | GACTGAGGT | X | | |
| 3 | 1 | 2 | AGCAACGTC | AGCAAA | GTGTCAGGA | X | | |
| 3 | 1 | 2 | AGCAGCATC | AGCAG | GAGTGTGAA | X | | |
| 3 | 1 | 2 | AGCAGCCTC | ATTGG | GAGTGAGTG | X | | |
| 3 | 1 | 2 | AGCAGGGTC | TTGGAT | GAGTTAAGA | X | | |
| 3 | 1 | 2 | AGCAGCGGC | AGACT | GAGCGAGCA | X | | |
| 3 | 1 | 2 | AGCAGGGTC | CTGTTG | GAGACAGGA | X | | |
| 3 | 1 | 2 | AGCAGCATC | AGCAT | CAGTTAGGA | X | | |
| 3 | 1 | 2 | AGCAGAGTC | AGAAAT | GAGTGAAGC | X | | |
| 3 | 1 | 2 | AGCAGCGCC | CACCCT | TGGTGAGGA | X | | |

| # of mutations | | | (-) site | spacer | (+) site | VF2468 concentration | | |
|---|---|---|---|---|---|---|---|---|
| T (-) | (+) | (-) | | | | 4 nM | 2 nM | 10.5 nM |
| 3 | 1 | 2 | AGCAGCGGC | TGATG | GAGGCAGGA | X | | |
| 3 | 1 | 2 | AGCAGCCTC | GCTTTG | AGGTGAGGA | X | | |
| 3 | 1 | 2 | AGCATCGTC | ATCCTA | GAGTCAGCA | X | | |
| 3 | 1 | 2 | GGCAGCGTC | GGGCA | GAGGGAGAA | X | | |
| 3 | 1 | 2 | AGCAGCCTC | ATCCT | GTGAGAGGA | X | | |
| 3 | 1 | 2 | AGCAGTGTC | TTCCAT | GAGTGGGTA | X | | |
| 3 | 1 | 2 | GGCAGCGTC | CAATCT | CAGTGAGAA | X | | |
| 3 | 1 | 2 | AGCAGTGTC | ACCTCT | GAGTGGGTA | X | | |
| 3 | 1 | 2 | AGCAGCATC | TATAGC | GACTGAGGT | X | | |
| 3 | 1 | 2 | AGCAGTGTC | TGGTTT | GGGGGAGGA | X | | |
| 3 | 1 | 2 | AGCAGAGTC | GGAGT | GAGAGAGGG | X | | |
| 3 | 1 | 2 | AGTAGCGTC | TAGGC | AAGTGAGCA | X | | |
| 3 | 1 | 2 | AGCAGCCTC | TACAT | GAGTGAGAC | X | | |
| 3 | 1 | 2 | AGCAGTGTC | AATAA | GAGAGTGGA | X | | |
| 3 | 1 | 2 | AGCAGCGTT | TCTCA | AAGTGCGGA | X | | |
| 3 | 1 | 2 | AGCAGCGAC | TGTGA | AAGTGAGAA | X | | |
| 3 | 1 | 2 | AGCAGAGTC | CCTGT | GAGTGAAGG | X | | |
| 3 | 1 | 2 | GGCAGCGTC | CTTTC | CAGCGAGGA | X | | |
| 3 | 1 | 2 | AGCAGGGTC | AATGTC | TGGTGAGGA | X | | |
| 3 | 1 | 2 | AGCAGCATC | AGGCT | GAGTGTGGT | X | | |
| 3 | 1 | 2 | AGCAGTGTC | TCGTT | AGGTGAGGA | X | | |
| 3 | 1 | 2 | AGCAGGGTC | AGCAAA | GAATGAGGC | X | | |
| 3 | 1 | 2 | AGCAGAGTC | ACAAA | GAATGAGTA | X | | |
| 3 | 1 | 2 | AGCAGCGTG | GGGCTG | GAGGGAGAA | X | | |
| 3 | 1 | 2 | AGCAGCGTG | TTCATG | GAGTGCGGC | X | | |
| 3 | 1 | 2 | AGCAGCATC | TAACAG | GAGGGAGGG | X | | |
| 3 | 1 | 2 | AGCAGCCTC | CTAGG | GAGGGAGGG | X | | |
| 3 | 1 | 2 | AGCAGCTTC | TGAGC | TAGTGAAGA | X | | |
| 3 | 1 | 2 | ATCAGCGTC | TACTAA | GAGAGTGGA | X | | |
| 3 | 1 | 2 | AGCAGCATC | ACCTGC | GAGGGAGGG | X | | |
| 3 | 1 | 2 | AGCAGCATC | GAGTT | GGGTGAGGT | X | | |
| 3 | 1 | 2 | TGCAGCGTC | CAAGCT | CAGTGAGGC | X | | |
| 3 | 1 | 2 | AGCAGCTTC | ATTTT | GAATGAGGG | X | | |
| 3 | 1 | 2 | AGCAGCCTC | TTTTGG | GAGTGGGGG | X | | |
| 3 | 1 | 2 | AGCAGCGCC | TCCCA | GAGTGGGGC | X | | |
| 3 | 1 | 2 | AGCAGGGTC | CCCCA | GAGAAGGA | X | | |
| 3 | 1 | 2 | AGCAGCCTC | CCGGA | GAGGGAGGG | X | | |
| 3 | 1 | 2 | GGCAGCGTC | GGGTGG | GAGAGAGAA | X | | |
| 3 | 1 | 2 | AGCAGAGTC | TACCTT | GAGTGAAAA | X | | |
| 3 | 1 | 2 | AGCAGCGAC | CCAAG | GAGTAAGAA | X | | |
| 3 | 1 | 2 | AGCAGTGTC | TTTAGA | AAGTGAGCA | X | | |
| 3 | 1 | 2 | AGCAGGGTC | GGGCC | TGGTGAGGA | X | | |
| 3 | 1 | 2 | AGCAGCGGC | TGAATC | CTGTGAGGA | X | | |
| 3 | 1 | 2 | TGCAGCGTC | TGGCAT | GAGTGGGGC | X | | |
| 3 | 1 | 2 | AGAAGCGTC | ATGCT | GAGTGAAAA | X | | |
| 3 | 1 | 2 | AGCAGGGTC | CAGGGA | GAGGGAAGA | X | | |
| 3 | 1 | 2 | AGCAGCATC | CCTGT | GAGTGAGTG | X | | |
| 3 | 1 | 2 | AGTAGCGTC | AATGAT | AAGTGTGGA | X | | |
| 3 | 1 | 2 | AGCAGGGTC | CAGGT | AAGAGAGGA | X | | |
| 3 | 1 | 2 | AGCAGGGTC | CAGGT | AAGAGAGGA | X | | |
| 3 | 1 | 2 | AGCAGGGTC | CAGGT | AAGAGAGGA | X | | |
| 3 | 2 | 1 | AGCAACCTC | ACCCCA | GAGAGAGGA | X | | |
| 3 | 2 | 1 | AGCAACGTG | TGTTGG | GAGAGAGGA | X | | |
| 3 | 2 | 1 | ATCAGGGTC | AGGTTT | TAGTGAGGA | X | | |
| 3 | 2 | 1 | AGCAAAGTC | TGTAT | GAGTGAGCA | X | | |
| 3 | 2 | 1 | AGCAGTGTA | AAGGAG | TAGTGAGGA | X | | |
| 3 | 2 | 1 | AGCAGAGTA | AAGCAG | GTGTGAGGA | X | | |
| 3 | 2 | 1 | AGCAGCCTG | GGAGA | GAGTGAGGG | X | | |
| 3 | 2 | 1 | AGCAACCTC | CTGGGT | GAGAGAGGA | X | | |
| 3 | 2 | 1 | AACAGCTTC | AGTACA | CAGTGAGGA | X | | |
| 3 | 2 | 1 | AGTAGTGTC | AATGAA | GAGTGAAGA | X | | |
| 3 | 2 | 1 | ATCAGGGTC | TAGGGA | GAGTGTGGA | X | | |
| 3 | 2 | 1 | GGCAGGGTC | CCCGG | GAGGGAGGA | X | | |
| 3 | 2 | 1 | AGCTGGGTC | TGAAGG | GTGTGAGGA | X | | |
| 3 | 2 | 1 | AGCTGGGTC | CTCAG | GAGAGAGGA | X | | |
| 3 | 2 | 1 | AGCAGCTCC | AGGGCC | GAGTGAGAA | X | | |
| 3 | 2 | 1 | AGCAACATC | CGCTCT | GAGTGGGGA | X | | |
| 3 | 2 | 1 | AACAGCTTC | ACAGG | CAGTGAGGA | X | | |
| 3 | 2 | 1 | ATCAGCGCC | CAACAC | CAGTGAGGA | X | | |
| 3 | 2 | 1 | AGCAGGGGC | AGTGG | GAGTGAGTA | X | | |
| 3 | 2 | 1 | AGCATGGTC | TGGTT | GGGTGAGGA | X | | |

| # of mutations | | | | | | VF2468 concentration | | |
|---|---|---|---|---|---|---|---|---|
| T (−) | (+) | (−) site | spacer | (+) site | 4 nM | 2 nM | 10.5 nM |
| 3 | 2 | 1 | GGCAGCGTG | CTCTGA | GAGAGAGGA | X | | |
| 3 | 2 | 1 | AGCAGAGCC | CCCTG | GAGTGAGGG | X | | |
| 3 | 2 | 1 | AGCACCGTG | CTTCAA | AAGTGAGGA | X | | |
| 3 | 2 | 1 | CCCAGCGTC | AGCAG | GAGTCAGGA | X | | |
| 3 | 2 | 1 | AGGAGCGTG | GACACA | GAGTGAGGT | X | | |
| 3 | 2 | 1 | AGCCGAGTC | TGTCCC | GAGTGTGGA | X | | |
| 3 | 2 | 1 | AGTAGAGTC | TCTGTT | GAGTGAGTA | X | | |
| 3 | 2 | 1 | ACCAGGGTC | ATGGC | AAGTGAGGA | X | | |
| 3 | 2 | 1 | TGCAGGGTC | AGATTG | AAGTGAGGA | X | | |
| 3 | 2 | 1 | AGCAGCGGG | GAGAGA | GAGCGAGGA | X | | |
| 3 | 2 | 1 | TGCAGCGCC | GAGGT | GAGTGAGGG | X | | |
| 3 | 2 | 1 | AGTAGAGTC | TGGCT | GAGGGAGGA | X | | |
| 3 | 2 | 1 | TGCAGCGCC | GAGGT | GAGTGAGGG | X | | |
| 3 | 2 | 1 | AGTAGGGTC | ACACTA | GAGTGAAGA | X | | |
| 3 | 2 | 1 | TGCAGCGCC | GAGGT | GAGTGAGGG | X | | |
| 3 | 2 | 1 | TGCAGCGCC | GAGGT | GAGTGAGGG | X | | |
| 3 | 2 | 1 | TGCAGCGCC | GAGGT | GAGTGAGGG | X | | |
| 3 | 2 | 1 | TGCAGCGCC | GAGGT | GAGTGAGGG | X | | |
| 3 | 2 | 1 | TGCAGCGCC | GAGGT | GAGTGAGGG | X | | |
| 3 | 2 | 1 | AGCAGGGTA | AAGCAA | GAGTGAGAA | X | | |
| 3 | 2 | 1 | AGCAGCGGG | GACCGG | GAGCGAGGA | X | | |
| 3 | 2 | 1 | AGCAGGTTC | AGTGTC | TAGTGAGGA | X | | |
| 3 | 2 | 1 | GGCATCGTC | TGCAGT | AAGTGAGGA | X | | |
| 3 | 2 | 1 | AATAGCGTC | AGCCCC | AAGTGAGGA | X | | |
| 3 | 2 | 1 | AGCAGCATG | GTATG | GAGGGAGGA | X | | |
| 3 | 2 | 1 | AGCAGCCTG | CTGCA | GAGTGAGGG | X | | |
| 3 | 2 | 1 | GGCAGCGTG | GTGGT | GAGAGAGGA | X | | |
| 3 | 2 | 1 | AGCAGAGTT | GGTGTC | TAGTGAGGA | X | | |
| 3 | 2 | 1 | AACAGAGTC | GGGAA | GAGTAAGGA | X | | |
| 3 | 2 | 1 | AACAGCGGC | GTCCT | GAGTGTGGA | X | | |
| 3 | 2 | 1 | AGCAGGGTG | TGAGA | GAGGGAGGA | X | | |
| 3 | 2 | 1 | AGCTGCATC | AAACT | TAGTGAGGA | X | | |
| 3 | 2 | 1 | GGCAGGGTC | TCCCG | GAGGGAGGA | X | | |
| 3 | 2 | 1 | AGCAGCTTT | TCAGA | GAGTGAAGA | X | | |
| 3 | 2 | 1 | AGCAGGGCC | CTGCT | GAGTGAGGG | X | | |
| 3 | 2 | 1 | AGCAGGGCC | CTGCT | GAGTGAGGG | X | | |
| 3 | 2 | 1 | GGCAGCGTT | GGGAT | GTGTGAGGA | X | | |
| 3 | 2 | 1 | AACAGAGTC | ACAGT | GAGTAAGGA | X | | |
| 3 | 2 | 1 | AGCAGGGCC | GGGCA | GAGTGAGGG | X | | |
| 3 | 2 | 1 | GGGAGCGTC | TGCCC | CAGTGAGGA | X | | |
| 3 | 2 | 1 | ATCAGTGTC | TAAAAT | GGGTGAGGA | X | | |
| 3 | 2 | 1 | AGCGGCTTC | TGCCT | GAGTGAGGG | X | | |
| 3 | 2 | 1 | AGCAATGTC | TGCCTT | GGGTGAGGA | X | | |
| 3 | 2 | 1 | AGCAAAGTC | ACCAG | GAGTGAGCA | X | | |
| 3 | 2 | 1 | AGCAATGTC | AATCAG | GAGAGAGGA | X | | |
| 3 | 2 | 1 | AGCAGGGTG | GAAAG | GAATGAGGA | X | | |
| 3 | 2 | 1 | ACCAGCCTC | CTGAGG | GAGTGAGGG | X | | |
| 3 | 2 | 1 | AGAAGCGGC | GTTGT | AAGTGAGGA | X | | |
| 3 | 2 | 1 | AGCAGTGTG | GTAGA | CAGTGAGGA | X | | |
| 3 | 2 | 1 | AGCAATGTC | AGTCT | GAGTTAGGA | X | | |
| 3 | 2 | 1 | AGCAGGGTG | TTGGAG | GAATGAGGA | X | | |
| 3 | 2 | 1 | AGCAGCATG | GAAAA | GAGGGAGGA | X | | |
| 3 | 2 | 1 | AGCAGCTTT | GTAGA | GAGTGAAGA | X | | |
| 3 | 2 | 1 | AGCAAGGTC | TGGGA | GAGTCAGGA | X | | |
| 3 | 2 | 1 | AGCAGCCTG | CCAAG | GAGTGAGGG | X | | |
| 3 | 2 | 1 | AGCAGTGGC | TAAGA | GAGTGAGCA | X | | |
| 3 | 2 | 1 | AACAGCGTG | TGTGA | AAGTGAGGA | X | | |
| 3 | 2 | 1 | AGCATCCTC | TATGCT | GTGTGAGGA | X | | |
| 3 | 2 | 1 | AGCAGAGCC | ATGAAG | GAGTGAGGC | X | | |
| 3 | 2 | 1 | AGCAGCCGC | CTGAG | CAGTGAGGA | X | | |
| 3 | 2 | 1 | AGCAGCGAG | GGAGG | AAGTGAGGA | X | | |
| 3 | 2 | 1 | AGCCGGGTC | TTCCG | AAGTGAGGA | X | | |
| 3 | 2 | 1 | AGCCTCGTC | CCCAGA | GAGGGAGGA | X | | |
| 3 | 2 | 1 | AGGAGAGTC | CCATGA | GAGTGAGAA | X | | |
| 3 | 2 | 1 | AGCAATGTC | AGATAG | GGGTGAGGA | X | | |
| 3 | 2 | 1 | AGCATCGGC | CTCTCT | GAGTGACGA | X | | |
| 3 | 2 | 1 | AGCATCTTC | AGTTG | AAGTGAGGA | X | | |
| 3 | 2 | 1 | GGCAGCGTG | TATGAT | GAGAGAGGA | X | | |
| 3 | 2 | 1 | AGCAGGGTA | AAGAGT | GAGTGAGAA | X | | |
| 3 | 2 | 1 | AACAGAGTC | AGCCCT | TAGTGAGGA | X | | |

-continued

| # of mutations | | | | | | VF2468 concentration | | |
|---|---|---|---|---|---|---|---|---|
| T (−) | (+) | (−) site | spacer | (+) site | 4 nM | 2 nM | 10.5 nM | |
| 3 2 | 1 | AGCACAGTC | CGGAT | GAGTGAGCA | X | | | |
| 3 2 | 1 | ATTAGCGTC | ACTTAG | AAGTGAGGA | X | | | |
| 3 2 | 1 | AACAGAGTC | AGAGA | TAGTGAGGA | X | | | |
| 3 2 | 1 | AGCAGCCTG | GCATG | GAGTGAGGG | X | | | |
| 3 2 | 1 | AACACCGTC | ACCTGT | GGGTGAGGA | X | | | |
| 3 2 | 1 | AGCAGCGGA | AATAA | GGGTGAGGA | X | | | |
| 3 2 | 1 | GGCAGCGTG | AACCCA | GAGTGAGTA | X | | | |
| 3 2 | 1 | AACACCGTC | CTGCCA | GTGTGAGGA | X | | | |
| 3 2 | 1 | AGCAGCGAT | GTTGT | AAGTGAGGA | X | | | |
| 3 2 | 1 | AGCAGGGTG | GGAAAG | GAGGGAGGA | X | | | |
| 3 2 | 1 | AGCTGGGTC | AGAGGT | GAGAGAGGA | X | | | |
| 3 2 | 1 | AGCAGCTCC | AGGGA | GAGTGAGAA | X | | | |
| 3 2 | 1 | AGCAATGTC | TTCCTT | GGGTGAGGA | X | | | |
| 3 2 | 1 | AGCACAGTC | TGAACA | GAGTGAGCA | X | | | |
| 3 2 | 1 | AGCAGCGGA | GGATCT | GGGTGAGGA | X | | | |
| 3 2 | 1 | AGCAGCTTT | TGGGA | GAGTGAGCA | X | | | |
| 3 2 | 1 | AGCAGCGAT | TTGAAG | AAGTGAGGA | X | | | |
| 3 2 | 1 | AGCAGCAGC | ACAAA | GAGTGAGTA | X | | | |
| 3 2 | 1 | AGGAGCGGC | AGGTGA | TAGTGAGGA | X | | | |
| 3 2 | 1 | AGCACGGTC | CAAAG | GAGAGAGGA | X | | | |
| 3 2 | 1 | AGCTGGGTC | ATTCCC | CAGTGAGGA | X | | | |
| 3 2 | 1 | AGCTGAGTC | AGCCAA | GTGTGAGGA | X | | | |
| 3 2 | 1 | AGTAGGGTC | AACGTT | GAGTGAAGA | X | | | |
| 3 2 | 1 | AGTAGAGTC | AACAGT | GAGTGATGA | X | | | |
| 3 2 | 1 | AGGAGAGTC | GCTCT | GAGTGAGAA | X | | | |
| 3 2 | 1 | AGCGCCGTC | TCTGG | AAGTGAGGA | X | | | |
| 3 2 | 1 | AGCTGTGTC | CCTCCT | GAGGGAGGA | X | | | |
| 3 2 | 1 | AGCTGCCTC | CGTGGG | GAGTGAGGC | X | | | |
| 3 2 | 1 | AGCAGCCTG | CTGCA | GAGTGAGGG | X | | | |
| 3 2 | 1 | AGCAGCCTG | CTGCA | GAGTGAGGG | X | | | |
| 3 2 | 1 | GGCAGAGTC | GTGCA | TAGTGAGGA | X | | | |
| 3 2 | 1 | AGCATTGTC | AATATT | GACTGAGGA | X | | | |
| 3 2 | 1 | AGCAGGGTG | GGTAA | GAGTGAGAA | X | | | |
| 3 2 | 1 | GGCAGGGTC | TCTGG | GAGGGAGGA | X | | | |
| 3 2 | 1 | AGTAGAGTC | CAGTA | GAGTGATGA | X | | | |
| 3 2 | 1 | AGCAGGGCC | CTGCT | GAGTGAGGG | X | | | |
| 3 2 | 1 | AGCAAAGTC | TTTAG | GAGAGAGGA | X | | | |
| 3 2 | 1 | AGCAGTGCC | CTGAA | GAGTGAGAA | X | | | |
| 3 2 | 1 | GGCAGGGTC | CGAGCC | CAGTGAGGA | X | | | |
| 3 2 | 1 | AGCTGGGTC | TGGCT | GAGTGTGGA | X | | | |
| 3 2 | 1 | AGCAGCTTT | CATGG | AAGTGAGGA | X | | | |
| 3 2 | 1 | ATCATCGTC | ATCGT | GAGAGAGGA | X | | | |
| 3 2 | 1 | AGCCGCGTG | AGGGC | AAGTGAGGA | X | | | |
| 3 2 | 1 | AGCAGGGTG | GGCAAG | GAGGGAGGA | X | | | |
| 3 2 | 1 | AGCATGGTC | AAGTTT | GGGTGAGGA | X | | | |
| 3 2 | 1 | ATCAGAGTC | AGAGA | AAGTGAGGA | X | | | |
| 3 2 | 1 | AGCAGTGGC | AGAAT | AAGTGAGGA | X | | | |
| 3 2 | 1 | AGGAGTGTC | TGCAA | AAGTGAGGA | X | | | |
| 3 2 | 1 | TGCAGGGTC | AAGCC | AAGTGAGGA | X | | | |
| 3 2 | 1 | AGCAGGTTC | AGTGTC | TAGTGAGGA | X | | | |
| 3 2 | 1 | AGCAGCGGA | AATAA | GGGTGAGGA | X | | | |
| 3 2 | 1 | AGCAGGGTG | CTCGG | GAGGGAGGA | X | | | |
| 3 2 | 1 | AGCAACCTC | CCCACA | GAGGGAGGA | X | | | |
| 3 2 | 1 | AGCAGGGTG | GGGGA | GAGGGAGGA | X | | | |
| 3 2 | 1 | AGCAACCTC | TGCTCA | GAGAGAGGA | X | | | |
| 3 2 | 1 | TGCAGGGTC | TGCGG | AAGTGAGGA | X | | | |
| 3 2 | 1 | AGCAGGTTC | AGACTG | AAGTGAGGA | X | | | |
| 3 2 | 1 | AGCAATGTC | ACCAT | GAGTGTGGA | X | | | |
| 3 2 | 1 | AGCACGGTC | CCCAAG | GAGGGAGGA | X | | | |
| 3 2 | 1 | AGCAGCGCT | CGGGC | GAGCGAGGA | X | | | |
| 3 2 | 1 | AGCAGGGAC | TGGTCA | GAGTGAGGT | X | | | |
| 3 2 | 1 | AGCAGCCAC | ACAATC | CAGTGAGGA | X | | | |
| 3 2 | 1 | AGTAGAGTC | AAGAGG | GAGTGAGTA | X | | | |
| 3 2 | 1 | AGCCTCGTC | TTGGT | GAGGGAGGA | X | | | |
| 3 2 | 1 | GGCAGCGGC | CTGGAG | GGGTGAGGA | X | | | |
| 3 2 | 1 | AGCAGAGTT | GGTTTC | TAGTGAGGA | X | | | |
| 3 2 | 1 | AGCATCTTC | ACCTG | AAGTGAGGA | X | | | |
| 3 2 | 1 | AGCAACATC | ATAAT | GAGTGGGGA | X | | | |
| 3 2 | 1 | AGCACAGTC | CCTAA | GAGTGAGCA | X | | | |
| 3 3 | 0 | AGGAGTTTC | CAGTT | GAGTGAGGA | X | | | |
| 3 3 | 0 | GGCAGCAGC | CATCA | GAGTGAGGA | X | | | |

| # of mutations | | | (−) site | spacer | (+) site | VF2468 concentration | | |
|---|---|---|---|---|---|---|---|---|
| T (−) | (+) | (−) | | | | 4 nM | 2 nM | 10.5 nM |
| 3 | 3 | 0 | AGCAGGTTG | TTGGAG | GAGTGAGGA | X | | |
| 3 | 3 | 0 | AACAGTGCC | CTGGT | GAGTGAGGA | X | | |
| 3 | 3 | 0 | TGGAGCGTG | GGGGA | GAGTGAGGA | X | | |
| 3 | 3 | 0 | TGGAGCGTG | GAAGAG | GAGTGAGGA | X | | |
| 3 | 3 | 0 | AGCTGAGGC | ACAGG | GAGTGAGGA | X | | |
| 3 | 3 | 0 | TGCAGGGTG | GACCCA | GAGTGAGGA | X | | |
| 3 | 3 | 0 | AACAGAGTG | AGGCT | GAGTGAGGA | X | | |
| 3 | 3 | 0 | AGCAACTTA | TTGCT | GAGTGAGGA | X | | |
| 3 | 3 | 0 | AGCACAATC | TTTTTG | GAGTGAGGA | X | | |
| 3 | 3 | 0 | TGGAGGGTC | GGTGGA | GAGTGAGGA | X | | |
| 3 | 3 | 0 | AGCCGTGTG | GCTACG | GAGTGAGGA | X | | |
| 3 | 3 | 0 | TGCTGCTTC | TGCCGT | GAGTGAGGA | X | | |
| 3 | 3 | 0 | AACAGAGTA | ACACA | GAGTGAGGA | X | | |
| 3 | 3 | 0 | ACCAACTTC | ATGTA | GAGTGAGGA | X | | |
| 3 | 3 | 0 | AGGAGAGTG | AGTGT | GAGTGAGGA | X | | |
| 3 | 3 | 0 | GGCAGGGTG | GCGAAG | GAGTGAGGA | X | | |
| 3 | 3 | 0 | GGCAGGGTG | GCCGGG | GAGTGAGGA | X | | |
| 3 | 3 | 0 | AGCAGGGCT | CCTGGT | GAGTGAGGA | X | | |
| 3 | 3 | 0 | TACAGTGTC | AGCAGT | GAGTGAGGA | X | | |
| 3 | 3 | 0 | ATCACCTTC | TTTCAT | GAGTGAGGA | X | | |
| 3 | 3 | 0 | TTCAGTGTC | TGACGG | GAGTGAGGA | X | | |
| 3 | 3 | 0 | AGCAGCTCA | GGTTAG | GAGTGAGGA | X | | |
| 3 | 3 | 0 | AGGAGAGTA | GGGCT | GAGTGAGGA | X | | |
| 3 | 3 | 0 | ACCTGGGTC | TGAGCA | GAGTGAGGA | X | | |
| 3 | 3 | 0 | ATCAGTGTG | TTTTT | GAGTGAGGA | X | | |
| 3 | 3 | 0 | TGGAGGGTC | AGAGGA | GAGTGAGGA | X | | |
| 3 | 3 | 0 | GGCAGGGTG | CGAGG | GAGTGAGGA | X | | |
| 3 | 3 | 0 | AGGAGAGTG | AATGT | GAGTGAGGA | X | | |
| 3 | 3 | 0 | AGCAGTGCA | CCCAA | GAGTGAGGA | X | | |
| 3 | 3 | 0 | AGCAGGTTG | AAGACT | GAGTGAGGA | X | | |
| 3 | 3 | 0 | AGGAGAGTG | AGAAGT | GAGTGAGGA | X | | |
| 3 | 3 | 0 | AGCAGCCGT | AACAAA | GAGTGAGGA | X | | |
| 3 | 3 | 0 | AGCAGGGCA | GGGCA | GAGTGAGGA | X | | |
| 3 | 3 | 0 | GCCAGCCTC | AGGCT | GAGTGAGGA | X | | |
| 3 | 3 | 0 | AGCAGGGCT | TGGTGG | GAGTGAGGA | X | | |
| 3 | 3 | 0 | AGTAGCAAC | TATTA | GAGTGAGGA | X | | |
| 3 | 3 | 0 | AACAGCGGA | GATTT | GAGTGAGGA | X | | |
| 3 | 3 | 0 | AGGACCATC | CGAGA | GAGTGAGGA | X | | |
| 3 | 3 | 0 | AGGACCATC | CCAGG | GAGTGAGGA | X | | |
| 3 | 3 | 0 | AGGACCATC | CCAGG | GAGTGAGGA | X | | |
| 3 | 3 | 0 | AGGACCATC | CCAGG | GAGTGAGGA | X | | |
| 3 | 3 | 0 | AGCAGGTTA | ACAGG | GAGTGAGGA | X | | |
| 3 | 3 | 0 | TGCAGGGTG | AGCCT | GAGTGAGGA | X | | |
| 3 | 3 | 0 | AGAAGGGTA | GAAAG | GAGTGAGGA | X | | |
| 3 | 3 | 0 | AGATGCGGC | CAGTA | GAGTGAGGA | X | | |
| 3 | 3 | 0 | AATAGGGTC | AGGTAG | GAGTGAGGA | X | | |
| 3 | 3 | 0 | AGCAGTGAA | GGTGG | GAGTGAGGA | X | | |
| 3 | 3 | 0 | AGAAACGTG | GAAAA | GAGTGAGGA | X | | |
| 3 | 3 | 0 | AACAGGGAC | CTTAT | GAGTGAGGA | X | | |
| 3 | 3 | 0 | AGCAAGGAC | TTAAA | GAGTGAGGA | X | | |
| 3 | 3 | 0 | AGCAGATGC | CCTTG | GAGTGAGGA | X | | |
| 3 | 3 | 0 | AGCAGCTGT | GCATA | GAGTGAGGA | X | | |
| 3 | 3 | 0 | AGAAGGGTT | TGTGCA | GAGTGAGGA | X | | |
| 3 | 3 | 0 | AACAGAGTG | GTTTA | GAGTGAGGA | X | | |
| 3 | 3 | 0 | GGCAGTGGC | AGTGG | GAGTGAGGA | X | | |
| 3 | 3 | 0 | AGCACCGAG | CCCCT | GAGTGAGGA | X | | |
| 3 | 3 | 0 | ATCAGCATG | AAATG | GAGTGAGGA | X | | |
| 3 | 3 | 0 | AGCTGTGTG | ACCCT | GAGTGAGGA | X | | |
| 3 | 3 | 0 | TGCAGGGTG | GGAATA | GAGTGAGGA | X | | |
| 3 | 3 | 0 | TGCAGGGTG | TAGTG | GAGTGAGGA | X | | |
| 3 | 3 | 0 | AGGAGGTTC | TGGGAG | GAGTGAGGA | X | | |
| 3 | 3 | 0 | AGGAATGTC | CTGGTC | GAGTGAGGA | X | | |
| 3 | 3 | 0 | AGTAGCTGC | CTTTGG | GAGTGAGGA | X | | |
| 3 | 3 | 0 | AGAAGGGTG | GGAGGG | GAGTGAGGA | X | | |
| 3 | 3 | 0 | AGTAGCTGC | CTTTGG | GAGTGAGGA | X | | |
| 3 | 3 | 0 | AGTAGCTGC | CTTTGG | GAGTGAGGA | X | | |
| 3 | 3 | 0 | AGTAGCTGC | CTTTGG | GAGTGAGGA | X | | |
| 3 | 3 | 0 | AGTAGCTGC | CTTTGG | GAGTGAGGA | X | | |
| 3 | 3 | 0 | AGTAGCTGC | CTTTGG | GAGTGAGGA | X | | |
| 3 | 3 | 0 | AGTAGCTGC | CTTTGG | GAGTGAGGA | X | | |

-continued

| # of mutations | | | | | | VF2468 concentration | | |
|---|---|---|---|---|---|---|---|---|
| T (−) | (+) | (−) site | spacer | (+) site | 4 nM | 2 nM | 10.5 nM |
| 3 3 | 0 | AGTAGAGGC | TGGAG | GAGTGAGGA | X | | |
| 3 3 | 0 | GGCAGCAGC | AATAGA | GAGTGAGGA | X | | |
| 3 3 | 0 | AGCAGCACA | AGCACT | GAGTGAGGA | X | | |
| 3 3 | 0 | TGCATCGTA | AGCAT | GAGTGAGGA | X | | |
| 3 3 | 0 | GGCAGGGTG | GGGGT | GAGTGAGGA | X | | |
| 3 3 | 0 | AGCAGCTGA | AAGAGG | GAGTGAGGA | X | | |
| 3 3 | 0 | TGGAGCGTG | GGAGGA | GAGTGAGGA | X | | |
| 3 3 | 0 | TCCAGGGTC | ACTAAT | GAGTGAGGA | X | | |
| 3 3 | 0 | TGCAGCGAA | AGGCA | GAGTGAGGA | X | | |
| 3 3 | 0 | AGCAGGTTG | GGGAA | GAGTGAGGA | X | | |
| 3 3 | 0 | AGCTGAGGC | TGGCA | GAGTGAGGA | X | | |
| 3 3 | 0 | AACAGTGGC | AAATGA | GAGTGAGGA | X | | |
| 3 3 | 0 | GGCAGTGCC | TGAAGG | GAGTGAGGA | X | | |
| 3 3 | 0 | GGCAGTGCC | TGAAGG | GAGTGAGGA | X | | |
| 3 3 | 0 | GGCAGTGCC | TGAAGG | GAGTGAGGA | X | | |
| 3 3 | 0 | AGGAGAGTA | TGGAG | GAGTGAGGA | X | | |
| 3 3 | 0 | CGCAGCATT | GCAGCG | GAGTGAGGA | X | | |
| 3 3 | 0 | GGAAGTGTC | CTTCAA | GAGTGAGGA | X | | |
| 3 3 | 0 | AGCTGCATA | AGGAAA | GAGTGAGGA | X | | |
| 3 3 | 0 | ACTAGGGTC | TTTGGA | GAGTGAGGA | X | | |
| 3 3 | 0 | AGCTGTGTG | CCAGG | GAGTGAGGA | X | | |
| 3 3 | 0 | ACCACTGTC | AGCTGT | GAGTGAGGA | X | | |
| 3 3 | 0 | GGTAGCTTC | TCCTG | GAGTGAGGA | X | | |
| 3 3 | 0 | AGCAGGGCT | GGGCAG | GAGTGAGGA | X | | |
| 3 3 | 0 | AGCTGTGTG | ATGGGA | GAGTGAGGA | X | | |
| 3 3 | 0 | TGAAGAGTC | CAAGG | GAGTGAGGA | X | | |
| 3 3 | 0 | TGAAGAGTC | CAAGG | GAGTGAGGA | X | | |
| 3 3 | 0 | ACGAGGGTC | CATAG | GAGTGAGGA | X | | |
| 3 3 | 0 | AGAAGCGGT | GGAGT | GAGTGAGGA | X | | |
| 3 3 | 0 | GGCAGAGTT | GTACTG | GAGTGAGGA | X | | |
| 3 3 | 0 | AGCAGTTAC | GGCAAA | GAGTGAGGA | X | | |
| 3 3 | 0 | TGCAGTGTG | CAAGGA | GAGTGAGGA | X | | |
| 3 3 | 0 | CTCTGCGTC | TGGAA | GAGTGAGGA | X | | |
| 3 3 | 0 | AGGAGAGTG | AGAGAA | GAGTGAGGA | X | | |
| 3 3 | 0 | AGGAGAGTG | AGAGAA | GAGTGAGGA | X | | |
| 3 3 | 0 | AATAGGGTC | AGGTAG | GAGTGAGGA | X | | |
| 4 0 | 4 | AGCAGCGTC | TCCGAA | GACTCATGT | X | | |
| 4 0 | 4 | AGCAGCGTC | ACATAA | TAGTGGAGC | X | | |
| 4 0 | 4 | AGCAGCGTC | CAGGA | GTGGAGTC | X | | |
| 4 0 | 4 | AGCAGCGTC | TGGTCT | GGCGGAGGC | X | | |
| 4 0 | 4 | AGCAGCGTC | TTAGA | AGGTGACAA | X | | |
| 4 0 | 4 | AGCAGCGTC | AGAGGA | GGGAGACCA | X | | |
| 4 0 | 4 | AGCAGCGTC | ACTGGT | AAGACATGA | X | | |
| 4 0 | 4 | AGCAGCGTC | CCTGG | CATGGAGCA | X | | |
| 4 0 | 4 | AGCAGCGTC | TGACAG | CAGTGAAAC | X | | |
| 4 0 | 4 | AGCAGCGTC | TCCAGG | GTGTGCTGC | X | | |
| 4 0 | 4 | AGCAGCGTC | TCAGA | GGTAGAGCA | X | | |
| 4 0 | 4 | AGCAGCGTC | GAGACC | CATGGAGCA | X | | |
| 4 0 | 4 | AGCAGCGTC | GTGGC | AGGGCAGGA | X | | |
| 4 0 | 4 | AGCAGCGTC | CTGGG | GAGCGCGTC | X | | |
| 4 0 | 4 | AGCAGCGTC | GTTCGG | GGCTGAGAT | X | | |
| 4 0 | 4 | AGCAGCGTC | AGGCT | GTGGGAGCC | X | | |
| 4 0 | 4 | AGCAGCGTC | CACTG | TGGTAAGCA | X | | |
| 4 0 | 4 | AGCAGCGTC | TGCATG | GTGTGTTGC | X | | |
| 4 0 | 4 | AGCAGCGTC | TAATAC | AATTGAGTT | X | | |
| 4 0 | 4 | AGCAGCGTC | AACTGT | GTGAGTTGA | X | | |
| 4 0 | 4 | AGCAGCGTC | AAGTCT | GTGTGCTGC | X | | |
| 4 0 | 4 | AGCAGCGTC | TACAGT | GACTGCCGT | X | | |
| 4 0 | 4 | AGCAGCGTC | TGTGC | CATGGAGCA | X | | |
| 4 0 | 4 | AGCAGCGTC | TCCTT | GAGCGGTGC | X | | |
| 4 0 | 4 | AGCAGCGTC | TCCTTG | GGCAGAGGT | X | | |
| 4 0 | 4 | AGCAGCGTC | ACGTG | CCGCTAGGA | X | | |
| 4 1 | 3 | AGCCGCGTC | GCGGA | GAGGGCGGC | X | | |
| 4 1 | 3 | AGCAGTGTC | CTGAGG | GTGTGAAGG | X | | |
| 4 1 | 3 | AGCAGTGTC | AGATT | AAGTGAGCC | X | | |
| 4 1 | 3 | AGCATCGTC | AATTA | CAGTGAAAA | X | | |
| 4 1 | 3 | AGCAGCGGC | TGTGG | CAGTGTGGT | X | | |
| 4 1 | 3 | AGCAACGTC | GTGACA | GAGCCTGGA | X | | |
| 4 1 | 3 | AGCAGTGTC | ACAGT | GTGTGAGAG | X | | |
| 4 1 | 3 | AGCAGCGGC | TCCCAG | GAGAGGGGC | X | | |
| 4 1 | 3 | AGCAACGTC | AGCAAA | GTCTCAGGA | X | | |

| # of mutations | | | | | | VF2468 concentration | | |
|---|---|---|---|---|---|---|---|---|
| T (−) | (+) | (−) site | spacer | (+) site | 4 nM | 2 nM | 10.5 nM |
| 4 | 1 | 3 | AGCAACGTC | AGCAAA | GTCTCAGGA | X | | |
| 4 | 1 | 3 | AGTAGCGTC | TCGCT | GTGTGAGTG | X | | |
| 4 | 1 | 3 | AGCAACGTC | AGCAGA | GTCTCAGGA | X | | |
| 4 | 1 | 3 | AGCAGCGTT | ATTCT | GAGTGATAT | X | | |
| 4 | 1 | 3 | AGCAGTGTC | CAGTA | GTGTAAGGT | X | | |
| 4 | 1 | 3 | AGCAACGTC | AGCAAA | GTCTCAGGA | X | | |
| 4 | 1 | 3 | AGCAACGTC | AGCAAA | GTCTCAGGA | X | | |
| 4 | 1 | 3 | GGCAGCGTC | GGGATA | TGGTGAGGG | X | | |
| 4 | 1 | 3 | AGCAACGTC | AGCAAA | GTCTCAGGA | X | | |
| 4 | 1 | 3 | AGCAGAGTC | GCTCA | CTGTGAGGC | X | | |
| 4 | 1 | 3 | AGCAGCGGC | AGCGGC | GAGGGCGGC | X | | |
| 4 | 1 | 3 | AGCAGTGTC | AGAGCA | GAGAGAGCC | X | | |
| 4 | 1 | 3 | AGCATCGTC | TGATCC | TTGTGAGGG | X | | |
| 4 | 1 | 3 | AGCAACGTC | AGCAAA | GTCTCAGGA | X | | |
| 4 | 1 | 3 | AGCAACGTC | AGCAAA | GTCTCAGGA | X | | |
| 4 | 1 | 3 | AGCAGGGTC | TCCTG | TAGTGAGTC | X | | |
| 4 | 1 | 3 | ACCAGCGTC | TGCTTC | TGGTGAGGC | X | | |
| 4 | 1 | 3 | AGCAACGTC | AGCAAA | GTCTCAGGA | X | | |
| 4 | 1 | 3 | AGCAGCATC | AGCTG | GAGGAAGGG | X | | |
| 4 | 1 | 3 | AGCAGCGGC | AACGAT | GAGCAAGAA | X | | |
| 4 | 1 | 3 | AGCAGTGTC | AGCAGC | AAGTGTGGT | X | | |
| 4 | 1 | 3 | AGCAACGTC | AGCAAA | GTCTCAGGA | X | | |
| 4 | 1 | 3 | AGCAGCGGC | CACAGA | GGTTGAGGC | X | | |
| 4 | 1 | 3 | AGCAGCGGC | ACCTG | GGGAGAGGC | X | | |
| 4 | 1 | 3 | AGCAGTGTC | AGTGGT | GGAGGAGGA | X | | |
| 4 | 1 | 3 | AGCAACGTC | AGCAAA | GTCTCAGGA | X | | |
| 4 | 1 | 3 | AGCAGAGTC | CTGGGA | GACTGAACA | X | | |
| 4 | 1 | 3 | AGCAGTGTC | AGATA | GAGGGAGCC | X | | |
| 4 | 1 | 3 | AGCAGTGTC | CATTTG | AAGGGAGGT | X | | |
| 4 | 1 | 3 | TGCAGCGTC | TGTGT | GAGTGTCGT | X | | |
| 4 | 1 | 3 | GGCAGCGTC | TGTCT | GTGTGAGCT | X | | |
| 4 | 1 | 3 | AGCAGCGTG | TTTTAA | GAGTGAAAG | X | | |
| 4 | 1 | 3 | AGCAGCGGC | TGTGAA | AGGTGAGGT | X | | |
| 4 | 1 | 3 | AGCAGTGTC | CAGGA | GGAGGAGGA | X | | |
| 4 | 1 | 3 | AGCAGTGTC | TTGCAT | GTGGGAGGT | X | | |
| 4 | 1 | 3 | ACCAGCGTC | TGCTTC | TGGTGAGGC | X | | |
| 4 | 1 | 3 | AGCAACGTC | CATCCT | GAGAGATGG | X | | |
| 4 | 1 | 3 | AGCAACGTC | AGCAAA | GTCTCAGGA | X | | |
| 4 | 1 | 3 | AGCAACGTC | ACAGGT | GAGTTGAGA | X | | |
| 4 | 1 | 3 | AGCAACGTC | CAGAA | AATTGAGCA | X | | |
| 4 | 1 | 3 | AGCAGTGTC | TTTTT | GAGTAGGCA | X | | |
| 4 | 1 | 3 | AGCAGCGGC | AGCAT | TAGGGAGGT | X | | |
| 4 | 1 | 3 | AGCAGTGTC | CTCATG | GGAGGAGGA | X | | |
| 4 | 1 | 3 | AGCAGCGGC | CAAGA | GAGTGAATT | X | | |
| 4 | 1 | 3 | AGCAACGTC | AGCAAA | GTCTCAGGA | X | | |
| 4 | 1 | 3 | AGCAGAGTC | AGGGA | GACTGAGTC | X | | |
| 4 | 1 | 3 | AGCAGTGTC | CAGCGT | GAGGGAGAT | X | | |
| 4 | 1 | 3 | AGCACCGTC | TGGGA | GTATGAGGC | X | | |
| 4 | 1 | 3 | ACCAGCGTC | CACTTC | TGGTGAGGC | X | | |
| 4 | 1 | 3 | AGCAACGTC | AGCAAA | GTCTCAGGA | X | | |
| 4 | 1 | 3 | AGCAACGTC | AGCAAA | GTCTCAGGA | X | | |
| 4 | 1 | 3 | AGCAACGTC | AGAAAA | GTCTCAGGA | X | | |
| 4 | 1 | 3 | AGCAGGGTC | CAAAA | GAGTGATTT | X | | |
| 4 | 1 | 3 | AGCAGTGTC | AGCCCA | GAGTGAATT | X | | |
| 4 | 1 | 3 | AGCAACGTC | AGCAAA | GTCTCAGGA | X | | |
| 4 | 1 | 3 | AGCAACGTC | AGCAAA | GTCTCAGGA | X | | |
| 4 | 1 | 3 | AGCAGTGTC | AACTAG | GAGTAGGCA | X | | |
| 4 | 1 | 3 | AGCAGCGGC | ATTAC | GAGTAAGCT | X | | |
| 4 | 1 | 3 | AGCAACGTC | AGCAAA | GTCTCAGGA | X | | |
| 4 | 1 | 3 | AGCAACGTC | AACAAA | GTCTCAGGA | X | | |
| 4 | 1 | 3 | AGCAGCTTC | CTCTG | GGGAGTGGA | X | | |
| 4 | 1 | 3 | AGCAGTGTC | TCCCC | GAGGGAAAA | X | | |
| 4 | 1 | 3 | AGCATCGTC | CGGGG | AGGTGAGAA | X | | |
| 4 | 1 | 3 | AGCAGCGGC | TCTCA | AAGTGTGGT | X | | |
| 4 | 1 | 3 | AGCATCGTC | CGGGG | AGGTGAGAA | X | | |
| 4 | 1 | 3 | AGCAGCGTT | CACACT | CAGAGAGGT | X | | |
| 4 | 1 | 3 | AGCAGCGGC | CGGAGC | AAGAGAGGG | X | | |
| 4 | 1 | 3 | AACAGCGTC | AATGT | GTGTGAGAG | X | | |
| 4 | 1 | 3 | AGCATCGTC | CGGGG | AGGTGAGAA | X | | |
| 4 | 1 | 3 | AGCATCGTC | CGGGG | AGGTGAGAA | X | | |
| 4 | 1 | 3 | AGCATCGTC | TGGGG | AGGTGAGAA | X | | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 4 | 1 | 3 AGCATCGTC | CGGGG | AGGTGAGAA | | X | | |
| 4 | 1 | 3 AGCAGCATC | AGCGA | GAGGAAGGG | | X | | |
| 4 | 1 | 3 AGCAACGTC | AGCAAA | GTCTCAGGA | | X | | |
| 4 | 1 | 3 AGCACCGTC | CAGTGT | GGGTGAAGC | | X | | |
| 4 | 1 | 3 AGCAACGTC | AGCAAA | GTCTCAGGA | | X | | |
| 4 | 1 | 3 AACAGCGTC | AACGT | GAGTGAATT | | X | | |
| 4 | 1 | 3 AGCAACGTC | AGCAAA | GTCTCAGGA | | X | | |
| 4 | 1 | 3 AGCAACGTC | AGCAAA | GTCTCAGGA | | X | | |
| 4 | 1 | 3 AGCACCGTC | TCCTGA | GGGTGAGTG | | X | | |
| 4 | 1 | 3 AGCACCGTC | CTTTCC | GTGTGGGGT | | X | | |
| 4 | 1 | 3 AGCAGGGTC | AAAAAG | TAGTGTTGA | | X | | |
| 4 | 1 | 3 AGCAACGTC | CCTCAT | GAATAAAGA | | X | | |
| 4 | 1 | 3 AGCAACGTC | AGCAAA | GTCTCAGGA | | X | | |
| 4 | 1 | 3 AGCAGCTTC | TCTGA | GGGAGTGGA | | X | | |
| 4 | 1 | 3 GGCAGCGTC | TGGGAT | GAGGAAGGC | | X | | |
| 4 | 1 | 3 AGCAACGTC | AGCAAA | GTCTCAGGA | | X | | |
| 4 | 1 | 3 AGCAGCGGC | AACTT | AAGAGTGGA | | X | | |
| 4 | 1 | 3 AGCAGCGGC | CTCAG | AAGTGAGCC | | X | | |
| 4 | 1 | 3 AGCAGTGTC | TGCACA | GAGTAGGCA | | X | | |
| 4 | 1 | 3 AGCAGTGTC | CCGAGG | CTGTGAGGC | | X | | |
| 4 | 1 | 3 AGCAACGTC | AGCAAA | GTCTCAGGA | | X | | |
| 4 | 1 | 3 AGCAACGTC | AGCAAA | GTCTCAGGA | | X | | |
| 4 | 1 | 3 AGCAGTGTC | CAGCA | CAGTGAGAT | | X | | |
| 4 | 1 | 3 AGCAACGTC | CAGAGG | GAGGAAAGA | | X | | |
| 4 | 1 | 3 AGCAGCGTG | TTAATT | AAGTGAGTC | | X | | |
| 4 | 1 | 3 AGCAGGGTC | TAAGG | GAGTGATTT | | X | | |
| 4 | 1 | 3 AGCACCGTC | TGGGA | GTTTCAGGA | | X | | |
| 4 | 1 | 3 AGCACCGTC | TGGGA | GTTTCAGGA | | X | | |
| 4 | 1 | 3 ATCAGCGTC | CAGCGT | GAGGTAGGC | | X | | |
| 4 | 1 | 3 AGCATCGTC | AATTA | TAGTGAGAC | | X | | |
| 4 | 1 | 3 AGCAACGTC | AGCAAA | GTCTCAGGA | | X | | |
| 4 | 1 | 3 AGCAGCGAC | ATCCT | GAGTGGGCT | | X | | |
| 4 | 1 | 3 AGCACCGTC | CAGACA | GAGCAGGGA | | X | | |
| 4 | 1 | 3 AGCAGTGTC | ATTTTC | TGGTGAGGG | | X | | |
| 4 | 1 | 3 AGCAGTGTC | CTGTG | GAGTGTTGG | | X | | |
| 4 | 1 | 3 AGCAGCGGC | GAGGT | TAGTGTGGT | | X | | |
| 4 | 1 | 3 AGCAGGGTC | CACAGT | GTGTGAGAT | | X | | |
| 4 | 2 | 2 AGCACCGGC | CGGCC | GAGGGAGGG | | X | | |
| 4 | 2 | 2 AGCAGAGTG | CCAGG | GAGTGAGAT | | X | | |
| 4 | 2 | 2 AGCAAGGTC | TGCATT | GAGAGAGGC | | X | | |
| 4 | 2 | 2 AGCATGGTC | CAGCA | GAGTGAGCC | | X | | |
| 4 | 2 | 2 ATCAGTGTC | ATCCTG | GAGTAAGGT | | X | | |
| 4 | 2 | 2 AGCATGGTC | GTGGA | AAGTGAGTA | | X | | |
| 4 | 2 | 2 AGCAATGTC | TGTGG | GAGGGAGGC | | X | | |
| 4 | 2 | 2 AGCATTGTC | TGCAGT | GAGTGTGGG | | X | | |
| 4 | 2 | 2 AGCATTGTC | TCCCTC | CAGTGAGGG | | X | | |
| 4 | 2 | 2 AGCAAGGTC | AGTGTC | TAGTGAGGG | | X | | |
| 4 | 2 | 2 AGCAGGGTA | GTGGT | GAGTAAGGT | | X | | |
| 4 | 2 | 2 AGCAGCGCA | GGCCG | GGGTGAGGG | | X | | |
| 4 | 2 | 2 AGCAGCATT | GACAT | GAGTGAGAT | | X | | |
| 4 | 2 | 2 AGCATGGTC | AGGTTC | CAGTGAGGG | | X | | |
| 4 | 2 | 2 AGCTGCATC | ACCTT | GAGTGAGTC | | X | | |
| 4 | 2 | 2 AGAAACGTC | CAGGTA | GAGTGAAAA | | X | | |
| 4 | 2 | 2 TGCAGTGTC | CCATG | GAGGGAGGT | | X | | |
| 4 | 2 | 2 AACAACGTC | CAGCAG | GAGTGTGAA | | X | | |
| 4 | 2 | 2 AGCAAGGTC | TTAAA | GAGCGAGTA | | X | | |
| 4 | 2 | 2 AGCAGTGTG | GGGCA | GTGTGAGGC | | X | | |
| 4 | 2 | 2 AGTAGTGTC | CTGTG | GAGGGAGGC | | X | | |
| 4 | 2 | 2 AGCAGGGTT | GGTTTC | TAGTGAGGC | | X | | |
| 4 | 2 | 2 AGCATGGTC | AGGTTC | CAGTGAGGG | | X | | |
| 4 | 2 | 2 AGCAGCATT | GACAT | GAGTGAGAT | | X | | |
| 4 | 2 | 2 AGCACCGTA | TTCTGC | TAGTGAGGG | | X | | |
| 4 | 2 | 2 AGCTGTGTC | TGGTGT | GAGTGAGAG | | X | | |
| 4 | 2 | 2 AGCCGGGTC | CCCAC | GAGTGAGTG | | X | | |
| 4 | 2 | 2 AACAGGGTC | AGAGAA | GAGTGAGAC | | X | | |
| 4 | 2 | 2 AGCACTGTC | TTGGA | AAGTGAGGG | | X | | |
| 4 | 2 | 2 AGCAACGTG | GCAGAG | GAGGGAGGT | | X | | |
| 4 | 2 | 2 AGCAGGGTG | GGAACT | GAGGGAGGT | | X | | |
| 4 | 2 | 2 AGCACAGTC | TTGGG | GAGAGAGGC | | X | | |
| 4 | 2 | 2 AGCATTGTC | ACACA | GAGTGAATA | | X | | |
| 4 | 2 | 2 ATCAGAGTC | AGCTTA | GAGTGAGAG | | X | | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 4 | 2 | 2 AGCAACCTC | CAGGT | GAGGGAGGC | | X | | |
| 4 | 2 | 2 AGCGGAGTC | GCTGGG | GAGAGAGGG | | X | | |
| 4 | 2 | 2 AGCATGGTC | CATTTC | TAGTGAGGC | | X | | |
| 4 | 2 | 2 TGCAGTGTC | CACAGC | AAGTGAGGT | | X | | |
| 4 | 2 | 2 GGCACCGTC | CTCCTG | GAGGGAGGC | | X | | |
| 4 | 2 | 2 AGCAAAGTC | TCTAAA | GAGTGTGGT | | X | | |
| 4 | 2 | 2 AGCAGCATT | GACAT | GAGTGAGAT | | X | | |
| 4 | 2 | 2 AGCAGCATT | GCACGG | GGGTGAGGT | | X | | |
| 4 | 2 | 2 AGCAGTGAC | AGCGG | GAGTGAGCC | | X | | |
| 4 | 2 | 2 AGCAGTGAC | CAATCT | GAGTGAGCC | | X | | |
| 4 | 2 | 2 AGCAATGTC | AACAGA | GGGTGAGGG | | X | | |
| 4 | 2 | 2 AGCAACATC | TACTAA | GAGTGAGCC | | X | | |
| 4 | 2 | 2 TGCAGGGTC | AGGGT | GTGTGAGGC | | X | | |
| 4 | 2 | 2 AGCAACGGC | GACTG | GAGTGACCA | | X | | |
| 4 | 2 | 2 AGCATGGTC | CAGTTC | CAGTGAGGG | | X | | |
| 4 | 2 | 2 GGCAGTGTC | CTCCCA | CAGTGAGGC | | X | | |
| 4 | 2 | 2 AGCACCGGC | CCTGGG | CAGTGAGGG | | X | | |
| 4 | 2 | 2 AACAGTGTC | TATAAA | TAGTGAGGG | | X | | |
| 4 | 2 | 2 AGCAAAGTC | AGAGG | GAGTGATGT | | X | | |
| 4 | 2 | 2 AGCAATGTC | TGCAT | GAGGGAGGT | | X | | |
| 4 | 2 | 2 AGCAGTCTC | CAGGC | GAGAGAGGG | | X | | |
| 4 | 2 | 2 AGCAAAGTC | CTTGGT | AAGTGAGGG | | X | | |
| 4 | 2 | 2 AGCAGCAGC | TTAGA | GAGTGAGCC | | X | | |
| 4 | 2 | 2 AACATCGTC | AGTGG | GAGTGTGAA | | X | | |
| 4 | 2 | 2 AGCAACATC | CTTGGG | GAGTGAAGT | | X | | |
| 4 | 2 | 2 AGCCCCGTC | AAGCA | GAGGGAGGC | | X | | |
| 4 | 2 | 2 AGCAGCGGT | TCTCA | GAGTGTGGC | | X | | |
| 4 | 2 | 2 AGCAAGGTC | TGAGAA | GAGTGGTGA | | X | | |
| 4 | 2 | 2 AACAGAGTC | AGAGAG | GTGTGAGGC | | X | | |
| 4 | 2 | 2 GGCAGCGTG | TGACAG | AAGTGAGGG | | X | | |
| 4 | 2 | 2 AGCATAGTC | TCCCA | GAGTGAGTG | | X | | |
| 4 | 2 | 2 AGCCGTGTC | CCCTT | AAGTGAGGG | | X | | |
| 4 | 2 | 2 AGCATGGTC | AGGTT | CAGTGAGGG | | X | | |
| 4 | 2 | 2 AGTAGTGTC | TGGTG | GAGTGAGTT | | X | | |
| 4 | 2 | 2 AGCAGCATT | GACAT | GAGTGAGAT | | X | | |
| 4 | 2 | 2 AGCAGCATT | TCAAGA | GAGTGAGAG | | X | | |
| 4 | 2 | 2 CGCAGTGTC | TGGTCA | CAGTGAGGC | | X | | |
| 4 | 2 | 2 AGCAGGGTG | GGGAA | GAGGGAGGT | | X | | |
| 4 | 2 | 2 AGCAGGGTA | ATGTGA | GAGTGAGTG | | X | | |
| 4 | 2 | 2 AGCATAGTC | ACTTA | GAGTGTGGG | | X | | |
| 4 | 2 | 2 AGCATGGTC | AGGTTC | CAGTGAGGG | | X | | |
| 4 | 2 | 2 TCCAGCGTC | GTGACA | GAGTGAGAC | | X | | |
| 4 | 2 | 2 AGCACTGTC | CTGTCA | GAGTGTGGC | | X | | |
| 4 | 2 | 2 AGCATAGTC | CAGTT | CAGTGAGGC | | X | | |
| 4 | 2 | 2 AGCAGTGTG | CACCAC | GAGAGAGGC | | X | | |
| 4 | 2 | 2 AGCAACGGC | AGGAGA | GAGAGGGGA | | X | | |
| 4 | 2 | 2 AGCCGGGTC | ACCGA | GAGTGAGTG | | X | | |
| 4 | 2 | 2 AGCAATGTC | AATTTT | CAGTGAGCA | | X | | |
| 4 | 2 | 2 AGCAACGTG | TGGAG | CAGTGAGGG | | X | | |
| 4 | 2 | 2 AGCACGGTC | AGTCTT | CAGTGAGGG | | X | | |
| 4 | 2 | 2 AGCATGGTC | ATGTTA | TAGTGAGTA | | X | | |
| 4 | 2 | 2 AGCAGGGTA | GGGAG | GAGTGAGTG | | X | | |
| 4 | 2 | 2 AGCGGTGTC | TGAAAA | AAGTGAGGG | | X | | |
| 4 | 2 | 2 AGCAAGGTC | CATCCA | GAGAGAGGC | | X | | |
| 4 | 2 | 2 AGCACCTTC | TAGGGA | GTGTGAGGC | | X | | |
| 4 | 2 | 2 AGCAAAGTC | TCACAG | GAGGGAGGC | | X | | |
| 4 | 2 | 2 AGCAAGGTC | TGGGA | GAGTGATGT | | X | | |
| 4 | 2 | 2 AGCAGCAGC | TGCCGG | GAGCGAGGC | | X | | |
| 4 | 2 | 2 AGCAACCTC | CTGGG | GAGTGTGGG | | X | | |
| 4 | 2 | 2 TGCAGCGAC | TGAAGT | GAGTGAGTG | | X | | |
| 4 | 2 | 2 GGCAGCTTC | CCAGT | GAGTAAGGT | | X | | |
| 4 | 2 | 2 AACAGTGTC | AGTGAT | TAGTGAGGG | | X | | |
| 4 | 2 | 2 AGCTTCGTC | CAGAG | CAGTGAGGG | | X | | |
| 4 | 2 | 2 AGCAGCATT | GACAT | GAGTGAGAT | | X | | |
| 4 | 2 | 2 AGCAACGTG | ATGAAA | GAGTGAGAT | | X | | |
| 4 | 2 | 2 AGCAATGTC | AGTCTC | AAGTGTGGA | | X | | |
| 4 | 2 | 2 TGCAGTGTC | CCTGG | GAGGGAGGT | | X | | |
| 4 | 2 | 2 AGCAACGGC | CAGTCC | CAGGGAGGA | | X | | |
| 4 | 2 | 2 AGCATCGGC | TCCTC | AAGTGAGGC | | X | | |
| 4 | 2 | 2 AGCATCGGC | TCCTC | AAGTGAGGC | | X | | |
| 4 | 2 | 2 AGCATCGGC | TCCTC | AAGTGAGGC | | X | | |

| # of mutations T (−) (+) (−) | site | spacer | (+) site | VF2468 concentration 4 nM | 2 nM | 10.5 nM |
|---|---|---|---|---|---|---|
| 4 2 2 | AGCAAGGTC | AGAGA | GTGTGAGGC | X | | |
| 4 2 2 | AGCGGAGTC | CAGAG | AAGTGAGGG | X | | |
| 4 2 2 | AGCACCATC | AGCAC | CAGTGAGGT | X | | |
| 4 2 2 | AGCTGCTTC | CCCTA | GAGTGAGAG | X | | |
| 4 2 2 | AGCAACATC | ACTTT | GAGTAAGGC | X | | |
| 4 2 2 | AACAGTGTC | AAATC | AAGTGAGGT | X | | |
| 4 2 2 | AGCATCGTA | CCTCAA | GAGACAGGA | X | | |
| 4 2 2 | AGCATGGTC | GGTTTC | CAGTGAGGG | X | | |
| 4 2 2 | AACAGCTTC | CCAGCT | TAGTGAGGC | X | | |
| 4 2 2 | AGCAACTTC | CCTGGA | GGGTGAGGG | X | | |
| 4 2 2 | AGCAGCATT | GACAT | GAGTGAGAT | X | | |
| 4 2 2 | AGCAGGGTG | GGGTGT | GAGGGAGGC | X | | |
| 4 2 2 | AGCATTGTC | TGAAG | GAGAGGGGA | X | | |
| 4 2 2 | GGCAGCGTG | TGTGA | GAGTGAGCT | X | | |
| 4 2 2 | AGCTGTGTC | CCCCA | GAGTGAGAG | X | | |
| 4 2 2 | AGCAGCATT | CATGT | GAGTGAGAT | X | | |
| 4 2 2 | AGCAGTGTT | TCTCT | GAGTGTGGC | X | | |
| 4 2 2 | AGCACAGTC | ACCCA | TAGTGAGGC | X | | |
| 4 2 2 | GGCAGCTTC | AGGGC | AAATGAGGA | X | | |
| 4 2 2 | AGCATTGTC | ATAATA | GAGAGAGGT | X | | |
| 4 2 2 | AGCATGGTC | ATGGA | AAGTGAGTA | X | | |
| 4 2 2 | AGCAGGGTG | GTAAA | GAGGGAGGT | X | | |
| 4 2 2 | AGCAACTTC | TCCAC | TAGTGAGGG | X | | |
| 4 2 2 | AGCAGCAGC | CGGTG | GTGTGAGGC | X | | |
| 4 2 2 | TGCAGGGTC | TCTTA | GAGTGAGTT | X | | |
| 4 2 2 | TGCAGCGTT | GGGCT | CAGTGAGGG | X | | |
| 4 2 2 | AGCAGCATA | TAATA | GAGTGAGTC | X | | |
| 4 2 2 | AGCAGTGTG | CTAAG | GAGAGAGGC | X | | |
| 4 2 2 | AACAGCATC | TCAGCT | GGGTGAGGC | X | | |
| 4 2 2 | AGCAGTGTG | CCTTGG | GTGTGAGGG | X | | |
| 4 2 2 | AACAGAGTC | GTTCA | GTGTGAGGG | X | | |
| 4 2 2 | AGCAACGTT | AGCAG | GAGTGTGGT | X | | |
| 4 2 2 | AGCAAAGTC | TGTAAA | GAGTGTGTA | X | | |
| 4 2 2 | TGCATCGTC | CTATG | GAGGGAGGT | X | | |
| 4 2 2 | AGCAAGGTC | TTGTTG | GAGGGAGGG | X | | |
| 4 2 2 | GGCACCGTC | ATCCT | GAGTGGGGC | X | | |
| 4 2 2 | AGCAGAGTA | AGGGAG | GAGTGAGAG | X | | |
| 4 2 2 | AGCAAAGTC | ACAGG | GAGTGAGCG | X | | |
| 4 2 2 | AGAAGTGTC | ACTGTC | CAGTGAGGC | X | | |
| 4 2 2 | AGCAGCATT | GACAT | GAGTGAGAT | X | | |
| 4 2 2 | AGCAAAGTC | AGCCA | GAGGGAGAA | X | | |
| 4 2 2 | AGCAAAGTC | TGGAGT | GAGTGTGTA | X | | |
| 4 2 2 | GGCAGTGTC | CGGCT | GAGGGAGGG | X | | |
| 4 2 2 | AGCAGCAAC | AGTGT | GAGTGAGTT | X | | |
| 4 2 2 | AGCATTGTC | TAGCA | GGGTGAGAA | X | | |
| 4 2 2 | AGCAAGGTC | ACTGAG | GAGGGAGGC | X | | |
| 4 2 2 | AGCATCGGC | AGCTTG | GAGAGAGGT | X | | |
| 4 2 2 | AGCAGGGTG | GTAGGG | GAGGGAGGT | X | | |
| 4 2 2 | AGCAGCGCT | TCTCA | AAGTGAGGC | X | | |
| 4 2 2 | AGCAGGGTG | GTGTGA | GAGTGAGTG | X | | |
| 4 2 2 | TGCAGCGTG | GCCACA | GAGTGAGAC | X | | |
| 4 2 2 | TGCAGTGTC | ATTTGA | GAGTAAGGT | X | | |
| 4 2 2 | AGCAGGGTG | AGCACT | AAGTGAGGC | X | | |
| 4 2 2 | AACAGGGTC | AGTGGG | GAGAGAGGC | X | | |
| 4 2 2 | AACAGCGGC | CTATT | GTGTGAGGG | X | | |
| 4 2 2 | AGCAACGTT | CAGCT | CAGTGAGGT | X | | |
| 4 2 2 | AGCAGTGTT | GCCCCA | GGGTGAGGT | X | | |
| 4 2 2 | AGCACCGTG | TGGGA | GAGGGAGGT | X | | |
| 4 2 2 | AGCAACGTT | CTGTG | GAATGAGCA | X | | |
| 4 2 2 | AGCCACGTC | GAATG | GATTGAGGG | X | | |
| 4 2 2 | AGCAGGGTG | GAGCGC | GAGGGAGGC | X | | |
| 4 2 2 | TGCAGCGGC | CTCAG | AAGTGAGGG | X | | |
| 4 2 2 | AGCATTGTC | TCCCTT | GAGTATGGA | X | | |
| 4 2 2 | GGCACCGTC | CTTTG | CAGTGAGGT | X | | |
| 4 2 2 | AGCATGGTC | GGGCAC | TAGTGAGGC | X | | |
| 4 2 2 | AGCACCTTC | ATGAAT | GTGTGAGGC | X | | |
| 4 2 2 | AGTAGTGTC | TAATAG | GTGTGAGGT | X | | |
| 4 2 2 | AGCACCATC | AAGATA | GTGTGAGGC | X | | |
| 4 2 2 | AGCCACGTC | ACCTG | AGGTGAGGA | X | | |
| 4 2 2 | AGCAACATC | TGTGTA | GAGCGAGGT | X | | |
| 4 2 2 | AGCCGAGTC | CTTGT | GGGTGAGGC | X | | |

| # of mutations T (-) (+) (-) | site | spacer | (+) site | VF2468 concentration 4 nM | 2 nM | 10.5 nM |
|---|---|---|---|---|---|---|
| 4 2 2 | ACCAGTGTC | CTGCAG | TAGTGAGGC | X | | |
| 4 2 2 | AGCAACGAC | GGGCT | GCGTGTGGA | X | | |
| 4 2 2 | AGCAGCATT | GACCT | GAGTGAGAT | X | | |
| 4 2 2 | AGCAGCATT | GACCT | GAGTGAGAT | X | | |
| 4 2 2 | CGCAGTGTC | TTCCC | CAGTGAGGC | X | | |
| 4 2 2 | TGCATCGTC | AGAGA | GTGTGAGGG | X | | |
| 4 2 2 | AGCTGAGTC | CCCGGC | AAGTGAGGC | X | | |
| 4 2 2 | AGCAACGTG | TGCCA | GTGTGAGGG | X | | |
| 4 2 2 | AGCAGTGGC | TGGGCA | TAGTGAGGC | X | | |
| 4 2 2 | AGCAGCATT | GACAT | GAGTGAGAT | X | | |
| 4 2 2 | AGCACCATC | TAGGCA | GAGGGAGGC | X | | |
| 4 2 2 | AGCACAGTC | ATGGTG | GAGTAAGGG | X | | |
| 4 2 2 | AGCATGGTC | AGGTTC | CAGTGAGGG | X | | |
| 4 2 2 | AGCATGGTC | AGGTTC | CAGTGAGGG | X | | |
| 4 2 2 | AGTAACGTC | ATTTCA | GAGTGCAGA | X | | |
| 4 2 2 | AGCAACTTC | TAGGAT | GAGTGTGAA | X | | |
| 4 2 2 | AGCAGCATT | GACAT | GAGTGAGAT | X | | |
| 4 2 2 | AGCAATGTC | TGCTGT | GGGTGAGGG | X | | |
| 4 2 2 | AGCAATGTC | TGCCAT | GAGTGTGAA | X | | |
| 4 2 2 | AGCAGATTC | GGAATT | GAGTGAGTG | X | | |
| 4 2 2 | CACAGCGTC | GGAGG | GAGGGAGGG | X | | |
| 4 2 2 | AGCAGCGAT | CTAAT | GAGGGAGAA | X | | |
| 4 2 2 | AGCACCGTG | AGACTT | GAGTGAGCC | X | | |
| 4 2 2 | ATCAGTGTC | CTGGG | GAGTGTGGT | X | | |
| 4 2 2 | AGCAACCTC | ACGGG | GAGGGAGGC | X | | |
| 4 2 2 | AGCAACTTC | AGAAGT | GAGTTAGGG | X | | |
| 4 2 2 | AGCAACTTC | CACTA | GAGAGAGGC | X | | |
| 4 2 2 | AGCAACGTG | GCAGAT | GAGAGAGGT | X | | |
| 4 2 2 | AACAGCATC | AAATGC | GGGTGAGGC | X | | |
| 4 2 2 | ACAAGCGTC | TGTAA | GAGTGAGTC | X | | |
| 4 2 2 | TCCAGCGTC | ACCTA | AAGTGAGGG | X | | |
| 4 2 2 | AGCAAGGTC | AGGAA | GAGAGAGGC | X | | |
| 4 2 2 | AGTAGCGTT | TTGTC | CAGTGAGGT | X | | |
| 4 2 2 | AGCAGTGTT | TGCTAA | CAGTGAGGC | X | | |
| 4 2 2 | AGCATGGTC | AGGTTC | CAGTGAGGG | X | | |
| 4 2 2 | AGCAGCGGA | GGTCA | GAGTGAGTT | X | | |
| 4 2 2 | AGCACCGAC | TCCAT | CAGTGAGGT | X | | |
| 4 2 2 | AGCAGTGAC | ATGAG | GAGTGAGCC | X | | |
| 4 2 2 | AGCAGGGTT | TCTGCA | GTGTGAGGT | X | | |
| 4 2 2 | AGCAGCATG | GTTAG | GAGTGAGAT | X | | |
| 4 2 2 | ATCAGAGTC | AAAGG | GAGGGAGGC | X | | |
| 4 2 2 | AGCAGGGTT | GGAAGA | AAGTGAGGG | X | | |
| 4 2 2 | AGCAGGGTG | GGCAA | GAGGGAGGC | X | | |
| 4 2 2 | GGCAGTGTC | TCAAAC | GAGGGAGGG | X | | |
| 4 2 2 | GGCATCGTC | ACTCTT | GAGTGAGAG | X | | |
| 4 2 2 | AGCACCGTG | ACTTC | GAGGGAGGT | X | | |
| 4 2 2 | AGCAGAGTT | TAAAA | TAGTGAGGG | X | | |
| 4 3 1 | GACAGCCTC | ATTAT | GAGTGAGGC | X | | |
| 4 3 1 | AGGGGGTC | TTGGGA | GAGTGAGGT | X | | |
| 4 3 1 | AGCCTGGTC | CGTGA | GTGTGAGGA | X | | |
| 4 3 1 | GGCAGCGAT | GAGATT | GAGTGAGGG | X | | |
| 4 3 1 | AACAAGGTC | ATAAA | GAGGGAGGA | X | | |
| 4 3 1 | AGCTGAGAC | TTAGA | GAGTGAGGT | X | | |
| 4 3 1 | AGCTGAGAC | TTAGA | GAGTGAGGT | X | | |
| 4 3 1 | GGCAGAGTG | GAGGAA | GAGTGAGGC | X | | |
| 4 3 1 | AGCTGGGTT | GGAGTG | GAGTGAGGG | X | | |
| 4 3 1 | AGCAAAGGC | TAAAGA | GTGTGAGGA | X | | |
| 4 3 1 | AGTAACGGC | GGGGCT | GAGGGAGGA | X | | |
| 4 3 1 | AGCATTGTT | CTCAG | AAGTGAGGA | X | | |
| 4 3 1 | CACAGCATC | AGCAG | GAGTGAGGG | X | | |
| 4 3 1 | AGCCACATC | AGTCT | GAGTAAGGA | X | | |
| 4 3 1 | AGCAGCACA | CAGGCC | GAGTGAGGT | X | | |
| 4 3 1 | AGCATTGCC | TTTTG | GAGTGAGGG | X | | |
| 4 3 1 | AGAAGTGCC | ATCTGG | GAGTGAGGG | X | | |
| 4 3 1 | ATCAGCATA | CAGGG | GAGTGAGGC | X | | |
| 4 3 1 | AGCAGGTAC | GTGCCT | GAGTGAGGC | X | | |
| 4 3 1 | AACTACGTC | CACCA | GAGTGGGGA | X | | |
| 4 3 1 | AGAAGTGCC | ATCTAG | GAGTGAGGG | X | | |
| 4 3 1 | AGGAGTCTC | ATACT | GAGTGAGGT | X | | |
| 4 3 1 | TCCAGCGGC | CACAG | GAGTGAGGT | X | | |
| 4 3 1 | AGCTCAGTC | TCCCA | GGGTGAGGA | X | | |

| # of mutations T (−) (+) (−) | site | spacer | (+) site | VF2468 concentration 4 nM | 2 nM | 10.5 nM |
|---|---|---|---|---|---|---|
| 4 3 1 | AGCTCAGTC | TCTCA | GGGTGAGGA | X | | |
| 4 3 1 | AACAGTATC | TATTCT | GAGTGAGGC | X | | |
| 4 3 1 | GGAAGTGTC | TTACTG | GAGTGAGGT | X | | |
| 4 3 1 | CTCAGAGTC | AAACA | GAGTGAGGT | X | | |
| 4 3 1 | AACAGTGTT | TTGGCC | GAGTGAGGG | X | | |
| 4 3 1 | CTCAGCTTC | CTGTG | GAGTGAGGC | X | | |
| 4 3 1 | AGCAGCTGT | AGGGA | GAGTGAGGT | X | | |
| 4 3 1 | AGCTGTGTG | ATCCT | GAGTGAGGG | X | | |
| 4 3 1 | AGGTGTGTC | TTTGGA | GAGTGAGGC | X | | |
| 4 3 1 | ATTAGAGTC | TGGGTT | GGGTGAGGA | X | | |
| 4 3 1 | AGCCGGCTC | GCGAGT | GAGTGAGGG | X | | |
| 4 3 1 | AGCACCAGC | CCGGGT | GAGTGAGGT | X | | |
| 4 3 1 | TTCAGCGTT | GTGAA | GAGTGAGGC | X | | |
| 4 3 1 | AGCTCCTTC | GAGGA | GAGTGAGGC | X | | |
| 4 3 1 | AAGAGTGTC | CTGGTT | GAGTGAGGC | X | | |
| 4 3 1 | TGCAGGGTA | GTTGG | GAGTGAGGT | X | | |
| 4 3 1 | AGGATCATC | CAGAGT | GAGTGAGGC | X | | |
| 4 3 1 | GTCTGCGTC | CGAAGG | GAGTGAGGG | X | | |
| 4 3 1 | ATGAGCGAC | TGATG | GAGTGAGGG | X | | |
| 4 3 1 | CCCAGGGTC | CACAGA | GAGTGAGGG | X | | |
| 4 3 1 | AGTACAGTC | CATTTG | GAGGGAGGA | X | | |
| 4 3 1 | AGCTTCCTC | CATCTT | GAGTGAGGG | X | | |
| 4 3 1 | AGAAGTGCC | TCCTG | GAGTGAGGG | X | | |
| 4 3 1 | GGCAGAGTG | GATCA | GAGTGAGGC | X | | |
| 4 3 1 | AGCAGTTCC | TAAAA | GAGTGAGGG | X | | |
| 4 3 1 | GGCACTGTC | GCTCA | GAGTGAGGT | X | | |
| 4 3 1 | AGCAGGCAC | AGCCTG | GAGTGAGGC | X | | |
| 4 3 1 | AGTGGAGTC | CCCTA | GAGTGAGAA | X | | |
| 4 3 1 | AGGACAGTC | GCAGA | GAGTGAGGC | X | | |
| 4 3 1 | AGCTGTGTG | CTGCCA | GAGTGAGGC | X | | |
| 4 3 1 | AGCAAGGTG | GGTGGC | GTGTGAGGA | X | | |
| 4 3 1 | TGCTGTGTC | CCCAGT | GAGTGAGGG | X | | |
| 4 3 1 | GGCACAGTC | TGACA | GAGAGAGGA | X | | |
| 4 3 1 | AGCTCAGTC | TCACA | GGGTGAGGA | X | | |
| 4 3 1 | GTCAGTGTC | ATGCTT | GAGTGAGGC | X | | |
| 4 3 1 | GGAAGGGTC | CCAGTG | GAGTGAGGT | X | | |
| 4 3 1 | AGGAGCAAC | AAAGA | GAGTGAGGG | X | | |
| 4 3 1 | AGCGGTTTC | AGTGA | GAGTGAGGC | X | | |
| 4 3 1 | AGCAGCACG | GGGTG | AAGTGAGGA | X | | |
| 4 3 1 | AGAAGGGTG | GAGAAG | GAGTGAGGT | X | | |
| 4 3 1 | TGCTGTGTC | CATCCA | GAGTGAGGG | X | | |
| 4 3 1 | AGCTCAGTC | AACTG | GGGTGAGGA | X | | |
| 4 3 1 | AGCAAGGTT | AGGTTC | TAGTGAGGA | X | | |
| 4 3 1 | AGCTCAGTC | TCTCA | GGGTGAGGA | X | | |
| 4 3 1 | AGCACGGTG | GTCAA | GAGTGAGGC | X | | |
| 4 3 1 | AGCAGGGAT | TTGCA | GAGTGAGGC | X | | |
| 4 3 1 | ATCAGCTTT | GGGGTT | GAGTGAGGT | X | | |
| 4 3 1 | AGCACAGAC | AGCAT | GAGTGAGGC | X | | |
| 4 3 1 | CCCAGCTTC | TCAGG | GAGTGAGGC | X | | |
| 4 3 1 | CGCCCGTC | TGGGA | AAGTGAGGA | X | | |
| 4 3 1 | AGCAGAGGT | TCCCA | GAGTGAGGC | X | | |
| 4 3 1 | AGCCACCTC | CCCTGC | GAGTAAGGA | X | | |
| 4 3 1 | AGCCCTGTC | TGTTAA | GAGTGAGGT | X | | |
| 4 3 1 | AGCAGCAGT | CTCTG | GAGTGAGGT | X | | |
| 4 3 1 | AGCCACTTC | TAGGGA | GAGTGAGTA | X | | |
| 4 3 1 | AGGTGCGGC | AGGTA | GAGTGAGGG | X | | |
| 4 3 1 | AGCTGTGTG | GTTGG | GAGTGAGGG | X | | |
| 4 3 1 | AGGCGCTTC | ATTTAT | GAGTGAGGT | X | | |
| 4 3 1 | AGGAGTCTC | ACGATA | GAGTGAGGT | X | | |
| 4 3 1 | ATCATCCTC | CGCACT | GAGTGAGGG | X | | |
| 4 3 1 | AGCCGGGTA | GGGGAT | GAGTGAGGC | X | | |
| 4 3 1 | AGCAACTGC | TTTGTG | GAGTGAGGT | X | | |
| 4 3 1 | GGCAGCATT | TGAAGG | GAGTGAGGG | X | | |
| 4 3 1 | CACAGCATC | TGAGGT | GAGTGAGGG | X | | |
| 4 3 1 | AGCTGAGAC | TTAGA | GAGTGAGGT | X | | |
| 4 3 1 | ACCCGTGTC | ACAGTT | GAGTGAGGG | X | | |
| 4 3 1 | AGCCCTGTC | TGCTGG | GAGTGAGGG | X | | |
| 4 3 1 | GGACGCGTC | AGGCT | GAGTGAGGT | X | | |
| 4 3 1 | AGGAACCTC | GTGCG | GAGTGAGGC | X | | |
| 4 3 1 | AGCTGTGTG | GCCTT | GAGTGAGGC | X | | |
| 4 3 1 | CGCTGCGAC | CTTCA | GAGTGAGGC | X | | |

| # of mutations | | | | | | VF2468 concentration | | |
|---|---|---|---|---|---|---|---|---|
| T (−) | (+) | (−) site | spacer | (+) site | | 4 nM | 2 nM | 10.5 nM |
| 4 3 | 1 | GGTAGAGTC | AGACA | GAGTGAGGG | | X | | |
| 4 3 | 1 | AGCTGAGAC | TTAGA | GAGTGAGGT | | X | | |
| 4 3 | 1 | ACCAACCTC | CTGTCA | GAGTGAGGC | | X | | |
| 4 3 | 1 | AGCAGTCTG | CTGCAG | GAGTGAGGG | | X | | |
| 4 3 | 1 | TGCTGTGTC | CTCACA | TAGTGAGGA | | X | | |
| 4 3 | 1 | AGAAACTTC | AAGAAG | GAGTGAGGT | | X | | |
| 4 3 | 1 | AACAATGTC | GTCACA | GAGTGAGTA | | X | | |
| 4 3 | 1 | AGAAGGGTG | AATAAG | GAGTGAGGT | | X | | |
| 4 3 | 1 | TGCAGCGGA | GGCAG | GAGTGAGGG | | X | | |
| 4 3 | 1 | AGCTGTGTG | ACCTC | GAGTGAGGC | | X | | |
| 4 3 | 1 | AATAGAGTC | CTGGG | GAGTGAGGC | | X | | |
| 4 3 | 1 | AGCTGAGAC | TTAGA | GAGTGAGGT | | X | | |
| 4 3 | 1 | AGCTGAGAC | TTAGA | GAGTGAGGT | | X | | |
| 4 3 | 1 | AGTAGCATT | TTTAGT | GAGTGAGGG | | X | | |
| 4 3 | 1 | ACCGGAGTC | ATCCCT | GAGTGAGGG | | X | | |
| 4 3 | 1 | AGCAGTCTG | AAGGG | GAGTGAGGG | | X | | |
| 4 3 | 1 | AGCAGCACA | CAGGCC | GAGTGAGGT | | X | | |
| 4 3 | 1 | AGCAGCCAT | CAGAG | GAGTGAGGC | | X | | |
| 4 3 | 1 | GCCAGGGTC | CAAATG | GAGTGAGGC | | X | | |
| 4 3 | 1 | AGCATCTTA | GTGAT | GAGTGAGGT | | X | | |
| 4 3 | 1 | AGGAGCAAC | AGAGA | GAGTGAGGG | | X | | |
| 4 3 | 1 | AGCAGGTTT | ATTAGG | GAGTGAGGG | | X | | |
| 4 3 | 1 | GACAGCCTC | TCCCA | GAGTGAGGC | | X | | |
| 4 3 | 1 | AGCAGCAAT | GGCAG | GAGTGAGGT | | X | | |
| 4 3 | 1 | GGCAGCGGT | AGAGA | TAGTGAGGA | | X | | |
| 4 3 | 1 | AGTGGAGTC | CTGGA | GAGTGAGTA | | X | | |
| 4 3 | 1 | AGCCTGGTC | TGGCC | GTGTGAGGA | | X | | |
| 4 3 | 1 | AGAACCGAC | CAGCCA | GAGTGAGGG | | X | | |
| 4 3 | 1 | AGCAACATG | ACCCA | GAGTGAGGG | | X | | |
| 4 3 | 1 | AGCTCAGTC | TTGCA | GGGTGAGGA | | X | | |
| 4 3 | 1 | AGCTCAGTC | TCACA | GGGTGAGGA | | X | | |
| 4 3 | 1 | TGCAATGTC | AAGCTT | GAGTGAGAA | | X | | |
| 4 3 | 1 | GGCCCCGTC | ACGGT | GAGTGAGGG | | X | | |
| 4 3 | 1 | AGCTCAGTC | TCACA | GGGTGAGGA | | X | | |
| 4 3 | 1 | AGCAATGTA | GGGAGG | GAGTGAGGG | | X | | |
| 4 3 | 1 | AGTAACATC | CTGTTT | GTGTGAGGA | | X | | |
| 4 3 | 1 | ATCATTGTC | TCCACT | GAGTGAGAA | | X | | |
| 4 3 | 1 | AGTAGAGTT | TAGGG | GAGTGAGGG | | X | | |
| 4 3 | 1 | AGCAGGGGT | CAGCTG | GAGTGAGGG | | X | | |
| 4 3 | 1 | TGCTGTGTC | TTCCTG | GAGTGAGGC | | X | | |
| 4 3 | 1 | ATTAGAGTC | AGAGCA | GGGTGAGGA | | X | | |
| 4 3 | 1 | AGAAGGGTG | AGCAA | GAGTGAGGT | | X | | |
| 4 3 | 1 | CTCAGTGTC | TCTGTG | AAGTGAGGA | | X | | |
| 4 3 | 1 | AGCTGTGTT | CTGGAT | GAGTGAGGT | | X | | |
| 4 3 | 1 | AGTACAGTC | TAGCCA | GAGGGAGGA | | X | | |
| 4 3 | 1 | AGCCGCTTT | ATTCAA | GAGTGAGGG | | X | | |
| 4 3 | 1 | ACCGGTGTC | GTCGT | GAGTGAGGG | | X | | |
| 4 3 | 1 | AGCAGTGCT | GAGGC | GAGTGAGGC | | X | | |
| 4 3 | 1 | AGCTCAGTC | TCACA | GGGTGAGGA | | X | | |
| 4 3 | 1 | ATCTGCATC | TCTCTT | GAGTGAGGT | | X | | |
| 4 3 | 1 | AGCACAATC | CCCCAA | GAGTGAGGG | | X | | |
| 4 3 | 1 | AGCTCAGTC | TCACA | GGGTGAGGA | | X | | |
| 4 3 | 1 | ATCATCATC | TTGGA | GAGTGAGGC | | X | | |
| 4 3 | 1 | GGTAGAGTC | ACTGTA | GAGTGAGGG | | X | | |
| 4 3 | 1 | AGCTGTGTG | CTGGGG | GAGTGAGGC | | X | | |
| 4 3 | 1 | ATGAGTGTC | AGGTG | GAGTGAGGG | | X | | |
| 4 3 | 1 | GGCAGAGTG | GTCCAG | GAGTGAGGC | | X | | |
| 4 3 | 1 | AGGAGTCTC | CAGGGG | GAGTGAGGC | | X | | |
| 4 3 | 1 | AGCCAAGTC | CTGAG | GGGTGAGGA | | X | | |
| 4 3 | 1 | CGCTGAGTC | CAGAG | GAGTGAGGC | | X | | |
| 4 3 | 1 | GGCTCCGTC | TTATGT | GAGTGAGGC | | X | | |
| 4 3 | 1 | AGCAGCAGT | GAGGA | GAGTGAGGC | | X | | |
| 4 3 | 1 | AGTACTGTC | AACTA | CAGTGAGGA | | X | | |
| 4 3 | 1 | ATGAGCGGC | CGGTAG | GAGTGAGGT | | X | | |
| 4 3 | 1 | TGCAAGGTC | AGGAT | AAGTGAGGA | | X | | |
| 4 3 | 1 | AGTACAGTC | ACTGT | TAGTGAGGA | | X | | |
| 4 3 | 1 | ATCATTGTC | AGGTT | GAGTGAGAA | | X | | |
| 4 3 | 1 | CTCAGCGGC | TGCTGT | GAGTGAGGG | | X | | |
| 4 3 | 1 | AGCAGTCCC | ATCCAA | GAGTGAGGG | | X | | |
| 4 3 | 1 | AGCACAGGC | TGGACA | GAGTGAGGT | | X | | |
| 4 3 | 1 | AGCAACCAC | CTCCTG | GAGGGAGGA | | X | | |

-continued

| # of mutations T (−) (+) (−) | site | spacer | (+) site | VF2468 concentration 4 nM | 2 nM | 10.5 nM |
|---|---|---|---|---|---|---|
| 4 3 1 | AGTAAGGTC | AAGGA | GAGGGAGGA | X | | |
| 4 3 1 | CGCCCCGTC | TGGAG | AAGTGAGGA | X | | |
| 4 3 1 | TGCACAGTC | ACATG | GTGTGAGGA | X | | |
| 4 3 1 | AGCAGCAAG | TGGCA | GAGTGAGGC | X | | |
| 4 3 1 | AGCTCAGTC | TCACA | GGGTGAGGA | X | | |
| 4 3 1 | GGCAGGGTT | TCTCA | GAGTGAGGT | X | | |
| 4 3 1 | AGGATGGTC | CTTCC | AAGTGAGGA | X | | |
| 4 3 1 | AGCAACCCC | ATTTT | GAGTGAGGG | X | | |
| 4 3 1 | AGAAGCCAC | ATCAGT | GAGTGAGGG | X | | |
| 4 3 1 | ACCAATGTC | ACCTGT | GTGTGAGGA | X | | |
| 4 3 1 | AGGTGCGTG | GAGTG | GAGTGAGGG | X | | |
| 4 3 1 | AGCAGTGAA | GGGAA | GAGTGAGGC | X | | |
| 4 3 1 | AGCTGAGTG | ACAGCT | GAGTGAGGG | X | | |
| 4 3 1 | AGCAGTGCG | TGCAT | GAGTGAGGG | X | | |
| 4 3 1 | GGCGGGGTC | TGCTC | GAGTGAGGC | X | | |
| 4 3 1 | AGAATAGTC | TTAGA | CAGTGAGGA | X | | |
| 4 3 1 | AGCAGGGAT | TTGCA | GAGTGAGGC | X | | |
| 4 3 1 | GGAAGTGTC | CAAGG | GAGTGAGGT | X | | |
| 4 3 1 | ATCAATGTC | CTCTGT | GAGTGAGGG | X | | |
| 4 3 1 | CCCAGCTTC | CTGGG | GAGTGAGGC | X | | |
| 4 3 1 | AGGTGCGGC | AGGTA | GAGTGAGGG | X | | |
| 4 3 1 | AGCTGAGAC | TTAGA | GAGTGAGGT | X | | |
| 4 3 1 | AGCAACATG | GCTCA | GAGTGAGGG | X | | |
| 4 3 1 | TGCGCCGTC | TACTAG | GAGTGAGGC | X | | |
| 4 3 1 | AGCAAAGTT | TAACAA | GAGTGAGAA | X | | |
| 4 3 1 | AGCAAAGTT | TAACAA | GAGTGAGAA | X | | |
| 4 3 1 | AGCAAAGTT | TAACAA | GAGTGAGAA | X | | |
| 4 3 1 | AGCAAAGTT | TAACAA | GAGTGAGAA | X | | |
| 4 3 1 | AGCAAAGTT | TAACAA | GAGTGAGAA | X | | |
| 4 3 1 | AGTATCATC | CGGCT | GAGTGAGGT | X | | |
| 4 3 1 | AGCTGAGAC | TTAGA | GAGTGAGGT | X | | |
| 4 3 1 | AGGAGCAAC | CACAGG | GAGTGAGGG | X | | |
| 4 3 1 | AGCAGCTCG | CTGAG | GAGTGAGGG | X | | |
| 4 3 1 | AGCTGAGAC | TTAGA | GAGTGAGGT | X | | |
| 4 3 1 | AGCAATGTG | AGTTGT | GAGTGAGGG | X | | |
| 4 3 1 | AGAAGCGGT | GCGTCT | GAGTGAGGT | X | | |
| 4 3 1 | AGAAGTGCC | ATCTGT | GAGTGAGGG | X | | |
| 4 4 0 | GGATGAGTC | TGGAG | GAGTGAGGA | X | | |
| 4 4 0 | ACAGGTGTC | CAAGAT | GAGTGAGGA | X | | |
| 4 4 0 | CTGGGCGTC | CCTCCA | GAGTGAGGA | X | | |
| 4 4 0 | CCCGGGGTC | TTCAGT | GAGTGAGGA | X | | |
| 4 4 0 | TGGCACGTC | TGAGG | GAGTGAGGA | X | | |
| 4 4 0 | AGCTCAGTA | CAAAAA | GAGTGAGGA | X | | |
| 4 4 0 | AAAAGGTTC | AGAGG | GAGTGAGGA | X | | |
| 4 4 0 | GACATCATC | AGAACT | GAGTGAGGA | X | | |
| 4 4 0 | AGCACTATT | CTATTA | GAGTGAGGA | X | | |
| 4 4 0 | CCCTGAGTC | TGAGG | GAGTGAGGA | X | | |
| 4 4 0 | TGGGGAGTC | AGTGC | GAGTGAGGA | X | | |
| 4 4 0 | AACAGGGCT | TCTGA | GAGTGAGGA | X | | |
| 4 4 0 | AGCAAAGCT | CGAGA | GAGTGAGGA | X | | |
| 4 4 0 | AACATTGTT | TCAGT | GAGTGAGGA | X | | |
| 4 4 0 | AGACACTTC | ATGAAT | GAGTGAGGA | X | | |
| 4 4 0 | GCCCACGTC | TTCGTG | GAGTGAGGA | X | | |
| 4 4 0 | AACATGGTT | GTGTGG | GAGTGAGGA | X | | |
| 4 4 0 | GGTACAGTC | TTCGCC | GAGTGAGGA | X | | |
| 4 4 0 | GGCATGGTG | AGAGTG | GAGTGAGGA | X | | |
| 4 4 0 | GGAAGTCTC | AGGAT | GAGTGAGGA | X | | |
| 4 4 0 | ATCTTGGTC | AGGGCA | GAGTGAGGA | X | | |
| 4 4 0 | ATCAGGTCC | CAATT | GAGTGAGGA | X | | |
| 4 4 0 | GGCATGGTG | TAAAGA | GAGTGAGGA | X | | |
| 4 4 0 | TGAAACGTT | GCAGG | GAGTGAGGA | X | | |
| 4 4 0 | TGAATCGGC | AACAA | GAGTGAGGA | X | | |
| 4 4 0 | ATACACGTC | TCCTG | GAGTGAGGA | X | | |
| 4 4 0 | GGGAAGGTC | CTTGG | GAGTGAGGA | X | | |
| 4 4 0 | CACTGTGTC | GGGTGA | GAGTGAGGA | X | | |
| 4 4 0 | ATCTTTGTC | TTCCT | GAGTGAGGA | X | | |
| 4 4 0 | CTGAGGGTC | ATTGG | GAGTGAGGA | X | | |
| 4 4 0 | ATGTGAGTC | TTCTT | GAGTGAGGA | X | | |
| 4 4 0 | AAAGTCGTC | AGCTAT | GAGTGAGGA | X | | |
| 4 4 0 | AACAATGTT | CGCCT | GAGTGAGGA | X | | |
| 4 4 0 | GGGAAGGTC | CTATGG | GAGTGAGGA | X | | |

-continued

| # of mutations T | (+) | (−) | (−) site | spacer | (+) site | VF2468 concentration 4 nM | 2 nM | 10.5 nM |
|---|---|---|---|---|---|---|---|---|
| 4 | 4 | 0 | GGATGTGTC | TTCAGG | GAGTGAGGA | X | | |
| 4 | 4 | 0 | TCCACAGTC | TGGGT | GAGTGAGGA | X | | |
| 4 | 4 | 0 | AGCAAAGCT | ATATGG | GAGTGAGGA | X | | |
| 4 | 4 | 0 | CCCTGGGTC | CCAGGG | GAGTGAGGA | X | | |
| 4 | 4 | 0 | GTGAGGGTC | TCTGGA | GAGTGAGGA | X | | |
| 4 | 4 | 0 | AGCCAGGTT | GAAAAG | GAGTGAGGA | X | | |
| 4 | 4 | 0 | AGCATGGCT | TATGG | GAGTGAGGA | X | | |
| 4 | 4 | 0 | AGCTCAGGC | AGGGG | GAGTGAGGA | X | | |
| 4 | 4 | 0 | CCCTGGGTC | TGCTG | GAGTGAGGA | X | | |
| 4 | 4 | 0 | AGCAACAGA | TGAAG | GAGTGAGGA | X | | |
| 4 | 4 | 0 | AGCATGGCT | GGAATG | GAGTGAGGA | X | | |
| 4 | 4 | 0 | AGCTAAGTT | CTTGTA | GAGTGAGGA | X | | |
| 4 | 4 | 0 | AACTTTGTC | CTGAA | GAGTGAGGA | X | | |
| 4 | 4 | 0 | AACATGGTT | CCTTCT | GAGTGAGGA | X | | |
| 4 | 4 | 0 | CGCCACGGC | TGGGAG | GAGTGAGGA | X | | |
| 4 | 4 | 0 | CTCATTGTC | CAGGA | GAGTGAGGA | X | | |
| 4 | 4 | 0 | CCCTGGGTC | ATGTGA | GAGTGAGGA | X | | |
| 5 | 1 | 4 | AGCAACGTC | AAAGAT | CACTGATCA | X | | |
| 5 | 1 | 4 | AGCAGCGGC | GACAGC | AGAGGAGGA | X | | |
| 5 | 1 | 4 | AGCAGCGGC | AAGTGG | GAGTAGGAT | X | | |
| 5 | 1 | 4 | AGCAGCGGC | GGCACC | ACGTGCGCA | X | | |
| 5 | 1 | 4 | AGCACCGTC | AATCAG | GTGCGAGTC | X | | |
| 5 | 1 | 4 | AGCACCGTC | AAGAGT | CAGTGTTTA | X | | |
| 5 | 2 | 3 | AGCACAGTC | ACCTCT | GAGTGACAC | X | | |
| 5 | 2 | 3 | AGCAACGTA | TCGAT | GAGGGTAGA | X | | |
| 5 | 2 | 3 | AGCATCGGC | AGGCA | GAGTAAGTC | X | | |
| 5 | 2 | 3 | AACAACGTC | CTGAAC | GTGAGAGAA | X | | |
| 5 | 2 | 3 | AGCATAGTC | CGTGTA | GTGAGAGAA | X | | |
| 5 | 2 | 3 | AGCATGGTC | TTAATG | GAGTGATAG | X | | |
| 5 | 2 | 3 | AGCTGTGTC | TGCCTT | GGGTGATGC | X | | |
| 5 | 2 | 3 | AGCAATGTC | ATGTC | CAGTGAGCC | X | | |
| 5 | 2 | 3 | AGCATTGTC | CAAGGA | GAGTAAGTG | X | | |
| 5 | 2 | 3 | AGCAGCTGC | TCTCAA | GAGTATGGG | X | | |
| 5 | 2 | 3 | TGCAGTGTC | TGGAGT | GTGTCAGGC | X | | |
| 5 | 2 | 3 | AGCATTGTC | CTCCTC | TGGTGAGGT | X | | |
| 5 | 2 | 3 | AGCATTGTC | CCAAAA | GTGAGGGA | X | | |
| 5 | 2 | 3 | AGCAATGTC | TACCA | CAGTGAGAC | X | | |
| 5 | 2 | 3 | AGCAACGTT | CTTTAT | GTAAGAGGA | X | | |
| 5 | 2 | 3 | AGCAACTTC | ACTTAG | GCGTGGGAA | X | | |
| 5 | 3 | 2 | AGGCGAGTC | TCTTTA | GTGTGAGGC | X | | |
| 5 | 3 | 2 | AGCCACGTT | AGGGGT | AAGTGAGGG | X | | |
| 5 | 3 | 2 | AGTATCGTG | ATTGA | AAGTGAGGC | X | | |
| 5 | 3 | 2 | AGCAAGGTA | GCTTG | GAGTGAGAC | X | | |
| 5 | 3 | 2 | TGCAGCTGC | AAAAG | AAGTGAGGG | X | | |
| 5 | 3 | 2 | AGTATCTTC | TGGTGT | GAGTGAGAT | X | | |
| 5 | 3 | 2 | TGCAGTTTC | TCAAAG | GAGAGTGGA | X | | |
| 5 | 3 | 2 | ATCAGGGGC | CCACTA | GAGTAAGGG | X | | |
| 5 | 3 | 2 | AGTTGCTTC | TGCATT | GAGTAACGA | X | | |
| 5 | 3 | 2 | AGCTACGTG | CCCGGC | CAGTGAGGG | X | | |
| 5 | 3 | 2 | AGCTTAGTC | TGAGT | GTGTGAGGT | X | | |
| 5 | 3 | 2 | ATCAGGGGC | TGAAG | GAGTAAGGG | X | | |
| 5 | 3 | 2 | ATCAGGGGC | TGAAG | GAGTAAGGG | X | | |
| 5 | 3 | 2 | AGCAACCCC | TCTGCT | GAGGGAGGC | X | | |
| 5 | 3 | 2 | AGCATGGTA | TGATGT | AAGTGAGGG | X | | |
| 5 | 3 | 2 | CATAGCGTC | AGATTG | GAGTAAGGT | X | | |
| 5 | 3 | 2 | TGCAGCTGC | TGTCAG | AAGTGAGGG | X | | |
| 5 | 3 | 2 | AGCTAGGTC | CCCTG | CAGTGAGGG | X | | |
| 5 | 3 | 2 | AGCTTGGTC | AGTGAA | GAGAGAGGT | X | | |
| 5 | 3 | 2 | AGCAACTAC | ATATCT | GTGTGAGGC | X | | |
| 5 | 3 | 2 | AGCAACCCC | TCTGCT | GAGGGAGGC | X | | |
| 5 | 3 | 2 | GTCAGTGTC | CTGGAA | AAGTGAGGG | X | | |
| 5 | 3 | 2 | TGCAGTGTA | GCTGGA | GAGGGAGGT | X | | |
| 5 | 3 | 2 | CTCATCGTC | CAGGCT | GAGTGAGTC | X | | |
| 5 | 3 | 2 | AGTAACATC | AAGTCA | TAGTGAGGC | X | | |
| 5 | 3 | 2 | AGCTATGTC | CTAAAG | AAGTGAGGG | X | | |
| 5 | 3 | 2 | GTCCGCGTC | TTGTTT | GAGTAAGGG | X | | |
| 5 | 3 | 2 | AGCCTTGTC | ACTGA | AAGTGAGGC | X | | |
| 5 | 3 | 2 | AGCACAGCC | ACATCT | GTGTGAGGC | X | | |
| 5 | 3 | 2 | AGCAACATT | CTAAGC | GAGTGAGTC | X | | |
| 5 | 4 | 1 | AGTGTGGTC | GGAGCA | GAGTGAGGG | X | | |
| 5 | 4 | 1 | ACTAATGTC | ATGCTA | GAGTGAGGT | X | | |

-continued

| # of mutations T | (-) | (+) | (-) site | spacer | (+) site | VF2468 concentration 4 nM | 2 nM | 10.5 nM |
|---|---|---|---|---|---|---|---|---|
| 5 | 4 | 1 | TACATTGTC | TAGGAG | GAGTGAGGG | X | | |
| 5 | 4 | 1 | ATCAATGGC | CAGAT | GAGTGAGGG | X | | |
| 5 | 4 | 1 | CGGGGAGTC | CCAGGG | GAGTGAGGG | X | | |
| 5 | 4 | 1 | AGCAGGTCA | CATCG | GAGTGAGGG | X | | |
| 5 | 4 | 1 | AGCTAGGTT | GGCCC | GAGTGAGGC | X | | |
| 5 | 4 | 1 | AGTGTGGTC | AGAGAG | AAGTGAGGA | X | | |
| 5 | 4 | 1 | AGTATGGTA | ACAGCA | GAGTGAGGG | X | | |
| 5 | 4 | 1 | ATCCGTCTC | TTCTG | GTGTGAGGA | X | | |
| 5 | 4 | 1 | AACAGTATT | GCAAT | GAGTGAGGG | X | | |
| 5 | 4 | 1 | ATCAGCAGT | GAACA | AAGTGAGGA | X | | |
| 5 | 4 | 1 | GGCCAAGTC | AGCGG | GAGTGAGGC | X | | |
| 5 | 4 | 1 | GCCAGTGTT | TCTCA | GAGTGAGGT | X | | |
| 5 | 4 | 1 | ATCAGGGCA | GGCCAG | GAGTGAGGG | X | | |
| 5 | 4 | 1 | AGTAGATGC | AGTTA | GAGTGAGGT | X | | |
| 5 | 4 | 1 | GGCCTGGTC | AGGAGG | GAGTGAGGG | X | | |
| 5 | 4 | 1 | AGCAACTCA | TTCTGT | GAGTGAGGG | X | | |
| 5 | 4 | 1 | GGGGGAGTC | TTGCGG | GAGTGAGGT | X | | |
| 5 | 4 | 1 | ATCAGTCTA | GCAGCA | GAGTGAGGG | X | | |
| 5 | 4 | 1 | AGTAGATGC | ATAGG | GAGTGAGGT | X | | |
| 5 | 4 | 1 | ACCAGTGGT | GGGGT | GAGTGAGGT | X | | |
| 5 | 4 | 1 | GGCCTTGTC | CCCTA | GAGTGAGGG | X | | |
| 5 | 4 | 1 | CTCATTGTC | TTGCTG | GAGTGAGGC | X | | |
| 5 | 4 | 1 | AGTATGGTA | AAAGGA | GAGTGAGGG | X | | |
| 5 | 4 | 1 | AGAGAGGTC | AGGGTA | GAGTGAGGG | X | | |
| 5 | 4 | 1 | GGCCTGGTC | AGATTT | GAGTGAGGG | X | | |
| 5 | 4 | 1 | TGTTGAGTC | CGTATG | GAGTGAGGG | X | | |
| 5 | 4 | 1 | AGCACCACT | GACAG | GAGTGAGGG | X | | |
| 5 | 4 | 1 | AAAACAGTC | ATCCT | GAGTGAGGG | X | | |
| 5 | 4 | 1 | AACAGTATT | AAGGA | GAGTGAGGG | X | | |
| 5 | 4 | 1 | GCCAACATC | CACAT | GAGTGAGGT | X | | |
| 5 | 4 | 1 | GGCCAAGTC | TCTCA | GAGTGAGGC | X | | |
| 5 | 4 | 1 | AAAACAGTC | TTTCGA | GAGTGAGGG | X | | |
| 5 | 4 | 1 | AATCCCGTC | ATGGA | GAGTGAGGT | X | | |
| 6 | 4 | 2 | GGTTACGTC | CGGAA | AAGTGAGGG | X | | |
| 6 | 4 | 2 | AGTTACTTC | TATAA | AAGTGAGGG | X | | |
| 6 | 4 | 2 | AGTTACTTC | CCTCA | AAGTGAGGG | X | | |
| 3 | 2 | 1 | GGCATCGTC | CACTC | CAGTGAGGA | | X | X |
| 4 | 2 | 2 | ATCAGGGTC | CAGCT | CAGTGAGGC | | X | X |
| 4 | 3 | 1 | AGCTCAGTC | ACTCCT | GAGTGAGGG | | X | X |
| 4 | 3 | 1 | AGCTCAGTC | CTGGG | GAGTGAGGG | | X | X |
| 4 | 3 | 1 | AGCATGGTT | TTCTG | GAGTGAGGC | | X | X |
| 4 | 3 | 1 | AGATGGGTC | TTGCT | GAGTGAGGC | | X | | X |
| 4 | 3 | 1 | AGATGGGTC | TTGCT | GAGTGAGGC | | X | | X |
| 2 | 1 | 1 | AGCAGAGTC | AGGAT | GAATGAGGA | | X | |
| 2 | 1 | 1 | AGCAGAGTC | ATGAA | GATTGAGGA | | X | |
| 3 | 0 | 3 | AGCAGCGTC | TGAAAG | TAGAGATGA | | X | |
| 3 | 0 | 3 | AGCAGCGTC | AGCTTC | AAGTATGGA | | X | |
| 3 | 0 | 3 | AGCAGCGTC | AACATT | TAGTAATGA | | X | |
| 3 | 0 | 3 | AGCAGCGTC | AACATT | TAGTAATGA | | X | |
| 3 | 1 | 2 | AGCAGTGTC | TTAGGA | AAGAGAGGA | | X | |
| 3 | 1 | 2 | AGCAGCTTC | AGATGG | GAGAGAGAA | | X | |
| 3 | 1 | 2 | AGCAGTGTC | CAGCA | AAGAGAGGA | | X | |
| 3 | 1 | 2 | TGCAGCGTC | AATGT | GAGTGAAAA | | X | |
| 3 | 1 | 2 | AGCAGTGTC | AGGTAT | GAGAGGGA | | X | |
| 3 | 1 | 2 | AGCAGCTTC | AGGGA | GAGTGTGGG | | X | |
| 3 | 1 | 2 | AGCAGTGTC | CTTGCC | GAAGGAGGA | | X | |
| 3 | 1 | 2 | AGCAGCTTC | ATGAAG | GAGAGAGAA | | X | |
| 3 | 1 | 2 | AGCAGCGTG | GAGGT | GAGTGGGGT | | X | |
| 3 | 1 | 2 | AGCAGCGTT | ACTCAG | GAGAGAGAA | | X | |
| 3 | 1 | 2 | AGAAGCGTC | ACTGA | GAGTGAGTT | | X | |
| 3 | 1 | 2 | AGCAGCATC | TTGAG | GGGTGAGGC | | X | |
| 3 | 1 | 2 | AGCAGCGGC | ACAAA | GAGGGACGA | | X | |
| 3 | 1 | 2 | AGCATCGTC | TGAAG | GGGTGAGCA | | X | |
| 3 | 1 | 2 | AGCAGCTTC | CACCA | GAGGGAGTA | | X | |
| 3 | 1 | 2 | AGCAGCGTT | CTGTCT | AAGTGAAGA | | X | |
| 3 | 1 | 2 | AGCAGCATC | TGCTTC | GGGTGAGGC | | X | |
| 3 | 1 | 2 | AGCAGGGTC | GGGGA | GGGTGAGAA | | X | |
| 3 | 1 | 2 | AGCAGGGTC | AGCTGG | GAGTAAGAA | | X | |
| 3 | 1 | 2 | AGCAGCGCC | GGAAGA | GAGCGAGGG | | X | |
| 3 | 1 | 2 | AGCACCGTC | CCTAA | GACTGAGCA | | X | |
| 3 | 1 | 2 | AGCAGAGTC | ACAGCT | GAATGAGGC | | X | |

-continued

| # of mutations T | (+) | (-) | (-) site | spacer | (+) site | 4 nM | 2 nM | 10.5 nM |
|---|---|---|---|---|---|---|---|---|
| 3 | 1 | 2 | AGCAGCGTG | GACCCA | AAGAGAGGA | X | | |
| 3 | 1 | 2 | AGCAGGGTC | CACAT | GAGTCAGGG | X | | |
| 3 | 1 | 2 | AGCAGGGTC | GGGGTG | GAGGGAGAA | X | | |
| 3 | 1 | 2 | GGCAGCGTC | CAGGTA | GACTGAGGG | X | | |
| 3 | 1 | 2 | AGCAGTGTC | CTAAAG | GAAGGAGGA | X | | |
| 3 | 1 | 2 | AGCAGCCTC | TTCTG | TAATGAGGA | X | | |
| 3 | 1 | 2 | AGCAGCGTT | GGGAA | GAGAGAGAA | X | | |
| 3 | 1 | 2 | AGCAGCGAC | AGGGCA | GAATGAGGC | X | | |
| 3 | 1 | 2 | AGCAGAGTC | GAGCA | AGGTGAGGA | X | | |
| 3 | 1 | 2 | AGCAGCATC | GAGTGG | AAGTGGGGA | X | | |
| 3 | 2 | 1 | AGCTGAGTC | CAGAA | GAGTGGGGA | X | | |
| 3 | 2 | 1 | GGCAGTGTC | AGTAG | GTGTGAGGA | X | | |
| 3 | 2 | 1 | AGCAACTTC | AGAAT | GAGTTAGGA | X | | |
| 3 | 2 | 1 | AGCATCTTC | AGCTA | TAGTGAGGA | X | | |
| 3 | 2 | 1 | GGCAGGGTC | ACCCGA | AAGTGAGGA | X | | |
| 3 | 2 | 1 | AGCAGTGTG | TGCCCA | GAGTGAGTA | X | | |
| 3 | 2 | 1 | AGCAGTGTA | CCATGC | GAGTGAGCA | X | | |
| 3 | 2 | 1 | AGCTGGGTC | TATTTG | GAGTCAGGA | X | | |
| 3 | 2 | 1 | AGCAGCGAG | GTGGG | GAGTGAGTA | X | | |
| 3 | 2 | 1 | AGCAGCTTG | GATTCA | GAGTGAGAA | X | | |
| 3 | 2 | 1 | AGCAGCAGC | AACGAG | GAGCGAGGA | X | | |
| 3 | 2 | 1 | AGCACCATC | TTTGAA | AAGTGAGGA | X | | |
| 3 | 2 | 1 | AGCAGAGTT | TGAATT | GAGTTAGGA | X | | |
| 3 | 2 | 1 | GGCAGGGTC | AAGGA | AAGTGAGGA | X | | |
| 3 | 2 | 1 | GGCAGTGTC | CAGGAG | GTGTGAGGA | X | | |
| 3 | 2 | 1 | TGCAACGTC | ACAAGT | GAGAGAGGA | X | | |
| 3 | 2 | 1 | AACAGTGTC | TTTCAA | AAGTGAGGA | X | | |
| 3 | 2 | 1 | AGCAGTGTA | GACCCA | GAGTGAGCA | X | | |
| 3 | 2 | 1 | AGCTGTGTC | CCCTT | GAGAGAGGA | X | | |
| 3 | 2 | 1 | AGCAGCGGA | GGTGGG | GAGGGAGGA | X | | |
| 3 | 2 | 1 | AACAGCTTC | TCATT | GAGTGAGTA | X | | |
| 3 | 2 | 1 | AGTAGAGTC | AGGCCT | GAATGAGGA | X | | |
| 3 | 2 | 1 | AGCAGCGAA | GCCGG | AAGTGAGGA | X | | |
| 3 | 2 | 1 | AACTGCGTC | CCAGG | AAGTGAGGA | X | | |
| 3 | 2 | 1 | AGAAGCCTC | TGCTAT | GAGTGAGGC | X | | |
| 3 | 2 | 1 | AGCAGTGTG | CAATG | GAGTGAGTA | X | | |
| 3 | 2 | 1 | AGTAGAGTC | CCTGG | GAGTGAGCA | X | | |
| 3 | 2 | 1 | GGCAGTGTC | ATGTGT | GAGGGAGGA | X | | |
| 3 | 2 | 1 | AGCACTGTC | ACTGTT | GAGTGATGA | X | | |
| 3 | 2 | 1 | AGCTGGGTC | TGGGAG | GAGTCAGGA | X | | |
| 3 | 2 | 1 | AGCAGCTTT | CCAAGA | GAGTGAGAA | X | | |
| 3 | 2 | 1 | AGCAGTGTA | GACCCA | GAGTGAGCA | X | | |
| 3 | 2 | 1 | GGCAGCGTG | GGGATG | CAGTGAGGA | X | | |
| 3 | 2 | 1 | AGCAGCAGC | AGAGG | GAGCGAGGA | X | | |
| 3 | 2 | 1 | AGTAGCTTC | CCTCT | GTGTGAGGA | X | | |
| 3 | 2 | 1 | TGCGGCGTC | TCCTGG | GAGTGAAGA | X | | |
| 3 | 2 | 1 | AACAGAGTC | TGGCA | GAGTGAGCA | X | | |
| 3 | 2 | 1 | GGCAGCGGC | CTGGG | GAGTGTGGA | X | | |
| 3 | 2 | 1 | AGCAGGCTC | CTTGT | TAGTGAGGA | X | | |
| 3 | 3 | 0 | ATCACCATC | ATACCT | GAGTGAGGA | X | | |
| 3 | 3 | 0 | AGCAGTTTA | ATTCT | GAGTGAGGA | X | | |
| 3 | 3 | 0 | AACAGCAAC | AAAAA | GAGTGAGGA | X | | |
| 3 | 3 | 0 | AGCTGAGTA | GAATG | GAGTGAGGA | X | | |
| 3 | 3 | 0 | AGCAACCTG | GGGCT | GAGTGAGGA | X | | |
| 3 | 3 | 0 | AGCAACCTG | GAAAA | GAGTGAGGA | X | | |
| 3 | 3 | 0 | TGCAGGCTC | CTGTG | GAGTGAGGA | X | | |
| 3 | 3 | 0 | CGCAGTATC | CCACT | GAGTGAGGA | X | | |
| 3 | 3 | 0 | AGAAACATC | AGATG | GAGTGAGGA | X | | |
| 3 | 3 | 0 | ACCTGTGTC | TCCTG | GAGTGAGGA | X | | |
| 3 | 3 | 0 | GGCAGGGCC | TCAAGG | GAGTGAGGA | X | | |
| 3 | 3 | 0 | AGAAACATC | TAAGAG | GAGTGAGGA | X | | |
| 3 | 3 | 0 | AGGTGCATC | CCTCA | GAGTGAGGA | X | | |
| 3 | 3 | 0 | GGCAGGGCC | TTCTT | GAGTGAGGA | X | | |
| 3 | 3 | 0 | GGCAGCTGC | TTTTT | GAGTGAGGA | X | | |
| 3 | 3 | 0 | AGCATGGCC | CAGGAG | GAGTGAGGA | X | | |
| 4 | 0 | 4 | AGCAGCGTC | TTCAGC | AAGTGGAGG | X | | |
| 4 | 0 | 4 | AGCAGCGTC | TGGGGC | AGTGGAGGA | X | | |
| 4 | 0 | 4 | AGCAGCGTC | TCATA | GAGTTAACC | X | | |
| 4 | 0 | 4 | AGCAGCGTC | CCTGA | AATTGTGCA | X | | |
| 4 | 1 | 3 | AGCAACGTC | AGGGAA | GAGGGACCA | X | | |
| 4 | 1 | 3 | AGCAGGGTC | CACTCA | GAGGGAGTC | X | | |

| # of mutations | | | | | | VF2468 concentration | | |
|---|---|---|---|---|---|---|---|---|
| T (−) | (+) | (−) site | spacer | (+) site | 4 nM | 2 nM | 10.5 nM | |
| 4 | 1 | 3 | AGCAGCGTG | TGGCT | GTGTGTGGC | X | | |
| 4 | 1 | 3 | AGCAGCGTT | GGCTGA | AAGTGAGGT | X | | |
| 4 | 1 | 3 | AGCAACGTC | TCCAGG | GACTGAAGC | X | | |
| 4 | 1 | 3 | AGCAGGGTC | ATTTAG | GAGTGACAT | X | | |
| 4 | 1 | 3 | AGCAGTGTC | TTGTCA | GAGTGTGTC | X | | |
| 4 | 1 | 3 | AGCAACGTC | CTCAAG | GAGGCAAGA | X | | |
| 4 | 1 | 3 | AGCATCGTC | CACCTG | GCGAGAGGC | X | | |
| 4 | 1 | 3 | AGCAGCTTC | TAACA | AAGTGAGAC | X | | |
| 4 | 1 | 3 | AGCAACGTC | AGGGAG | GAGAGGGCA | X | | |
| 4 | 1 | 3 | AGCAGCGTT | TTCAT | GTGTGTGTA | X | | |
| 4 | 1 | 3 | AGCAGCGTT | TAACT | GAGTGAAAG | X | | |
| 4 | 1 | 3 | AGCAGGGTC | AGCAG | GAGGGAGTC | X | | |
| 4 | 1 | 3 | AGCAGTGTC | ATTAC | GAGTGCGAC | X | | |
| 4 | 1 | 3 | AGCAGTGTC | AGTGC | AAGTGCGGG | X | | |
| 4 | 1 | 3 | AGCAGCTTC | CATCG | TGGTGTGGA | X | | |
| 4 | 1 | 3 | GGCAGCGTC | TAGGG | GTGTGATAA | X | | |
| 4 | 1 | 3 | AGCAGCTTC | CGGTC | GAGTGATTT | X | | |
| 4 | 1 | 3 | AGCAGGGTC | CGGCTT | GTGTGCGGC | X | | |
| 4 | 1 | 3 | AGCAGCGGC | AAGAA | GAGGGTGGT | X | | |
| 4 | 1 | 3 | AGCAGCCTC | ACTCA | GAGTGGGAC | X | | |
| 4 | 1 | 3 | AGCAACGTC | TCCACA | GAGACAGGC | X | | |
| 4 | 1 | 3 | AGCAGCGTG | GGGGA | GTGTGGGGG | X | | |
| 4 | 1 | 3 | AGCAGGGTC | TGCAGG | GACTGAGAG | X | | |
| 4 | 1 | 3 | AGCAGTGTC | TTTTC | CAGTAAGGT | X | | |
| 4 | 1 | 3 | AGCAGCGGC | AAGCAC | AAGCAAGGA | X | | |
| 4 | 1 | 3 | AGCAGCTTC | CTCCAG | GGGAGAGGT | X | | |
| 4 | 1 | 3 | AGCAGCTTC | GCCTGC | TGGTGTGGA | X | | |
| 4 | 1 | 3 | AGCAGCGAC | TCACAC | AAGTGAGAT | X | | |
| 4 | 1 | 3 | AGCAGCGGC | CCCAGC | GAGTGTGTC | X | | |
| 4 | 1 | 3 | AGCAGTGTC | TGCAAC | TAGTGAGCT | X | | |
| 4 | 1 | 3 | AGCAGCGGC | CTGGGG | ACGAGAGGA | X | | |
| 4 | 1 | 3 | AGCAGCGGC | TGCCA | GAGGGTGGT | X | | |
| 4 | 1 | 3 | AGCAACGTC | CATTCT | GAGGCAAGA | X | | |
| 4 | 2 | 2 | AGCATTGTC | GGATTC | TGGTGAGGA | X | | |
| 4 | 2 | 2 | AGCATGGTC | ACAAA | GGGTGAGGT | X | | |
| 4 | 2 | 2 | AGCAACATC | ACAGA | GAGAGAGGG | X | | |
| 4 | 2 | 2 | AGCAATGTC | CCTTG | GAGTGTGGG | X | | |
| 4 | 2 | 2 | AGCAGCTGC | CAGAG | GAGGGAGGC | X | | |
| 4 | 2 | 2 | AGCTGGGTC | CTAGA | AAGTGAGGT | X | | |
| 4 | 2 | 2 | AGCAGCTGC | AGTGA | GAGTGAGCT | X | | |
| 4 | 2 | 2 | AGCATTGTC | AATGA | CAGTGAGAA | X | | |
| 4 | 2 | 2 | AGCAAAGTC | TAAGA | GAGTGTGGC | X | | |
| 4 | 2 | 2 | AGCAGGGTG | GAGAA | GAGCGAGGG | X | | |
| 4 | 2 | 2 | ATCAACGTC | CTTTGA | GAGAAAGGA | X | | |
| 4 | 2 | 2 | AGCAGCTTT | TTTCC | GAGTGAGAG | X | | |
| 4 | 2 | 2 | GGCAGCGTT | TCCTGT | GAGCAAGGA | X | | |
| 4 | 2 | 2 | AGCACCATC | AGGAG | GAGGGAGGG | X | | |
| 4 | 2 | 2 | ATCAGAGTC | TGCAG | GCGTGAGGC | X | | |
| 4 | 2 | 2 | AGCACCGGC | CTCTTG | GAGGGAGGT | X | | |
| 4 | 2 | 2 | GGCAGGGTC | AGTGG | GAGTGAGTC | X | | |
| 4 | 2 | 2 | AGCACCTTC | TCCTGG | TAGTGAGGC | X | | |
| 4 | 2 | 2 | AGCGGTGTC | ATCCAG | GAGTGAGCG | X | | |
| 4 | 2 | 2 | AGCAATGTC | TATAA | AAGTGAGGC | X | | |
| 4 | 2 | 2 | AGCAGGGTA | AGTAC | AAGTGAGGC | X | | |
| 4 | 2 | 2 | AGCAACGTG | ATCGG | GAGGGAGGG | X | | |
| 4 | 2 | 2 | AGCAGGGTA | GATGG | GAGAGAGGG | X | | |
| 4 | 2 | 2 | AGCAATGTC | TGGGT | GAGTGTGGG | X | | |
| 4 | 2 | 2 | AGCAATGTC | TGAAA | TAGTGAGTA | X | | |
| 4 | 2 | 2 | TGCAGAGTC | AAGGAA | GAGTGAGAT | X | | |
| 4 | 2 | 2 | AGCATAGTC | TCCTAG | GAGAGAGGC | X | | |
| 4 | 2 | 2 | AGCAGGGTA | ATGGG | GAGAGAGGG | X | | |
| 4 | 2 | 2 | ATCACCGTC | GAGGG | GAGGGAGGG | X | | |
| 4 | 2 | 2 | GGCAGCTTC | GGTGTC | CAGTGAGGC | X | | |
| 4 | 2 | 2 | AGCTGGGTC | TCATTG | CAGTGAGGT | X | | |
| 4 | 2 | 2 | AGCAACGTA | CTGTT | AAGTGAGAA | X | | |
| 4 | 2 | 2 | AGCAAAGTC | AAGAA | GAGTGAAAA | X | | |
| 4 | 2 | 2 | GGCAGGGTC | TCTCA | AAGTGAGGT | X | | |
| 4 | 2 | 2 | TGCAGGGTC | ATGCAA | GTGTGAGGT | X | | |
| 4 | 2 | 2 | AGCAAAGTC | AGAGCT | GAGTGAGCC | X | | |
| 4 | 2 | 2 | GGCAGTGTC | ATTTTT | GAGTAAGGG | X | | |
| 4 | 2 | 2 | AGCAGCTGC | TGTGG | GAGGGAGGC | X | | |

| # of mutations T | (−) | (+) | (−) site | spacer | (+) site | VF2468 concentration 4 nM | 2 nM | 10.5 nM |
|---|---|---|---|---|---|---|---|---|
| 4 | 2 | 2 | AGCAGCGGT | GGTATC | TAGTGAGGC | | X | |
| 4 | 2 | 2 | AGCAACATC | TGGAAC | GAGTGAATA | | X | |
| 4 | 2 | 2 | AGCAGTGTG | ATCTT | GAGTAAGGC | | X | |
| 4 | 2 | 2 | GGCAGCTTC | AGCAC | CAGTGAGGC | | X | |
| 4 | 2 | 2 | AGCAGAGTT | GCTTAA | GAGTGAGAG | | X | |
| 4 | 2 | 2 | AGCACCTTC | TGCCAA | GAGTGAGAT | | X | |
| 4 | 2 | 2 | AGCAGCTGC | GGGCA | GAGTGAGCT | | X | |
| 4 | 2 | 2 | AGTAGAGTC | TTTGTT | GTGTGAGGT | | X | |
| 4 | 2 | 2 | AGCATGGTC | GTTGGG | GGGTGAGGC | | X | |
| 4 | 2 | 2 | AGCATTGTC | TCTTGT | GTGTGAGGT | | X | |
| 4 | 2 | 2 | ATCAGAGTC | AATTTG | TAGTGAGGT | | X | |
| 4 | 2 | 2 | AGCAGCTTA | GAGGG | GAGAGAGGT | | X | |
| 4 | 2 | 2 | GACAGCGTC | CTCCG | GGGTGAGGC | | X | |
| 4 | 2 | 2 | TGCAGAGTC | AGCCCT | GAGTGAGAT | | X | |
| 4 | 2 | 2 | AGCAGAGTT | GGAAG | GAGTGAGAG | | X | |
| 4 | 2 | 2 | AGCAGGGTA | GGTCA | GAGAGAGGG | | X | |
| 4 | 3 | 1 | TGCAGTGAC | TGTCCA | GAGTGAGGC | | X | |
| 4 | 3 | 1 | AGCAGAGGT | GAGGT | GAGTGAGGG | | X | |
| 4 | 3 | 1 | AGCAGTTTA | AATTT | GAGTGAGGC | | X | |
| 4 | 3 | 1 | AGAAAGGTC | ATAAT | GAGTGAGGG | | X | |
| 4 | 3 | 1 | AGCACAATC | CCAAAG | GAGTGAGGC | | X | |
| 4 | 3 | 1 | AGCAAAGGC | AGGAG | GAGTGAGGT | | X | |
| 4 | 3 | 1 | AGCCACATC | CCCTA | GAGTGAGGT | | X | |
| 4 | 3 | 1 | TGCTGGGTC | TACAG | GAGTGAGGC | | X | |
| 4 | 3 | 1 | GGCAGTGTG | AGCTG | GAGTGAGGG | | X | |
| 4 | 3 | 1 | AGTAGTGTG | CTGAA | GAGTGAGGG | | X | |
| 4 | 3 | 1 | TGCATGGTC | AGAGGT | GAGTGAGGG | | X | |
| 4 | 3 | 1 | AGCATAGTT | TAGGAT | CAGTGAGGA | | X | |
| 4 | 3 | 1 | AGCAGCAGG | ATGAGA | GAGTGAGGC | | X | |
| 4 | 3 | 1 | AGCACCATT | AAATTG | GAGTGAGGC | | X | |
| 4 | 3 | 1 | ATCAGGGTT | AAGCA | GAGTGAGGC | | X | |
| 4 | 3 | 1 | AGCAAAGTG | GAGAG | GAGGGAGGA | | X | |
| 4 | 3 | 1 | AGCAACACC | AATGAA | GAGTGAAGA | | X | |
| 4 | 3 | 1 | GGCAGTGGC | TCTGT | GAGTGAGGT | | X | |
| 4 | 3 | 1 | AGTATCGGC | TGTGGT | GAGTGAGGG | | X | |
| 4 | 3 | 1 | GGCAGCTCC | GCCTCC | GAGTGAGGG | | X | |
| 4 | 3 | 1 | AGCAAAGGC | TGGGTG | GAGTGAGGT | | X | |
| 4 | 3 | 1 | AGCAAGTTC | CACTG | GAGTGTGGA | | X | |
| 4 | 3 | 1 | AGCAAAGGC | AGTCA | GAGTGAGGG | | X | |
| 4 | 3 | 1 | CGCAGCAAC | GCTCTG | GAGTGAGGC | | X | |
| 4 | 3 | 1 | GGCAGCGGT | TGGGG | GAGTGAGGC | | X | |
| 4 | 3 | 1 | AGCAACTGC | TTTTA | GAGTGAGCA | | X | |
| 4 | 3 | 1 | AGAAGAGTA | AAGCA | GAGTGAGGT | | X | |
| 4 | 3 | 1 | AGCAACATA | ATAACA | GAGTGAGGT | | X | |
| 4 | 3 | 1 | CGCACCTTC | CTGTAT | GAGTGAGGC | | X | |
| 4 | 3 | 1 | GTCCGCGTC | GCCCA | GAGTGAGAA | | X | |
| 4 | 3 | 1 | GGCAGTGTG | CTTGAT | GAGTGAGGG | | X | |
| 4 | 3 | 1 | CCCACCGTC | CTAAAG | AAGTGAGGA | | X | |
| 4 | 3 | 1 | AACAACGTG | AAACCA | GAGTGAGGC | | X | |
| 4 | 3 | 1 | AGCAACCAC | AAAAA | AAGTGAGGA | | X | |
| 4 | 3 | 1 | AGCCCCTTC | AGCATA | GAGTGAGGG | | X | |
| 4 | 3 | 1 | AGCCGCTGC | AGCAGG | GAGTGAGGT | | X | |
| 4 | 3 | 1 | AGCCGCTGC | AGCAGG | GAGTGAGGT | | X | |
| 4 | 3 | 1 | AGCCGCTGC | AGCAGG | GAGTGAGGT | | X | |
| 4 | 3 | 1 | AGCCGCTGC | AGCAGG | GAGTGAGGT | | X | |
| 4 | 3 | 1 | AGAGGGTC | TGCAG | GAGTGAGGG | | X | |
| 4 | 3 | 1 | AGCAAAGGC | AAATA | GAGTGAGGG | | X | |
| 4 | 3 | 1 | GGCAACTTC | CAAGA | AAGTGAGGA | | X | |
| 4 | 3 | 1 | GCCAGCTTC | CATACA | GAGTGAGGC | | X | |
| 4 | 3 | 1 | AGAAGGGTG | ATTAG | GAGTGAGGC | | X | |
| 4 | 3 | 1 | AGCTACGAC | TCAGGA | GAGTGAGGT | | X | |
| 4 | 3 | 1 | AGCAAGGTG | GGCGG | GAGTGAGGG | | X | |
| 4 | 3 | 1 | AGGAGAGTT | AGAAGA | GAGTGAGGT | | X | |
| 4 | 3 | 1 | TGCTCCGTC | CTGGCT | GAGTGAGGT | | X | |
| 4 | 3 | 1 | AGCACTGTT | TGCCC | GAGTGAGGC | | X | |
| 4 | 3 | 1 | AGTACCATC | AGGGCT | GAGTGAGGC | | X | |
| 4 | 3 | 1 | AGCAGCAGG | GCAGT | GAGTGAGGC | | X | |
| 4 | 3 | 1 | GGCAGGGAC | CATAT | GAGTGAGGC | | X | |
| 4 | 3 | 1 | AGCAAGGTT | CCCCG | GAGTGAGTA | | X | |
| 4 | 3 | 1 | AGCATGGGC | AGGGG | GAGTGAGGC | | X | |
| 4 | 3 | 1 | AGCTGAGTA | GCTAA | GAGTGAGGC | | X | |

| # of mutations T (−) (+) (−) | site | spacer | (+) site | VF2468 concentration 4 nM | 2 nM | 10.5 nM |
|---|---|---|---|---|---|---|
| 4 3 1 | AGCGACTTC | ATATCT | GAGTGAGGT | X | | |
| 4 3 1 | AGGAGAGTT | TAAAG | GAGTGAGGT | X | | |
| 4 3 1 | GACAGCATC | AGTCTG | GAGTGAGGG | X | | |
| 4 3 1 | AGCAACTCC | ATTTC | GAGTGAGGC | X | | |
| 4 3 1 | AGTCGCTTC | ACTTTG | GAGTGAGAA | X | | |
| 4 3 1 | AGTAACATC | TTTACT | GAGGGAGGA | X | | |
| 4 3 1 | AGCAACTGC | AATGGT | GAGTGAGCA | X | | |
| 4 3 1 | AGCATTGTG | CTAGG | CAGTGAGGA | X | | |
| 4 3 1 | AGAAAAGTC | TTGAAG | GAGTGAGGG | X | | |
| 4 3 1 | GGCAGTGTA | GGGAG | GAGTGAGGT | X | | |
| 4 3 1 | AGCAAGGTA | AAGGAG | GAGTGAGGT | X | | |
| 4 3 1 | AGCATCTGC | AGATG | GAGTGAGGC | X | | |
| 4 3 1 | TGCATAGTC | TTGGG | GAGTGAGGG | X | | |
| 4 3 1 | AGAAGGGTG | AGGTGG | GAGTGAGGC | X | | |
| 4 3 1 | AGCCGAGTG | GTTAA | GAGTGAGGG | X | | |
| 4 3 1 | CTCAGGGTC | ATTAGT | GAGTGAGGG | X | | |
| 4 3 1 | AACAGGGTT | GGCCT | GAGTGAGGC | X | | |
| 4 3 1 | AGCCTAGTC | ACACCT | GAGTGAGGG | X | | |
| 4 3 1 | AGCAATGTT | TTGCT | GAGTGAGAA | X | | |
| 4 3 1 | AGCAGCAAA | TCTGCT | GAGTGAGGT | X | | |
| 4 3 1 | AGCAGTCCC | TGCCCA | GAGTGAGGC | X | | |
| 4 3 1 | TGCAATGTC | TTTGA | GAGTGAGGT | X | | |
| 4 3 1 | TGCAGGTTC | TTTGG | GAGTGAGGG | X | | |
| 4 3 1 | AGCTAAGTC | TGTAGG | CAGTGAGGA | X | | |
| 4 3 1 | AGCATAGTT | GGGAG | CAGTGAGGA | X | | |
| 4 3 1 | AGCATGGTA | GAGACT | GAGTGAGGG | X | | |
| 4 3 1 | AGCAAGGAC | TGGGCT | GAGTGAGGC | X | | |
| 4 3 1 | AGGTGGGTC | CCCAGA | GAGTGAGGC | X | | |
| 4 3 1 | AGCAGCTGT | CAATCA | GAGTGAGGC | X | | |
| 4 3 1 | TGCATGGTC | CTGGAG | GAGTGAGGG | X | | |
| 4 3 1 | AGCATAGTA | CTTAA | GAGTGAGGG | X | | |
| 4 3 1 | AGCAAGGTA | ATTAG | GAGTGAGTA | X | | |
| 4 3 1 | TGCACCTTC | ATGCCT | GAGTGAGGG | X | | |
| 4 3 1 | AGCACCGAG | GTCGGA | GAGTGAGGG | X | | |
| 4 3 1 | TGGAGAGTC | AGCAG | GAGTGAGTA | X | | |
| 4 3 1 | AGAAGAGTT | AGGTGG | GAGTGAGGT | X | | |
| 4 3 1 | ATCAGGGTT | AGGAT | GAGTGAGGG | X | | |
| 4 3 1 | GGCAGTGCC | CAGCAG | GAGTGAGGC | X | | |
| 4 3 1 | AGTAAGGTC | TTAAA | TAGTGAGGA | X | | |
| 4 3 1 | AGCAGCAGG | CCAGT | GAGTGAGGC | X | | |
| 4 4 0 | AGCCATGTG | CAAGT | GAGTGAGGA | X | | |
| 4 4 0 | GGTAGTGTT | ATGAAT | GAGTGAGGA | X | | |
| 4 4 0 | TACAAAGTC | GATGA | GAGTGAGGA | X | | |
| 4 4 0 | AGCCATGTA | CATGT | GAGTGAGGA | X | | |
| 4 4 0 | GACTGGGTC | TGTCAT | GAGTGAGGA | X | | |
| 4 4 0 | AGCACAGCA | GATGA | GAGTGAGGA | X | | |
| 4 4 0 | TGAATAGTC | TTGGAA | GAGTGAGGA | X | | |
| 4 4 0 | GTCAGGTTC | ACACAT | GAGTGAGGA | X | | |
| 4 4 0 | GGTAAAGTC | TGGTCA | GAGTGAGGA | X | | |
| 4 4 0 | AGTATAGTG | GCAGA | GAGTGAGGA | X | | |
| 4 4 0 | ATGGGGTC | AGAGGG | GAGTGAGGA | X | | |
| 4 4 0 | CCCAAAGTC | GTAAG | GAGTGAGGA | X | | |
| 4 4 0 | CAAATCGTC | TACAT | GAGTGAGGA | X | | |
| 4 4 0 | AATAAGGTC | ATAGCA | GAGTGAGGA | X | | |
| 4 4 0 | AGTATAGTT | CAGAT | GAGTGAGGA | X | | |
| 4 4 0 | AGAGAGGTC | AAGGA | GAGTGAGGA | X | | |
| 4 4 0 | TGGTGAGTC | ACCAC | GAGTGAGGA | X | | |
| 4 4 0 | TGCCTGGTC | ACTTGG | GAGTGAGGA | X | | |
| 4 4 0 | AGCCATGTG | GGAAG | GAGTGAGGA | X | | |
| 4 4 0 | AACAGGTT | CGCAGA | GAGTGAGGA | X | | |
| 4 4 0 | AGCAATTTA | TGTACA | GAGTGAGGA | X | | |
| 4 4 0 | AGGCATGTC | TCAGCA | GAGTGAGGA | X | | |
| 4 4 0 | TACAAAGTC | CTTAG | GAGTGAGGA | X | | |
| 4 4 0 | AATAAGGTC | AGAGAG | GAGTGAGGA | X | | |
| 4 4 0 | AATAAGTC | AGATAG | GAGTGAGGA | X | | |
| 4 4 0 | AATAAGGTC | AGATAG | GAGTGAGGA | X | | |
| 4 4 0 | AATAAGGTC | AAATAG | GAGTGAGGA | X | | |
| 4 4 0 | AATAAGGTC | AGATG | GAGTGAGGA | X | | |
| 4 4 0 | AATAAGGTC | AGATAG | GAGTGAGGA | X | | |
| 4 4 0 | AGCACAGCA | GGCAG | GAGTGAGGA | X | | |
| 4 4 0 | GGAAAGGTC | AGTTAT | GAGTGAGGA | X | | |

| # of mutations | | | | | | VF2468 concentration | | |
|---|---|---|---|---|---|---|---|---|
| T (−) | (+) | (−) | site | spacer | (+) site | 4 nM | 2 nM | 10.5 nM |
| 4 | 4 | 0 | AGCCATTTC | AACAA | GAGTGAGGA | X | | |
| 4 | 4 | 0 | AATAAGGTC | ACGGTG | GAGTGAGGA | X | | |
| 4 | 4 | 0 | ATCAGCACT | TCAGA | GAGTGAGGA | X | | |
| 4 | 4 | 0 | GGTGGGGTC | ATGGA | GAGTGAGGA | X | | |
| 4 | 4 | 0 | CACACAGTC | AGTGTA | GAGTGAGGA | X | | |
| 4 | 4 | 0 | AATATTGTC | TCTGT | GAGTGAGGA | X | | |
| 4 | 4 | 0 | GGAATAGTC | TGGTTA | GAGTGAGGA | X | | |
| 4 | 4 | 0 | AGCAACAAT | CGTAC | GAGTGAGGA | X | | |
| 4 | 4 | 0 | AATAAGGTC | ACAGTG | GAGTGAGGA | X | | |
| 4 | 4 | 0 | GACTGTGTC | CTTCA | GAGTGAGGA | X | | |
| 4 | 4 | 0 | AATAAAGTC | AGATAG | GAGTGAGGA | X | | |
| 4 | 4 | 0 | AATAAGGTC | AGAGAG | GAGTGAGGA | X | | |
| 4 | 4 | 0 | AATAAGGTC | AGACAA | GAGTGAGGA | X | | |
| 4 | 4 | 0 | AATAAGGTC | AGATAG | GAGTGAGGA | X | | |
| 4 | 4 | 0 | AATAAGGTC | AGATG | GAGTGAGGA | X | | |
| 5 | 1 | 4 | AGCAGCTTC | CCCTG | CAGAAAGGT | X | | |
| 5 | 2 | 3 | GGCAACGTC | ATCTC | TAGTGAGAC | X | | |
| 5 | 2 | 3 | AGCAGTTTC | TTTTAC | TTGTGAGGG | X | | |
| 5 | 2 | 3 | AGCAGTTTC | AGTATC | TTGTGAGGG | X | | |
| 5 | 2 | 3 | AGCAGCAGC | CGAAC | GAGGGAGAT | X | | |
| 5 | 2 | 3 | AGCAGCAGC | CCAGG | GAGGGAGAT | X | | |
| 5 | 2 | 3 | AGCAACTTC | TCTAA | TTGTGAGGT | X | | |
| 5 | 2 | 3 | AGCAACTTC | CACAG | TTGTGAGGT | X | | |
| 5 | 2 | 3 | AGCAAGGTC | AGTGA | TAGTGAATA | X | | |
| 5 | 2 | 3 | AGCAGTTTC | GGTGTT | TTGTGAGGG | X | | |
| 5 | 2 | 3 | AGCAGCAGC | AGGAA | GAGGGAGAT | X | | |
| 5 | 2 | 3 | AGCATTGTC | TTAGA | AAGTAAGGG | X | | |
| 5 | 3 | 2 | AGCCCAGTC | TCAGG | GAGTGAGAG | X | | |
| 5 | 3 | 2 | AGCTACATC | TGCATT | GAGTGAGTC | X | | |
| 5 | 3 | 2 | AGCATGGTT | TGAAAG | GAGTGAGCC | X | | |
| 5 | 3 | 2 | GACAGGGTC | CACTTG | GAGTGAGTC | X | | |
| 5 | 3 | 2 | ATCCTCGTC | CTGCA | GAGTGAGTC | X | | |
| 5 | 3 | 2 | CAGAGCGTC | CAGGT | GAGTGAGTC | X | | |
| 5 | 3 | 2 | AGCAAAGGC | CTGAAG | GAGTAAGGG | X | | |
| 5 | 3 | 2 | AGCATCGAT | TAAAA | GAGTGAGAG | X | | |
| 5 | 3 | 2 | ATCATGGTC | ACTTT | GAGGGAGGG | X | | |
| 5 | 3 | 2 | AGCCCAGTC | CCCCTA | GAGTGAGAG | X | | |
| 5 | 3 | 2 | TGCATAGTC | AATTT | GAGTGAGAT | X | | |
| 5 | 3 | 2 | AGCCATGTC | AGCTT | GAGGGAGGT | X | | |
| 5 | 3 | 2 | AGCATTGTA | GGGGAC | GAGTGTGGT | X | | |
| 5 | 3 | 2 | ATCATGGTC | CAGGA | GAGGGAGGG | X | | |
| 5 | 3 | 2 | AGCAAAGGC | CAAGT | GAGTAAGGG | X | | |
| 5 | 3 | 2 | ATAAGAGTC | ATGCAG | GAGTGAGTG | X | | |
| 5 | 3 | 2 | AGCCATGTC | CCAAGG | GAGGGAGGT | X | | |
| 5 | 3 | 2 | AGCAAAGGC | AATGA | GAGTAAGGG | X | | |
| 5 | 3 | 2 | AGCCCAGTC | AGGAT | GAGTGAGAG | X | | |
| 5 | 4 | 1 | TTCCACGTC | AACAT | GAGTGAGGG | X | | |
| 5 | 4 | 1 | AGTCAGGTC | CCCACA | GAGTGAGGT | X | | |
| 5 | 4 | 1 | CTGAGGGTC | GGTAG | GAGTGAGGC | X | | |
| 5 | 4 | 1 | ATGACAGTC | TATGCA | GAGTGAGGC | X | | |
| 5 | 4 | 1 | AACAGTCTA | CCTGA | GAGTGAGGC | X | | |
| 5 | 4 | 1 | CTCAGTTTC | CTGAG | GAGTGAGGG | X | | |
| 5 | 4 | 1 | AGTCAGGTC | TTCCAT | GAGTGAGGG | X | | |
| 5 | 4 | 1 | GTGGGCGTC | CACTAA | GAGTGAGGC | X | | |
| 5 | 4 | 1 | GGTGGGGTC | CTTGAA | GAGTGAGGC | X | | |
| 5 | 4 | 1 | AGTTAAGTC | TCTAGA | GAGTGAGGG | X | | |
| 5 | 4 | 1 | TTCACCTTC | CACCAT | GAGTGAGGC | X | | |
| 5 | 4 | 1 | TCCTGAGTC | TTGGTA | GAGTGAGGC | X | | |
| 5 | 4 | 1 | ATAATAGTC | TCCAT | GAGTGAGGC | X | | |
| 5 | 4 | 1 | AGCAAAGGT | GGGGTG | GAGTGAGGT | X | | |
| 5 | 4 | 1 | AGTTTAGTC | CTTGG | GAGTGAGGT | X | | |
| 5 | 4 | 1 | ACAAAGGTC | CTCCA | GAGTGAGGC | X | | |
| 5 | 4 | 1 | TGCAGTCCC | AATCA | GAGTGAGGT | X | | |
| 5 | 4 | 1 | AGTCATGTC | GTTAA | GAGTGAGGC | X | | |
| 5 | 4 | 1 | CACCACGTC | AAGGTA | GAGAGAGGA | X | | |
| 5 | 4 | 1 | CTCAGTTTC | AAAAGC | GAGTGAGGG | X | | |
| 5 | 4 | 1 | GAAAGTGTC | CAAGTG | GAGTGAGGC | X | | |
| 5 | 4 | 1 | GGGTGGGTC | TAGAGG | GAGTGAGGT | X | | |
| 5 | 4 | 1 | AGAGTTGTC | CCCCAA | GAGTGAGGC | X | | |
| 6 | 4 | 2 | AGAAGGGGT | AGGAG | GAGTGAGAG | X | | |
| 3 | 1 | 2 | AGCAGAGTC | ATATT | GAGTCAGGG | | | X |

| # of mutations | | | VF2468 concentration | | | | |
|---|---|---|---|---|---|---|---|
| T | (−) | (+) | (−) site | spacer | (+) site | 4 nM | 2 nM | 10.5 nM |
| 3 | 3 | 0 | ACCATCTTC | ATCAG | GAGTGAGGA | | | X |
| 4 | 2 | 2 | AGGAACGTC | TCCAA | GGGTGAGGG | | | X |
| 4 | 2 | 2 | AGCACCTTC | AGAGG | GAGTGTGGC | | | X |
| 4 | 2 | 2 | GGCAGGGTC | GGTCA | GAGTGAGAG | | | X |
| 4 | 2 | 2 | GGCAGGGTC | ACAGGT | GAGTGAGAG | | | X |
| 4 | 2 | 2 | AGCACAGTC | AAGCT | GAGGGAGGT | | | X |
| 4 | 2 | 2 | GGCAGGGTC | TAGGCA | GAGTGAGAG | | | X |
| 4 | 2 | 2 | AGCAAGGTC | TACTCG | GGGTGAGGC | | | X |
| 4 | 3 | 1 | AGCAAGTTC | CGTTAA | GAGTGAGGT | | | X |
| 4 | 3 | 1 | AGCAGTTTT | TGCAGT | GAGTGAGGC | | | X |
| 2 | 1 | 1 | AGCTGCGTC | ACATG | GACTGAGGA | X | | |
| 3 | 1 | 2 | AGCAGGGTC | TGAGCT | GTGTGGGGA | | | X |
| 3 | 1 | 2 | AGCAGGGTC | AGCTG | GTGTGGGGA | | | X |
| 3 | 2 | 1 | AGAAGCCTC | AAGGAT | GAGTGAGGT | X | | |
| 3 | 2 | 1 | AGAAGCCTC | ATAAGT | GAGTGAGGT | | | X |
| 3 | 3 | 0 | AGCATTTTC | AATTT | GAGTGAGGA | | | X |
| 4 | 0 | 4 | AGCAGCGTC | CCTCC | GACACTGGA | | | X |
| 4 | 1 | 3 | AGCAGTGTC | ACCGAC | AGGTGAGGC | | | X |
| 4 | 1 | 3 | AGCAGTGTC | TGGGA | GAGGGTAGA | | | X |
| 4 | 2 | 2 | AGCAACTTC | TTCCT | GGGTGAGGC | | | X |
| 4 | 3 | 1 | AGCCCGGTC | TGAAAG | GAGTGAAGA | | | X |
| 4 | 3 | 1 | AGTAACTTC | TGAGTG | GAGTGAGGC | | | X |
| 4 | 3 | 1 | AGTAACTTC | AAAAT | GAGTGAGGC | | | X |
| 4 | 3 | 1 | ACCTGCTTC | AAAGT | GAGTGAGGG | | | X |
| 4 | 3 | 1 | AGCATTTTC | CCCCTA | AAGTGAGGA | | | X |
| 4 | 3 | 1 | AGTAACTTC | AGTATA | GAGTGAGGC | | | X |
| 4 | 3 | 1 | AGCAATGTT | TGAGT | GAGTGATGA | | | X |
| 4 | 3 | 1 | AGCATTTTC | CTTTA | AAGTGAGGA | | | X |
| 4 | 3 | 1 | AGCCACGGC | TGCCTG | GAGTGAGGG | | | X |
| 4 | 4 | 0 | CCTAGAGTC | CAGGA | GAGTGAGGA | | | X |
| 5 | 4 | 1 | ATCATAGTG | ACCAC | GAGTGAGGC | | | X |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09322006B2). An electronic copy of the "Sequence Listing" will also be available from the USPTO upon request and payment of the fee set forth in 37 CFR 1.19(b)(3).

What is claimed is:

1. A method comprising
   (a) providing a dimeric nuclease that cuts one or more double-stranded target sites of a double-stranded nucleic acid and creates a 5' overhang on the double-stranded nucleic acid, wherein the dimeric nuclease comprises two nuclease monomers, and wherein each of the target sites comprises
      (i) a left-half site, wherein the left-half site comprises a nucleic acid sequence that is bound by one monomer of the dimeric nuclease;
      (ii) a right-half site, wherein the right-half site comprises a nucleic acid sequence that is bound by other monomer of the dimeric nuclease; and
      (iii) a spacer sequence between the left-half site and the right-half site;
   wherein the left-half site, the spacer sequence, and right-half site forms a 5'-[the left-half site]-[the spacer sequence]-[the right-half site]-3' (LSR) structure, and the cleavage site of the dimeric nuclease is located within the spacer sequence;
   (b) contacting the dimeric nuclease with a library of candidate nucleic acid molecules, wherein each of the candidate nucleic acid molecules comprises a concatemer containing multiple copies of identical DNA sequences, a plurality of the target sites and multiple constant insert sequences, each of the constant insert sequences is located between two target sites of the plurality of the target sites, and each of the multiple copies of the identical DNA sequences comprises a target site of the plurality of the target sites and a constant insert sequence of the multiple constant insert sequences, under conditions suitable for the dimeric nuclease to cut a candidate nucleic acid molecule of the library of candidate nucleic acid molecules; thereby generating one or more candidate nucleic acid molecules cut once, twice and multiple times by the dimeric nuclease, wherein the candidate nucleic acid molecules cut twice by the dimeric nuclease comprise a 5' overhang and the constant insert sequence flanked by the left half-site and a part of the spacer sequence from one of the plurality of the target sites, and flanked by the right half-site and a part of the spacer sequence from another of the plurality of the target sites, (c) filling in the 5' overhang of each of the one or more candidate nucleic acid molecules cut twice by the dimeric nuclease, thereby creating one or more candidate nucleic acid molecules with blunt ends; and (d) identifying the one or more target sites of the one or more candidate nucleic acid molecules cut twice by the dimeric nuclease by determining the sequence of the one or more candidate nucleic acid molecules with blunt ends created in step (c).

2. The method of claim 1, wherein step (d) further comprises ligating sequencing adapters to the blunt ends of the one or more candidate nucleic acid molecules with blunt ends and amplifying and/or sequencing the one or more candidate nucleic acid molecules with blunt ends.

3. The method of claim 2, wherein said amplifying the one or more candidate nucleic acid molecules with blunt ends is performed via PCR after said ligating the sequencing adapters.

4. The method of claim 1, further comprises a step of enriching more than one of the candidate nucleic acid molecules with blunt ends.

5. The method of claim 4, wherein the step of enriching the more than one of the candidate nucleic acid molecules with blunt ends comprises a size fractionation of the more than one of the candidate nucleic acid molecules with blunt ends.

6. The method of claim 5, wherein the size fractionation is done by gel purification.

7. The method of claim 1, wherein the nuclease is a homing endonuclease.

8. The method of claim 1, further comprising compiling more than one of the target sites identified in step (d), thereby generating a nuclease target site profile.

9. The method of claim 1, wherein the nuclease is a therapeutic nuclease which cuts one or more specific nuclease target sites in a gene associated with a disease.

10. The method of claim 9 further comprising determining a maximum concentration of the therapeutic nuclease at which the therapeutic nuclease cuts the specific nuclease target sites, and does not cut more than 10 of the specific nuclease target sites in a genome.

11. The method of claim 9 further comprising determining a maximum concentration of the therapeutic nuclease at which the therapeutic nuclease cuts the specific nuclease target sites, and does not cut more than 5 of the specific target sites in a genome.

12. The method of claim 9 further comprising determining a maximum concentration of the therapeutic nuclease at which the therapeutic nuclease cuts the specific nuclease target sites, and does not cut more than 2 of the specific target sites in a genome.

13. The method of claim 9 further comprising determining a maximum concentration of the therapeutic nuclease at which the therapeutic nuclease cuts a specific nuclease target site of the specific nuclease target sites, and does not cut more than 1 of the specific target sites in a genome.

14. The method of claim 9 further comprising determining a maximum concentration of the therapeutic nuclease at which the therapeutic nuclease cuts a specific nuclease target site of the specific nuclease target sites, and does not cut any additional specific nuclease target site of the specific nuclease target sites in a genome.

15. The method of claim 1, wherein the nuclease comprises an unspecific nucleic acid cleavage domain.

16. The method of claim 1, wherein the nuclease comprises a FokI cleavage domain.

17. The method of claim 1, wherein the nuclease comprises a nucleic acid cleavage domain that cleaves a target sequence upon dimerization of the nucleic acid cleavage domain.

18. The method of claim 1, wherein the nuclease comprises a binding domain that specifically binds a nucleic acid sequence.

19. The method of claim 18, wherein the binding domain comprises a zinc finger.

20. The method of claim 19, wherein the binding domain comprises at least 2 zinc fingers.

21. The method of claim 19, wherein the binding domain comprises at least 3 zinc fingers.

22. The method of claim 19, wherein the binding domain comprises at least 4 zinc fingers.

23. The method of claim 19, wherein the binding domain comprises at least 5 zinc fingers.

24. The method of claim 18, wherein the binding domain comprises a Transcriptional Activator-Like Element.

25. The method of claim 1, wherein the nuclease is a Zinc Finger Nuclease.

26. The method of claim 1, wherein the nuclease is a Transcriptional Activator-Like Element Nuclease (TALEN).

* * * * *